(12) United States Patent
Peterson

(10) Patent No.: US 12,110,540 B2
(45) Date of Patent: Oct. 8, 2024

(54) **COMPOSITIONS AND METHODS FOR DETECTING TOXIGENIC *CLOSTRIDIUM DIFFICILE***

(71) Applicant: Gen-Probe Incorporated

(72) Inventor: Patrick Lynn Peterson, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 739 days.

(21) Appl. No.: 16/769,229

(22) PCT Filed: Dec. 13, 2018

(86) PCT No.: PCT/US2018/065470
§ 371 (c)(1),
(2) Date: Jun. 2, 2020

(87) PCT Pub. No.: WO2019/118735
PCT Pub. Date: Jun. 20, 2019

(65) Prior Publication Data
US 2020/0318171 A1 Oct. 8, 2020

Related U.S. Application Data

(60) Provisional application No. 62/599,494, filed on Dec. 15, 2017.

(51) Int. Cl.
*C12Q 1/689* (2018.01)
*C12Q 1/6827* (2018.01)

(52) U.S. Cl.
CPC .......... *C12Q 1/6827* (2013.01); *C12Q 1/689* (2013.01); *C12Q 2537/143* (2013.01); *C12Q 2561/109* (2013.01); *C12Q 2565/101* (2013.01); *C12Q 2600/156* (2013.01); *C12Q 2600/166* (2013.01)

(58) Field of Classification Search
CPC ........ C12Q 2561/109; C12Q 2565/101; C12Q 2600/156; C12Q 2600/166
See application file for complete search history.

(56) References Cited

U.S. PATENT DOCUMENTS

2007/0202517 A1  8/2007  Agarwal et al.

FOREIGN PATENT DOCUMENTS

| CN | 104928376 A | 9/2015 | |
|---|---|---|---|
| GB | 2549799 A | 11/2017 | |
| WO | 2010116290 A1 | 10/2010 | |
| WO | WO-2019032809 A1 * | 2/2019 | ............. C12Q 1/689 |

OTHER PUBLICATIONS

Du et al. Sequence Variation in tcdA and tedB of Clostridium difficile: ST37 with Truncated tcdA Is a Potential Epidemic Strain in China. Journal of Clinical Microbiology 2014; 52(9): 3264-3270 + Supplementary Information (Year: 2014).*
Tadokoro et al.Classification of hepatitis B virus genotypes by the PCR-Invader method with genotype-specific probes. Journal of Virological Methods 2006; 138: 30-39 (Year: 2006).*
Tadokoro et al. Quantitation of viral load by real-time PCR-monitoring Invader reaction. Journal of Virological Methods 155: 182-186 (Year: 2009).*
Goorhuis et al., "Emergence of Clostridium difficile Infection Due to a New Hypervirulent Strain, Polymerase Chain Reaction Ribotype 078," Clinical Infectious Diseases, 47(9): 1162-1170 (2008).
Jensen et al., "Diagnosis of Clostridium difficile: real-time PCR detection of toxin genes in faecal samples is more sensitive compared to toxigenic culture," European Journal of Clinical Microbiology & Infectious Diseases, 34(4): 727-736 (2014).
Joost et al., "Characterisation of Clostridium difficile isolates by sIpA and tcdC gene sequencing," International Journal of Antimicrobial Agents, 33: S31-S18 (2009).
Office Action for European Application No. 18836749.4, dated Apr. 24, 2023, 9 pages.
Baron et al., "The Emerging Threat of Clostridium difficile Infection: New Insights into Diagnosis and Disease Management," 16 pages (2010).
Chevaliez et al., "Hepatitis Virus C RNA quantification by automated cobas ampliprep-cobas taqman 48 (CAP-CTM) real-time PCR assay: An evaluation of performance," Journal of Hepatology, 44(2): S195-S196 (2006).
Huang et al., "Comparison of a Commercial Multiplex Real-Time PCR to the Cell Cytotoxicity Neutralization Assay for Diagnosis of Clostridium difficile Infections," Journal of Clinical Microbiology, 47(11): 3729-3731 (2009).
International Search Report from PCT application No. PCT/US2018/065470, dated Mar. 19, 2019, 34 pages.
Ohno et al. "New Hepatitis C Virus (HCV) Genotyping System That Allows for Identification of HCV Genotypes 1a, 1b, 2a, 2b, 3a, 3b, 4, 5a, and 6a," Journal of Clinical Microbiology, 35(1): 201-207 (1997).
Stamper et al., "Comparison of a Commercial Real-Time PCR Assay for tcdB Detection to a Cell Culture Cytotoxicity Assay and Toxigenic Culture for Direct Detection of Toxin-Producing Clostridium difficile in Clinical Samples," Journal of Clinical Microbiology, 47(2): 373-378 (2009).

* cited by examiner

*Primary Examiner* — Angela M. Bertagna
(74) *Attorney, Agent, or Firm* — Michael J. Gilly; Adam M. Breier

(57) ABSTRACT

Provided herein are compositions, kits, and methods for detecting at least one of a *C. diffcile* tcdA, tcdB, tcdC, cdtA, or cdtB nucleic acid in a sample. In son embodiments, one or more alleles of tcdC such as 117del tcdC or 184T tcdC are detected.

12 Claims, No Drawings

Specification includes a Sequence Listing.

SEQUENCE LISTING

<160> NUMBER OF SEQ ID NOS: 339

<210> SEQ ID NO 1
<211> LENGTH: 681
<212> TYPE: DNA
<213> ORGANISM: Clostridioides difficile

<400> SEQUENCE: 1

```
atgttttcta aaaaaaatga gggtaacgaa tttagtaatg aaggaaaagg aagctctaag    60
aaaataatta aattctttaa gagcacaaag ggtattgctc tactggcatt tattttgggc   120
gtgttttttg gcaatatatc ctcaccagct tgttctgaag accatgagga ggtcatttct   180
aatcaaacat cagttataga ttctcaaaaa acagaaatag aaactttaaa tagcaaattg   240
tctgatgctg aaccatggtt caaaatgaaa gacgacgaaa agaaagctat tgaagctgaa   300
atcaacgta aagctgaaga agctaaaaag gctgaagaac aacgtaaaaa agaagaagaa   360
gagaagaaag gatatgatac tggtattact tatgaccaat tagctagaac acctgatgat   420
tataagtaca aaaaggtaaa atttgaaggt aaggttattc aagttattga gatggtgat   480
gaggtgcaaa taagattagc tgtgtctgga aattatgata aggtcgtact atgtagttat   540
aaaaaatcaa taactccttc aagagtgtta gaggatgatt acataactat aagaggtata   600
agtgctggaa ctataactta tgaatcaact atgggtggaa atataactat accagggata   660
gctgtagaga aaataaatta a                                              681
```

<210> SEQ ID NO 2
<211> LENGTH: 480
<212> TYPE: DNA
<213> ORGANISM: Clostridioides difficile

<400> SEQUENCE: 2

```
atgttttcta aaaaaaatga gggtaacgaa tttagtaatg aaggaaaagg aagctctaag    60
aaaataatta aattctttaa gagcacaaag ggtattgctc tactggcatt tattttaggc   120
gtgttttttg gcaatatatc ctcaccatct tgttctgaag accatgagga ggtcatttct   180
aaccaaacat cagttataga ttctcaaaaa acagaaatag aaactttaaa tagcaaattg   240
tctgatgctg aaccatggtt caaaatgaaa gacgacgaaa agaaagctat tgaagctgaa   300
atcaacgta aagctgaaga agctaaaaaa gctgaagaag ctaaaaaggc tgaagaacaa   360
cgcaaaaaag aagaaggagga gaagaaagga tatgatactg gtattactta tgaccaatta   420
gctagaacac ctgatgatta aagtacaaa aaggtaaaat ttgaaggtaa ggttattcaa   480
```

<210> SEQ ID NO 3
<211> LENGTH: 680
<212> TYPE: DNA
<213> ORGANISM: Clostridioides difficile

<400> SEQUENCE: 3

```
atgttttcta aaaaaaatga gggtaacgaa tttagtaatg aaggaaaagg aagctctaag    60
aaaataatta aattctttaa gagcacaaag ggtattgctc tactggcatt tattttggcg   120
tgttttttgg caatatatcc tcaccagctt gttctgaaga ccatgaggag gtcatttcta   180
atcaaacatc agttatagat tctcaaaaaa cagaaataga aactttaaat agcaaattgt   240
ctgatgctga accatggttc aaaatgaaag acgacgaaaa gaaagctatt gaagctgaaa   300
tcaacgtaa agctgaagaa gctaaaaagg ctgaagaaca acgtaaaaaa gaagaagaag   360
agaagaaagg atatgatact ggtattactt atgaccaatt agctagaaca cctgatgatt   420
ataagtacaa aaaggtaaaa tttgaaggta aggttattca agttattgaa gatggtgatg   480
aggtgcaaat aagattagct gtgtctggaa attatgataa ggtcgtacta tgtagttata   540
aaaaatcaat aactccttca agagtgttag aggatgatta cataactata agaggtataa   600
```

```
gtgctggaac tataacttat gaatcaacta tgggtggaaa tataactata ccagggatag     660
ctgtagagaa aataaattaa                                                 680

<210> SEQ ID NO 4
<211> LENGTH: 681
<212> TYPE: DNA
<213> ORGANISM: Clostridioides difficile

<400> SEQUENCE: 4
atgttttcta aaaaaatga gggtaacgaa tttagtaatg aaggaaaagg aagctctaag      60
aaaataatta aattctttaa gagcacaaag ggtattgctc tactggcatt tattttggc    120 gtgttttttg gcaatatatc ctcaccagct tgttctgaag accatgagga ggtcatttct    180
aatcaaacat cagttataga ttctcaaaaa acagaaatag aaactttaaa tagcaaattg    240
tctgatgctg aaccatggtt caaaatgaaa gacgacgaaa agaaagctat tgaagctgaa    300
aatcaacgta agctgaaga agctaaaaag gctgaagaac aacgtaaaaa agaagaagaa    360
gagaagaaag gatatgatac tggtattact tatgaccaat tagctagaac acctgatgat    420
tataagtaca aaaaggtaaa atttgaaggt aaggttattc aagttattga agatggtgat    480
gaggtgcaaa taagattagc tgtgtctgga aattatgata aggtcgtact atgtagttat    540
aaaaaatcaa taactccttc aagagtgtta gaggatgatt acataactat aagaggtata    600
agtgctggaa ctataactta tgaatcaact atgggtggaa atataactat accagggata    660
gctgtagaga aataaaatta a                                               681

<210> SEQ ID NO 5
<211> LENGTH: 681
<212> TYPE: DNA
<213> ORGANISM: Clostridioides difficile

<400> SEQUENCE: 5
atgttttcta aaaaaatga gggtaacgaa tttagtaatg aaggaaaagg aagctctaag      60
aaaataatta aattctttaa gagcacaaag ggtattgctc tactggcatt tattttggc    120 gtgttttttg gcaatatatc ctcaccagct tgttctgaag accatgagga ggtcatttct    180
aattaaacat cagttataga ttctcaaaaa acagaaatag aaactttaaa tagcaaattg    240
tctgatgctg aaccatggtt caaaatgaaa gacgacgaaa agaaagctat tgaagctgaa    300
aatcaacgta agctgaaga agctaaaaag gctgaagaac aacgtaaaaa agaagaagaa    360
gagaagaaag gatatgatac tggtattact tatgaccaat tagctagaac acctgatgat    420
tataagtaca aaaaggtaaa atttgaaggt aaggttattc aagttattga agatggtgat    480
gaggtgcaaa taagattagc tgtgtctgga aattatgata aggtcgtact atgtagttat    540
aaaaaatcaa taactccttc aagagtgtta gaggatgatt acataactat aagaggtata    600
agtgctggaa ctataactta tgaatcaact atgggtggaa atataactat accagggata    660
gctgtagaga aataaaatta a                                               681

<210> SEQ ID NO 6
<211> LENGTH: 2631
<212> TYPE: DNA
<213> ORGANISM: Clostridioides difficile

<400> SEQUENCE: 6
atgaaagtac aaatgaggaa taaaaaggta ttaagttttt taacacttac agccatagtt      60
agtcaagcat tagcatatcc tgtatatgct caaactagta caagtagcca ttctgataat    120
```

```
aaaaaagaaa ttataaatga agacatactc acaaacaacg gattaatggg atattatttc      180
acagacgaac actttaaaga tttaaaatta atggcaccca taaagatgg taatttaaaa        240 tttgaagaaa agaaagtaga taaacttcta aataaagaca aatcaaatgt aaaatctata       300
cgatggacag gaagaataat tccttctaag gatggtgaat atacattatc aactgataga      360
gatgatattt taatgcaagt aaataatgag agtactatat caaatacact taaagttaat     420
atgaaaaagg gtaaagaata taaatttaga atagagctac aagataaaaa tttaggttca      480
atagataatt tatcatcacc aaatctttat tgggaattag atggtattaa gaaaattata     540
ccagcagaaa atttattctt aagagattat tctaatatag aaaaaaatga tccatttatc     600
ccaaataaca atttctttga cccaaggttg atgtctgatt gggaagacga agatttggat     660
acagataatg ataatatacc agattcatat gaacgaaatg gatatactat taaggactta    720
attgcagtta agtgggaaga tagctttgca gaacaaggct ataagaaata tgtatcaaat    780
tatttagagt caaatactgc tggagatcca tatacagatt atgaaaaagc ttcaggttct    840
tttgacaagg ctataaagac cgaagcaaga gatccgttag ttgcagcgta tccaattgtt    900
ggagtaggta tggaaaaatt aattatatct acaaatgaac atgcctctac tgatcaaggt    960
aaaactgttt ccagagctac tactaacagt aaaactgaat ctaatacagc tggtgtttct     1020
gttaatgtag gatatcaaaa tggattcaca gctaatgtaa ctacaaatta ttcccataca    1080
acagataatt caactgccgt tcaagatagt aatggagaat catggaatac tggattaagt    1140
ataaacaaag gagaatctgc atatataaat gcaaatgtta gatattacaa cacaggtact    1200
gcacctatgt acaaagtgac accaacaaca aatttagtgt tagatggaga tacattatca     1260
actatcaaag cacaagaaaa tcaaattggc aataatctat ctcctggaga tacttatccc    1320
aaaaaagggc tttcacctct ggctcttaac acaatggatc aatttagctc tagactgatt    1380
cctataaatt atgatcaatt aaaaaaatta gatgctggaa agcaaattaa attgaaaaca    1440
acacaagtaa gtggaaattt tggtacaaaa aatagttctg gacaaatagt aacagaagga    1500
aatagttggt cagactatat aagtcaaatt gacagtattt ctgcatctat tatattagat    1560
acagagaatg aatcttacga aagaagagtt actgctaaaa atttacagaa tccagaagat    1620
aaaacacctg aacttacaat tggagaagca attgaaaaag cttttggcgc tactaaaaaa    1680
gatggtttgt tatattttaa tgatatacca atagatgaaa gttgtgttga actcatatt      1740 gatgataata cagccaataa gattaaagat agtttaaaaa ctttgtctga taaaagata      1800 tataatgtta aacttgaaag aggaatgaat atacttataa aaacaccaac ttactttact    1860
aattttgatg attacaataa ttaccctagt acatggagta atgtcaatac tacgaatcaa    1920
gatggtttac aaggctcagc aaataaatta atggtgaga caaagattaa aatacctatg      1980
tctaagctaa aaccttataa acgttatgtt tttagtggat attcaaagga tccctttaaca    2040 tctaattcaa taattgtaaa gataaaagca aagaagaaa aaacgggatta tttggtacca      2100 gaacaaggat atacaaagtt tagttatgaa tttgaaacta ctgaaaaaga ttcttctaat    2160
atagagataa cattaattgg tagtggtaca acatacttag ataacttatc tattacagaa    2220
ctgaatagta ctcctgaaat acttaatgaa ccagaagtta aaattccaac tgaccaagaa    2280
ataatagatg cacataaaat atattctgca gatttaaatt ttaatccaag tacaggaaat    2340
gcttatataa atggtatgta ttttacacca acacaaacta ataagaagc tctcgattat      2400 atccaaaaat atagagttga agctacttta caatattctg gattaaaga tattggaact     2460
```

-continued

| | |
|---|---|
| aaagataaag aaatgcgtaa ttatttagga gatccaaatc aacctaaaac taattatgtc | 2520 |
| aatcttagga gttattttac aggtggagaa aatattatga catacaagaa attaagaata | 2580 |
| tatgcaatta ctccagatga tagagagtta ttagttctta gtgttgatta g | 2631 |

<210> SEQ ID NO 7
<211> LENGTH: 8133
<212> TYPE: DNA
<213> ORGANISM: Clostridioides difficile

<400> SEQUENCE: 7

| | |
|---|---|
| atgtctttaa tatctaaaga agagttaata aaactcgcat atagcattag accaagagaa | 60 |
| aatgagtata aaactatact aactaattta gacgaatata ataagttaac tacaaacaat | 120 |
| aatgaaaata atatttaca attaaaaaaa ctaaatgaat caattgatgt ttttatgaat | 180 |
| aaatataaaa cttcaagcag aaatagagca ctctctaatc taaaaaaaga tatattaaaa | 240 |
| gaagtaattc ttattaaaaa ttccaataca agccctgtag aaaaaaattt acattttgta | 300 |
| tggataggtg gagaagtcag tgatattgct cttgaataca taaaacaatg ggctgatatt | 360 |
| aatgcagaat ataatattaa actgtggtat gatagtgaag cattcttagt aaatacacta | 420 |
| aaaaaggcta tagttgaatc ttctaccact gaagcattac agctactaga ggaagagatt | 480 |
| caaaatcctc aatttgataa tatgaaattt acaaaaaaaa ggatggaatt tatatatgat | 540 |
| agacaaaaaa ggtttataaa ttattataaa tctcaaatca ataaacctac agtacctaca | 600 |
| atagatgata ttataaagtc tcatctagta tctgaatata tagagatga aactgtatta | 660 |
| gaatcatata gaacaaattc tttgagaaaa ataaatagta atcatgggat agatatcagg | 720 |
| gctaatagtt tgtttacaga acaagagtta ttaaatattt atagtcagga gttgttaaat | 780 |
| cgtggaaatt tagctgcagc atctgacata gtaagattat tagccctaaa aaattttggc | 840 |
| ggagtatatt tagatgttga tatgcttcca ggtattcact ctgatttatt taaaacaata | 900 |
| tctagaccta gctctattgg actagaccgt tgggaaatga taaaattaga ggctattatg | 960 |
| aagtatataaa aatatataaa taattataca tcagaaaact ttgataaact tgatcaacaa | 1020 |
| ttaaaagata attttaaact cattatagaa agtaaaagtg aaaaatctga gatattttct | 1080 |
| aaattagaaa atttaaatgt atctgatctt gaaattaaaa tagctttcgc tttaggcagt | 1140 |
| gttataaaatc aagccttgat atcaaaacaa ggttcatatc ttactaacct agtaatagaa | 1200 |
| caagtaaaaa atagatatca atttttaaac caacacctta acccagccat agagtctgat | 1260 |
| aataacttca cagatactac taaaattttt catgattcat tatttaattc agctaccgca | 1320 |
| gaaaactcta tgtttttaac aaaaatagca ccatacttac aagtaggttt tatgccagaa | 1380 |
| gctcgctcca caataagttt aagtggtcca ggagcttatg cgtcagctta ctatgatttc | 1440 |
| ataaatttac aagaaaatac tatagaaaaa actttaaaag catcagattt aatagaattt | 1500 |
| aaattcccag aaaataatct atctcaattg acagaacaag aaataaatag tctatggagc | 1560 |
| tttgatcaag caagtgcaaa atatcaattt gagaaatatg taagagatta tactggtgga | 1620 |
| tctctcttctg aagacaatgg ggtagacttt aataaaaata ctgccctcga caaaaactat | 1680 |
| ttattaaata taaaaattcc atcaaacaat gtagaagaag ctggaagtaa aaattatgtt | 1740 |
| cattatatca tacagttaca aggagatgat ataagttatg aagcaacatg caatttattt | 1800 |
| tctaaaaatc ctaaaaatag tattattata caacgaaata tgaatgaaag tgcaaaaagc | 1860 |
| tactttttaa gtgatgatgg agaatctatt ttagaattaa ataaatatag gatacctgaa | 1920 |
| agattaaaaa ataaggaaaa agtaaaagta acctttattg gacatggtaa agatgaattc | 1980 |

```
aacacaagcg aatttgctag attaagtgta gattcacttt ccaatgagat aagttcattt    2040
ttagatacca taaaattaga tatatcacct aaaaatgtag aagtaaactt acttggatgt    2100
aatatgttta gttatgattt taatgttgaa gaaacttatc ctgggaagtt gctattaagt    2160
attatggaca aaattacttc cactttacct gatgtaaata aaaattctat tactatagga    2220
gcaaatcaat atgaagtaag aattaatagt gagggaagaa aagaacttct ggctcactca    2280
ggtaaatgga taaataaaga agaagctatt atgagcgatt tatctagtaa agaatacatt    2340 tttttttgatt ctatagataa taagctaaaa gcaaagtcca agaatattcc aggattagca   2400
tcaatatcag aagatataaa aacattatta cttgatgcaa gtgttagtcc tgatacaaaa    2460
tttattttaa ataatcttaa gcttaatatt gaatcttcta ttggtgatta catttattat    2520
gaaaaattag agcctgttaa aaatataatt cacaattcta tagatgattt aatagatgag    2580
ttcaatctac ttgaaaatgt atctgatgaa ttatatgaat taaaaaaatt aaataatcta    2640
gatgagaagt atttaatatc tttttgaagat atctcaaaaa ataattcaac ttactctgta   2700
agatttatta acaaaagtaa tggtgagtca gtttatgtag aaacagaaaa agaaatttttt   2760 tcaaaatata gcgaacatat tacaaaagaa ataagtacta taagaatag tataattaca     2820 gatgttaatg gtaatttatt ggataatata cagttagatc atacttctca agttaataca    2880
ttaaacgcag cattctttat tcaatcatta atagattata gtagcaataa agatgtactg    2940
aatgatttaa gtacctcagt taaggttcaa ctttatgctc aactatttag tacaggttta    3000
aatactatat atgactctat ccaattagta aatttaatat caaatgcagt aaatgatact    3060
ataaatgtac tacctacaat aacagagggg atacctattg tatctactat attagacgga    3120
ataaacttag gtgcagcaat taaggaatta ctagacgaac atgacccatt actaaaaaaa    3180
gaattagaag ctaaggtggg tgttttagca ataaatatgt cattatctat agctgcaact    3240
gtagcttcaa ttgttggaat aggtgctgaa gttactattt tcttattacc tatagctggt    3300
atatctgcag gaataccttc attagttaat aatgaattaa tattgcatga taaggcaact    3360
tcagtggtaa actatttttaa tcatttgtct gaatctaaaa aatatggccc tcttaaaaca   3420
gaagatgata aaattttagt tcctattgat gatttagtaa tatcagaaat agattttaat    3480
aataattcga taaaactagg aacatgtaat atattagcaa tggagggggg atcaggacac    3540
acagtgactg gtaatataga tcactttttc tcatctccat ctataagttc tcatattcct    3600
tcattatcaa tttattctgc aataggtata gaaacagaaa atctagattt ttcaaaaaaa    3660
ataatgatgt tacctaatgc tccttcaaga gtgttttggt gggaaactgg agcagttcca    3720
ggtttaagat cattggaaaa tgacggaact agattacttg attcaataag agatttatac    3780
ccaggtaaat tttactggag attctatgct tttttcgatt atgcaataac tacattaaaa    3840
ccagtttatg aagacactaa tattaaaatt aaactagata agatactag aaacttcata    3900 atgccaacta taactactaa cgaaattaga aacaaattat cttattcatt tgatggagca    3960
ggaggaactt actctttatt attatcttca tatccaatat caacgaatat aaatttatct    4020
aaagatgatt tatggatatt taatattgat aatgaagtaa gagaaatatc tatagaaaat    4080
ggtactatta aaaaaggaaa gttaataaaa gatgttttaa gtaaaattga tataaataaa    4140
aataaactta ttataggcaa tcaaacaata gattttcag gcgatataga taataaagat    4200
agatatatat tcttgacttg tgagttagat gataaaatta gtttaataat agaaataaat    4260
cttgttgcaa aatcttatag tttgttattg tctggggata aaaattattt gatatccaat    4320
```

```
ttatctaata ctattgagaa aatcaatact ttaggcctag atagtaaaaa tatagcgtac    4380
aattacactg atgaatctaa taataaatat tttggagcta tatctaaaac aagtcaaaaa    4440
agcataatac attataaaaa agacagtaaa aatatattag aattttataa tgacagtaca    4500
ttagaattta acagtaaaga ttttattgct gaagatataa atgtatttat gaaagatgat    4560
attaatacta taacaggaaa atactatgtt gataataata ctgataaaag tatagatttc    4620
tctatttctt tagttagtaa aaatcaagta aaagtaaatg gattatattt aaatgaatcc    4680
gtatactcat cttaccttga ttttgtgaaa aattcagatg gacaccataa tacttctaat    4740
tttatgaatt tatttttgga caatataagt ttctggaaat tgtttgggtt tgaaaatata    4800
aattttgtaa tcgataaata ctttacccct gttggtaaaa ctaatcttgg atatgtagaa    4860
tttatttgtg acaataataa aaatatagat atatatttg gtgaatggaa aacatcgtca    4920
tctaaaagca ctatatttag cggaaatggt agaaatgttg tagtagagcc tatatataat    4980
cctgatacgg gtgaagatat atctacttca ctagatttt cctatgaacc tctctatgga    5040
atagatagat atataaataa agtattgata gcacctgatt tatatacaag tttaataaat    5100
attaatacca attattattc aaatgagtac taccctgaga ttatagttct aacccaaat    5160 acattccaca aaaagtaaa tataaattta gatagttctt cttttgagta taatggtct    5220 acagaaggaa gtgactttat tttagttaga tacttagaag aaagtaataa aaaaatatta    5280
caaaaaataa gaatcaaagg tatcttatct aatactcaat catttaataa aatgagtata    5340
gattttaaag atattaaaaa actatcatta ggatatataa tgagtaattt taaatcattt    5400
aattctgaaa atgaattaga tagagatcat ttaggattta aaataataga taataaaact    5460
tattactatg atgaagatag taaattagtt aaaggattaa tcaatataaa taattcatta    5520
ttctattttg atcctataga atttaactta gtaactggat ggcaaactat caatggtaaa    5580
aaatattatt ttgatataaa tactggagca gctttaacta gttataaaat tattaatggt    5640
aaacactttt atttttaataa tgatggtgtg atgcagttgg gagtatttaa aggacctgat    5700
ggatttgaat attttgcacc tgccaatact caaaataata acatagaagg tcaggctata    5760
gtttatcaaa gtaaattctt aactttgaat ggcaaaaaat attattttga taatgactca    5820
aaagcagtca ctggatggag aattattaac aatgagaaat attactttaa tcctaataat    5880
gctattgctg cagtcggatt gcaagtaatt gacaataata gtattatttt caatcctgac    5940
actgctatca tctcaaaagg ttggcagact gttaatggta gtagatacta ctttgatact    6000
gataccgcta ttgccttaa tggttataaa actattgatg gtaaacactt ttattttgat    6060
agtgattgtg tagtgaaaat aggtgtgttt agtacctcta atggatttga atattttgca    6120
cctgctaata cttataataa taacatagaa ggtcaggcta tagtttatca agtaaattc    6180 ttaactttga atggtaaaaa atattacttt gataataact caaaagcagt taccggatgg    6240
caaactattg atagtaaaaa atattacttt aatactaaca ctgctgaagc agctactgga    6300
tggcaaacta ttgatggtaa aaaatattac tttaatacta acactgctga agcagctact    6360
ggatggcaaa ctattgatgg taaaaaatat tactttaata ctaacactgc tatagcttca    6420
actggttata caattattaa tggtaaacat ttttatttta atactgatgg tattatgcag    6480
ataggagtgt ttaaaggacc taatggattt gaatattttg cacctgctaa tacggatgct    6540
aacaacatag aaggtcaagc tatactttac caaaatgaat tcttaacttt gaatagtaaa    6600
aaatattact ttggtagtga ctcaaaagca gttactggat ggagaattat taacaataag    6660
aaatattact ttaatcctaa taatgctatt gctgcaattc atctatgcac tataaataat    6720
```

```
gacaagtatt actttagtta tgatggaatt cttcaaaatg gatatattac tattgaaaga    6780
aataatttct attttgatgc taataatgaa tctaaaatgg taacaggagt atttaaagga    6840
cctaatggat ttgagtattt tgcacctgct aatactcaca ataataacat agaaggtcag    6900
gctatagttt accagaacaa attcttaact ttgaatggca aaaatattta ttttgataat    6960
gactcaaaag cagttactgg atggcaaacc attgatggta aaaatatta ctttaatctt    7020 aacactgctg aagcagctac tggatggcaa actattgatg gtaaaaaata ttactttaat    7080
cttaacactg ctgaagcagc tactggatgg caaactattg atggtaaaaa atattacttt    7140
aatactaaca ctttcatagc ctcaactggt tatacaagta ttaatggtaa acatttttat    7200
tttaatactg atggtattat gcagatagga gtgtttaaag gacctaatgg atttgaatac    7260
tttgcacctg ctaatactca taataataac atagaaggtc aagctatact ttaccaaaat    7320
aaattcttaa ctttgaatgg taaaaaatat tactttggta gtgactcaaa agcagttacc    7380
ggattgcgaa ctattgatgg taaaaaatat tactttaata ctaacactgc tgttgcagtt    7440
actggatggc aaactattaa tggtaaaaaa tactacttta atactaacac ttctatagct    7500
tcaactggtt atacaattat tagtggtaaa cattttatt ttaatactga tggtattatg    7560
cagataggag tgtttaaagg acctgatgga tttgaatact ttgcacctgc taatacagat    7620
gctaacaata tagaaggtca agctatacgt tatcaaaata gattcctata tttcacatgac    7680 aatatatatt attttggtaa taattcaaaa gcggctactg gttgggtaac tattgatggt    7740
aatagatatt acttcgagcc taatacagct atgggtgcga atggttataa aactattgat    7800
aataaaaact tttactttag aaatggttta cctcagatag gagtgtttaa agggtctaat    7860
ggatttgaat actttgcacc tgctaatacg gatgctaaca atatagaagg tcaagctata    7920
cgttatcaaa atagattcct acatttactt ggaaaaatat attactttgg taataattca    7980
aaagcagtta ctggatggca aactattaat ggtaaagtat attactttat gcctgatact    8040
gctatggctg cagctggtgg acttttcgag attgatggtg ttatatattt ctttggtgtt    8100
gatggagtaa agcccctgg gatatatggc taa                                 8133
```

<210> SEQ ID NO 8
<211> LENGTH: 7101
<212> TYPE: DNA
<213> ORGANISM: Clostridioides difficile

<400> SEQUENCE: 8

```
atgagtttag ttaatagaaa acagttagaa aaaatggcaa atgtaagatt tcgtactcaa     60
gaagatgaat atgttgcaat attggatgct ttagaagaat atcataatat gtcagagaat    120
actgtagtcg aaaatatttt aaaattaaaa gatataaata gttaacaga tatttatata    180 gatacatata aaaaatctgg tagaaataaa gccttaaaaa aatttaagga atatctagtt    240
acagaagtat tagagctaaa gaataataat ttaactccag ttgagaaaaa tttcactttt    300
gtttggattg gaggtcaaat aaatgacact gctattaatt atataaatca atggaaagat    360
gtaaatagtg attataatgt taatgttttt tatgatagta atgcattttt gataaacaca    420
ttgaaaaaaa ctgtagtaga atcagcaata aatgatacac ttgaatcatt tagagaaaac    480
ttaaatgacc ctagatttga ctataataaa ttcttcagaa acgtatggaa ataatttat    540 gataaacaga aaaatttcat aaactactat aaagctcaaa gagaagaaaa tcctgaactt    600
ataattgatg atattgtaaa gacatatctt tcaaatgagt attcaaagga gatagatgaa    660
```

```
cttaataacct atattgaaga atccttaaat aaaattacac agaatagtgg aaatgatgtt    720
agaaactttg aagaatttaa aaatggagag tcattcaact tatatgaaca agagttggta    780
gaaaggtgga atttagctgc tgcttctgac atattaagaa tatctgcatt aaaagaaatt    840
ggtggtatgt atttagatgt tgatatgtta ccaggaatac aaccagactt atttgagtct    900
atagagaaac ctagttcagt aacagtggat ttttgggaaa tgacaaagtt agaagctata    960
atgaaataca aagaatatat accagaatat acctcagaac attttgacat gttagacgaa   1020
gaagttcaaa gtagttttga atctgttcta gcttctaagt cagataaatc agaaatattc   1080
tcatcacttg gtgatatgga ggcatcacca ctagaagtta aaattgcatt taatagtaag   1140
ggtattataa atcaagggct aatttctgtg aaagactcat attgtagcaa tttaatagta   1200
aaacaaatcg agaatagata taaaatattg aataatagtt aaatccagc tattagcgag    1260 gataatgatt ttaatactac aacgaatacc tttattgata gtataatggc tgaagctaat   1320
gcagataatg gtagatttat gatgaaacta ggaaagtatt taagagttgg tttcttccca   1380
gatgttaaaa ctactattaa cttaagtggc cctgaagcat atgcggcagc ttatcaagat   1440
ttattaatgt ttaaagaagg cagtatgaat atccatttga tagaagctga tttaagaaac   1500
tttgaaatct ctaaaactaa tatttctcaa tcaactgaac aagaaatggc tagcttatgg   1560
tcatttgacg atgcaagagc taaagctcaa tttgaagaat ataaaaggaa ttattttgaa   1620
ggttctcttg gtgaagatga taatcttgat ttttctcaaa atatagtagt tgacaaggag   1680 tatctttag aaaaatatc ttcattagca agaagttcag agagaggata tatacactat    1740
attgttcagt tacaaggaga taaaattagt tatgaagcag catgtaactt atttgcaaag   1800
actccttatg atagtgtact gtttcagaaa aatatagaag attcagaaat tgcatattat   1860
tataatcctg gagatggtga aatacaagaa atagacaagt ataaaattcc aagtataatt   1920
tctgatagac ctaagattaa attaacattt attggtcatg gtaaagatga atttaatact   1980
gatatatttg caggttttga tgtagattca ttatccacag aaatagaagc agcaatagat   2040
ttagctaaag aggatatttc tcctaagtca atagaaataa atttattagg atgtaatatg   2100
tttagctact ctatcaacgt agaggagact tatcctggaa aattattact taaagttaaa   2160
gataaaatat cagaattaat gccatctata agtcaagact ctattatagt aagtgcaaat   2220
caatatgaag ttagaataaa tagtgaagga agaagagaat tattggatca ttctggtgaa   2280 tggataaaata aagaagaaag tattataaag gatatttcat caaaagaata tatatcattt   2340
aatcctaaag aaaataaaat tacagtaaaa tctaaaaatt tacctgagct atctacatta   2400
ttacaagaaa ttagaaataa ttctaattca agtgatattg aactagaaga aaaagtaatg   2460 ttaacgaat gtgagataaa tgttatttca aatatagata cgcaaattgt tgaggaaagg   2520
attgaagaag ctaagaattt aacttctgac tctattaatt atataaaaga tgaatttaaa   2580
ctaatagaat ctatttctga tgcactatgt gacttaaaac aacagaatga attagaagat   2640 tctcattta tatcttttga ggacatatca gagactgatg agggatttag tataagattt    2700
attaataaag aaactggaga atctatattt gtagaaactg aaaaaacaat attctctgaa   2760
tatgctaatc atataactga agagatttct aagataaaag gtactatatt tgatactgta   2820
aatggtaagt tagtaaaaaa agtaaattta gatactacac acgaagtaaa tactttaaat   2880
gctgcatttt ttatacaatc attaatagaa tataatagtt ctaaagaatc tcttagtaat   2940
ttaagtgtag caatgaaagt ccaagtttac gctcaattat ttagtactgg tttaaatact   3000
attacagatg cagccaaagt tgttgaatta gtatcaactg cattagatga aactatagac   3060
```

```
ttacttccta cattatctga aggattacct ataattgcaa ctattataga tggtgtaagt    3120
ttaggtgcag caatcaaaga gctaagtgaa acgagtgacc cattattaag acaagaaata    3180
gaagctaaga taggtataat ggcagtaaat ttaacaacag ctacaactgc aatcattact    3240
tcatctttgg ggatagctag tggatttagt atacttttag ttcctttagc aggaatttca    3300
gcaggtatac caagcttagt aaacaatgaa cttgtacttc gagataaggc aacaaaggtt    3360
gtagattatt ttaaacatgt ttcattagtt gaaactgaag gagtatttac tttattagat    3420
gataaaataa tgatgccaca agatgattta gtgatatcag aaatagattt taataataat    3480
tcaatagttt taggtaaatg tgaaatctgg agaatggaag gtggttcagg tcatactgta    3540
actgatgata tagatcactt cttttcagca ccatcaataa catatagaga gccacactta    3600
tctatatatg acgtattgga agtacaaaaa gaagaacttg atttgtcaaa agatttaatg    3660
gtattaccta atgctccaaa tagagtattt gcttgggaaa caggatggac accaggttta    3720
agaagcttag aaaatgatgg cacaaaactg ttagaccgta taagagataa ctatgaaggt    3780
gagttttatt ggagatattt tgcttttata gctgatgctt taataacaac attaaaacca    3840
agatatgaag atactaatat aagaataaat ttagatagta atactagaag ttttatagtt    3900
ccaataataa ctacagaata tataagagaa aaattatcat attctttcta tggttcagga    3960
ggaacttatg cattgtctct ttctcaatat aaatatggta taaatataga attaagtgaa    4020
agtgatgttt ggattataga tgttgataat gttgtgagag atgtaactat agaatctgat    4080
aaaattaaaa aaggtgattt aatagaaggt attttatcta cactaagtat tgaagagaat    4140
aaaattatct taaatagcca tgagattaat ttttctggtg aggtaaatgg aagtaatgga    4200
tttgtttctt taacattttc aattttagaa ggaataaatg caattataga agttgattta    4260
ttatctaaat catataaatt acttatttct ggcgaattaa aaatattgat gttaaattca    4320
aatcatattc aacagaaaat agattatata ggattcaata gcgaattaca gaaaaatata    4380
ccatatagct ttgtagatag tgaaggaaaa gagaatggtt ttattaatgg ttcaacaaaa    4440
gaaggtttat ttgtatctga attacctgat gtagttctta taagtaaggt ttatatggat    4500
gatagtaagc cttcatttgg atattatagt aataatttga aagatgtcaa agttataact    4560
aaagataatg ttaatatatt aacaggttat tatcttaagg atgatataaa aatctctctt    4620
tctttgactc tacaagatga aaaaactata aagttaaata gtgtgcattt agatgaaagt    4680
ggagtagctg agattttgaa gttcatgaat agaaaggta atacaaatac ttcagattct    4740
ttaatgagct ttttagaaag tatgaatata aaagtatttt tcgttaattt cttacaatct    4800
aatattaagt ttatattaga tgctaatttt ataataagtg gtactacttc tattggccaa    4860
tttgagttta tttgtgatga aaatgataat atacaaccat atttcattaa gtttaataca    4920
ctagaaacta attatacttt atatgtagga aatagacaaa atatgatagt ggaaccaaat    4980
tatgatttag atgattctgg agatatatct tcaactgtta tcaatttctc tcaaaagtat    5040
ctttatggaa tagacagttg tgttaataaa gttgtaattt caccaaatat ttatacagat    5100
gaaataaata taacgcctgt atatgaaaca aataatactt atccagaagt tattgtatta    5160
gatgcaaatt atataaatga aaaaataaat gttaatatca atgatctatc tatacgatat    5220
gtatggagta atgatggtaa tgattttatt cttatgtcaa ctagtgaaga aaataaggtg    5280
tcacaagtta aaataagatt cgttaatgtt tttaaagata agactttggc aaataagcta    5340
tcttttaact ttagtgataa acaagatgta cctgtaagtg aaataatctt atcatttaca    5400
```

-continued

```
ccttcatatt atgaggatgg attgattggc tatgatttgg gtctagtttc tttatataat        5460
gagaaatttt atattaataa ctttggaatg atggtatctg gattaatata tattaatgat        5520
tcattatatt atttttaaacc accagtaaat aatttgataa ctggatttgt gactgtaggc       5580
gatgataaat actactttaa tccaattaat ggtggagctg cttcaattgg agagacaata       5640
attgatgaca aaaattatta tttcaaccaa agtggagtgt tacaaacagg tgtatttagt       5700
acagaagatg gatttaaata ttttgcccca gctaatacac ttgatgaaaa cctagaagga       5760
gaagcaattg attttactgg aaaattaatt attgacgaaa atatttatta ttttgatgat       5820
aattatagag gagctgtaga atggaaagaa ttagatggtg aaatgcacta ttttagccca       5880
gaaacaggta aagcttttaa aggtctaaat caaataggtg atgataaata ctatttcaat       5940
tctgatggag ttatgcaaaa aggatttgtt agtataaatg ataataaaca ctattttgat       6000
gattctggtg ttatgaaagt aggttacact gaaatagatg gcaagcattt ctactttgct       6060
gaaaacggag aaatgcaaat aggagtattt aatacagaag atggatttaa atatttttgct     6120 catcataatg aagatttagg aaatgaagaa ggtgaagaaa tctcatattc tggtatatta     6180
aatttcaata ataaaattta ctattttgat gattcattta cagctgtagt tggatggaaa      6240
gatttagagg atggttcaaa gtattatttt gatgaagata cagcagaagc atatataggt      6300
ttgtcattaa taaatgatgg tcaatattat tttaatgatg atggaattat gcaagttgga       6360
tttgtcacta taaatgataa agtcttctac ttttctgact ctggaattat agaatctgga       6420
gtacaaaaca tagatgacaa ttatttctat atagatgata atggtatagt tcaaattggt       6480
gtatttgata cttcagatgg atataaatat tttgcacctg ctaatactgt aaatgataat       6540
atttacggac aagcagttga atatagtggt ttagttagag ttggggaaga tgtatattat       6600
tttggagaaa catatacaat tgagactgga tggatatatg atatgaaaaa tgaaagtgat       6660
aaatattatt tcaatccaga aactaaaaaa gcatgcaaag gtattaattt aattgatgat       6720 ataaatatt attttgatga aagggcata atgagaacgg tcttatatc atttgaaaat         6780 aataattatt actttaatga gaatggtgaa atgcaatttg gttatataaa atagaagat       6840 aagatgttct attttggtga agatggtgtc atgcagattg gagtatttaa tacaccagat      6900
ggatttaaat actttgcaca tcaaaatact ttggatgaga attttgaggg agaatcaata      6960
aactatactg gttggttaga tttagatgaa aagagatatt attttacaga tgaatatatt      7020
gcagcaactg gttcagttat tattgatggt gaggagtatt attttgatcc tgatacagct      7080
caattagtga ttagtgaata g                                                  7101
```

<210> SEQ ID NO 9
<211> LENGTH: 1392
<212> TYPE: DNA
<213> ORGANISM: Clostridioides difficile

<400> SEQUENCE: 9

```
atgaaaaaat ttagaaaaca taaaagtatt agtaattgta tatctatatt gttgatatta        60
tatctaactt taggtagttt gttacctaat aacatttatg cacaagactt acaaagctat       120
agtgaaaaag tttgcaatac tacttacaag gctcctatag aaagaccaga agattttctt       180
aaagataaag aaagggctaa agaatgggaa agaaagaag cagaaagaat agagcaaaaa        240
cttgaaagat ctgaaaaaga agcattagaa tcatataaaa aagattctgt agaaataaat        300
aaatattctc agacaagaaa ttatttttat gattatcaaa tagaagcaaa ttctcgagaa       360
aaagaatata gagaacttcg aaatgctata tcaaaaaata aatagataa acctatgtat        420
```

```
gtctattatt ttgaatctcc agaaaaattt gcatttaata aagtaataag aacagaaaat    480
caaaacgaaa tttcattaga aaatttaat gagtttaaag aaactataca aaacaaatta    540
tttaagcaag atggatttaa agaaatttct ttatatgaac ctggaaaagg tgatgaagaa    600
cctacaccat tacttatgca cttaaaatta cctagaaata ctggtatgtt accatataca    660
aatactaaca atgtaagtac attaatagag caaggatata gtataaaaat agataaaatt    720
gttcgtatag ttatagatgg gaaacattat attaaagcag aagcatctgt tgtaagtagt    780
cttgatttta aggatgatgt aagtaagggg gactcttggg gtaaagcaaa ttataatgat    840
tggagtaata aattaacacc taatgaactt gctgatgtaa atgattatat gcgtggagga    900
tatactgcaa ttaataatta tttaatatca aatggtccag taaataaccc taacccagaa    960
ttagattcta aaatcacaaa cattgaaaat gcattaaaac gtgaacctat tccaactaat   1020
ttaactgtat atagaagatc tggtcctcaa gaatttggtt taacccttac ttcccctgaa   1080
tatgatttta acaaaccaga aaatatagat gcttttaaat caaatgggaa aggacaaaca   1140
ctgtcttatc caaactttat tagtactagt attggtagtg tgaatatgag tgcatttgct   1200
aaaagaaaaa tagtactacg tataactata cctaaaggtt ctcctggagc ctatctatca   1260
gctattccag gttatgcagg tgaatatgaa gtacttttaa atcatggaag caaatttaaa   1320
atcagtaaaa ttgattctta caaagatggc gctataacaa aattaattgt tgatgcaaca   1380
ttgataccct aa                                                       1392
```

<210> SEQ ID NO 10
<211> LENGTH: 35
<212> TYPE: DNA
<213> ORGANISM: Artificial Sequence
<220> FEATURE:
<223> OTHER INFORMATION: Exemplary cdtB FRET cassette
<220> FEATURE:
<221> NAME/KEY: misc_feature
<222> LOCATION: (1)..(1)
<223> OTHER INFORMATION: Redmond Red fluorophore labeled
<220> FEATURE:
<221> NAME/KEY: misc_feature
<222> LOCATION: (4)..(4)
<223> OTHER INFORMATION: Eclipse Quencher
<220> FEATURE:
<221> NAME/KEY: misc_feature
<222> LOCATION: (35)..(35)
<223> OTHER INFORMATION: 3'-terminal Hexanediol

<400> SEQUENCE: 10

```
tctagccggt tttccggctg agacgtccgt ggcct                               35
```

<210> SEQ ID NO 11
<211> LENGTH: 34
<212> TYPE: DNA
<213> ORGANISM: Artificial Sequence
<220> FEATURE:
<223> OTHER INFORMATION: Exemplary tcdC FRET cassette
<220> FEATURE:
<221> NAME/KEY: misc_feature
<222> LOCATION: (1)..(1)
<223> OTHER INFORMATION: Hexochloro-Fluorescein labeled
<220> FEATURE:
<221> NAME/KEY: misc_feature
<222> LOCATION: (4)..(4)
<223> OTHER INFORMATION: Blackberry Quencher 650 dT
<220> FEATURE:
<221> NAME/KEY: misc_feature
<222> LOCATION: (34)..(34)
<223> OTHER INFORMATION: 3'-terminal Hexanediol

<400> SEQUENCE: 11
tcttagccgg ttttccggct gagacctcgg cgcg                       34

<210> SEQ ID NO 12
<211> LENGTH: 36
<212> TYPE: DNA
<213> ORGANISM: Artificial Sequence
<220> FEATURE:
<223> OTHER INFORMATION: Exemplary tcdB/tcdA FRET cassette
<220> FEATURE:
<221> NAME/KEY: misc_feature
<222> LOCATION: (1)..(1)
<223> OTHER INFORMATION: Fluorescein labeled
<220> FEATURE:
<221> NAME/KEY: misc_feature
<222> LOCATION: (4)..(4)
<223> OTHER INFORMATION: Blackberry Quencher 650 dT
<220> FEATURE:
<221> NAME/KEY: misc_feature
<222> LOCATION: (36)..(36)
<223> OTHER INFORMATION: 3'-terminal Hexanediol

<400> SEQUENCE: 12
tcttagccgg ttttccggct gagactccgc gtccgt                     36

<210> SEQ ID NO 13
<211> LENGTH: 53
<212> TYPE: DNA
<213> ORGANISM: Artificial Sequence
<220> FEATURE:
<223> OTHER INFORMATION: cdtA Forward Primer

<400> SEQUENCE: 13
gagcaaggat atagtataaa aatagataaa attgttcgta tagttataga tgg     53

<210> SEQ ID NO 14
<211> LENGTH: 38
<212> TYPE: DNA
<213> ORGANISM: Artificial Sequence
<220> FEATURE:
<223> OTHER INFORMATION: cdtA Invader

<400> SEQUENCE: 14
tatattaaag cagaagcatc tgttgtaagt agtcttgt                   38

<210> SEQ ID NO 15
<211> LENGTH: 38
<212> TYPE: DNA
<213> ORGANISM: Artificial Sequence
<220> FEATURE:
<223> OTHER INFORMATION: cdtA Invader

<400> SEQUENCE: 15
tatattaaag cagaagcatc tgttgtaagt agtcttgc                   38

<210> SEQ ID NO 16
<211> LENGTH: 27
<212> TYPE: DNA
<213> ORGANISM: Artificial Sequence
<220> FEATURE:
<223> OTHER INFORMATION: THS for cdtA probe

<400> SEQUENCE: 16
attttaagga tgatgtaagt aagggag                               27

<210> SEQ ID NO 17
<211> LENGTH: 27

```
<212> TYPE: DNA
<213> ORGANISM: Artificial Sequence
<220> FEATURE:
<223> OTHER INFORMATION: THS for cdtA probe

<400> SEQUENCE: 17
cgattttaag gatgatgtaa gtaaggg                                            27

<210> SEQ ID NO 18
<211> LENGTH: 37
<212> TYPE: DNA
<213> ORGANISM: Artificial Sequence
<220> FEATURE:
<223> OTHER INFORMATION: cdtA Primary Probe
<220> FEATURE:
<221> NAME/KEY: misc_feature
<222> LOCATION: (37)..(37)
<223> OTHER INFORMATION: 3'-terminal Hexanediol

<400> SEQUENCE: 18
cgcgaggccg attttaagga tgatgtaagt aagggag                                 37

<210> SEQ ID NO 19
<211> LENGTH: 39
<212> TYPE: DNA
<213> ORGANISM: Artificial Sequence
<220> FEATURE:
<223> OTHER INFORMATION: cdtA Primary Probe
<220> FEATURE:
<221> NAME/KEY: misc_feature
<222> LOCATION: (39)..(39)
<223> OTHER INFORMATION: 3'-terminal Hexanediol

<400> SEQUENCE: 19
aggccacgga cgattttaag gatgatgtaa gtaagggag                               39

<210> SEQ ID NO 20
<211> LENGTH: 37
<212> TYPE: DNA
<213> ORGANISM: Artificial Sequence
<220> FEATURE:
<223> OTHER INFORMATION: cdtA Primary Probe
<220> FEATURE:
<221> NAME/KEY: misc_feature
<222> LOCATION: (37)..(37)
<223> OTHER INFORMATION: 3'-terminal Hexanediol

<400> SEQUENCE: 20
aggccacgga cgattttaag gatgatgtaa gtaaggg                                 37

<210> SEQ ID NO 21
<211> LENGTH: 32
<212> TYPE: DNA
<213> ORGANISM: Artificial Sequence
<220> FEATURE:
<223> OTHER INFORMATION: cdtA Reverse Primer

<400> SEQUENCE: 21
actccaatca ctataatttg ctttaccccca ag                                     32

<210> SEQ ID NO 22
<211> LENGTH: 36
<212> TYPE: DNA
<213> ORGANISM: Artificial Sequence
<220> FEATURE:
<223> OTHER INFORMATION: cdtA Reverse Primer
```

-continued

<400> SEQUENCE: 22
cgcatataat catttacatc agcaagttca ttaggt         36

<210> SEQ ID NO 23
<211> LENGTH: 25
<212> TYPE: DNA
<213> ORGANISM: Artificial Sequence
<220> FEATURE:
<223> OTHER INFORMATION: cdtA Reverse Primer

<400> SEQUENCE: 23
atttgcttta ccccaagagt ctccc         25

<210> SEQ ID NO 24
<211> LENGTH: 21
<212> TYPE: DNA
<213> ORGANISM: Artificial Sequence
<220> FEATURE:
<223> OTHER INFORMATION: cdtA Reverse Primer

<400> SEQUENCE: 24
gctttacccc aagagtctcc c         21

<210> SEQ ID NO 25
<211> LENGTH: 36
<212> TYPE: DNA
<213> ORGANISM: Artificial Sequence
<220> FEATURE:
<223> OTHER INFORMATION: cdtA Reverse Primer

<400> SEQUENCE: 25
actccaatca ctataatttg ctttacccca agagtc         36

<210> SEQ ID NO 26
<211> LENGTH: 32
<212> TYPE: DNA
<213> ORGANISM: Artificial Sequence
<220> FEATURE:
<223> OTHER INFORMATION: cdtA Reverse Primer

<400> SEQUENCE: 26
caatcactat aatttgcttt accccaagag tc         32

<210> SEQ ID NO 27
<211> LENGTH: 42
<212> TYPE: DNA
<213> ORGANISM: Artificial Sequence
<220> FEATURE:
<223> OTHER INFORMATION: cdtA Reverse Primer

<400> SEQUENCE: 27
aggtgttaat ttattactcc aatcactata atttgcttta cc         42

<210> SEQ ID NO 28
<211> LENGTH: 39
<212> TYPE: DNA
<213> ORGANISM: Artificial Sequence
<220> FEATURE:
<223> OTHER INFORMATION: cdtA Reverse Primer

<400> SEQUENCE: 28
tgttaattta ttactccaat cactataatt tgctttacc         39

<210> SEQ ID NO 29

```
<211> LENGTH: 43
<212> TYPE: DNA
<213> ORGANISM: Artificial Sequence
<220> FEATURE:
<223> OTHER INFORMATION: cdtA Reverse Primer

<400> SEQUENCE: 29
gttcattagg tgttaattta ttactccaat cactataatt tgc          43

<210> SEQ ID NO 30
<211> LENGTH: 32
<212> TYPE: DNA
<213> ORGANISM: Artificial Sequence
<220> FEATURE:
<223> OTHER INFORMATION: Forward Primer

<400> SEQUENCE: 30
gttgatgtct gattgggaag acgaagattt gg                       32

<210> SEQ ID NO 31
<211> LENGTH: 27
<212> TYPE: DNA
<213> ORGANISM: Artificial Sequence
<220> FEATURE:
<223> OTHER INFORMATION: Forward Primer

<400> SEQUENCE: 31
tttgacccaa ggttgatgtc tgattgg                             27

<210> SEQ ID NO 32
<211> LENGTH: 24
<212> TYPE: DNA
<213> ORGANISM: Artificial Sequence
<220> FEATURE:
<223> OTHER INFORMATION: Forward Primer

<400> SEQUENCE: 32
gacccaaggt tgatgtctga ttgg                                24

<210> SEQ ID NO 33
<211> LENGTH: 28
<212> TYPE: DNA
<213> ORGANISM: Artificial Sequence
<220> FEATURE:
<223> OTHER INFORMATION: Forward Primer

<400> SEQUENCE: 33
ctttgaccca aggttgatgt ctgattgg                            28

<210> SEQ ID NO 34
<211> LENGTH: 32
<212> TYPE: DNA
<213> ORGANISM: Artificial Sequence
<220> FEATURE:
<223> OTHER INFORMATION: THS for cdtB probe

<400> SEQUENCE: 34
cgttcatatg aatctggtat attatcatta tc                       32

<210> SEQ ID NO 35
<211> LENGTH: 32
<212> TYPE: DNA
<213> ORGANISM: Artificial Sequence
<220> FEATURE:
<223> OTHER INFORMATION: THS for cdtB probe
```

-continued

```
<400> SEQUENCE: 35
gttcatatga atctggtata ttatcattat ct                                      32

<210> SEQ ID NO 36
<211> LENGTH: 26
<212> TYPE: DNA
<213> ORGANISM: Artificial Sequence
<220> FEATURE:
<223> OTHER INFORMATION: THS for cdtB probe

<400> SEQUENCE: 36
cgttcatatg aatctggtat attatc                                             26

<210> SEQ ID NO 37
<211> LENGTH: 44
<212> TYPE: DNA
<213> ORGANISM: Artificial Sequence
<220> FEATURE:
<223> OTHER INFORMATION: cdtB Primary Probe
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (44)..(44)
<223> OTHER INFORMATION: 3'-terminal Hexanediol

<400> SEQUENCE: 37
aggccacgga cgcgttcata tgaatctggt atattatcat tatc                         44

<210> SEQ ID NO 38
<211> LENGTH: 44
<212> TYPE: DNA
<213> ORGANISM: Artificial Sequence
<220> FEATURE:
<223> OTHER INFORMATION: cdtB Primary Probe
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (44)..(44)
<223> OTHER INFORMATION: 3'-terminal Hexanediol

<400> SEQUENCE: 38
aggccacgga cggttcatat gaatctggta tattatcatt atct                         44

<210> SEQ ID NO 39
<211> LENGTH: 38
<212> TYPE: DNA
<213> ORGANISM: Artificial Sequence
<220> FEATURE:
<223> OTHER INFORMATION: cdtB Primary Probe
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (38)..(38)
<223> OTHER INFORMATION: 3'-terminal Hexanediol

<400> SEQUENCE: 39
aggccacgga cgcgttcata tgaatctggt atattatc                                38

<210> SEQ ID NO 40
```

```
<211> LENGTH: 40
<212> TYPE: DNA
<213> ORGANISM: Artificial Sequence
<220> FEATURE:
<223> OTHER INFORMATION: cdtB Reverse iPrimer

<400> SEQUENCE: 40
cacttaactg caattaagtc cttaatagta tatccatttc                                40

<210> SEQ ID NO 41
<211> LENGTH: 40
<212> TYPE: DNA
<213> ORGANISM: Artificial Sequence
<220> FEATURE:
<223> OTHER INFORMATION: cdtB Reverse iPrimer

<400> SEQUENCE: 41
acttaactgc aattaagtcc ttaatagtat atccatttcg                                40

<210> SEQ ID NO 42
<211> LENGTH: 40
<212> TYPE: DNA
<213> ORGANISM: Artificial Sequence
<220> FEATURE:
<223> OTHER INFORMATION: cdtB Invader

<400> SEQUENCE: 42
acttaactgc aattaagtcc ttaatagtat atccatttct                                40

<210> SEQ ID NO 43
<211> LENGTH: 21
<212> TYPE: DNA
<213> ORGANISM: Artificial Sequence
<220> FEATURE:
<223> OTHER INFORMATION: THS for cdtB probe

<400> SEQUENCE: 43
ggaagacgaa gatttggata c                                                    21

<210> SEQ ID NO 44
<211> LENGTH: 33
<212> TYPE: DNA
<213> ORGANISM: Artificial Sequence
<220> FEATURE:
<223> OTHER INFORMATION: THS for cdtB probe

<400> SEQUENCE: 44
gatacagata atgataatat accagattca tat                                       33

<210> SEQ ID NO 45
<211> LENGTH: 32
<212> TYPE: DNA
<213> ORGANISM: Artificial Sequence
<220> FEATURE:
<223> OTHER INFORMATION: THS for cdtB probe

<400> SEQUENCE: 45
gttcatatga atctggtata ttatcattat ct                                        32

<210> SEQ ID NO 46
<211> LENGTH: 31
<212> TYPE: DNA
<213> ORGANISM: Artificial Sequence
<220> FEATURE:
<223> OTHER INFORMATION: cdtB Primary Probe
<220> FEATURE:
<221> NAME/KEY: misc_feature
```

<222> LOCATION: (31)..(31)
<223> OTHER INFORMATION: 3'-terminal Hexanediol

<400> SEQUENCE: 46
cgcgaggccg ggaagacgaa gatttggata c                              31

<210> SEQ ID NO 47
<211> LENGTH: 43
<212> TYPE: DNA
<213> ORGANISM: Artificial Sequence
<220> FEATURE:
<223> OTHER INFORMATION: cdtB Primary Probe
<220> FEATURE:
<221> NAME/KEY: misc_feature
<222> LOCATION: (43)..(43)
<223> OTHER INFORMATION: 3'-terminal Hexanediol

<400> SEQUENCE: 47
cgcgaggccg gatacagata atgataatat accagattca tat                 43

<210> SEQ ID NO 48
<211> LENGTH: 42
<212> TYPE: DNA
<213> ORGANISM: Artificial Sequence
<220> FEATURE:
<223> OTHER INFORMATION: cdtB Primary Probe
<220> FEATURE:
<221> NAME/KEY: misc_feature
<222> LOCATION: (42)..(42)
<223> OTHER INFORMATION: 3'-terminal Hexanediol

<400> SEQUENCE: 48
cgcgaggccg gttcatatga atctggtata ttatcattat ct                  42

<210> SEQ ID NO 49
<211> LENGTH: 37
<212> TYPE: DNA
<213> ORGANISM: Artificial Sequence
<220> FEATURE:
<223> OTHER INFORMATION: cdtB Reverse Primer

<400> SEQUENCE: 49
cataatctgt atatggatct ccagcagtat ttgactc                        37

<210> SEQ ID NO 50
<211> LENGTH: 44
<212> TYPE: DNA
<213> ORGANISM: Artificial Sequence
<220> FEATURE:
<223> OTHER INFORMATION: cdtB Reverse Primer

<400> SEQUENCE: 50
gactctaaat aatttgatac atatttctta tagccttgtt ctgc                44

<210> SEQ ID NO 51
<211> LENGTH: 21
<212> TYPE: DNA
<213> ORGANISM: Artificial Sequence
<220> FEATURE:
<223> OTHER INFORMATION: cdtB Primary Probe

<400> SEQUENCE: 51
ggaagacgaa gatttggata c                                         21

<210> SEQ ID NO 52
<211> LENGTH: 22
<212> TYPE: DNA

```
<213> ORGANISM: Artificial Sequence
<220> FEATURE:
<223> OTHER INFORMATION: cdtB Primary Probe

<400> SEQUENCE: 52
ggaagacgaa gatttggata ca                                            22

<210> SEQ ID NO 53
<211> LENGTH: 33
<212> TYPE: DNA
<213> ORGANISM: Artificial Sequence
<220> FEATURE:
<223> OTHER INFORMATION: cdtB Primary Probe
<220> FEATURE:
<221> NAME/KEY: misc_feature
<222> LOCATION: (33)..(33)
<223> OTHER INFORMATION: 3'-terminal Hexanediol

<400> SEQUENCE: 53
aggccacgga cgggaagacg aagatttgga tac                                33

<210> SEQ ID NO 54
<211> LENGTH: 34
<212> TYPE: DNA
<213> ORGANISM: Artificial Sequence
<220> FEATURE:
<223> OTHER INFORMATION: cdtB Primary Probe
<220> FEATURE:
<221> NAME/KEY: misc_feature
<222> LOCATION: (34)..(34)
<223> OTHER INFORMATION: 3'-terminal Hexanediol

<400> SEQUENCE: 54
aggccacgga cgggaagacg aagatttgga taca                               34

<210> SEQ ID NO 55
<211> LENGTH: 21
<212> TYPE: DNA
<213> ORGANISM: Artificial Sequence
<220> FEATURE:
<223> OTHER INFORMATION: cdtB Forward Primer

<400> SEQUENCE: 55
gatccattta tcccaaataa c                                             21

<210> SEQ ID NO 56
<211> LENGTH: 24
<212> TYPE: DNA
<213> ORGANISM: Artificial Sequence
<220> FEATURE:
<223> OTHER INFORMATION: cdtB Reverse Primer

<400> SEQUENCE: 56
catatttctt atagccttgt tctg                                          24

<210> SEQ ID NO 57
<211> LENGTH: 21
<212> TYPE: DNA
<213> ORGANISM: Artificial Sequence
<220> FEATURE:
<223> OTHER INFORMATION: THS for tcdA Probe

<400> SEQUENCE: 57
gaataaactt aggtgcagca a                                             21

<210> SEQ ID NO 58
<211> LENGTH: 32
```

```
<212> TYPE: DNA
<213> ORGANISM: Artificial Sequence
<220> FEATURE:
<223> OTHER INFORMATION: tcdA Primary Probe
<220> FEATURE:
<221> NAME/KEY: misc_feature
<222> LOCATION: (32)..(32)
<223> OTHER INFORMATION: 3'-terminal Hexanediol

<400> SEQUENCE: 58
tccgcgcgtc cgaataaact taggtgcagc aa                                    32

<210> SEQ ID NO 59
<211> LENGTH: 23
<212> TYPE: DNA
<213> ORGANISM: Artificial Sequence
<220> FEATURE:
<223> OTHER INFORMATION: tcdA Forward Primer

<400> SEQUENCE: 59
ctttatgctc aactatttag tac                                              23

<210> SEQ ID NO 60
<211> LENGTH: 27
<212> TYPE: DNA
<213> ORGANISM: Artificial Sequence
<220> FEATURE:
<223> OTHER INFORMATION: tcdA Forward Primer

<400> SEQUENCE: 60
cagtaaatga tactataaat gtactac                                          27

<210> SEQ ID NO 61
<211> LENGTH: 19
<212> TYPE: DNA
<213> ORGANISM: Artificial Sequence
<220> FEATURE:
<223> OTHER INFORMATION: THS for tcdA Probe

<400> SEQUENCE: 61
ctagacgaac atgacccat                                                   19

<210> SEQ ID NO 62
<211> LENGTH: 31
<212> TYPE: DNA
<213> ORGANISM: Artificial Sequence
<220> FEATURE:
<223> OTHER INFORMATION: tcdA Primary Probe
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (31)..(31)
<223> OTHER INFORMATION: 3'-terminal Hexanediol

<400> SEQUENCE: 62
acggacgcgg agctagacga acatgaccca t                                     31

<210> SEQ ID NO 63
<211> LENGTH: 31
<212> TYPE: DNA
<213> ORGANISM: Artificial Sequence
<220> FEATURE:
<223> OTHER INFORMATION: tcdA Invader
<220> FEATURE:
<221> NAME/KEY: misc_feature
<222> LOCATION: (31)..(31)
```

```
<223> OTHER INFORMATION: RNA

<400> SEQUENCE: 63
ataaacttag gtgcagcaat taaggaatta a                                      31

<210> SEQ ID NO 64
<211> LENGTH: 37
<212> TYPE: DNA
<213> ORGANISM: Artificial Sequence
<220> FEATURE:
<223> OTHER INFORMATION: tcdA Forward iPrimer

<400> SEQUENCE: 64
cagaggggat acctattgta tctactatat tagacgg                                37

<210> SEQ ID NO 65
<211> LENGTH: 35
<212> TYPE: DNA
<213> ORGANISM: Artificial Sequence
<220> FEATURE:
<223> OTHER INFORMATION: tcdA Forward iPrimer

<400> SEQUENCE: 65
gaggggatac ctattgtatc tactatatta gacgg                                  35

<210> SEQ ID NO 66
<211> LENGTH: 19
<212> TYPE: DNA
<213> ORGANISM: Artificial Sequence
<220> FEATURE:
<223> OTHER INFORMATION: THS for tcdA Probe

<400> SEQUENCE: 66
ctagacgaac atgacccat                                                    19

<210> SEQ ID NO 67
<211> LENGTH: 21
<212> TYPE: DNA
<213> ORGANISM: Artificial Sequence
<220> FEATURE:
<223> OTHER INFORMATION: THS for tcdA Probe

<400> SEQUENCE: 67
gaataaactt aggtgcagca a                                                 21

<210> SEQ ID NO 68
<211> LENGTH: 29
<212> TYPE: DNA
<213> ORGANISM: Artificial Sequence
<220> FEATURE:
<223> OTHER INFORMATION: tcdA Primary Probe
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (29)..(29)
<223> OTHER INFORMATION: 3'-terminal Hexanediol

<400> SEQUENCE: 68
cgcgccgagg ctagacgaac atgacccat                                         29

<210> SEQ ID NO 69
<211> LENGTH: 33
<212> TYPE: DNA
<213> ORGANISM: Artificial Sequence
```

```
<220> FEATURE:
<223> OTHER INFORMATION: tcdA Primary Probe
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (33)..(33)
<223> OTHER INFORMATION: 3'-terminal Hexanediol

<400> SEQUENCE: 69
acggacgcgg aggaataaac ttaggtgcag caa                                   33

<210> SEQ ID NO 70
<211> LENGTH: 35
<212> TYPE: DNA
<213> ORGANISM: Artificial Sequence
<220> FEATURE:
<223> OTHER INFORMATION: tcdA Reverse Primer

<400> SEQUENCE: 70
gtaacttcag cacctattcc aacaattgaa gctac                                 35

<210> SEQ ID NO 71
<211> LENGTH: 30
<212> TYPE: DNA
<213> ORGANISM: Artificial Sequence
<220> FEATURE:
<223> OTHER INFORMATION: tcdA Reverse Primer

<400> SEQUENCE: 71
agtaatgggt catgttcgtc tagtaattcc                                       30

<210> SEQ ID NO 72
<211> LENGTH: 35
<212> TYPE: DNA
<213> ORGANISM: Artificial Sequence
<220> FEATURE:
<223> OTHER INFORMATION: tcdA Reverse Primer

<400> SEQUENCE: 72
gacatattta ttgctaaaac acccaccta gcttc                                  35

<210> SEQ ID NO 73
<211> LENGTH: 24
<212> TYPE: DNA
<213> ORGANISM: Artificial Sequence
<220> FEATURE:
<223> OTHER INFORMATION: tcdA Reverse Primer

<400> SEQUENCE: 73
gatataccag ctataggtaa taag                                             24

<210> SEQ ID NO 74
<211> LENGTH: 29
<212> TYPE: DNA
<213> ORGANISM: Artificial Sequence
<220> FEATURE:
<223> OTHER INFORMATION: tcdC 117 Invader
<220> FEATURE:
<221> NAME/KEY: misc_feature
<222> LOCATION: (29)..(29)
<223> OTHER INFORMATION: RNA

<400> SEQUENCE: 74
ggtgaggata tattgccaaa aaacacgcg                                        29
```

```
<210> SEQ ID NO 75
<211> LENGTH: 33
<212> TYPE: DNA
<213> ORGANISM: Artificial Sequence
<220> FEATURE:
<223> OTHER INFORMATION: tcdC 117 Invader
<220> FEATURE:
<221> NAME/KEY: misc_feature
<222> LOCATION: (33)..(33)
<223> OTHER INFORMATION: RNA

<400> SEQUENCE: 75
acaaagggta ttgctctact ggcatttatt ttc                              33

<210> SEQ ID NO 76
<211> LENGTH: 33
<212> TYPE: DNA
<213> ORGANISM: Artificial Sequence
<220> FEATURE:
<223> OTHER INFORMATION: tcdC 117 Iprimer
<220> FEATURE:
<221> NAME/KEY: misc_feature
<222> LOCATION: (33)..(33)
<223> OTHER INFORMATION: n is a, c, g, or t

<400> SEQUENCE: 76
acaaagggta ttgctctact ggcatttatt ttn                              33

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000
```

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86
<211> LENGTH: 29
<212> TYPE: DNA
<213> ORGANISM: Artificial Sequence
<220> FEATURE:
<223> OTHER INFORMATION: tcdC 117del Invader
<220> FEATURE:
<221> NAME/KEY: misc_feature
<222> LOCATION: (29)..(29)
<223> OTHER INFORMATION: RNA

<400> SEQUENCE: 86
ggtgaggata tattgccaaa aaacacacg                                      29

<210> SEQ ID NO 87
<211> LENGTH: 30
<212> TYPE: DNA
<213> ORGANISM: Artificial Sequence
<220> FEATURE:
<223> OTHER INFORMATION: tcdC 117del Reverse iPrimer

<400> SEQUENCE: 87
ggtgaggata tattgccaaa aaacacacca                                     30

<210> SEQ ID NO 88
<211> LENGTH: 29
<212> TYPE: DNA
<213> ORGANISM: Artificial Sequence
<220> FEATURE:
<223> OTHER INFORMATION: tcdC 117del Reverse iPrimer

<400> SEQUENCE: 88
ggtgaggata tattgccaaa aaacacacc                                      29

<210> SEQ ID NO 89
<211> LENGTH: 28
<212> TYPE: DNA
<213> ORGANISM: Artificial Sequence
<220> FEATURE:
<223> OTHER INFORMATION: tcdC 117del Reverse iPrimer

<400> SEQUENCE: 89
ggtgaggata tattgccaaa aaacacgc                                       28

<210> SEQ ID NO 90
<211> LENGTH: 28
<212> TYPE: DNA
<213> ORGANISM: Artificial Sequence
<220> FEATURE:

```
-continued

<223> OTHER INFORMATION: tcdC 117del Reverse iPrimer

<400> SEQUENCE: 90
ggtgaggata tattgccaaa aaacacac                                28

<210> SEQ ID NO 91
<211> LENGTH: 27
<212> TYPE: DNA
<213> ORGANISM: Artificial Sequence
<220> FEATURE:
<223> OTHER INFORMATION: tcdC 117del Reverse iPrimer

<400> SEQUENCE: 91
ggtgaggata tattgccaaa aaacacg                                 27

<210> SEQ ID NO 92
<211> LENGTH: 27
<212> TYPE: DNA
<213> ORGANISM: Artificial Sequence
<220> FEATURE:
<223> OTHER INFORMATION: tcdC 117del Reverse iPrimer

<400> SEQUENCE: 92
ggtgaggata tattgccaaa aaacaca                                 27

<210> SEQ ID NO 93
<211> LENGTH: 21
<212> TYPE: DNA
<213> ORGANISM: Artificial Sequence
<220> FEATURE:
<223> OTHER INFORMATION: THS for tcdC 117del Probe

<400> SEQUENCE: 93
caaaataaat gccagtagag c                                       21

<210> SEQ ID NO 94
<211> LENGTH: 25
<212> TYPE: DNA
<213> ORGANISM: Artificial Sequence
<220> FEATURE:
<223> OTHER INFORMATION: THS for tcdC 117del Probe

<400> SEQUENCE: 94
aaaataaatg ccagtagagc aatat                                   25

<210> SEQ ID NO 95
<211> LENGTH: 26
<212> TYPE: DNA
<213> ORGANISM: Artificial Sequence
<220> FEATURE:
<223> OTHER INFORMATION: THS for tcdC 117del Probe

<400> SEQUENCE: 95
aaaataaatg ccagtagagc aatatc                                  26

<210> SEQ ID NO 96
<211> LENGTH: 20
<212> TYPE: DNA
<213> ORGANISM: Artificial Sequence
<220> FEATURE:
<223> OTHER INFORMATION: THS for tcdC 117del Probe

<400> SEQUENCE: 96
caaaataaat gccagtagag                                         20
```

```
<210> SEQ ID NO 97
<211> LENGTH: 19
<212> TYPE: DNA
<213> ORGANISM: Artificial Sequence
<220> FEATURE:
<223> OTHER INFORMATION: THS for tcdC 117del Probe

<400> SEQUENCE: 97
caaaataaat gccagtaga                                                  19

<210> SEQ ID NO 98
<211> LENGTH: 23
<212> TYPE: DNA
<213> ORGANISM: Artificial Sequence
<220> FEATURE:
<223> OTHER INFORMATION: THS for tcdC 117del Probe

<400> SEQUENCE: 98
caaaataaat gccagtagag caa                                             23

<210> SEQ ID NO 99
<211> LENGTH: 26
<212> TYPE: DNA
<213> ORGANISM: Artificial Sequence
<220> FEATURE:
<223> OTHER INFORMATION: THS for tcdC 117del Probe

<400> SEQUENCE: 99
caaaataaat gccagtagag caatac                                          26

<210> SEQ ID NO 100
<211> LENGTH: 22
<212> TYPE: DNA
<213> ORGANISM: Artificial Sequence
<220> FEATURE:
<223> OTHER INFORMATION: THS for tcdC 117del Probe

<400> SEQUENCE: 100
caaataaatg ccagtagagc aa                                              22

<210> SEQ ID NO 101
<211> LENGTH: 21
<212> TYPE: DNA
<213> ORGANISM: Artificial Sequence
<220> FEATURE:
<223> OTHER INFORMATION: THS for tcdC 117del Probe

<400> SEQUENCE: 101
caataaatgc cagtagagca a                                               21

<210> SEQ ID NO 102
<211> LENGTH: 20
<212> TYPE: DNA
<213> ORGANISM: Artificial Sequence
<220> FEATURE:
<223> OTHER INFORMATION: THS for tcdC 117del Probe

<400> SEQUENCE: 102
cataaatgcc agtagagcaa                                                 20

<210> SEQ ID NO 103
<211> LENGTH: 23
<212> TYPE: DNA
<213> ORGANISM: Artificial Sequence
<220> FEATURE:
<223> OTHER INFORMATION: THS for tcdC 117del Probe w/methoxy
<220> FEATURE:
```

```
<221> NAME/KEY: misc_feature
<222> LOCATION: (6)..(6)
<223> OTHER INFORMATION: n is U

<400> SEQUENCE: 103
caaaanaaat gccagtagag caa                                               23

<210> SEQ ID NO 104
<211> LENGTH: 23
<212> TYPE: DNA
<213> ORGANISM: Artificial Sequence
<220> FEATURE:
<223> OTHER INFORMATION: THS for tcdC 117del Probe w/methoxy
<220> FEATURE:
<221> NAME/KEY: misc_feature
<222> LOCATION: (4)..(4)
<223> OTHER INFORMATION: n is 2-O-Methyladenosine

<400> SEQUENCE: 104
caanataaat gccagtagag caa                                               23

<210> SEQ ID NO 105
<211> LENGTH: 23
<212> TYPE: DNA
<213> ORGANISM: Artificial Sequence
<220> FEATURE:
<223> OTHER INFORMATION: THS for tcdC 117del Probe w/methoxy
<220> FEATURE:
<221> NAME/KEY: misc_feature
<222> LOCATION: (3)..(3)
<223> OTHER INFORMATION: n is 2-O-Methyladenosine

<400> SEQUENCE: 105
canaataaat gccagtagag caa                                               23

<210> SEQ ID NO 106
<211> LENGTH: 22
<212> TYPE: DNA
<213> ORGANISM: Artificial Sequence
<220> FEATURE:
<223> OTHER INFORMATION: THS for tcdC 117del Probe w/methoxy
<220> FEATURE:
<221> NAME/KEY: misc_feature
<222> LOCATION: (5)..(5)
<223> OTHER INFORMATION: n is U

<400> SEQUENCE: 106
caaanaaatg ccagtagagc aa                                                22

<210> SEQ ID NO 107
<211> LENGTH: 21
<212> TYPE: DNA
<213> ORGANISM: Artificial Sequence
<220> FEATURE:
<223> OTHER INFORMATION: THS for tcdC 117del Probe w/methoxy
<220> FEATURE:
<221> NAME/KEY: misc_feature
<222> LOCATION: (4)..(4)
<223> OTHER INFORMATION: n is U

<400> SEQUENCE: 107
caanaaatgc cagtagagca a                                                 21

<210> SEQ ID NO 108
<211> LENGTH: 20
<212> TYPE: DNA
<213> ORGANISM: Artificial Sequence
<220> FEATURE:
<223> OTHER INFORMATION: THS for tcdC 117del Probe w/methoxy
```

```
<220> FEATURE:
<221> NAME/KEY: misc_feature
<222> LOCATION: (3)..(3)
<223> OTHER INFORMATION: n is U

<400> SEQUENCE: 108
canaaatgcc agtagagcaa                                                        20

<210> SEQ ID NO 109
<211> LENGTH: 22
<212> TYPE: DNA
<213> ORGANISM: Artificial Sequence
<220> FEATURE:
<223> OTHER INFORMATION: THS for tcdC 117del Probe w/methoxy
<220> FEATURE:
<221> NAME/KEY: misc_feature
<222> LOCATION: (4)..(4)
<223> OTHER INFORMATION: n is 2-O-Methyladenosine
<220> FEATURE:
<221> NAME/KEY: misc_feature
<222> LOCATION: (5)..(5)
<223> OTHER INFORMATION: n is U

<400> SEQUENCE: 109
caannaaatg ccagtagagc aa                                                     22

<210> SEQ ID NO 110
<211> LENGTH: 22
<212> TYPE: DNA
<213> ORGANISM: Artificial Sequence
<220> FEATURE:
<223> OTHER INFORMATION: THS for tcdC 117del Probe w/methoxy
<220> FEATURE:
<221> NAME/KEY: misc_feature
<222> LOCATION: (5)..(5)
<223> OTHER INFORMATION: n is U
<220> FEATURE:
<221> NAME/KEY: misc_feature
<222> LOCATION: (6)..(6)
<223> OTHER INFORMATION: n is 2-O-Methyladenosine

<400> SEQUENCE: 110
caaannaatg ccagtagagc aa                                                     22

<210> SEQ ID NO 111
<211> LENGTH: 22
<212> TYPE: DNA
<213> ORGANISM: Artificial Sequence
<220> FEATURE:
<223> OTHER INFORMATION: THS for tcdC 117del Probe w/methoxy
<220> FEATURE:
<221> NAME/KEY: misc_feature
<222> LOCATION: (4)..(4)
<223> OTHER INFORMATION: n is 2-O-Methyladenosine
<220> FEATURE:
<221> NAME/KEY: misc_feature
<222> LOCATION: (5)..(5)
<223> OTHER INFORMATION: n is U
<220> FEATURE:
<221> NAME/KEY: misc_feature
<222> LOCATION: (6)..(6)
<223> OTHER INFORMATION: n is 2-O-Methyladenosine

<400> SEQUENCE: 111
caannnaatg ccagtagagc aa                                                     22

<210> SEQ ID NO 112
<211> LENGTH: 22
<212> TYPE: DNA
<213> ORGANISM: Artificial Sequence
<220> FEATURE:
```

-continued

```
<223> OTHER INFORMATION: THS for tcdC 117del Probe w/methoxy
<220> FEATURE:
<221> NAME/KEY: misc_feature
<222> LOCATION: (2)..(2)
<223> OTHER INFORMATION: n is 2-O-Methyladenosine

<400> SEQUENCE: 112
cnaataaatg ccagtagagc aa                                          22

<210> SEQ ID NO 113
<211> LENGTH: 23
<212> TYPE: DNA
<213> ORGANISM: Artificial Sequence
<220> FEATURE:
<223> OTHER INFORMATION: THS for tcdC 117del Probe w/methoxy
<220> FEATURE:
<221> NAME/KEY: misc_feature
<222> LOCATION: (2)..(2)
<223> OTHER INFORMATION: n is 2-O-Methyladenosine

<400> SEQUENCE: 113
cnaaataaat gccagtagag caa                                         23

<210> SEQ ID NO 114
<211> LENGTH: 22
<212> TYPE: DNA
<213> ORGANISM: Artificial Sequence
<220> FEATURE:
<223> OTHER INFORMATION: THS for tcdC 117del Probe w/methoxy
<220> FEATURE:
<221> NAME/KEY: misc_feature
<222> LOCATION: (2)..(2)
<223> OTHER INFORMATION: n is 2-O-Methyladenosine
<220> FEATURE:
<221> NAME/KEY: misc_feature
<222> LOCATION: (5)..(5)
<223> OTHER INFORMATION: n is U

<400> SEQUENCE: 114
cnaanaaatg ccagtagagc aa                                          22

<210> SEQ ID NO 115
<211> LENGTH: 23
<212> TYPE: DNA
<213> ORGANISM: Artificial Sequence
<220> FEATURE:
<223> OTHER INFORMATION: THS for tcdC 117del Probe w/methoxy
<220> FEATURE:
<221> NAME/KEY: misc_feature
<222> LOCATION: (2)..(2)
<223> OTHER INFORMATION: n is 2-O-Methyladenosine
<220> FEATURE:
<221> NAME/KEY: misc_feature
<222> LOCATION: (6)..(6)
<223> OTHER INFORMATION: n is U

<400> SEQUENCE: 115
cnaaanaaat gccagtagag caa                                         23

<210> SEQ ID NO 116
<211> LENGTH: 24
<212> TYPE: DNA
<213> ORGANISM: Artificial Sequence
<220> FEATURE:
<223> OTHER INFORMATION: THS for tcdC 117del Probe w/methoxy
<220> FEATURE:
<221> NAME/KEY: misc_feature
<222> LOCATION: (5)..(5)
<223> OTHER INFORMATION: n is U
<220> FEATURE:
<221> NAME/KEY: misc_feature
```

```
<222> LOCATION: (6)..(6)
<223> OTHER INFORMATION: n is 2-O-Methyladenosine

<400> SEQUENCE: 116
caaannaatg ccagtagagc aata                                          24

<210> SEQ ID NO 117
<211> LENGTH: 25
<212> TYPE: DNA
<213> ORGANISM: Artificial Sequence
<220> FEATURE:
<223> OTHER INFORMATION: THS for tcdC 117del Probe w/methoxy
<220> FEATURE:
<221> NAME/KEY: misc_feature
<222> LOCATION: (5)..(5)
<223> OTHER INFORMATION: n is U
<220> FEATURE:
<221> NAME/KEY: misc_feature
<222> LOCATION: (6)..(6)
<223> OTHER INFORMATION: n is 2-O-Methyladenosine

<400> SEQUENCE: 117
caaannaatg ccagtagagc aatac                                         25

<210> SEQ ID NO 118
<211> LENGTH: 26
<212> TYPE: DNA
<213> ORGANISM: Artificial Sequence
<220> FEATURE:
<223> OTHER INFORMATION: THS for tcdC 117del Probe w/methoxy
<220> FEATURE:
<221> NAME/KEY: misc_feature
<222> LOCATION: (5)..(5)
<223> OTHER INFORMATION: n is U
<220> FEATURE:
<221> NAME/KEY: misc_feature
<222> LOCATION: (6)..(6)
<223> OTHER INFORMATION: n is 2-O-Methyladenosine

<400> SEQUENCE: 118
caaannaatg ccagtagagc aatacc                                        26

<210> SEQ ID NO 119
<211> LENGTH: 27
<212> TYPE: DNA
<213> ORGANISM: Artificial Sequence
<220> FEATURE:
<223> OTHER INFORMATION: THS for tcdC 117del Probe w/methoxy
<220> FEATURE:
<221> NAME/KEY: misc_feature
<222> LOCATION: (5)..(5)
<223> OTHER INFORMATION: n is U
<220> FEATURE:
<221> NAME/KEY: misc_feature
<222> LOCATION: (6)..(6)
<223> OTHER INFORMATION: n is 2-O-Methyladenosine

<400> SEQUENCE: 119
caaannaatg ccagtagagc aataccc                                       27

<210> SEQ ID NO 120
<211> LENGTH: 24
<212> TYPE: DNA
<213> ORGANISM: Artificial Sequence
<220> FEATURE:
<223> OTHER INFORMATION: THS for tcdC 117del Probe w/methoxy
<220> FEATURE:
<221> NAME/KEY: misc_feature
<222> LOCATION: (5)..(5)
<223> OTHER INFORMATION: n is U
<220> FEATURE:
```

```
<221> NAME/KEY: misc_feature
<222> LOCATION: (6)..(6)
<223> OTHER INFORMATION: n is 2-O-Methyladenosine
<220> FEATURE:
<221> NAME/KEY: misc_feature
<222> LOCATION: (11)..(12)
<223> OTHER INFORMATION: n is 5-methylated cytosine
<220> FEATURE:
<221> NAME/KEY: misc_feature
<222> LOCATION: (20)..(20)
<223> OTHER INFORMATION: n is 5-methylated cytosine

<400> SEQUENCE: 120
caaannaatg nnagtagagn aata                                              24

<210> SEQ ID NO 121
<211> LENGTH: 24
<212> TYPE: DNA
<213> ORGANISM: Artificial Sequence
<220> FEATURE:
<223> OTHER INFORMATION: THS for tcdC 117del Probe w/methoxy
<220> FEATURE:
<221> NAME/KEY: misc_feature
<222> LOCATION: (1)..(1)
<223> OTHER INFORMATION: n is 5-methylated cytosine
<220> FEATURE:
<221> NAME/KEY: misc_feature
<222> LOCATION: (5)..(5)
<223> OTHER INFORMATION: n is U
<220> FEATURE:
<221> NAME/KEY: misc_feature
<222> LOCATION: (6)..(6)
<223> OTHER INFORMATION: n is 2-O-Methyladenosine
<220> FEATURE:
<221> NAME/KEY: misc_feature
<222> LOCATION: (11)..(12)
<223> OTHER INFORMATION: n is 5-methylated cytosine
<220> FEATURE:
<221> NAME/KEY: misc_feature
<222> LOCATION: (20)..(20)
<223> OTHER INFORMATION: n is 5-methylated cytosine

<400> SEQUENCE: 121
naaannaatg nnagtagagn aata                                              24

<210> SEQ ID NO 122
<211> LENGTH: 24
<212> TYPE: DNA
<213> ORGANISM: Artificial Sequence
<220> FEATURE:
<223> OTHER INFORMATION: THS for tcdC 117del Probe w/methoxy
<220> FEATURE:
<221> NAME/KEY: misc_feature
<222> LOCATION: (1)..(1)
<223> OTHER INFORMATION: n is 5-methylated cytosine
<220> FEATURE:
<221> NAME/KEY: misc_feature
<222> LOCATION: (5)..(5)
<223> OTHER INFORMATION: n is U
<220> FEATURE:
<221> NAME/KEY: misc_feature
<222> LOCATION: (6)..(6)
<223> OTHER INFORMATION: n is 2-O-Methyladenosine

<400> SEQUENCE: 122
naaannaatg ccagtagagc aata                                              24

<210> SEQ ID NO 123
<211> LENGTH: 21
<212> TYPE: DNA
<213> ORGANISM: Artificial Sequence
<220> FEATURE:
<223> OTHER INFORMATION: THS for tcdC 117del Probe
```

```
<400> SEQUENCE: 123
caaaataaat gccagtagag c                                          21

<210> SEQ ID NO 124
<211> LENGTH: 21
<212> TYPE: DNA
<213> ORGANISM: Artificial Sequence
<220> FEATURE:
<223> OTHER INFORMATION: THS for tcdC 117del Probe

<400> SEQUENCE: 124
caaaataaat gccagtagag c                                          21

<210> SEQ ID NO 125
<211> LENGTH: 20
<212> TYPE: DNA
<213> ORGANISM: Artificial Sequence
<220> FEATURE:
<223> OTHER INFORMATION: THS for tcdC 117del Probe

<400> SEQUENCE: 125
caaaataaat gccagtagag                                            20

<210> SEQ ID NO 126
<211> LENGTH: 19
<212> TYPE: DNA
<213> ORGANISM: Artificial Sequence
<220> FEATURE:
<223> OTHER INFORMATION: THS for tcdC 117del Probe

<400> SEQUENCE: 126
caaaataaat gccagtaga                                             19

<210> SEQ ID NO 127
<211> LENGTH: 25
<212> TYPE: DNA
<213> ORGANISM: Artificial Sequence
<220> FEATURE:
<223> OTHER INFORMATION: THS for tcdC 117del Probe

<400> SEQUENCE: 127
aaaataaatg ccagtagagc aatac                                      25

<210> SEQ ID NO 128
<211> LENGTH: 25
<212> TYPE: DNA
<213> ORGANISM: Artificial Sequence
<220> FEATURE:
<223> OTHER INFORMATION: THS for tcdC 117del Probe

<400> SEQUENCE: 128
aaaataaatg ccagtagagc aatat                                      25

<210> SEQ ID NO 129
<211> LENGTH: 26
<212> TYPE: DNA
<213> ORGANISM: Artificial Sequence
<220> FEATURE:
<223> OTHER INFORMATION: THS for tcdC 117del Probe

<400> SEQUENCE: 129
aaaataaatg ccagtagagc aatatc                                     26

<210> SEQ ID NO 130
```

```
<211> LENGTH: 22
<212> TYPE: DNA
<213> ORGANISM: Artificial Sequence
<220> FEATURE:
<223> OTHER INFORMATION: THS for tcdC 117del Probe with abasic linker
<220> FEATURE:
<221> NAME/KEY: misc_feature
<222> LOCATION: (1)..(2)
<223> OTHER INFORMATION: (abasic)-linker follows position 1

<400> SEQUENCE: 130
caaataaatg ccagtagagc aa                                              22

<210> SEQ ID NO 131
<211> LENGTH: 22
<212> TYPE: DNA
<213> ORGANISM: Artificial Sequence
<220> FEATURE:
<223> OTHER INFORMATION: THS for tcdC 117del Probe with abasic linker
<220> FEATURE:
<221> NAME/KEY: misc_feature
<222> LOCATION: (2)..(3)
<223> OTHER INFORMATION: (abasic)-linker follows position 2

<400> SEQUENCE: 131
caaataaatg ccagtagagc aa                                              22

<210> SEQ ID NO 132
<211> LENGTH: 22
<212> TYPE: DNA
<213> ORGANISM: Artificial Sequence
<220> FEATURE:
<223> OTHER INFORMATION: THS for tcdC 117del Probe with C9 linker
<220> FEATURE:
<221> NAME/KEY: misc_feature
<222> LOCATION: (1)..(2)
<223> OTHER INFORMATION: (sp9)-linker follows position 1

<400> SEQUENCE: 132
caaataaatg ccagtagagc aa                                              22

<210> SEQ ID NO 133
<211> LENGTH: 22
<212> TYPE: DNA
<213> ORGANISM: Artificial Sequence
<220> FEATURE:
<223> OTHER INFORMATION: THS for tcdC 117del Probe with C9 linker
<220> FEATURE:
<221> NAME/KEY: misc_feature
<222> LOCATION: (2)..(3)
<223> OTHER INFORMATION: (sp9)-linker follows position 2

<400> SEQUENCE: 133
caaataaatg ccagtagagc aa                                              22

<210> SEQ ID NO 134
<211> LENGTH: 20
<212> TYPE: DNA
<213> ORGANISM: Artificial Sequence
<220> FEATURE:
<223> OTHER INFORMATION: THS for tcdC 117del Probe with abasic linker
<220> FEATURE:
<221> NAME/KEY: misc_feature
<222> LOCATION: (1)..(2)
<223> OTHER INFORMATION: (abasic)-linker follows position 1

<400> SEQUENCE: 134
caaataaatg ccagtagagc                                                 20
```

```
<210> SEQ ID NO 135
<211> LENGTH: 20
<212> TYPE: DNA
<213> ORGANISM: Artificial Sequence
<220> FEATURE:
<223> OTHER INFORMATION: THS for tcdC 117del Probe with abasic linker
<220> FEATURE:
<221> NAME/KEY: misc_feature
<222> LOCATION: (2)..(3)
<223> OTHER INFORMATION: (abasic)-linker follows position 2

<400> SEQUENCE: 135
caaataaatg ccagtagagc                                              20

<210> SEQ ID NO 136
<211> LENGTH: 20
<212> TYPE: DNA
<213> ORGANISM: Artificial Sequence
<220> FEATURE:
<223> OTHER INFORMATION: THS for tcdC 117del Probe with C9 linker
<220> FEATURE:
<221> NAME/KEY: misc_feature
<222> LOCATION: (1)..(2)
<223> OTHER INFORMATION: (sp9)-linker follows position 1

<400> SEQUENCE: 136
caaataaatg ccagtagagc                                              20

<210> SEQ ID NO 137
<211> LENGTH: 20
<212> TYPE: DNA
<213> ORGANISM: Artificial Sequence
<220> FEATURE:
<223> OTHER INFORMATION: THS for tcdC 117del Probe with C9 linker
<220> FEATURE:
<221> NAME/KEY: misc_feature
<222> LOCATION: (2)..(3)
<223> OTHER INFORMATION: (sp9)-linker follows position 2

<400> SEQUENCE: 137
caaataaatg ccagtagagc                                              20

<210> SEQ ID NO 138
<211> LENGTH: 31
<212> TYPE: DNA
<213> ORGANISM: Artificial Sequence
<220> FEATURE:
<223> OTHER INFORMATION: tcdC 117del Primary Probe
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (31)..(31)
<223> OTHER INFORMATION: 3'-terminal Hexanediol

<400> SEQUENCE: 138
cgcgccgagg caaataaat gccagtagag c                                  31

<210> SEQ ID NO 139
<211> LENGTH: 35
<212> TYPE: DNA
<213> ORGANISM: Artificial Sequence
<220> FEATURE:
<223> OTHER INFORMATION: tcdC 117del Primary Probe
<220> FEATURE:
<221> NAME/KEY: misc_feature
<222> LOCATION: (1)..(10)
<223> OTHER INFORMATION: RNA
<220> FEATURE:
```

<221> NAME/KEY: misc_feature
<222> LOCATION: (35)..(35)
<223> OTHER INFORMATION: 3'-terminal Hexanediol

<400> SEQUENCE: 139
cgcgccgagg aaaataaatg ccagtagagc aatat            35

<210> SEQ ID NO 140
<211> LENGTH: 36
<212> TYPE: DNA
<213> ORGANISM: Artificial Sequence
<220> FEATURE:
<223> OTHER INFORMATION: tcdC 117del Primary Probe
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (36)..(36)
<223> OTHER INFORMATION: 3'-terminal Hexanediol

<400> SEQUENCE: 140
cgcgccgagg aaaataaatg ccagtagagc aatatc           36

<210> SEQ ID NO 141
<211> LENGTH: 30
<212> TYPE: DNA
<213> ORGANISM: Artificial Sequence
<220> FEATURE:
<223> OTHER INFORMATION: tcdC 117del Primary Probe
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (30)..(30)
<223> OTHER INFORMATION: 3'-terminal Hexanediol

<400> SEQUENCE: 141
cgcgccgagg caaaataaat gccagtagag            30

<210> SEQ ID NO 142
<211> LENGTH: 29
<212> TYPE: DNA
<213> ORGANISM: Artificial Sequence
<220> FEATURE:
<223> OTHER INFORMATION: tcdC 117del Primary Probe
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (29)..(29)
<223> OTHER INFORMATION: 3'-terminal Hexanediol

<400> SEQUENCE: 142
cgcgccgagg caaaataaat gccagtaga            29

<210> SEQ ID NO 143
<211> LENGTH: 33
<212> TYPE: DNA
<213> ORGANISM: Artificial Sequence
<220> FEATURE:
<223> OTHER INFORMATION: tcdC 117del Primary Probe
<220> FEATURE:
<221> NAME/KEY: misc_feature
<222> LOCATION: (1)..(10)
<223> OTHER INFORMATION: RNA

```
<220> FEATURE:
<221> NAME/KEY: misc_feature
<222> LOCATION: (33)..(33)
<223> OTHER INFORMATION: 3'-terminal Hexanediol

<400> SEQUENCE: 143
cgcgccgagg caaaataaat gccagtagag caa                                    33

<210> SEQ ID NO 144
<211> LENGTH: 36
<212> TYPE: DNA
<213> ORGANISM: Artificial Sequence
<220> FEATURE:
<223> OTHER INFORMATION: tcdC 117del Primary Probe
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (36)..(36)
<223> OTHER INFORMATION: 3'-terminal Hexanediol

<400> SEQUENCE: 144
cgcgccgagg caaaataaat gccagtagag caatac                                 36

<210> SEQ ID NO 145
<211> LENGTH: 32
<212> TYPE: DNA
<213> ORGANISM: Artificial Sequence
<220> FEATURE:
<223> OTHER INFORMATION: tcdC 117del Primary Probe
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (32)..(32)
<223> OTHER INFORMATION: 3'-terminal Hexanediol

<400> SEQUENCE: 145
cgcgccgagg caaataaatg ccagtagagc aa                                     32

<210> SEQ ID NO 146
<211> LENGTH: 31
<212> TYPE: DNA
<213> ORGANISM: Artificial Sequence
<220> FEATURE:
<223> OTHER INFORMATION: tcdC 117del Primary Probe
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (31)..(31)
<223> OTHER INFORMATION: 3'-terminal Hexanediol

<400> SEQUENCE: 146
cgcgccgagg caataaatgc cagtagagca a                                      31

<210> SEQ ID NO 147
<211> LENGTH: 30
<212> TYPE: DNA
<213> ORGANISM: Artificial Sequence
<220> FEATURE:
<223> OTHER INFORMATION: tcdC 117del Primary Probe
<220> FEATURE:
<221> NAME/KEY: misc_feature
<222> LOCATION: (1)..(10)
```

<223> OTHER INFORMATION: RNA
<220> FEATURE:
<221> NAME/KEY: misc_feature
<222> LOCATION: (30)..(30)
<223> OTHER INFORMATION: 3'-terminal Hexanediol

<400> SEQUENCE: 147
cgcgccgagg cataaatgcc agtagagcaa                                    30

<210> SEQ ID NO 148
<211> LENGTH: 33
<212> TYPE: DNA
<213> ORGANISM: Artificial Sequence
<220> FEATURE:
<223> OTHER INFORMATION: tcdC 117del Primary Probe w/methoxy
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (16)..(16)
<223> OTHER INFORMATION: n is U
<220> FEATURE:
<221> NAME/KEY: misc_feature
<222> LOCATION: (33)..(33)
<223> OTHER INFORMATION: 3'-terminal Hexanediol

<400> SEQUENCE: 148
cgcgccgagg caaanaaat gccagtagag caa                                 33

<210> SEQ ID NO 149
<211> LENGTH: 33
<212> TYPE: DNA
<213> ORGANISM: Artificial Sequence
<220> FEATURE:
<223> OTHER INFORMATION: tcdC 117del Primary Probe w/methoxy
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (14)..(14)
<223> OTHER INFORMATION: n is 2-O-Methyladenosine
<220> FEATURE:
<221> NAME/KEY: misc_feature
<222> LOCATION: (33)..(33)
<223> OTHER INFORMATION: 3'-terminal Hexanediol

<400> SEQUENCE: 149
cgcgccgagg caanataaat gccagtagag caa                                33

<210> SEQ ID NO 150
<211> LENGTH: 33
<212> TYPE: DNA
<213> ORGANISM: Artificial Sequence
<220> FEATURE:
<223> OTHER INFORMATION: tcdC 117del Primary Probe w/methoxy
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (13)..(13)
<223> OTHER INFORMATION: n is 2-O-Methyladenosine
<220> FEATURE:
<221> NAME/KEY: misc_feature
<222> LOCATION: (33)..(33)
<223> OTHER INFORMATION: 3'-terminal Hexanediol

<400> SEQUENCE: 150
cgcgccgagg canaataaat gccagtagag caa                                33

<210> SEQ ID NO 151
<211> LENGTH: 32
<212> TYPE: DNA
<213> ORGANISM: Artificial Sequence
<220> FEATURE:
<223> OTHER INFORMATION: tcdC 117del Primary Probe w/methoxy
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (15)..(15)
<223> OTHER INFORMATION: n is U
<220> FEATURE:
<221> NAME/KEY: misc_feature
<222> LOCATION: (32)..(32)
<223> OTHER INFORMATION: 3'-terminal Hexanediol

<400> SEQUENCE: 151
cgcgccgagg caaanaaatg ccagtagagc aa                                 32

<210> SEQ ID NO 152
<211> LENGTH: 31
<212> TYPE: DNA
<213> ORGANISM: Artificial Sequence
<220> FEATURE:
<223> OTHER INFORMATION: tcdC 117del Primary Probe w/methoxy
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (14)..(14)
<223> OTHER INFORMATION: n is U
<220> FEATURE:
<221> NAME/KEY: misc_feature
<222> LOCATION: (31)..(31)
<223> OTHER INFORMATION: 3'-terminal Hexanediol

<400> SEQUENCE: 152
cgcgccgagg caanaaatgc cagtagagca a                                  31

<210> SEQ ID NO 153
<211> LENGTH: 30
<212> TYPE: DNA
<213> ORGANISM: Artificial Sequence
<220> FEATURE:
<223> OTHER INFORMATION: tcdC 117del Primary Probe w/methoxy
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (13)..(13)
<223> OTHER INFORMATION: n is U
<220> FEATURE:
<221> NAME/KEY: misc_feature
<222> LOCATION: (30)..(30)
<223> OTHER INFORMATION: 3'-terminal Hexanediol

<400> SEQUENCE: 153
cgcgccgagg canaaatgcc agtagagcaa                                    30

<210> SEQ ID NO 154

```
<211> LENGTH: 32
<212> TYPE: DNA
<213> ORGANISM: Artificial Sequence
<220> FEATURE:
<223> OTHER INFORMATION: tcdC 117del Primary Probe w/methoxy
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (14)..(14)
<223> OTHER INFORMATION: n is 2-O-Methyladenosine
<220> FEATURE:
<221> NAME/KEY: misc_feature
<222> LOCATION: (15)..(15)
<223> OTHER INFORMATION: n is U
<220> FEATURE:
<221> NAME/KEY: misc_feature
<222> LOCATION: (32)..(32)
<223> OTHER INFORMATION: 3'-terminal Hexanediol

<400> SEQUENCE: 154
cgcgccgagg caannaaatg ccagtagagc aa                                32

<210> SEQ ID NO 155
<211> LENGTH: 32
<212> TYPE: DNA
<213> ORGANISM: Artificial Sequence
<220> FEATURE:
<223> OTHER INFORMATION: tcdC 117del Primary Probe w/methoxy
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (14)..(14)
<223> OTHER INFORMATION: n is U
<220> FEATURE:
<221> NAME/KEY: misc_feature
<222> LOCATION: (15)..(15)
<223> OTHER INFORMATION: n is 2-O-Methyladenosine
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (32)..(32)
<223> OTHER INFORMATION: 3'-terminal Hexanediol

<400> SEQUENCE: 155
cgcgccgagg caaannaatg ccagtagagc aa                                32

<210> SEQ ID NO 156
<211> LENGTH: 32
<212> TYPE: DNA
<213> ORGANISM: Artificial Sequence
<220> FEATURE:
<223> OTHER INFORMATION: tcdC 117del Primary Probe w/methoxy
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (14)..(14)
<223> OTHER INFORMATION: n is 2-O-Methyladenosine
<220> FEATURE:
<221> NAME/KEY: misc_feature
<222> LOCATION: (15)..(15)
<223> OTHER INFORMATION: n is U
<220> FEATURE:
<221> NAME/KEY: misc_feature
```

-continued

```
<222> LOCATION: (16)..(16)
<223> OTHER INFORMATION: n is 2-O-Methyladenosine
<220> FEATURE:
<221> NAME/KEY: misc_feature
<222> LOCATION: (32)..(32)
<223> OTHER INFORMATION: 3'-terminal Hexanediol

<400> SEQUENCE: 156
cgcgccgagg caannnaatg ccagtagagc aa                                  32

<210> SEQ ID NO 157
<211> LENGTH: 32
<212> TYPE: DNA
<213> ORGANISM: Artificial Sequence
<220> FEATURE:
<223> OTHER INFORMATION: tcdC 117del Primary Probe w/methoxy
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (12)..(12)
<223> OTHER INFORMATION: n is 2-O-Methyladenosine
<220> FEATURE:
<221> NAME/KEY: misc_feature
<222> LOCATION: (32)..(32)
<223> OTHER INFORMATION: 3'-terminal Hexanediol

<400> SEQUENCE: 157
cgcgccgagg cnaataaatg ccagtagagc aa                                  32

<210> SEQ ID NO 158
<211> LENGTH: 33
<212> TYPE: DNA
<213> ORGANISM: Artificial Sequence
<220> FEATURE:
<223> OTHER INFORMATION: tcdC 117del Primary Probe w/methoxy
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (12)..(12)
<223> OTHER INFORMATION: n is 2-O-Methyladenosine
<220> FEATURE:
<221> NAME/KEY: misc_feature
<222> LOCATION: (33)..(33)
<223> OTHER INFORMATION: 3'-terminal Hexanediol

<400> SEQUENCE: 158
cgcgccgagg cnaaataaat gccagtagag caa                                 33

<210> SEQ ID NO 159
<211> LENGTH: 32
<212> TYPE: DNA
<213> ORGANISM: Artificial Sequence
<220> FEATURE:
<223> OTHER INFORMATION: tcdC 117del Primary Probe w/methoxy
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (12)..(12)
<223> OTHER INFORMATION: n is 2-O-Methyladenosine
<220> FEATURE:
<221> NAME/KEY: misc_feature
<222> LOCATION: (15)..(15)
<223> OTHER INFORMATION: n is U
<220> FEATURE:
```

```
<221> NAME/KEY: misc_feature
<222> LOCATION: (32)..(32)
<223> OTHER INFORMATION: 3'-terminal Hexanediol

<400> SEQUENCE: 159
cgcgccgagg cnaanaaatg ccagtagagc aa                                    32

<210> SEQ ID NO 160
<211> LENGTH: 33
<212> TYPE: DNA
<213> ORGANISM: Artificial Sequence
<220> FEATURE:
<223> OTHER INFORMATION: tcdC 117del Primary Probe w/methoxy
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (12)..(12)
<223> OTHER INFORMATION: n is 2-O-Methyladenosine
<220> FEATURE:
<221> NAME/KEY: misc_feature
<222> LOCATION: (16)..(16)
<223> OTHER INFORMATION: n is U
<220> FEATURE:
<221> NAME/KEY: misc_feature
<222> LOCATION: (33)..(33)
<223> OTHER INFORMATION: 3'-terminal Hexanediol

<400> SEQUENCE: 160
cgcgccgagg cnaaanaaat gccagtagag caa                                   33

<210> SEQ ID NO 161
<211> LENGTH: 34
<212> TYPE: DNA
<213> ORGANISM: Artificial Sequence
<220> FEATURE:
<223> OTHER INFORMATION: tcdC 117del Primary Probe w/methoxy
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (15)..(15)
<223> OTHER INFORMATION: n is U
<220> FEATURE:
<221> NAME/KEY: misc_feature
<222> LOCATION: (16)..(16)
<223> OTHER INFORMATION: n is 2-O-Methyladenosine
<220> FEATURE:
<221> NAME/KEY: misc_feature
<222> LOCATION: (34)..(34)
<223> OTHER INFORMATION: 3'-terminal Hexanediol

<400> SEQUENCE: 161
cgcgccgagg caaannaatg ccagtagagc aata                                  34

<210> SEQ ID NO 162
<211> LENGTH: 35
<212> TYPE: DNA
<213> ORGANISM: Artificial Sequence
<220> FEATURE:
<223> OTHER INFORMATION: tcdC 117del Primary Probe w/methoxy
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (15)..(15)
<223> OTHER INFORMATION: n is U
```

```
<220> FEATURE:
<221> NAME/KEY: misc_feature
<222> LOCATION: (16)..(16)
<223> OTHER INFORMATION: n is 2-O-Methyladenosine
<220> FEATURE:
<221> NAME/KEY: misc_feature
<222> LOCATION: (35)..(35)
<223> OTHER INFORMATION: 3'-terminal Hexanediol

<400> SEQUENCE: 162
cgcgccgagg caaannaatg ccagtagagc aatac                                  35

<210> SEQ ID NO 163
<211> LENGTH: 36
<212> TYPE: DNA
<213> ORGANISM: Artificial Sequence
<220> FEATURE:
<223> OTHER INFORMATION: tcdC 117del Primary Probe w/methoxy
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (15)..(15)
<223> OTHER INFORMATION: n is U
<220> FEATURE:
<221> NAME/KEY: misc_feature
<222> LOCATION: (16)..(16)
<223> OTHER INFORMATION: n is 2-O-Methyladenosine
<220> FEATURE:
<221> NAME/KEY: misc_feature
<222> LOCATION: (36)..(36)
<223> OTHER INFORMATION: 3'-terminal Hexanediol

<400> SEQUENCE: 163
cgcgccgagg caaannaatg ccagtagagc aatacc                                 36

<210> SEQ ID NO 164
<211> LENGTH: 37
<212> TYPE: DNA
<213> ORGANISM: Artificial Sequence
<220> FEATURE:
<223> OTHER INFORMATION: tcdC 117del Primary Probe w/methoxy
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (15)..(15)
<223> OTHER INFORMATION: n is U
<220> FEATURE:
<221> NAME/KEY: misc_feature
<222> LOCATION: (16)..(16)
<223> OTHER INFORMATION: n is 2-O-Methyladenosine
<220> FEATURE:
<221> NAME/KEY: misc_feature
<222> LOCATION: (37)..(37)
<223> OTHER INFORMATION: 3'-terminal Hexanediol

<400> SEQUENCE: 164
cgcgccgagg caaannaatg ccagtagagc aataccc                                37

<210> SEQ ID NO 165
<211> LENGTH: 34
<212> TYPE: DNA
<213> ORGANISM: Artificial Sequence
<220> FEATURE:
<223> OTHER INFORMATION: tcdC 117del Primary Probe w/methoxy
<220> FEATURE:
<221> NAME/KEY: misc_feature
<222> LOCATION: (1)..(10)
```

<223> OTHER INFORMATION: RNA
<220> FEATURE:
<221> NAME/KEY: misc_feature
<222> LOCATION: (15)..(15)
<223> OTHER INFORMATION: n is U
<220> FEATURE:
<221> NAME/KEY: misc_feature
<222> LOCATION: (16)..(16)
<223> OTHER INFORMATION: n is 2-O-Methyladenosine
<220> FEATURE:
<221> NAME/KEY: misc_feature
<222> LOCATION: (21)..(22)
<223> OTHER INFORMATION: n is 5-methylated cytosine
<220> FEATURE:
<221> NAME/KEY: misc_feature
<222> LOCATION: (30)..(30)
<223> OTHER INFORMATION: n is 5-methylated cytosine
<220> FEATURE:
<221> NAME/KEY: misc_feature
<222> LOCATION: (34)..(34)
<223> OTHER INFORMATION: 3'-terminal Hexanediol

<400> SEQUENCE: 165
cgcgccgagg caaannaatg nnagtagagn aata                                34

<210> SEQ ID NO 166
<211> LENGTH: 34
<212> TYPE: DNA
<213> ORGANISM: Artificial Sequence
<220> FEATURE:
<223> OTHER INFORMATION: tcdC 117del Primary Probe w/methoxy
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (11)..(11)
<223> OTHER INFORMATION: n is 5-methylated cytosine
<220> FEATURE:
<221> NAME/KEY: misc_feature
<222> LOCATION: (15)..(15)
<223> OTHER INFORMATION: n is U
<220> FEATURE:
<221> NAME/KEY: misc_feature
<222> LOCATION: (16)..(16)
<223> OTHER INFORMATION: n is 2-O-Methyladenosine
<220> FEATURE:
<221> NAME/KEY: misc_feature
<222> LOCATION: (21)..(22)
<223> OTHER INFORMATION: n is 5-methylated cytosine
<220> FEATURE:
<221> NAME/KEY: misc_feature
<222> LOCATION: (30)..(30)
<223> OTHER INFORMATION: n is 5-methylated cytosine
<220> FEATURE:
<221> NAME/KEY: misc_feature
<222> LOCATION: (34)..(34)
<223> OTHER INFORMATION: 3'-terminal Hexanediol

<400> SEQUENCE: 166
cgcgccgagg naaannaatg nnagtagagn aata                                34

<210> SEQ ID NO 167
<211> LENGTH: 34
<212> TYPE: DNA
<213> ORGANISM: Artificial Sequence
<220> FEATURE:
<223> OTHER INFORMATION: tcdC 117del Primary Probe w/methoxy
<220> FEATURE:
<221> NAME/KEY: misc_feature
<222> LOCATION: (1)..(10)
<223> OTHER INFORMATION: RNA
<220> FEATURE:
<221> NAME/KEY: misc_feature

```
<222> LOCATION: (11)..(11)
<223> OTHER INFORMATION: n is 5-methylated cytosine
<220> FEATURE:
<221> NAME/KEY: misc_feature
<222> LOCATION: (15)..(15)
<223> OTHER INFORMATION: n is U
<220> FEATURE:
<221> NAME/KEY: misc_feature
<222> LOCATION: (16)..(16)
<223> OTHER INFORMATION: n is 2-O-Methyladenosine
<220> FEATURE:
<221> NAME/KEY: misc_feature
<222> LOCATION: (34)..(34)
<223> OTHER INFORMATION: 3'-terminal Hexanediol

<400> SEQUENCE: 167
cgcgccgagg naaannaatg ccagtagagc aata                                    34

<210> SEQ ID NO 168
<211> LENGTH: 35
<212> TYPE: DNA
<213> ORGANISM: Artificial Sequence
<220> FEATURE:
<223> OTHER INFORMATION: tcdC 117del Primary Probe
<220> FEATURE:
<221> NAME/KEY: misc_feature
<222> LOCATION: (1)..(14)
<223> OTHER INFORMATION: RNA
<220> FEATURE:
<221> NAME/KEY: misc_feature
<222> LOCATION: (35)..(35)
<223> OTHER INFORMATION: 3'-terminal Hexanediol

<400> SEQUENCE: 168
atgacgtggc agaccaaaat aaatgccagt agagc                                   35

<210> SEQ ID NO 169
<211> LENGTH: 33
<212> TYPE: DNA
<213> ORGANISM: Artificial Sequence
<220> FEATURE:
<223> OTHER INFORMATION: tcdC 117del Primary Probe
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (33)..(33)
<223> OTHER INFORMATION: 3'-terminal Hexanediol

<400> SEQUENCE: 169
acggacgcgg agcaaaataa atgccagtag agc                                     33

<210> SEQ ID NO 170
<211> LENGTH: 32
<212> TYPE: DNA
<213> ORGANISM: Artificial Sequence
<220> FEATURE:
<223> OTHER INFORMATION: tcdC 117del Primary Probe
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (32)..(32)
<223> OTHER INFORMATION: 3'-terminal Hexanediol

<400> SEQUENCE: 170
acggacgcgg agcaaaataa atgccagtag ag                                      32
```

<210> SEQ ID NO 171
<211> LENGTH: 31
<212> TYPE: DNA
<213> ORGANISM: Artificial Sequence
<220> FEATURE:
<223> OTHER INFORMATION: tcdC 117del Primary Probe
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (31)..(31)
<223> OTHER INFORMATION: 3'-terminal Hexanediol

<400> SEQUENCE: 171
acggacgcgg agcaaaataa atgccagtag a                                      31

<210> SEQ ID NO 172
<211> LENGTH: 37
<212> TYPE: DNA
<213> ORGANISM: Artificial Sequence
<220> FEATURE:
<223> OTHER INFORMATION: tcdC 117del Primary Probe
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (37)..(37)
<223> OTHER INFORMATION: 3'-terminal Hexanediol

<400> SEQUENCE: 172
acggacgcgg agaaaataaa tgccagtaga gcaatac                                37

<210> SEQ ID NO 173
<211> LENGTH: 37
<212> TYPE: DNA
<213> ORGANISM: Artificial Sequence
<220> FEATURE:
<223> OTHER INFORMATION: tcdC 117del Primary Probe
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (37)..(37)
<223> OTHER INFORMATION: 3'-terminal Hexanediol

<400> SEQUENCE: 173
acggacgcgg agaaaataaa tgccagtaga gcaatat                                37

<210> SEQ ID NO 174
<211> LENGTH: 38
<212> TYPE: DNA
<213> ORGANISM: Artificial Sequence
<220> FEATURE:
<223> OTHER INFORMATION: tcdC 117del Primary Probe
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (38)..(38)
<223> OTHER INFORMATION: 3'-terminal Hexanediol

<400> SEQUENCE: 174
acggacgcgg agaaaataaa tgccagtaga gcaatatc                               38

```
<210> SEQ ID NO 175
<211> LENGTH: 34
<212> TYPE: DNA
<213> ORGANISM: Artificial Sequence
<220> FEATURE:
<223> OTHER INFORMATION: tcdC 117del Primary Probe with abasic linker
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (13)..(14)
<223> OTHER INFORMATION: (abasic)-linker follows position 13
<220> FEATURE:
<221> NAME/KEY: misc_feature
<222> LOCATION: (34)..(34)
<223> OTHER INFORMATION: 3'-terminal Hexanediol

<400> SEQUENCE: 175
acggacgcgg agcaaataaa tgccagtaga gcaa                                34

<210> SEQ ID NO 176
<211> LENGTH: 34
<212> TYPE: DNA
<213> ORGANISM: Artificial Sequence
<220> FEATURE:
<223> OTHER INFORMATION: tcdC 117del Primary Probe with abasic linker
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (14)..(15)
<223> OTHER INFORMATION: (abasic)-linker follows position 14
<220> FEATURE:
<221> NAME/KEY: misc_feature
<222> LOCATION: (34)..(34)
<223> OTHER INFORMATION: 3'-terminal Hexanediol

<400> SEQUENCE: 176
acggacgcgg agcaaataaa tgccagtaga gcaa                                34

<210> SEQ ID NO 177
<211> LENGTH: 34
<212> TYPE: DNA
<213> ORGANISM: Artificial Sequence
<220> FEATURE:
<223> OTHER INFORMATION: tcdC 117del Primary Probe with C9 linker
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (13)..(14)
<223> OTHER INFORMATION: (sp9)-linker follows position 13
<220> FEATURE:
<221> NAME/KEY: misc_feature
<222> LOCATION: (34)..(34)
<223> OTHER INFORMATION: 3'-terminal Hexanediol

<400> SEQUENCE: 177
acggacgcgg agcaaataaa tgccagtaga gcaa                                34

<210> SEQ ID NO 178
<211> LENGTH: 34
<212> TYPE: DNA
<213> ORGANISM: Artificial Sequence
<220> FEATURE:
```

```
<223> OTHER INFORMATION: tcdC 117del Primary Probe with C9 linker
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (14)..(15)
<223> OTHER INFORMATION: (sp9)-linker follows position 14
<220> FEATURE:
<221> NAME/KEY: misc_feature
<222> LOCATION: (34)..(34)
<223> OTHER INFORMATION: 3'-terminal Hexanediol

<400> SEQUENCE: 178
acggacgcgg agcaaataaa tgccagtaga gcaa                                    34

<210> SEQ ID NO 179
<211> LENGTH: 32
<212> TYPE: DNA
<213> ORGANISM: Artificial Sequence
<220> FEATURE:
<223> OTHER INFORMATION: tcdC 117del Primary Probe with abasic linker
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (13)..(14)
<223> OTHER INFORMATION: (abasic)-linker follows position 13
<220> FEATURE:
<221> NAME/KEY: misc_feature
<222> LOCATION: (32)..(32)
<223> OTHER INFORMATION: 3'-terminal Hexanediol

<400> SEQUENCE: 179
acggacgcgg agcaaataaa tgccagtaga gc                                      32

<210> SEQ ID NO 180
<211> LENGTH: 32
<212> TYPE: DNA
<213> ORGANISM: Artificial Sequence
<220> FEATURE:
<223> OTHER INFORMATION: tcdC 117del Primary Probe with abasic linker
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (14)..(15)
<223> OTHER INFORMATION: (abasic)-linker follows position 14
<220> FEATURE:
<221> NAME/KEY: misc_feature
<222> LOCATION: (32)..(32)
<223> OTHER INFORMATION: 3'-terminal Hexanediol

<400> SEQUENCE: 180
acggacgcgg agcaaataaa tgccagtaga gc                                      32

<210> SEQ ID NO 181
<211> LENGTH: 32
<212> TYPE: DNA
<213> ORGANISM: Artificial Sequence
<220> FEATURE:
<223> OTHER INFORMATION: tcdC 117del Primary Probe with C9 linker
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
```

```
<222> LOCATION: (13)..(14)
<223> OTHER INFORMATION: (sp9)-linker follows position 13
<220> FEATURE:
<221> NAME/KEY: misc_feature
<222> LOCATION: (32)..(32)
<223> OTHER INFORMATION: 3'-terminal Hexanediol

<400> SEQUENCE: 181
acggacgcgg agcaaataaa tgccagtaga gc                                        32

<210> SEQ ID NO 182
<211> LENGTH: 32
<212> TYPE: DNA
<213> ORGANISM: Artificial Sequence
<220> FEATURE:
<223> OTHER INFORMATION: tcdC 117del Primary Probe with C9 linker
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (14)..(15)
<223> OTHER INFORMATION: (sp9)-linker follows position 14
<220> FEATURE:
<221> NAME/KEY: misc_feature
<222> LOCATION: (32)..(32)
<223> OTHER INFORMATION: 3'-terminal Hexanediol

<400> SEQUENCE: 182
acggacgcgg agcaaataaa tgccagtaga gc                                        32

<210> SEQ ID NO 183
<211> LENGTH: 32
<212> TYPE: DNA
<213> ORGANISM: Artificial Sequence
<220> FEATURE:
<223> OTHER INFORMATION: tcdC 117del Invader
<220> FEATURE:
<221> NAME/KEY: misc_feature
<222> LOCATION: (32)..(32)
<223> OTHER INFORMATION: RNA

<400> SEQUENCE: 183
acaaagggta ttgctctact ggcatttatt tc                                        32

<210> SEQ ID NO 184
<211> LENGTH: 21
<212> TYPE: DNA
<213> ORGANISM: Artificial Sequence
<220> FEATURE:
<223> OTHER INFORMATION: THS for tcdC 117del Primary Probe
<220> FEATURE:
<221> NAME/KEY: misc_feature
<222> LOCATION: (4)..(4)
<223> OTHER INFORMATION: RNA

<400> SEQUENCE: 184
tggtgtgttt tttggcaata t                                                    21

<210> SEQ ID NO 185
<211> LENGTH: 23
<212> TYPE: DNA
<213> ORGANISM: Artificial Sequence
<220> FEATURE:
<223> OTHER INFORMATION: THS for tcdC 117del Primary Probe
<220> FEATURE:
<221> NAME/KEY: misc_feature
<222> LOCATION: (3)..(3)
<223> OTHER INFORMATION: RNA
```

<400> SEQUENCE: 185
ggtgtgtttt ttggcaatat atc                                          23

<210> SEQ ID NO 186
<211> LENGTH: 20
<212> TYPE: DNA
<213> ORGANISM: Artificial Sequence
<220> FEATURE:
<223> OTHER INFORMATION: THS for tcdC 117del Primary Probe

<400> SEQUENCE: 186
ggtgtgtttt ttggcaatat                                              20

<210> SEQ ID NO 187
<211> LENGTH: 23
<212> TYPE: DNA
<213> ORGANISM: Artificial Sequence
<220> FEATURE:
<223> OTHER INFORMATION: THS for tcdC 117del Primary Probe

<400> SEQUENCE: 187
ggtgtgtttt ttggcaatat atc                                          23

<210> SEQ ID NO 188
<211> LENGTH: 33
<212> TYPE: DNA
<213> ORGANISM: Artificial Sequence
<220> FEATURE:
<223> OTHER INFORMATION: tcdC 117del Primary Probe
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (16)..(16)
<223> OTHER INFORMATION: RNA
<220> FEATURE:
<221> NAME/KEY: misc_feature
<222> LOCATION: (33)..(33)
<223> OTHER INFORMATION: 3'-terminal Hexanediol

<400> SEQUENCE: 188
acggacgcgg agtggtgtgt tttttggcaa tat                               33

<210> SEQ ID NO 189
<211> LENGTH: 37
<212> TYPE: DNA
<213> ORGANISM: Artificial Sequence
<220> FEATURE:
<223> OTHER INFORMATION: tcdC 117del Primary Probe
<220> FEATURE:
<221> NAME/KEY: misc_feature
<222> LOCATION: (1)..(14)
<223> OTHER INFORMATION: RNA
<220> FEATURE:
<221> NAME/KEY: misc_feature
<222> LOCATION: (17)..(17)
<223> OTHER INFORMATION: RNA
<220> FEATURE:
<221> NAME/KEY: misc_feature
<222> LOCATION: (37)..(37)
<223> OTHER INFORMATION: 3'-terminal Hexanediol

<400> SEQUENCE: 189
atgacgtggc agacggtgtg tttttggca atatatc                            37

<210> SEQ ID NO 190
<211> LENGTH: 34

```
-continued

<212> TYPE: DNA
<213> ORGANISM: Artificial Sequence
<220> FEATURE:
<223> OTHER INFORMATION: tcdC 117del Primary Probe
<220> FEATURE:
<221> NAME/KEY: misc_feature
<222> LOCATION: (1)..(14)
<223> OTHER INFORMATION: RNA
<220> FEATURE:
<221> NAME/KEY: misc_feature
<222> LOCATION: (17)..(17)
<223> OTHER INFORMATION: RNA
<220> FEATURE:
<221> NAME/KEY: misc_feature
<222> LOCATION: (34)..(34)
<223> OTHER INFORMATION: 3'-terminal Hexanediol

<400> SEQUENCE: 190
atgacgtggc agacggtgtg ttttttggca atat                              34

<210> SEQ ID NO 191
<211> LENGTH: 35
<212> TYPE: DNA
<213> ORGANISM: Artificial Sequence
<220> FEATURE:
<223> OTHER INFORMATION: tcdC 117del Primary Probe
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (15)..(15)
<223> OTHER INFORMATION: RNA
<220> FEATURE:
<221> NAME/KEY: misc_feature
<222> LOCATION: (35)..(35)
<223> OTHER INFORMATION: 3'-terminal Hexanediol

<400> SEQUENCE: 191
acggacgcgg agggtgtgtt ttttggcaat atatc                             35

<210> SEQ ID NO 192
<211> LENGTH: 29
<212> TYPE: DNA
<213> ORGANISM: Artificial Sequence
<220> FEATURE:
<223> OTHER INFORMATION: tcdC 117del Reverse iPrimer

<400> SEQUENCE: 192
ggtgaggata tattgccaaa aaacacgcc                                    29

<210> SEQ ID NO 193
<211> LENGTH: 30
<212> TYPE: DNA
<213> ORGANISM: Artificial Sequence
<220> FEATURE:
<223> OTHER INFORMATION: tcdC 117del Reverse iPrimer

<400> SEQUENCE: 193
ggtgaggata tattgccaaa aaacacgcca                                   30

<210> SEQ ID NO 194
<211> LENGTH: 30
<212> TYPE: DNA
<213> ORGANISM: Artificial Sequence
<220> FEATURE:
<223> OTHER INFORMATION: tcdC 183/184 Invader
<220> FEATURE:
<221> NAME/KEY: misc_feature
<222> LOCATION: (30)..(30)
```

<223> OTHER INFORMATION: RNA

<400> SEQUENCE: 194
ctgaagacca tgaggaggtc atttctaata                30

<210> SEQ ID NO 195
<211> LENGTH: 32
<212> TYPE: DNA
<213> ORGANISM: Artificial Sequence
<220> FEATURE:
<223> OTHER INFORMATION: tcdC 183/184 Invader

<400> SEQUENCE: 195
gttctgaaga ccatgaggag gtcatttcta ag             32

<210> SEQ ID NO 196
<211> LENGTH: 33
<212> TYPE: DNA
<213> ORGANISM: Artificial Sequence
<220> FEATURE:
<223> OTHER INFORMATION: tcdC 183/184 Invader

<400> SEQUENCE: 196
gttctgaaga ccatgaggag gtcatttcta atg            33

<210> SEQ ID NO 197
<211> LENGTH: 23
<212> TYPE: DNA
<213> ORGANISM: Artificial Sequence
<220> FEATURE:
<223> OTHER INFORMATION: THS for tcdC 183/184 CC>TT Primary Probe

<400> SEQUENCE: 197
ttaaacatca gttatagatt ctc                       23

<210> SEQ ID NO 198
<211> LENGTH: 22
<212> TYPE: DNA
<213> ORGANISM: Artificial Sequence
<220> FEATURE:
<223> OTHER INFORMATION: THS for tcdC 183/184 CC>TT Primary Probe

<400> SEQUENCE: 198
taaacatcag ttatagattc tc                        22

<210> SEQ ID NO 199
<211> LENGTH: 23
<212> TYPE: DNA
<213> ORGANISM: Artificial Sequence
<220> FEATURE:
<223> OTHER INFORMATION: THS for tcdC 183/184 CC>TT Primary Probe

<400> SEQUENCE: 199
ttaaacatca gttatagatt ctc                       23

<210> SEQ ID NO 200
<211> LENGTH: 22
<212> TYPE: DNA
<213> ORGANISM: Artificial Sequence
<220> FEATURE:
<223> OTHER INFORMATION: THS for tcdC 183/184 CC>TT Primary Probe
<220> FEATURE:
<221> NAME/KEY: misc_feature
<222> LOCATION: (5)..(5)
<223> OTHER INFORMATION: n is 5-methylated cytosine

```
<400> SEQUENCE: 200
taaanatcag ttatagattc tc                                              22

<210> SEQ ID NO 201
<211> LENGTH: 33
<212> TYPE: DNA
<213> ORGANISM: Artificial Sequence
<220> FEATURE:
<223> OTHER INFORMATION: tcdC 183/184 CC>TT Primary Probe
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (33)..(33)
<223> OTHER INFORMATION: 3'-terminal Hexanediol

<400> SEQUENCE: 201
cgcgccgagg ttaaacatca gttatagatt ctc                                  33

<210> SEQ ID NO 202
<211> LENGTH: 32
<212> TYPE: DNA
<213> ORGANISM: Artificial Sequence
<220> FEATURE:
<223> OTHER INFORMATION: tcdC 183/184 CC>TT Primary Probe
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (32)..(32)
<223> OTHER INFORMATION: 3'-terminal Hexanediol

<400> SEQUENCE: 202
cgcgccgagg taaacatcag ttatagattc tc                                   32

<210> SEQ ID NO 203
<211> LENGTH: 33
<212> TYPE: DNA
<213> ORGANISM: Artificial Sequence
<220> FEATURE:
<223> OTHER INFORMATION: tcdC 183/184 CC>TT Primary Probe
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (33)..(33)
<223> OTHER INFORMATION: 3'-terminal Hexanediol

<400> SEQUENCE: 203
cgcgccgagg ttaaacatca gttatagatt ctc                                  33

<210> SEQ ID NO 204
<211> LENGTH: 32
<212> TYPE: DNA
<213> ORGANISM: Artificial Sequence
<220> FEATURE:
<223> OTHER INFORMATION: tcdC 183/184 CC>TT Primary Probe
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (15)..(15)
```

```
<223> OTHER INFORMATION: n is 5-methylated cytosine
<220> FEATURE:
<221> NAME/KEY: misc_feature
<222> LOCATION: (32)..(32)
<223> OTHER INFORMATION: 3'-terminal Hexanediol

<400> SEQUENCE: 204
cgcgccgagg taaanatcag ttatagattc tc                                    32

<210> SEQ ID NO 205
<211> LENGTH: 41
<212> TYPE: DNA
<213> ORGANISM: Artificial Sequence
<220> FEATURE:
<223> OTHER INFORMATION: tcdC 184 Invader
<220> FEATURE:
<221> NAME/KEY: misc_feature
<222> LOCATION: (41)..(41)
<223> OTHER INFORMATION: RNA

<400> SEQUENCE: 205
gtttctattt ctgttttttg agaatctata actgatgttt t                          41

<210> SEQ ID NO 206
<211> LENGTH: 23
<212> TYPE: DNA
<213> ORGANISM: Artificial Sequence
<220> FEATURE:
<223> OTHER INFORMATION: THS for tcdC 183C>T 184C>T Primary Probe

<400> SEQUENCE: 206
aattagaaat gacctcctca tgg                                              23

<210> SEQ ID NO 207
<211> LENGTH: 23
<212> TYPE: DNA
<213> ORGANISM: Artificial Sequence
<220> FEATURE:
<223> OTHER INFORMATION: THS for tcdC 183C>T 184C>T Primary Probe

<400> SEQUENCE: 207
attagaaatg acctcctcat ggt                                              23

<210> SEQ ID NO 208
<211> LENGTH: 19
<212> TYPE: DNA
<213> ORGANISM: Artificial Sequence
<220> FEATURE:
<223> OTHER INFORMATION: THS for tcdC 183C>T 184C>T Primary Probe

<400> SEQUENCE: 208
aattagaaat gacctcctc                                                   19

<210> SEQ ID NO 209
<211> LENGTH: 18
<212> TYPE: DNA
<213> ORGANISM: Artificial Sequence
<220> FEATURE:
<223> OTHER INFORMATION: THS for tcdC 183C>T 184C>T Primary Probe

<400> SEQUENCE: 209
attagaaatg acctcctc                                                    18

<210> SEQ ID NO 210
<211> LENGTH: 23
<212> TYPE: DNA
<213> ORGANISM: Artificial Sequence
```

```
<220> FEATURE:
<223> OTHER INFORMATION: THS for tcdC 183C>T 184C>T Primary Probe

<400> SEQUENCE: 210
aattagaaat gacctcctca tgg                                              23

<210> SEQ ID NO 211
<211> LENGTH: 23
<212> TYPE: DNA
<213> ORGANISM: Artificial Sequence
<220> FEATURE:
<223> OTHER INFORMATION: THS for tcdC 183C>T 184C>T Primary Probe

<400> SEQUENCE: 211
aattagaaat gacctcctca tgg                                              23

<210> SEQ ID NO 212
<211> LENGTH: 23
<212> TYPE: DNA
<213> ORGANISM: Artificial Sequence
<220> FEATURE:
<223> OTHER INFORMATION: THS for tcdC 183C>T 184C>T Primary Probe

<400> SEQUENCE: 212
attagaaatg acctcctcat ggt                                              23

<210> SEQ ID NO 213
<211> LENGTH: 33
<212> TYPE: DNA
<213> ORGANISM: Artificial Sequence
<220> FEATURE:
<223> OTHER INFORMATION: tcdC 183C>T 184C>T Primary Probe
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (33)..(33)
<223> OTHER INFORMATION: 3'-terminal Hexanediol

<400> SEQUENCE: 213
cgcgccgagg aattagaaat gacctcctca tgg                                   33

<210> SEQ ID NO 214
<211> LENGTH: 33
<212> TYPE: DNA
<213> ORGANISM: Artificial Sequence
<220> FEATURE:
<223> OTHER INFORMATION: tcdC 183C>T 184C>T Primary Probe
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (33)..(33)
<223> OTHER INFORMATION: 3'-terminal Hexanediol

<400> SEQUENCE: 214
cgcgccgagg attagaaatg acctcctcat ggt                                   33

<210> SEQ ID NO 215
<211> LENGTH: 29
<212> TYPE: DNA
<213> ORGANISM: Artificial Sequence
<220> FEATURE:
<223> OTHER INFORMATION: tcdC 183C>T 184C>T Primary Probe
<220> FEATURE:
```

<221> NAME/KEY: misc_feature
<222> LOCATION: (1)..(10)
<223> OTHER INFORMATION: RNA
<220> FEATURE:
<221> NAME/KEY: misc_feature
<222> LOCATION: (29)..(29)
<223> OTHER INFORMATION: 3'-terminal Hexanediol

<400> SEQUENCE: 215
cgcgccgagg aattagaaat gacctcctc        29

<210> SEQ ID NO 216
<211> LENGTH: 28
<212> TYPE: DNA
<213> ORGANISM: Artificial Sequence
<220> FEATURE:
<223> OTHER INFORMATION: tcdC 183C>T 184C>T Primary Probe
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (28)..(28)
<223> OTHER INFORMATION: 3'-terminal Hexanediol

<400> SEQUENCE: 216
cgcgccgagg attagaaatg acctcctc        28

<210> SEQ ID NO 217
<211> LENGTH: 37
<212> TYPE: DNA
<213> ORGANISM: Artificial Sequence
<220> FEATURE:
<223> OTHER INFORMATION: tcdC 183C>T 184C>T Primary Probe
<220> FEATURE:
<221> NAME/KEY: misc_feature
<222> LOCATION: (1)..(14)
<223> OTHER INFORMATION: RNA
<220> FEATURE:
<221> NAME/KEY: misc_feature
<222> LOCATION: (37)..(37)
<223> OTHER INFORMATION: 3'-terminal Hexanediol

<400> SEQUENCE: 217
atgacgtggc agacaattag aaatgacctc ctcatgg        37

<210> SEQ ID NO 218
<211> LENGTH: 35
<212> TYPE: DNA
<213> ORGANISM: Artificial Sequence
<220> FEATURE:
<223> OTHER INFORMATION: tcdC 183C>T 184C>T Primary Probe
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (35)..(35)
<223> OTHER INFORMATION: 3'-terminal Hexanediol

<400> SEQUENCE: 218
acggacgcgg agaattagaa atgacctcct catgg        35

<210> SEQ ID NO 219
<211> LENGTH: 35
<212> TYPE: DNA
<213> ORGANISM: Artificial Sequence
<220> FEATURE:
<223> OTHER INFORMATION: tcdC 183C>T 184C>T Primary Probe

```
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (35)..(35)
<223> OTHER INFORMATION: 3'-terminal Hexanediol

<400> SEQUENCE: 219
acggacgcgg agattagaaa tgacctcctc atggt                               35

<210> SEQ ID NO 220
<211> LENGTH: 35
<212> TYPE: DNA
<213> ORGANISM: Artificial Sequence
<220> FEATURE:
<223> OTHER INFORMATION: tcdC 183T Forward iPrimer (+)

<400> SEQUENCE: 220
cttgttctga agaccatgag gaggtcattt ctaat                               35

<210> SEQ ID NO 221
<211> LENGTH: 42
<212> TYPE: DNA
<213> ORGANISM: Artificial Sequence
<220> FEATURE:
<223> OTHER INFORMATION: tcdC 184 Forward iPrimer (-)

<400> SEQUENCE: 221
gtttctattt ctgttttttg agaatctata actgatgttt aa                       42

<210> SEQ ID NO 222
<211> LENGTH: 30
<212> TYPE: DNA
<213> ORGANISM: Artificial Sequence
<220> FEATURE:
<223> OTHER INFORMATION: tcdC 184 Forward Primer

<400> SEQUENCE: 222
gcaatatatc ctcaccagct tgttctgaag                                     30

<210> SEQ ID NO 223
<211> LENGTH: 28
<212> TYPE: DNA
<213> ORGANISM: Artificial Sequence
<220> FEATURE:
<223> OTHER INFORMATION: tcdC 184 Invader

<400> SEQUENCE: 223
gaagaccatg aggaggtcat ttctaaca                                       28

<210> SEQ ID NO 224

<400> SEQUENCE: 224

000

<210> SEQ ID NO 225
<211> LENGTH: 41
<212> TYPE: DNA
<213> ORGANISM: Artificial Sequence
<220> FEATURE:
<223> OTHER INFORMATION: tcdC 184 Iprimer 2 (-)

<400> SEQUENCE: 225
gtttctattt ctgttttttg agaatctata actgatgttt a                        41
```

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233
<211> LENGTH: 22
<212> TYPE: DNA
<213> ORGANISM: Artificial Sequence
<220> FEATURE:
<223> OTHER INFORMATION: THS for tcdC 184C>T Primary Probe

<400> SEQUENCE: 233
agttagaaat gacctcctca tg                                              22

<210> SEQ ID NO 234
<211> LENGTH: 29
<212> TYPE: DNA
<213> ORGANISM: Artificial Sequence
<220> FEATURE:
<223> OTHER INFORMATION: THS for tcdC 184C>T Primary Probe

<400> SEQUENCE: 234
taaacatcag ttatagattc tcaaaaagc                                       29

<210> SEQ ID NO 235
<211> LENGTH: 29
<212> TYPE: DNA
<213> ORGANISM: Artificial Sequence

```
<220> FEATURE:
<223> OTHER INFORMATION: THS for tcdC 184C>T Primary Probe

<400> SEQUENCE: 235
taaacatcag ttatagattc tcaaaaagc                                         29

<210> SEQ ID NO 236
<211> LENGTH: 22
<212> TYPE: DNA
<213> ORGANISM: Artificial Sequence
<220> FEATURE:
<223> OTHER INFORMATION: THS for tcdC 184C>T Primary Probe

<400> SEQUENCE: 236
agttagaaat gacctcctca tg                                                22

<210> SEQ ID NO 237
<211> LENGTH: 22
<212> TYPE: DNA
<213> ORGANISM: Artificial Sequence
<220> FEATURE:
<223> OTHER INFORMATION: THS for tcdC 184C>T Primary Probe

<400> SEQUENCE: 237
taaacatcag ttatagattc tc                                                22

<210> SEQ ID NO 238
<211> LENGTH: 36
<212> TYPE: DNA
<213> ORGANISM: Artificial Sequence
<220> FEATURE:
<223> OTHER INFORMATION: tcdC 184C>T Primary Probe
<220> FEATURE:
<221> NAME/KEY: misc_feature
<222> LOCATION: (1)..(14)
<223> OTHER INFORMATION: RNA
<220> FEATURE:
<221> NAME/KEY: misc_feature
<222> LOCATION: (36)..(36)
<223> OTHER INFORMATION: 3'-terminal Hexanediol

<400> SEQUENCE: 238
atgacgtggc agacagttag aaatgacctc ctcatg                                 36

<210> SEQ ID NO 239
<211> LENGTH: 43
<212> TYPE: DNA
<213> ORGANISM: Artificial Sequence
<220> FEATURE:
<223> OTHER INFORMATION: tcdC 184C>T Primary Probe
<220> FEATURE:
<221> NAME/KEY: misc_feature
<222> LOCATION: (1)..(14)
<223> OTHER INFORMATION: RNA
<220> FEATURE:
<221> NAME/KEY: misc_feature
<222> LOCATION: (43)..(43)
<223> OTHER INFORMATION: 3'-terminal Hexanediol

<400> SEQUENCE: 239
atgacgtggc agactaaaca tcagttatag attctcaaaa agc                         43

<210> SEQ ID NO 240
<211> LENGTH: 41
<212> TYPE: DNA
<213> ORGANISM: Artificial Sequence
<220> FEATURE:
<223> OTHER INFORMATION: tcdC 184C>T Primary Probe
<220> FEATURE:
```

```
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (41)..(41)
<223> OTHER INFORMATION: 3'-terminal Hexanediol

<400> SEQUENCE: 240
acggacgcgg agtaaacatc agttatagat tctcaaaaag c                 41

<210> SEQ ID NO 241
<211> LENGTH: 34
<212> TYPE: DNA
<213> ORGANISM: Artificial Sequence
<220> FEATURE:
<223> OTHER INFORMATION: tcdC 184C>T Primary Probe
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (34)..(34)
<223> OTHER INFORMATION: 3'-terminal Hexanediol

<400> SEQUENCE: 241
acggacgcgg agagttagaa atgacctcct catg                         34

<210> SEQ ID NO 242
<211> LENGTH: 34
<212> TYPE: DNA
<213> ORGANISM: Artificial Sequence
<220> FEATURE:
<223> OTHER INFORMATION: tcdC 184C>T Primary Probe
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (34)..(34)
<223> OTHER INFORMATION: 3'-terminal Hexanediol

<400> SEQUENCE: 242
acggacgcgg agtaaacatc agttatagat tctc                         34

<210> SEQ ID NO 243
<211> LENGTH: 42
<212> TYPE: DNA
<213> ORGANISM: Artificial Sequence
<220> FEATURE:
<223> OTHER INFORMATION: tcdC Forward Primer

<400> SEQUENCE: 243
ggaaaaggaa gctctaagaa aataattaaa ttctttaaga gc                42

<210> SEQ ID NO 244
<211> LENGTH: 44
<212> TYPE: DNA
<213> ORGANISM: Artificial Sequence
<220> FEATURE:
<223> OTHER INFORMATION: tcdC Forward Primer

<400> SEQUENCE: 244
ggaagctcta agaaaataat taaattcttt aagagcacaa aggg              44

<210> SEQ ID NO 245
<211> LENGTH: 21
```

```
<212> TYPE: DNA
<213> ORGANISM: Artificial Sequence
<220> FEATURE:
<223> OTHER INFORMATION: tcdC Forward Primer
<220> FEATURE:
<221> NAME/KEY: misc_feature
<222> LOCATION: (6)..(6)
<223> OTHER INFORMATION: n is 5-methylated cytosine

<400> SEQUENCE: 245
ggtaangaat ttagtaatga a                                         21

<210> SEQ ID NO 246
<211> LENGTH: 21
<212> TYPE: DNA
<213> ORGANISM: Artificial Sequence
<220> FEATURE:
<223> OTHER INFORMATION: tcdC Forward Primer
<220> FEATURE:
<221> NAME/KEY: misc_feature
<222> LOCATION: (6)..(6)
<223> OTHER INFORMATION: n is 5-methylated cytosine

<400> SEQUENCE: 246
ggtaangaat ttagtaatga a                                         21

<210> SEQ ID NO 247
<211> LENGTH: 43
<212> TYPE: DNA
<213> ORGANISM: Artificial Sequence
<220> FEATURE:
<223> OTHER INFORMATION: tcdC Forward Primer

<400> SEQUENCE: 247
ggaagctcta agaaaataat taaattcttt aagagcacaa agg                  43

<210> SEQ ID NO 248
<211> LENGTH: 33
<212> TYPE: DNA
<213> ORGANISM: Artificial Sequence
<220> FEATURE:
<223> OTHER INFORMATION: tcdC Forward Primer

<400> SEQUENCE: 248
ggtaacgaat ttagtaatga aggaaaagga agc                             33

<210> SEQ ID NO 249
<211> LENGTH: 40
<212> TYPE: DNA
<213> ORGANISM: Artificial Sequence
<220> FEATURE:
<223> OTHER INFORMATION: tcdC Reverse Primer

<400> SEQUENCE: 249
gttcagcatc agacaatttg ctatttaaag tttctatttc                      40

<210> SEQ ID NO 250
<211> LENGTH: 29
<212> TYPE: DNA
<213> ORGANISM: Artificial Sequence
<220> FEATURE:
<223> OTHER INFORMATION: tcdC Reverse Primer

<400> SEQUENCE: 250
gaaccatggt tcagcatcag acaatttgc                                  29

<210> SEQ ID NO 251
```

```
<211> LENGTH: 34
<212> TYPE: DNA
<213> ORGANISM: Artificial Sequence
<220> FEATURE:
<223> OTHER INFORMATION: tcdC Reverse Primer

<400> SEQUENCE: 251
ctttcttttc gtcgtctttc attttgaacc atgg                                   34

<210> SEQ ID NO 252
<211> LENGTH: 36
<212> TYPE: DNA
<213> ORGANISM: Artificial Sequence
<220> FEATURE:
<223> OTHER INFORMATION: tcdC Reverse Primer

<400> SEQUENCE: 252
caatagcttt cttttcgtcg tctttcattt tgaacc                                 36

<210> SEQ ID NO 253
<211> LENGTH: 25
<212> TYPE: DNA
<213> ORGANISM: Artificial Sequence
<220> FEATURE:
<223> OTHER INFORMATION: tcdC Reverse Primer

<400> SEQUENCE: 253
tcataagtaa taccagtatc atatc                                             25

<210> SEQ ID NO 254
<211> LENGTH: 26
<212> TYPE: DNA
<213> ORGANISM: Artificial Sequence
<220> FEATURE:
<223> OTHER INFORMATION: tcdC Reverse Primer

<400> SEQUENCE: 254
tcataagtaa taccagtatc atatcc                                            26

<210> SEQ ID NO 255
<211> LENGTH: 30
<212> TYPE: DNA
<213> ORGANISM: Artificial Sequence
<220> FEATURE:
<223> OTHER INFORMATION: tcdC Reverse Primer

<400> SEQUENCE: 255
gtcgtctttc attttgaacc atggttcagc                                        30

<210> SEQ ID NO 256
<211> LENGTH: 42
<212> TYPE: DNA
<213> ORGANISM: Artificial Sequence
<220> FEATURE:
<223> OTHER INFORMATION: tcdC Reverse Primer

<400> SEQUENCE: 256
gtttctattt ctgttttttg agaatctata actgatgttt ga                          42

<210> SEQ ID NO 257
<211> LENGTH: 24
<212> TYPE: DNA
<213> ORGANISM: Artificial Sequence
<220> FEATURE:
<223> OTHER INFORMATION: tcdC Reverse Primer
```

```
<400> SEQUENCE: 257
cctcctcatg gtcttcagaa caag                                            24

<210> SEQ ID NO 258
<211> LENGTH: 25
<212> TYPE: DNA
<213> ORGANISM: Artificial Sequence
<220> FEATURE:
<223> OTHER INFORMATION: tcdC Reverse Primer

<400> SEQUENCE: 258
cctcctcatg gtcttcagaa caagc                                           25

<210> SEQ ID NO 259
<211> LENGTH: 26
<212> TYPE: DNA
<213> ORGANISM: Artificial Sequence
<220> FEATURE:
<223> OTHER INFORMATION: tcdC Reverse Primer

<400> SEQUENCE: 259
gacctcctca tggtcttcag aacaag                                          26

<210> SEQ ID NO 260
<211> LENGTH: 29
<212> TYPE: DNA
<213> ORGANISM: Artificial Sequence
<220> FEATURE:
<223> OTHER INFORMATION: tcdB Forward iPrimer

<400> SEQUENCE: 260
gtaagtttag gtgcagcaat caaagagct                                       29

<210> SEQ ID NO 261
<211> LENGTH: 29
<212> TYPE: DNA
<213> ORGANISM: Artificial Sequence
<220> FEATURE:
<223> OTHER INFORMATION: tcdB Forward iPrimer

<400> SEQUENCE: 261
gtaagtttag gtgcagcaat caaagagtt                                       29

<210> SEQ ID NO 262
<211> LENGTH: 39
<212> TYPE: DNA
<213> ORGANISM: Artificial Sequence
<220> FEATURE:
<223> OTHER INFORMATION: tcdB Forward iPrimer

<400> SEQUENCE: 262
ggattacctg taattgctac tattatagat ggtgtaagt                            39

<210> SEQ ID NO 263
<211> LENGTH: 38
<212> TYPE: DNA
<213> ORGANISM: Artificial Sequence
<220> FEATURE:
<223> OTHER INFORMATION: tcdB Forward iPrimer

<400> SEQUENCE: 263
gattacctgt aattgctact attatagatg gtgtaagt                             38

<210> SEQ ID NO 264
```

```
<211> LENGTH: 29
<212> TYPE: DNA
<213> ORGANISM: Artificial Sequence
<220> FEATURE:
<223> OTHER INFORMATION: tcdB Forward Primer

<400> SEQUENCE: 264
gtgtaagttt aggtgcagca atcaaagag                                29

<210> SEQ ID NO 265
<211> LENGTH: 18
<212> TYPE: DNA
<213> ORGANISM: Artificial Sequence
<220> FEATURE:
<223> OTHER INFORMATION: tcdB Forward Primer

<400> SEQUENCE: 265
ggtgcagcaa tcaaagag                                            18

<210> SEQ ID NO 266
<211> LENGTH: 31
<212> TYPE: DNA
<213> ORGANISM: Artificial Sequence
<220> FEATURE:
<223> OTHER INFORMATION: tcdB Forward Primer

<400> SEQUENCE: 266
tggtgtaagt taggtgcag caatcaaaga g                              31

<210> SEQ ID NO 267
<211> LENGTH: 34
<212> TYPE: DNA
<213> ORGANISM: Artificial Sequence
<220> FEATURE:
<223> OTHER INFORMATION: tcdB Forward Primer

<400> SEQUENCE: 267
gattggaggt caaataaatg acactgctat taat                          34

<210> SEQ ID NO 268
<211> LENGTH: 30
<212> TYPE: DNA
<213> ORGANISM: Artificial Sequence
<220> FEATURE:
<223> OTHER INFORMATION: tcdB Forward Primer

<400> SEQUENCE: 268
atagatggtg taagtttagg tgcagcaatc                               30

<210> SEQ ID NO 269
<211> LENGTH: 31
<212> TYPE: DNA
<213> ORGANISM: Artificial Sequence
<220> FEATURE:
<223> OTHER INFORMATION: tcdB Forward Primer

<400> SEQUENCE: 269
tggtgtaagt ttaggtgcat caattaaaga g                             31

<210> SEQ ID NO 270
<211> LENGTH: 25
<212> TYPE: DNA
<213> ORGANISM: Artificial Sequence
<220> FEATURE:
<223> OTHER INFORMATION: tcdB Forward Primer
```

```
<400> SEQUENCE: 270
ggtgcagcaa tcaaagagct aagtg                                          25

<210> SEQ ID NO 271
<211> LENGTH: 34
<212> TYPE: DNA
<213> ORGANISM: Artificial Sequence
<220> FEATURE:
<223> OTHER INFORMATION: tcdB Forward Primer

<400> SEQUENCE: 271
gtaagtttag gtgcatcaat taaagagttg agtg                                34

<210> SEQ ID NO 272
<211> LENGTH: 36
<212> TYPE: DNA
<213> ORGANISM: Artificial Sequence
<220> FEATURE:
<223> OTHER INFORMATION: tcdB Forward Primer

<400> SEQUENCE: 272
gtgtaagttt aggtgcatca attaaagagt tgagtg                              36

<210> SEQ ID NO 273
<211> LENGTH: 24
<212> TYPE: DNA
<213> ORGANISM: Artificial Sequence
<220> FEATURE:
<223> OTHER INFORMATION: tcdB Forward Primer

<400> SEQUENCE: 273
gtggatttag tatactttta gttc                                           24

<210> SEQ ID NO 274
<211> LENGTH: 35
<212> TYPE: DNA
<213> ORGANISM: Artificial Sequence
<220> FEATURE:
<223> OTHER INFORMATION: tcdB Forward Primer

<400> SEQUENCE: 274
gtattaccta atgctccaaa tagagtattt gcttg                               35

<210> SEQ ID NO 275
<211> LENGTH: 29
<212> TYPE: DNA
<213> ORGANISM: Artificial Sequence
<220> FEATURE:
<223> OTHER INFORMATION: tcdB Forward Primer

<400> SEQUENCE: 275
cctaatgccc cagatagagt atttggctg                                      29

<210> SEQ ID NO 276
<211> LENGTH: 23
<212> TYPE: DNA
<213> ORGANISM: Artificial Sequence
<220> FEATURE:
<223> OTHER INFORMATION: tcdB Forward Primer

<400> SEQUENCE: 276
gccccagata gaatctttgg ctg                                            23
```

<210> SEQ ID NO 277
<211> LENGTH: 28
<212> TYPE: DNA
<213> ORGANISM: Artificial Sequence
<220> FEATURE:
<223> OTHER INFORMATION: tcdB Forward Primer

<400> SEQUENCE: 277
ctaatgcccc agatagaatc tttggctg                                      28

<210> SEQ ID NO 278
<211> LENGTH: 24
<212> TYPE: DNA
<213> ORGANISM: Artificial Sequence
<220> FEATURE:
<223> OTHER INFORMATION: tcdB Forward Primer

<400> SEQUENCE: 278
cttgatttgt caaaagattt aatg                                          24

<210> SEQ ID NO 279
<211> LENGTH: 24
<212> TYPE: DNA
<213> ORGANISM: Artificial Sequence
<220> FEATURE:
<223> OTHER INFORMATION: tcdB Forward Primer
<220> FEATURE:
<221> NAME/KEY: misc_feature
<222> LOCATION: (1)..(1)
<223> OTHER INFORMATION: n is 5-methylated cytosine
<220> FEATURE:
<221> NAME/KEY: misc_feature
<222> LOCATION: (11)..(11)
<223> OTHER INFORMATION: n is 5-methylated cytosine

<400> SEQUENCE: 279
nttgatttat naaaagattt aatg                                          24

<210> SEQ ID NO 280
<211> LENGTH: 35
<212> TYPE: DNA
<213> ORGANISM: Artificial Sequence
<220> FEATURE:
<223> OTHER INFORMATION: tcdB Invader

<400> SEQUENCE: 280
tttactgcca ttatacctat cttagcttct attta                              35

<210> SEQ ID NO 281
<211> LENGTH: 22
<212> TYPE: DNA
<213> ORGANISM: Artificial Sequence
<220> FEATURE:
<223> OTHER INFORMATION: THS for tcdB Primary Probe

<400> SEQUENCE: 281
cttgtcttaa taatgggtca ct                                            22

<210> SEQ ID NO 282
<211> LENGTH: 35
<212> TYPE: DNA
<213> ORGANISM: Artificial Sequence
<220> FEATURE:
<223> OTHER INFORMATION: THS for tcdB Primary Probe

```
<400> SEQUENCE: 282
taattatata aatcaatgga aagatgtaaa tagtg                              35

<210> SEQ ID NO 283
<211> LENGTH: 17
<212> TYPE: DNA
<213> ORGANISM: Artificial Sequence
<220> FEATURE:
<223> OTHER INFORMATION: THS for tcdB Primary Probe

<400> SEQUENCE: 283
gggaaagagg atggacg                                                 17

<210> SEQ ID NO 284
<211> LENGTH: 18
<212> TYPE: DNA
<213> ORGANISM: Artificial Sequence
<220> FEATURE:
<223> OTHER INFORMATION: THS for tcdB Primary Probe

<400> SEQUENCE: 284
gggaaagagg atggacgc                                                18

<210> SEQ ID NO 285
<211> LENGTH: 16
<212> TYPE: DNA
<213> ORGANISM: Artificial Sequence
<220> FEATURE:
<223> OTHER INFORMATION: THS for tcdB Primary Probe

<400> SEQUENCE: 285
gggaaagagg atggac                                                  16

<210> SEQ ID NO 286
<211> LENGTH: 21
<212> TYPE: DNA
<213> ORGANISM: Artificial Sequence
<220> FEATURE:
<223> OTHER INFORMATION: THS for tcdB Primary Probe

<400> SEQUENCE: 286
gggaaagagg atggacgcca g                                            21

<210> SEQ ID NO 287
<211> LENGTH: 19
<212> TYPE: DNA
<213> ORGANISM: Artificial Sequence
<220> FEATURE:
<223> OTHER INFORMATION: THS for tcdB Primary Probe

<400> SEQUENCE: 287
gggaaacagg atggacacc                                               19

<210> SEQ ID NO 288
<211> LENGTH: 19
<212> TYPE: DNA
<213> ORGANISM: Artificial Sequence
<220> FEATURE:
<223> OTHER INFORMATION: THS for tcdB Primary Probe

<400> SEQUENCE: 288
gggaaagagg atggacgcc                                               19

<210> SEQ ID NO 289
```

```
<211> LENGTH: 38
<212> TYPE: DNA
<213> ORGANISM: Artificial Sequence
<220> FEATURE:
<223> OTHER INFORMATION: THS for tcdB Primary Probe

<400> SEQUENCE: 289
attatagtca ctatttacat ctttccattg atttatat                            38

<210> SEQ ID NO 290
<211> LENGTH: 25
<212> TYPE: DNA
<213> ORGANISM: Artificial Sequence
<220> FEATURE:
<223> OTHER INFORMATION: THS for tcdB Primary Probe

<400> SEQUENCE: 290
caaagagcta agtgaaacca gtgac                                          25

<210> SEQ ID NO 291
<211> LENGTH: 26
<212> TYPE: DNA
<213> ORGANISM: Artificial Sequence
<220> FEATURE:
<223> OTHER INFORMATION: THS for tcdB Primary Probe

<400> SEQUENCE: 291
caaagagcta agtgaaacca gtgacc                                         26

<210> SEQ ID NO 292
<211> LENGTH: 27
<212> TYPE: DNA
<213> ORGANISM: Artificial Sequence
<220> FEATURE:
<223> OTHER INFORMATION: THS for tcdB Primary Probe

<400> SEQUENCE: 292
caaagagcta agtgaaacca gtgaccc                                        27

<210> SEQ ID NO 293
<211> LENGTH: 30
<212> TYPE: DNA
<213> ORGANISM: Artificial Sequence
<220> FEATURE:
<223> OTHER INFORMATION: THS for tcdB Primary Probe

<400> SEQUENCE: 293
taagtgaaac cagtgaccca ttattaagac                                     30

<210> SEQ ID NO 294
<211> LENGTH: 22
<212> TYPE: DNA
<213> ORGANISM: Artificial Sequence
<220> FEATURE:
<223> OTHER INFORMATION: THS for tcdB Primary Probe

<400> SEQUENCE: 294
cttgtcttaa taatgggtca ct                                             22

<210> SEQ ID NO 295
<211> LENGTH: 30
<212> TYPE: DNA
<213> ORGANISM: Artificial Sequence
<220> FEATURE:
<223> OTHER INFORMATION: THS for tcdB Primary Probe
```

-continued

```
<400> SEQUENCE: 295
tgagtgaaac cagtgaccca ttattaagac                                    30

<210> SEQ ID NO 296
<211> LENGTH: 25
<212> TYPE: DNA
<213> ORGANISM: Artificial Sequence
<220> FEATURE:
<223> OTHER INFORMATION: THS for tcdB Primary Probe

<400> SEQUENCE: 296
tttaggtgca tcaattaaag agttg                                         25

<210> SEQ ID NO 297
<211> LENGTH: 25
<212> TYPE: DNA
<213> ORGANISM: Artificial Sequence
<220> FEATURE:
<223> OTHER INFORMATION: THS for tcdB Primary Probe

<400> SEQUENCE: 297
tttaggtgca gcaattaaag agtta                                         25

<210> SEQ ID NO 298
<211> LENGTH: 22
<212> TYPE: DNA
<213> ORGANISM: Artificial Sequence
<220> FEATURE:
<223> OTHER INFORMATION: THS for tcdB Primary Probe
<220> FEATURE:
<221> NAME/KEY: misc_feature
<222> LOCATION: (6)..(6)
<223> OTHER INFORMATION: n is 5-methylated cytosine
<220> FEATURE:
<221> NAME/KEY: misc_feature
<222> LOCATION: (19)..(19)
<223> OTHER INFORMATION: n is 5-methylated cytosine
<220> FEATURE:
<221> NAME/KEY: misc_feature
<222> LOCATION: (21)..(21)
<223> OTHER INFORMATION: n is 5-methylated cytosine

<400> SEQUENCE: 298
cttgtnttaa taatgggtna nt                                            22

<210> SEQ ID NO 299
<211> LENGTH: 32
<212> TYPE: DNA
<213> ORGANISM: Artificial Sequence
<220> FEATURE:
<223> OTHER INFORMATION: tcdB Primary Probe
<220> FEATURE:
<221> NAME/KEY: misc_feature
<222> LOCATION: (1)..(10)
<223> OTHER INFORMATION: RNA
<220> FEATURE:
<221> NAME/KEY: misc_feature
<222> LOCATION: (32)..(32)
<223> OTHER INFORMATION: 3'-terminal Hexanediol

<400> SEQUENCE: 299
cgcgccgagg cttgtcttaa taatgggtca ct                                 32

<210> SEQ ID NO 300
<211> LENGTH: 47
<212> TYPE: DNA
<213> ORGANISM: Artificial Sequence
<220> FEATURE:
```

```
<223> OTHER INFORMATION: tcdB Primary Probe
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (47)..(47)
<223> OTHER INFORMATION: 3'-terminal Hexanediol

<400> SEQUENCE: 300
acggacgcgg agtaattata taaatcaatg gaaagatgta aatagtg                47

<210> SEQ ID NO 301
<211> LENGTH: 29
<212> TYPE: DNA
<213> ORGANISM: Artificial Sequence
<220> FEATURE:
<223> OTHER INFORMATION: tcdB Primary Probe
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (29)..(29)
<223> OTHER INFORMATION: 3'-terminal Hexanediol

<400> SEQUENCE: 301
acggacgcgg aggggaaaga ggatggacg                                    29

<210> SEQ ID NO 302
<211> LENGTH: 30
<212> TYPE: DNA
<213> ORGANISM: Artificial Sequence
<220> FEATURE:
<223> OTHER INFORMATION: tcdB Primary Probe
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (30)..(30)
<223> OTHER INFORMATION: 3'-terminal Hexanediol

<400> SEQUENCE: 302
acggacgcgg aggggaaaga ggatggacgc                                   30

<210> SEQ ID NO 303
<211> LENGTH: 28
<212> TYPE: DNA
<213> ORGANISM: Artificial Sequence
<220> FEATURE:
<223> OTHER INFORMATION: tcdB Primary Probe
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (28)..(28)
<223> OTHER INFORMATION: 3'-terminal Hexanediol

<400> SEQUENCE: 303
acggacgcgg aggggaaaga ggatggac                                     28

<210> SEQ ID NO 304
<211> LENGTH: 33
<212> TYPE: DNA
<213> ORGANISM: Artificial Sequence
```

```
<220> FEATURE:
<223> OTHER INFORMATION: tcdB Primary Probe
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (33)..(33)
<223> OTHER INFORMATION: 3'-terminal Hexanediol

<400> SEQUENCE: 304
acggacgcgg aggggaaaga ggatggacgc cag                                    33

<210> SEQ ID NO 305
<211> LENGTH: 31
<212> TYPE: DNA
<213> ORGANISM: Artificial Sequence
<220> FEATURE:
<223> OTHER INFORMATION: tcdB Primary Probe
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (31)..(31)
<223> OTHER INFORMATION: 3'-terminal Hexanediol

<400> SEQUENCE: 305
acggacgcgg aggggaaaca ggatggacac c                                      31

<210> SEQ ID NO 306
<211> LENGTH: 31
<212> TYPE: DNA
<213> ORGANISM: Artificial Sequence
<220> FEATURE:
<223> OTHER INFORMATION: tcdB Primary Probe
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (31)..(31)
<223> OTHER INFORMATION: 3'-terminal Hexanediol

<400> SEQUENCE: 306
acggacgcgg aggggaaaga ggatggacgc c                                      31

<210> SEQ ID NO 307
<211> LENGTH: 50
<212> TYPE: DNA
<213> ORGANISM: Artificial Sequence
<220> FEATURE:
<223> OTHER INFORMATION: tcdB Primary Probe
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (50)..(50)
<223> OTHER INFORMATION: 3'-terminal Hexanediol

<400> SEQUENCE: 307
acggacgcgg agattatagt cactatttac atctttccat tgatttatat                  50

<210> SEQ ID NO 308
<211> LENGTH: 37
<212> TYPE: DNA
```

```
<213> ORGANISM: Artificial Sequence
<220> FEATURE:
<223> OTHER INFORMATION: tcdB Primary Probe
<220> FEATURE:
<221> NAME/KEY: misc_feature
<222> LOCATION: (37)..(37)
<223> OTHER INFORMATION: 3'-terminal Hexanediol

<400> SEQUENCE: 308
acggacgcgg agcaaagagc taagtgaaac cagtgac                              37

<210> SEQ ID NO 309
<211> LENGTH: 38
<212> TYPE: DNA
<213> ORGANISM: Artificial Sequence
<220> FEATURE:
<223> OTHER INFORMATION: tcdB Primary Probe
<220> FEATURE:
<221> NAME/KEY: misc_feature
<222> LOCATION: (38)..(38)
<223> OTHER INFORMATION: 3'-terminal Hexanediol

<400> SEQUENCE: 309
acggacgcgg agcaaagagc taagtgaaac cagtgacc                             38

<210> SEQ ID NO 310
<211> LENGTH: 39
<212> TYPE: DNA
<213> ORGANISM: Artificial Sequence
<220> FEATURE:
<223> OTHER INFORMATION: tcdB Primary Probe
<220> FEATURE:
<221> NAME/KEY: misc_feature
<222> LOCATION: (39)..(39)
<223> OTHER INFORMATION: 3'-terminal Hexanediol

<400> SEQUENCE: 310
acggacgcgg agcaaagagc taagtgaaac cagtgaccc                            39

<210> SEQ ID NO 311
<211> LENGTH: 42
<212> TYPE: DNA
<213> ORGANISM: Artificial Sequence
<220> FEATURE:
<223> OTHER INFORMATION: tcdB Primary Probe
<220> FEATURE:
<221> NAME/KEY: misc_feature
<222> LOCATION: (42)..(42)
<223> OTHER INFORMATION: 3'-terminal Hexanediol

<400> SEQUENCE: 311
acggacgcgg agtaagtgaa accagtgacc cattattaag ac                        42

<210> SEQ ID NO 312
<211> LENGTH: 34
<212> TYPE: DNA
<213> ORGANISM: Artificial Sequence
<220> FEATURE:
<223> OTHER INFORMATION: tcdB Primary Probe
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (34)..(34)
<223> OTHER INFORMATION: 3'-terminal Hexanediol

<400> SEQUENCE: 312
acggacgcgg agcttgtctt aataatgggt cact                                 34
```

<210> SEQ ID NO 313
<211> LENGTH: 42
<212> TYPE: DNA
<213> ORGANISM: Artificial Sequence
<220> FEATURE:
<223> OTHER INFORMATION: tcdB Primary Probe
<220> FEATURE:
<221> NAME/KEY: misc_feature
<222> LOCATION: (42)..(42)
<223> OTHER INFORMATION: 3'-terminal Hexanediol

<400> SEQUENCE: 313
acggacgcgg agtgagtgaa accagtgacc cattattaag ac          42

<210> SEQ ID NO 314
<211> LENGTH: 37
<212> TYPE: DNA
<213> ORGANISM: Artificial Sequence
<220> FEATURE:
<223> OTHER INFORMATION: tcdB Primary Probe
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (37)..(37)
<223> OTHER INFORMATION: 3'-terminal Hexanediol

<400> SEQUENCE: 314
acggacgcgg agtttaggtg catcaattaa agagttg          37

<210> SEQ ID NO 315
<211> LENGTH: 37
<212> TYPE: DNA
<213> ORGANISM: Artificial Sequence
<220> FEATURE:
<223> OTHER INFORMATION: tcdB Primary Probe
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (37)..(37)
<223> OTHER INFORMATION: 3'-terminal Hexanediol

<400> SEQUENCE: 315
acggacgcgg agtttaggtg cagcaattaa agagtta          37

<210> SEQ ID NO 316
<211> LENGTH: 34
<212> TYPE: DNA
<213> ORGANISM: Artificial Sequence
<220> FEATURE:
<223> OTHER INFORMATION: tcdB Primary Probe
<220> FEATURE:
<221> NAME/KEY: misc_feature
<222> LOCATION: (1)..(12)
<223> OTHER INFORMATION: RNA
<220> FEATURE:
<221> NAME/KEY: misc_feature
<222> LOCATION: (18)..(18)
<223> OTHER INFORMATION: n is 5-methylated cytosine
<220> FEATURE:
<221> NAME/KEY: misc_feature
<222> LOCATION: (31)..(31)
<223> OTHER INFORMATION: n is 5-methylated cytosine
<220> FEATURE:
<221> NAME/KEY: misc_feature
<222> LOCATION: (33)..(33)

```
<223> OTHER INFORMATION: n is 5-methylated cytosine
<220> FEATURE:
<221> NAME/KEY: misc_feature
<222> LOCATION: (34)..(34)
<223> OTHER INFORMATION: 3'-terminal Hexanediol

<400> SEQUENCE: 316
acggacgcgg agcttgtntt aataatgggt nant                                34

<210> SEQ ID NO 317
<211> LENGTH: 35
<212> TYPE: DNA
<213> ORGANISM: Artificial Sequence
<220> FEATURE:
<223> OTHER INFORMATION: tcdB Reverse iPrimer

<400> SEQUENCE: 317
tttactgcca ttatacctat cttagcttct atttc                               35

<210> SEQ ID NO 318
<211> LENGTH: 36
<212> TYPE: DNA
<213> ORGANISM: Artificial Sequence
<220> FEATURE:
<223> OTHER INFORMATION: tcdB Reverse Primer

<400> SEQUENCE: 318
ctgccattat acctatctta gcttctattt cttgtc                              36

<210> SEQ ID NO 319
<211> LENGTH: 34
<212> TYPE: DNA
<213> ORGANISM: Artificial Sequence
<220> FEATURE:
<223> OTHER INFORMATION: tcdB Reverse Primer

<400> SEQUENCE: 319
ctgccattat acctatctta gcttctattt cttg                                34

<210> SEQ ID NO 320
<211> LENGTH: 34
<212> TYPE: DNA
<213> ORGANISM: Artificial Sequence
<220> FEATURE:
<223> OTHER INFORMATION: tcdB Reverse Primer

<400> SEQUENCE: 320
ctgccattat acctattttt gcttctattt cttg                                34

<210> SEQ ID NO 321
<211> LENGTH: 29
<212> TYPE: DNA
<213> ORGANISM: Artificial Sequence
<220> FEATURE:
<223> OTHER INFORMATION: tcdB Forward Primer

<400> SEQUENCE: 321
gtaagtttag gtgcatcaat taaagagtt                                      29

<210> SEQ ID NO 322
<211> LENGTH: 28
<212> TYPE: DNA
<213> ORGANISM: Artificial Sequence
<220> FEATURE:
<223> OTHER INFORMATION: tcdB Reverse Primer
```

```
<400> SEQUENCE: 322
gaactaaaag tatactaaat ccactagc                                          28

<210> SEQ ID NO 323
<211> LENGTH: 47
<212> TYPE: DNA
<213> ORGANISM: Artificial Sequence
<220> FEATURE:
<223> OTHER INFORMATION: tcdB Reverse iPrimer

<400> SEQUENCE: 323
tcaatgtgtt tatcaaaaat gcattactat cataaaaaac attaaca                     47

<210> SEQ ID NO 324
<211> LENGTH: 35
<212> TYPE: DNA
<213> ORGANISM: Artificial Sequence
<220> FEATURE:
<223> OTHER INFORMATION: tcdB Reverse iPrimer

<400> SEQUENCE: 324
tttactgcca ttatacctat ttttgcttct atttc                                  35

<210> SEQ ID NO 325
<211> LENGTH: 35
<212> TYPE: DNA
<213> ORGANISM: Artificial Sequence
<220> FEATURE:
<223> OTHER INFORMATION: tcdB Reverse iPrimer

<400> SEQUENCE: 325
tttactgcca ttatacctat tttggcttct atttc                                  35

<210> SEQ ID NO 326
<211> LENGTH: 36
<212> TYPE: DNA
<213> ORGANISM: Artificial Sequence
<220> FEATURE:
<223> OTHER INFORMATION: tcdB Reverse iPrimer

<400> SEQUENCE: 326
gtttactgcc attataccta ttttggcttc tatttc                                 36

<210> SEQ ID NO 327
<211> LENGTH: 47
<212> TYPE: DNA
<213> ORGANISM: Artificial Sequence
<220> FEATURE:
<223> OTHER INFORMATION: tcdB Reverse Primer

<400> SEQUENCE: 327
caatgtgttt atcaaaaatg cattactatc ataaaaaaca ttaacat                     47

<210> SEQ ID NO 328
<211> LENGTH: 36
<212> TYPE: DNA
<213> ORGANISM: Artificial Sequence
<220> FEATURE:
<223> OTHER INFORMATION: tcdB Reverse Primer

<400> SEQUENCE: 328
ctatttcttg tcttaataat gggtcacttg tttcac                                 36

<210> SEQ ID NO 329
```

```
<211> LENGTH: 30
<212> TYPE: DNA
<213> ORGANISM: Artificial Sequence
<220> FEATURE:
<223> OTHER INFORMATION: tcdB Reverse Primer

<400> SEQUENCE: 329
cttgtcttaa taatgggtca cttgtttcac                                        30

<210> SEQ ID NO 330
<211> LENGTH: 36
<212> TYPE: DNA
<213> ORGANISM: Artificial Sequence
<220> FEATURE:
<223> OTHER INFORMATION: tcdB Reverse Primer

<400> SEQUENCE: 330
ctatttcttg tcttaataat gggtcactag tttcac                                 36

<210> SEQ ID NO 331
<211> LENGTH: 30
<212> TYPE: DNA
<213> ORGANISM: Artificial Sequence
<220> FEATURE:
<223> OTHER INFORMATION: tcdB Reverse Primer

<400> SEQUENCE: 331
cttgtcttaa taatgggtca ctagtttcac                                        30

<210> SEQ ID NO 332
<211> LENGTH: 44
<212> TYPE: DNA
<213> ORGANISM: Artificial Sequence
<220> FEATURE:
<223> OTHER INFORMATION: tcdB Reverse Primer

<400> SEQUENCE: 332
cctgctgaaa ttcctgctaa aggaactaaa agtatactaa atcc                        44

<210> SEQ ID NO 333
<211> LENGTH: 43
<212> TYPE: DNA
<213> ORGANISM: Artificial Sequence
<220> FEATURE:
<223> OTHER INFORMATION: tcdB Reverse Primer

<400> SEQUENCE: 333
cctgctgaaa ttcctgctaa aggaactaaa agtatactaa atc                         43

<210> SEQ ID NO 334
<211> LENGTH: 38
<212> TYPE: DNA
<213> ORGANISM: Artificial Sequence
<220> FEATURE:
<223> OTHER INFORMATION: tcdB Reverse Primer

<400> SEQUENCE: 334
acctgctgaa attcctgcta aaggaactaa aagtatac                               38

<210> SEQ ID NO 335
<211> LENGTH: 35
<212> TYPE: DNA
<213> ORGANISM: Artificial Sequence
<220> FEATURE:
<223> OTHER INFORMATION: tcdB Reverse Primer
```

```
<400> SEQUENCE: 335
agttttgtac catcattttc taagcttctt aaacc                              35

<210> SEQ ID NO 336
<211> LENGTH: 36
<212> TYPE: DNA
<213> ORGANISM: Artificial Sequence
<220> FEATURE:
<223> OTHER INFORMATION: tcdB Reverse Primer

<400> SEQUENCE: 336
cagttttgtg ccatcatttt ctaagcttct taaacc                             36

<210> SEQ ID NO 337
<211> LENGTH: 19
<212> TYPE: DNA
<213> ORGANISM: Artificial Sequence
<220> FEATURE:
<223> OTHER INFORMATION: tcdB Reverse Primer

<400> SEQUENCE: 337
ctcttatacg gtctaacag                                                19

<210> SEQ ID NO 338
<211> LENGTH: 19
<212> TYPE: DNA
<213> ORGANISM: Artificial Sequence
<220> FEATURE:
<223> OTHER INFORMATION: tcdB Reverse Primer
<220> FEATURE:
<221> NAME/KEY: misc_feature
<222> LOCATION: (1)..(1)
<223> OTHER INFORMATION: n is 5-methylated cytosine
<220> FEATURE:
<221> NAME/KEY: misc_feature
<222> LOCATION: (9)..(9)
<223> OTHER INFORMATION: n is 5-methylated cytosine

<400> SEQUENCE: 338
ntcttatang gtctaatag                                                19

<210> SEQ ID NO 339
<211> LENGTH: 33
<212> TYPE: DNA
<213> ORGANISM: Artificial Sequence
<220> FEATURE:
<223> OTHER INFORMATION: tcdB Forward Primer

<400> SEQUENCE: 339
tggattggag gtcaaataaa tgatactgct att                                33
```

COMPOSITIONS AND METHODS FOR DETECTING TOXIGENIC *CLOSTRIDIUM DIFFICILE*

CROSS-REFERENCE TO RELATED APPLICATION

This application is a national stage entry under 35 U.S.C. § 371 of International Patent Application No. PCT/US2018/065470, filed Dec. 13, 2018, which claims the benefit under 35 U.S.C. § 119(e) of U.S. Provisional Application No. 62/599,494, filed Dec. 15, 2017, the contents of which are hereby incorporated by reference herein.

SEQUENCE LISTING

The present application is filed with a Sequence Listing in electronic format. The Sequence Listing is provided as a file entitled "2020-06-01 01159-0015-00US_Seq_List_ST25.txt" created on Jun. 1, 2020, which is 116,855 bytes in size. The information in the electronic format of the sequence listing is incorporated herein by reference in its entirety.

INTRODUCTION AND SUMMARY

The embodiments herein are directed to the field of detecting infectious agents, more specifically by using compositions and methods to detect toxigenic *Costridium difficile* nucleic acids. *Costridium difficile* as used herein is synonymous with *Clostridioides difficile*.

*C. difficile* is a gram-positive bacterium responsible for gastrointestinal infections, diarrhea including antibiotic-associated diarrhea, and pseudomembranous colitis. *C. difficile* can also colonize individuals asymptomatically. It can undergo sporulation to form spores that are resistant to many conditions that would kill vegetative bacteria, including heat, antibiotic exposure, and more. As such, spores in a patient's gastrointestinal tract (which may or may not have been associated with symptomatic infection as opposed to asymptomatic colonization) can survive antibiotic treatment and then germinate to cause a subsequent illness. The difficulty of inactivating *C. difficile* spores, which are excreted in feces and also naturally occurring in soil, means that some decontamination procedures such as antiseptic solutions and ultraviolet treatment may not be effective, and thus contamination following fecal or soil exposure can persist and serve to spread infections.

*C. difficile* strains can produce various toxins that contribute to diarrhea and other symptoms. These include toxin A and toxin B, encoded by the tcdA and tcdB genes, respectively, and found in the Pathogenic Locus, and the binary toxin, which has two subunits encoded by the cdtA and cdtB genes in the Cdt locus. Not all toxin genes occur in all strains. Non-toxinogenic strains do not express the toxins and have been suggested based on animal data to confer a protective effect, perhaps by competing with pathogenic strains for colonization in the gastrointestinal tract. Toxins A and B were characterized earlier than the binary toxin and were historically considered necessary for pathogenicity, although pathogenicity has recently been reported in a strain designated RA09-70, which is negative for Toxin B. See Monot et al., Sci Rep. 2015; 5: 15023, available in PubMed Central as PMCID: PMC4597214.

Furthermore, certain mutations in the tcdC gene, which encodes a regulator of tcdA and tcdB expression, can result in increased levels of toxins A and B and a hypervirulent phenotype. Some relatively recent reports have indicated that the binary toxin can in some cases suffice to cause colitis in the absence of toxins A and B. Presence of both the Cdt locus and the Pathogenic Locus has also been linked to more serious disease.

Rapid and reliable identification of toxigenic *C. difficile*, including hypervirulent *C. difficile* in particular, is important for facilitating appropriate responses to both treat infected subjects and contain and limit spread of the bacterial infection, including antibiotic therapy and other infection control measures such as rigorous disinfection and hygienic precautions. Thus, compositions and methods for rapid and reliable nucleic acid-based detection of toxigenic *C. difficile* are desirable.

Nucleic acid-based detection of *C. difficile* is, however, complicated by several factors. As noted above, non-toxinogenic strains are not thought to cause disease and may be protective, so nucleic-acid based approaches logically focus on the toxin-coding genes and tcdC, the genotype of which can contribute to hypervirulence. Because other *Clostridium* species (e.g., *C. soldelli*) can carry related toxin genes, cross-reactivity with sequences from other *Clostridium* species can be an issue. Furthermore, a number of different alleles of the genes present in the PaLoc and CdtLoc exist in different *C. difficile* strains, which can further complicate their detection. For example, sequence variants of tcdB can result in false negatives if they fail to hybridize sufficiently with amplification or detection oligomers. As a further example, at least four tcdC variants at position 117 have been described, only one of which results in hypervirulence. Efforts have been made to specifically detect alleles of tcdC associated with hypervirulence, but these may be subject to erroneous results. For example, 117T tcdC alleles do not promote hypervirulence but in some assays may give rise to a false positive signal indicating hypervirulence. Additionally, some assays do not detect the two tcdC alleles that are associated with hypervirulence, 117del and 184T, making the assays prone to false negative results.

Accordingly, there is a need for compositions and methods that can provide rapid and sensitive amplification of various alleles of the *C. difficile* toxin and toxin-related target sequences, which can be used for accurate identification of toxigenic *C. difficile* despite its intraspecific heterogeneity, and which can discriminate alleles that are associated with hypervirulence from those that are not, thereby assisting in the identification of hypervirulent and non-hypervirulent strains. In various embodiments, this disclosure aims to meet these needs, provide other benefits, or at least provide the public with a useful choice.

Provided herein are the following embodiments. Embodiment 1 is a composition or kit comprising forward and reverse tcdC amplification oligomers and further comprising one or both of a first and a second tcdC detection oligomer, wherein: the first tcdC detection oligomer, if present, is configured to specifically hybridize to a first tcdC sequence at a site comprising position 117 thereof but exhibits distinguishably different hybridization to a second tcdC sequence, wherein the first tcdC sequence is the sequence of SEQ ID NO: 3 and the second tcdC sequence is the sequence of SEQ ID NO: 4; the second tcdC detection oligomer, if present, is configured to specifically hybridize to the sequence of a third tcdC sequence at a site comprising position 184 thereof but exhibits distinguishably different hybridization to the sequence of a fourth tcdC sequence, wherein the third tcdC sequence is the sequence of SEQ ID NO: 5 and the fourth tcdC sequence is the sequence of SEQ ID NO: 2; and the forward and reverse tcdC amplification oligomers are configured to produce a tcdC amplicon, wherein the tcdC amplicon comprises position 117 of SEQ ID NO: 3 or SEQ ID NO: 4 if the first tcdC detection oligomer is present and/or position 184 of SEQ ID NO: 5 if the second tcdC detection oligomer is present.

Embodiment 2 is a composition comprising forward and reverse tcdC amplification oligomers, one or both of a first tcdC detection oligomer and a second tcdC detection oligomer, forward and reverse tcdA amplification oligomers, and at least one tcdA detection oligomer, wherein: the first tcdC detection oligomer, if present, is configured to specifically hybridize to a first tcdC sequence, which is the sequence of SEQ ID NO: 3, at a site comprising position 117 thereof; the second tcdC detection oligomer, if present, is configured to specifically hybridize to a third tcdC sequence, which is the sequence of SEQ ID NO: 5, at a site comprising position 184 thereof; the forward and reverse tcdC amplification oligomers are configured to produce a tcdC amplicon, wherein the tcdC amplicon comprises position 117 of SEQ ID NO: 3 if the first tcdC detection oligomer is present and/or position 184 of SEQ ID NO: 5 if the second tcdC detection oligomer is present, the forward and reverse tcdA amplification oligomers are configured to produce a tcdA amplicon having a size of from 80 to 400 nucleotides; and the tcdA detection oligomer is configured to specifically hybridize to the tcdA amplicon.

Embodiment 3 is a method of detecting a *C. difficile* tcdC allele, the *C. difficile* tcdC allele comprising a 117del mutation or a 184T mutation, the method comprising: preparing a composition according to embodiment 1 or 2 which further comprises a sample comprising or suspected of comprising *C. difficile* nucleic acid; subjecting the composition to amplification conditions; and detecting the presence of the *C. difficile* 117del tcdC allele or 184T tcdC allele in the sample by determining whether at least one of the first tcdC detection oligomer or the second tcdC detection oligomer hybridized to a tcdC amplicon.

Embodiment 4 is a composition or kit comprising either or both of (i) a first tcdC detection oligomer and a first tcdC primary probe oligomer, and (ii) a second tcdC detection oligomer and a second tcdC primary probe oligomer, wherein: the at least one first tcdC detection oligomer, if present, is an invader oligomer configured to specifically hybridize to a first tcdC sequence at a site comprising position 117 thereof but exhibits distinguishably different hybridization to a second tcdC sequence, wherein the first tcdC sequence is the sequence of SEQ ID NO: 3 and the second tcdC sequence is the sequence of SEQ ID NO: 4; the first tcdC primary probe oligomer, if present, is configured to form an invasive cleavage substrate with the first tcdC detection oligomer in the presence of the first tcdC sequence; the second tcdC detection oligomer, if present, is an invader oligomer configured to specifically hybridize to the sequence of a third tcdC sequence at a site comprising position 184 thereof, but exhibits distinguishably different hybridization to the sequence of a fourth tcdC sequence, wherein the third tcdC sequence is the sequence of SEQ ID NO: 5 and the fourth tcdC sequence is the sequence of SEQ ID NO: 2; and the second tcdC primary probe oligomer, if present, is configured to form an invasive cleavage substrate with the second tcdC detection oligomer in the presence of the third tcdC sequence.

Embodiment 5 is a method of detecting a *C. difficile* tcdC allele, the *C. difficile* tcdC allele comprising a 117del mutation or a 184T mutation, the method comprising: preparing a composition according to embodiment 4 which further comprises a sample comprising or suspected of comprising *C. difficile* nucleic acid; subjecting the composition to invasive cleavage reaction conditions; and detecting the presence of the mutant *C. difficile* tcdC sequence in the sample by determining whether at least one of the first tcdC primary probe or the second tcdC primary probe underwent cleavage.

Embodiment 6 is the method of any one of embodiments 3 or 5, wherein the *C. difficile* tcdC allele comprises at least one of a 117del mutation and a 184T mutation.

Embodiment 7 is the method of anyone of embodiments 3, 5, or 6, wherein the method is configured to generate a positive signal in the presence of 117del mutant tcdC.

Embodiment 8 is the method of any one of embodiments 3 or 5-7, wherein the method is configured not to generate a positive signal in the presence of 117T tcdC.

Embodiment 9 is the method of any one of embodiments 3 or 5-8, wherein the method is configured not to generate a positive signal in the presence of 117D tcdC.

Embodiment 10 is the composition, kit, or method of any one of the preceding embodiments, wherein the first tcdC detection oligomer is present.

Embodiment 11 is the composition, kit, or method of embodiment 10, wherein the first tcdC detection oligomer competes for hybridization to a tcdC nucleic acid under stringent conditions with an oligomer having a sequence consisting of SEQ ID NO: 86-92, 183, 192, or 193.

Embodiment 12 is the composition, kit, or method of embodiment 10 or 11, wherein the first tcdC detection oligomer comprises the sequence of any one of SEQ ID NOs: 87-92, with up to two mismatches.

Embodiment 13 is the composition, kit, or method of embodiment 12, wherein the first tcdC detection oligomer comprises the sequence of SEQ ID NO: 88, with up to two mismatches.

Embodiment 14 is the composition, kit, or method of embodiment 10 or 11, wherein the first tcdC detection oligomer comprises the sequence of SEQ ID NO: 192 or 193, with up to two mismatches.

Embodiment 15 is the composition, kit, or method of embodiment 10 or 11, wherein the first tcdC detection oligomer comprises the sequence of SEQ ID NO: 86 with up to two mismatches.

Embodiment 16 is the composition, kit, or method of embodiment 10 or 11, wherein the first tcdC detection oligomer comprises the sequence of SEQ ID NO: 183 with up to two mismatches.

Embodiment 17 is the composition, kit, or method of any one embodiments 10-16, wherein the first tcdC detection oligomer has no mismatches to the 1, 2, 3, 4, 5, 6, 7, 8, 9, or 10 3'-terminal nucleotides of SEQ ID NO: 86-92, 183, 192, or 193.

Embodiment 18 is the composition, kit, or method of embodiment 17, wherein the first tcdC detection oligomer comprises the sequence of of SEQ ID NO: 86 or 183.

Embodiment 19 is the composition, kit, or method of embodiment 11, wherein the first tcdC detection oligomer comprises the sequence of any one of SEQ ID NOs: 87-92, 192, or 193.

Embodiment 20 is the composition, kit, or method of embodiment 19, wherein: (the first tcdC detection oligomer comprises the sequence any one of SEQ ID NOs: 89-92; and (ii) the composition or kit further comprises an additional first tcdC detection oligomer that comprises the sequence any one of SEQ ID NOs: 89-92, which is different from the first tcdC detection oligomer.

Embodiment 21 is the composition, kit, or method of any one of the preceding embodiments, wherein the composition or kit further comprises at least one first tcdC primary probe oligomer that is configured to form an invasive cleavage structure in the presence of the first tcdC detection oligomer and a polynucleotide comprising the sequence of SEQ ID NO: 3.

Embodiment 22 is the composition, kit, or method of embodiment 21, wherein the first tcdC primary probe oligomer comprises the sequence of any one of SEQ ID NOs: 93-137 or 184-187, with up to two mismatches.

Embodiment 23 is the composition, kit, or method of embodiment 21 or 22, wherein the first tcdC primary probe oligomer competes for hybridization to a tcdC nucleic acid under stringent conditions with an oligomer having a sequence consisting of SEQ ID NO: 138-182 or 188-191.

Embodiment 24 is the composition, kit, or method of any one of embodiments 21-23, wherein the first tcdC primary probe oligomer comprises the sequence of SEQ ID NO: 115, with up to two mismatches.

Embodiment 25 is the composition, kit, or method of any one of embodiments 21-23, wherein the first tcdC primary probe oligomer comprises the sequence of SEQ ID NO: 122, with up to two mismatches.

Embodiment 26 is the composition, kit, or method of any one of embodiments 21-23, wherein the first tcdC primary probe oligomer comprises the sequence of SEQ ID NO: 185, with up to two mismatches.

Embodiment 27 is the composition, kit, or method of any one of embodiments 21-26, wherein the first tcdC primary probe oligomer has no mismatches to the 1, 2, 3, 4, 5, 6, 7, 8, 9, or 10 5'-terminal nucleotides of SEQ ID NO: 93-137 or 184-187.

Embodiment 28 is the composition, kit, or method of embodiment 27, wherein the first tcdC primary probe oligomer comprises the sequence of any one of SEQ ID NOs: 93-137 or 184-187.

Embodiment 29 is the composition, kit, or method of any one of embodiments 21-28, wherein the first tcdC primary probe oligomer comprises the sequence of any one of SEQ ID NOs: 138-182 or 188-191, with up to two mismatches.

Embodiment 30 is the composition, kit, or method of embodiment 29, wherein the first tcdC primary probe oligomer comprises the sequence of any one of SEQ ID NOs: 138-182 or 188-191.

Embodiment 31 is the method of any one of embodiments 3 or 5-30, wherein the method is configured to generate a positive signal in the presence of 184T mutant tcdC.

Embodiment 32 is the composition, kit, or method of any one of the preceding embodiments, wherein the second tcdC detection oligomer is present and is configured to specifically hybridize to the sequence of a third tcdC sequence at a site comprising position 184 thereof but exhibits distinguishably different hybridization to the sequence of a fourth tcdC sequence, wherein the third tcdC sequence is the sequence of SEQ ID NO: 5 and the fourth tcdC sequence is the sequence of SEQ ID NO: 2.

Embodiment 33 is the composition, kit, or method of embodiment 32, wherein the second tcdC detection oligomer comprises the sequence of any one of SEQ ID NOs: 194-196 or 205, with up to two mismatches.

Embodiment 34 is the composition, kit, or method of embodiment 32, wherein the second tcdC detection oligomer comprises the sequence of SEQ ID NO: 196, with up to two mismatches.

Embodiment 35 is the composition, kit, or method of embodiment 32, wherein the second tcdC detection oligomer comprises the sequence of SEQ ID NO: 205, with up to two mismatches.

Embodiment 36 is the composition, kit, or method of any one of embodiments 32-35, wherein the second tcdC detection oligomer has no mismatches to the 1, 2, 3, 4, 5, 6, 7, 8, 9, or 10 3'-terminal nucleotides of SEQ ID NO: 194-196 or 205.

Embodiment 37 is the composition, kit, or method of embodiment 36, wherein the second tcdC detection oligomer comprises the sequence of any one of SEQ ID NOs: 194-196 or 205.

Embodiment 38 is the composition, kit, or method of any one of embodiments 32-37, wherein the composition or kit further comprises at least one second tcdC primary probe oligomer that is configured to form an invasive cleavage structure in the presence of the second tcdC detection oligomer and a polynucleotide comprising the sequence of SEQ ID NO: 5.

Embodiment 39 is the composition, kit, or method of embodiment 38, wherein the second tcdC primary probe oligomer comprises the sequence of any one of SEQ ID NOs: 197-200, 206-212, or 233-237, with up to two mismatches.

Embodiment 40 is the composition, kit, or method of embodiment 38 or 39, wherein the second tcdC primary probe oligomer competes for hybridization to a tcdC nucleic acid under stringent conditions with an oligomer having a sequence consisting of SEQ ID NO: 201-204, 213-219, or 238-242.

Embodiment 41 is the composition, kit, or method of embodiment 39 or 40, wherein the second tcdC primary probe oligomer comprises the sequence of SEQ ID NO: 200, with up to two mismatches.

Embodiment 42 is the composition, kit, or method of embodiment 39 or 40, wherein the second tcdC primary probe oligomer comprises the sequence of SEQ ID NO: 209, with up to two mismatches.

Embodiment 43 is the composition, kit, or method of any one of embodiments 38-42, wherein the second tcdC primary probe oligomer has no mismatches to the 1, 2, 3, 4, 5, 6, 7, 8, 9, or 10 5'-terminal nucleotides of SEQ ID NO: 197-200, 206-212, or 233-237.

Embodiment 44 is the composition, kit, or method of embodiment 43, wherein the second tcdC primary probe oligomer comprises the sequence of any one of SEQ ID NOs: 197-200, 206-212, or 233-237.

Embodiment 45 is the composition, kit, or method of any one of embodiments 38-44, wherein the second tcdC primary probe oligomer comprises the sequence of any one of SEQ ID NOs: 201-204, 213-219, or 238-242 with up to two mismatches.

Embodiment 46 is the composition, kit, or method of embodiment 45, wherein the second tcdC primary probe oligomer comprises the sequence of any one of SEQ ID NOs: 201-204, 213-219, or 238-242.

Embodiment 47 is the method of embodiment 3 or 5, wherein the method is configured not to generate a positive signal in the presence of 117T 184C tcdC.

Embodiment 48 is the method of embodiment 47, wherein the method is configured not to generate a positive signal in the presence of 117D 184C tcdC.

Embodiment 49 is the composition, kit, or method of any one of embodiments 4-48, wherein the composition or kit further comprises at least forward and reverse tcdC amplification oligomers, wherein the forward and reverse tcdC amplification oligomers are configured to produce a tcdC amplicon comprising position 117 of SEQ ID NO: 3 or SEQ ID NO: 4 if the first tcdC detection oligomer is present and/or position 184 of SEQ ID NO: 5 or SEQ ID NO: 2 if the second tcdC detection oligomer is present.

Embodiment 50 is the composition, kit, or method of any one of embodiments 4-48, wherein the first detection oligomer is an iPrimer and the composition or kit further comprises a first additional amplification oligomer wherein the iPrimer is a forward amplification oligomer and the first additional amplification oligomer is a reverse amplification oligomer, or the iPrimer is a reverse amplification oligomer and the first additional amplification oligomer is a forward amplification oligomer, and wherein the first additional amplification oligomer and first detection oligomer are configured to produce a tcdC amplicon comprising position 117 of SEQ ID NO: 3 or SEQ ID NO: 4.

Embodiment 51 is the composition, kit, or method of any one of embodiments 4-48, wherein the second detection oligomer is an iPrimer and the composition or kit further comprises a second additional amplification oligomer wherein the iPrimer is a forward amplification oligomer and the second additional amplification oligomer is a reverse amplification oligomer, or the iPrimer is a reverse amplification oligomer and the second additional amplification oligomer is a forward amplification oligomer and wherein the second additional amplification oligomer and second detection oligomer are configured to produce a tcdC amplicon comprising position 184 of SEQ ID NO: 5 or SEQ ID NO: 2.

Embodiment 52 is the composition, kit, or method of any one of embodiments 1-3 or 49-51, wherein the forward tcdC amplification oligomer comprises the sequence of any one of SEQ ID NOs: 243-248, with up to two mismatches.

Embodiment 53 is the composition, kit, or method of any one of embodiments 1-3 or 49-52, wherein the forward tcdC amplification oligomer competes for hybridization to a tcdC nucleic acid under stringent conditions with an oligomer having a sequence consisting of SEQ ID NO: 243-248.

Embodiment 54 is the composition, kit, or method of embodiment 52 or 53, wherein the forward tcdC amplification oligomer comprises the sequence of SEQ ID NO: 245, with up to two mismatches.

Embodiment 55 is the composition, kit, or method of embodiment 52 or 53, wherein the forward tcdC amplification oligomer comprises the sequence of SEQ ID NO: 247, with up to two mismatches.

Embodiment 56 is the composition, kit, or method of any one of embodiments 1-3 or 49-55, wherein the forward tcdC amplification oligomer has no mismatches to the 1, 2, 3, 4, 5, 6, 7, 8, 9, or 10 3'-terminal nucleotides of any one of SEQ ID NO: 243-248.

Embodiment 57 is the composition, kit, or method of embodiment 56, wherein the forward tcdC amplification oligomer comprises the sequence of any one of SEQ ID NOs: 243-248.

Embodiment 58 is the composition, kit, or method of any one of embodiments 1-3 or 49-57, wherein the reverse tcdC amplification oligomer comprising the sequence of any one of SEQ ID NOs: 249-259, with up to two mismatches.

Embodiment 59 is the composition, kit, or method of any one of embodiments 1-3 or 49-58, wherein the reverse tcdC amplification oligomer competes for hybridization to a tcdC nucleic acid under stringent conditions with an oligomer having a sequence consisting of SEQ ID NO: 249-259.

Embodiment 60 is the composition, kit, or method of embodiment 58 or 59, wherein the reverse tcdC amplification oligomer comprises the sequence of SEQ ID NO: 255, with up to two mismatches.

Embodiment 61 is the composition, kit, or method of embodiment 58 or 59, wherein the reverse tcdC amplification oligomer comprises the sequence of SEQ ID NO: 258, with up to two mismatches.

Embodiment 62 is the composition, kit, or method of any one of embodiments 1-3 or 49-61, wherein the reverse tcdC amplification oligomer has no mismatches to the 1, 2, 3, 4, 5, 6, 7, 8, 9, or 10 3'-terminal nucleotides of any one of SEQ ID NO: 249-259.

Embodiment 63 is the composition, kit, or method of embodiment 62, wherein the reverse tcdC amplification oligomer comprises the sequence of any one of SEQ ID NOs: 249-259.

Embodiment 64 is the composition, kit, or method of any one of embodiments 1 or 3-63, wherein the composition or kit further comprises at least forward and reverse tcdA amplification oligomers, and at least one tcdA detection oligomer, wherein:
the forward and reverse tcdA amplification oligomers are configured to produce a tcdA amplicon having a size of from 80 to 400 nucleotides; and
the tcdA detection oligomer is configured to specifically hybridize to the tcdA amplicon.

Embodiment 65 is the method of embodiment 64, further comprising detecting the presence of a *C. difficile* pathogenic locus based at least in part on whether the tcdA detection oligomer hybridized to the tcdA amplicon.

Embodiment 66 is the composition, kit, or method of any one of embodiments 2-65, wherein the forward or reverse tcdA amplification oligomer is an iPrimer and the tcdA detection oligomer is a primary probe.

Embodiment 67 is the composition, kit, or method of any one of embodiments 2-65, wherein the tcdA detection oligomer is a primary probe and the composition or kit further comprises an invader oligomer.

Embodiment 68 is the composition, kit, or method of any one of embodiments 2-67, wherein the forward tdA amplification oligomer comprises the sequence of any one of SEQ ID NOs: 59-60, 64, or 65, with up to two mismatches.

Embodiment 69 is the composition, kit, or method of any one of embodiments 2-68, wherein the forward tdA amplification oligomer competes for hybridization to a tcdA nucleic acid under stringent conditions with an oligomer having a sequence consisting of SEQ ID NO: 59-60, 64, or 65.

Embodiment 70 is the composition, kit, or method of embodiment 68 or 69, wherein the forward tcdA amplification oligomer comprises the sequence of SEQ ID NO: 64, with up to two mismatches.

Embodiment 71 is the composition, kit, or method of embodiment 68 or 69, wherein the forward tcdA amplification oligomer comprises the sequence of SEQ ID NO: 65, with up to two mismatches.

Embodiment 72 is the composition, kit, or method of any one of embodiments 2-71, wherein the forward tdA amplification oligomer has no mismatches to the 1, 2, 3, 4, 5, 6, 7, 8, 9, or 10 3'-terminal nucleotides of any one of SEQ ID NO: 59-60, 64, or 65.

Embodiment 73 is the composition, kit, or method of embodiment 72, wherein the forward tcdA amplification oligomer comprises the sequence of any one of SEQ ID NOs: 59-60, 64, or 65.

Embodiment 74 is the composition, kit, or method of any one of embodiments 2-73, wherein the reverse tcdA amplification oligomer comprises the sequence of any one of SEQ ID NOs: 70-73, with up to two mismatches.

Embodiment 75 is the composition, kit, or method of any one of embodiments 2-74, wherein the reverse tcdA amplification oligomer competes for hybridization to a tcdA nucleic acid under stringent conditions with an oligomer having a sequence consisting of SEQ ID NO: 70-73.

Embodiment 76 is the composition, kit, or method of embodiment 74 or 75, wherein the reverse tcdA amplification oligomer comprises the sequence of SEQ ID NO: 70, with up to two mismatches.

Embodiment 77 is the composition, kit, or method of embodiment 74 or 75, wherein the reverse tcdA amplification oligomer comprises the sequence of SEQ ID NO: 72, with up to two mismatches.

Embodiment 78 is the composition, kit, or method of any one of embodiments 2-77, wherein the reverse tcdA amplification oligomer has no mismatches to the 1, 2, 3, 4, 5, 6, 7, 8, 9, or 10 3'-terminal nucleotides of any one of SEQ ID NO: 70-73.

Embodiment 79 is the composition, kit, or method of embodiment 78, wherein the reverse tcdA amplification oligomer comprises the sequence of any one of SEQ ID NOs: 70-73.

Embodiment 80 is the composition, kit, or method of any one of embodiments 2-93, wherein the tcdA detection oligomer comprises the sequence of any one of SEQ ID NOs: 57, 61, 66, or 67, with up to two mismatches.

Embodiment 81 is the composition, kit, or method of any one of embodiments 2-80, wherein the tcdA detection oligomer competes for hybridization to a tcdA nucleic acid under stringent conditions with an oligomer having a sequence consisting of SEQ ID NO: 58, 62, 68, or 69.

Embodiment 82 is the composition, kit, or method of embodiment 80 or 81, wherein the tcdA detection oligomer comprises the sequence of SEQ ID NO: 66, with up to two mismatches.

Embodiment 83 is the composition, kit, or method of embodiment 80 or 81, wherein the tcdA detection oligomer comprises the sequence of SEQ ID NO: 67, with up to two mismatches.

Embodiment 84 is the composition, kit, or method of any one of embodiments 2-83, wherein the tcdA detection oligomer has no mismatches to the 1, 2, 3, 4, 5, 6, 7, 8, 9, or 10 5'-terminal nucleotides of any one of SEQ ID NO: 57, 61, 66, or 67.

Embodiment 85 is the composition, kit, or method of embodiment 84, wherein the tcdA detection oligomer comprises the sequence of any one of SEQ ID NOs: 57, 61, 66, or 67.

Embodiment 86 is the composition, kit, or method of embodiment 84, wherein the tcdA detection oligomer comprises the sequence of any one of SEQ ID NOs: 58, 62, 68, or 69.

Embodiment 87 is the composition, kit, or method of any one of embodiments 2-86, wherein the composition or kit further comprises a tcdA invader oligomer, wherein the tcdA invader oligomer competes for hybridization to a tcdA nucleic acid under stringent conditions with an oligomer having a sequence consisting of SEQ ID NO: 63, and/or the tcdA invader oligomer comprises the sequence of SEQ ID NO: 63, with up to two mismatches.

Embodiment 88 is the composition, kit, or method of embodiment 87, wherein the tcdA invader oligomer has no mismatches to the 1, 2, 3, 4, 5, 6, 7, 8, 9, or 10 3'-terminal nucleotides of any one of SEQ ID NO: 63.

Embodiment 89 is the composition, kit, or method of any one of the preceding embodiments, wherein the composition or kit further comprises forward and reverse tcdB amplification oligomers, wherein: the forward and reverse tcdB amplification oligomers are configured to produce a tcdB amplicon having a size of from 80 to 400 nucleotides; and the tcdB detection oligomer is configured to specifically hybridize to the tcdB amplicon.

Embodiment 90 is a composition or kit comprising a forward tcdB amplification oligomer, an additional forward tcdB amplification oligomer, and a reverse amplification oligomer, wherein the forward tcdB amplification oligomer competes for hybridization to a tcdB nucleic acid under stringent conditions with an oligomer having a sequence consisting of SEQ ID NO: 260-279 or 339 and/or the forward tcdB amplification oligomer comprises the sequence of any one of SEQ ID NOs: 260-279 or 339 with up to two mismatches; wherein the additional forward tcdB amplification oligomer competes for hybridization to a tcdB nucleic acid under stringent conditions with an oligomer having a sequence consisting of SEQ ID NO: 260-279 or 339 and/or the additional forward tcdB amplification oligomer comprises the sequence of any one of SEQ ID NOs: 260-279 or 339 with up to two mismatches; wherein the additional forward tcdB amplification oligomer is different from the forward tcdB amplification oligomer, and wherein the forward tcdB amplification oligomer, additional forward tcdB amplification oligomer, and reverse amplification oligomer are collectively configured to produce a tcdB amplicon having a size of from 80 to 400 nucleotides.

Embodiment 91 is the composition, kit, or method of embodiment 89, wherein the forward and reverse tcdB amplification oligomers are as recited in embodiment 90 and the composition or kit further comprises the additional forward tcdB amplification oligomer as recited in embodiment 90.

Embodiment 92 is a method of detecting tcdB, comprising preparing a composition according to any one of embodiments 89-91, which further comprises a sample comprising or suspected of comprising *C. difficile* nucleic acid; subjecting the composition to amplification conditions; and detecting the presence of at least one tcdB amplicon.

Embodiment 93 is the composition, kit, or method of any one of embodiments 89-92, wherein the composition or kit further comprises a tcdB detection oligomer configured to specifically hybridize to at least one tcdB amplicon.

Embodiment 94 is the method of embodiment 93, further comprising detecting the presence of a *C. difficile* pathogenic locus based at least in part on whether the tcdB detection oligomer hybridized to the tcdB amplicon.

Embodiment 95 is the composition, kit, or method of any one of embodiments 89-94, wherein the forward or reverse tcdB amplification oligomer is an iPrimer and the tcdB detection oligomer is a primary probe.

Embodiment 96 is the composition, kit, or method of any one of embodiments 89-95, wherein the tcdB detection oligomer is a primary probe and the composition or kit further comprises an invader oligomer.

Embodiment 97 is the composition, kit, or method of any one of embodiments 89-96, wherein the forward tcdB amplification oligomer comprises the sequence of any one of SEQ ID NOs: 260-279 or 339, with up to two mismatches.

Embodiment 98 is the composition, kit, or method of any one of embodiments 89-97, wherein the forward tcdB amplification oligomer competes for hybridization to a tcdB nucleic acid under stringent conditions with an oligomer having a sequence consisting of SEQ ID NO: 260-279 or 339.

Embodiment 99 is the composition, kit, or method of embodiment 97 or 98, wherein the forward tcdB amplification oligomer comprises the sequence of SEQ ID NO: 274, with up to two mismatches.

Embodiment 100 is the composition, kit, or method of embodiment 97 or 98, wherein the forward tcdB amplification oligomer comprises the sequence of SEQ ID NO: 277, with up to two mismatches.

Embodiment 101 is the composition, kit, or method of embodiment 97 or 98, wherein the forward tcdB amplification oligomer comprises the sequence of SEQ ID NO: 279, with up to two mismatches.

Embodiment 102 is the composition, kit, or method of embodiment 97 or 98, wherein the forward tcdB amplification oligomer comprises the sequence of SEQ ID NO: 339, with up to two mismatches.

Embodiment 103 is the composition, kit, or method of any one of embodiments 89-102, wherein the forward tcdB amplification oligomer has no mismatches to the 1, 2, 3, 4, 5, 6, 7, 8, 9, or 10 3'-terminal nucleotides of any one of SEQ ID NO: 260-279 or 339.

Embodiment 104 is the composition, kit, or method of embodiment 103, wherein the forward tcdB amplification oligomer comprises the sequence of any one of SEQ ID NOs: 260-279 or 339.

Embodiment 105 is the composition, kit, or method of any one of embodiments 90-104, wherein the additional forward tcdB amplification oligomer is present and comprises the sequence of any one of SEQ ID NOs: 274, 277, 279, or 339.

Embodiment 106 is the composition, kit, or method of any one of embodiments 89-105, wherein the reverse tcdB amplification oligomer comprises the sequence of any one of SEQ ID NOs: 317-338, with up to two mismatches.

Embodiment 107 is the composition, kit, or method of any one of embodiments 89-106, wherein the reverse tcdB amplification oligomer competes for hybridization to a tcdB nucleic acid under stringent conditions with an oligomer having a sequence consisting of SEQ ID NO: 317-338.

Embodiment 108 is the composition, kit, or method of embodiment 106 or 107, wherein the reverse tcdB amplification oligomer comprises the sequence of SEQ ID NO: 317, with up to two mismatches.

Embodiment 109 is the composition, kit, or method of embodiment 106 or 107, wherein the reverse tcdB amplification oligomer comprises the sequence of SEQ ID NO: 324 or 325, with up to two mismatches, optionally wherein the composition or kit comprises at least two reverse tcdB amplification oligomers comprising the sequences of SEQ ID NO: 324 with up to two mismatches and of SEQ ID NO: 325 with up to two mismatches, respectively.

Embodiment 110 is the composition, kit, or method of embodiment 106 or 107, wherein the reverse dB amplification oligomer comprises the sequence of SEQ ID NO: 336, with up to two mismatches.

Embodiment 111 is the composition, kit, or method of embodiment 106 or 107, wherein the reverse dB amplification oligomer comprises the sequence of SEQ ID NO: 338, with up to two mismatches.

Embodiment 112 is the composition, kit, or method of any one of embodiments 89-111, wherein at least one or at least two reverse tcdB amplification oligomers have no mismatches to the 1, 2, 3, 4, 5, 6, 7, 8, 9, or 10 3'-terminal nucleotides of any one of SEQ ID NO: 317-338.

Embodiment 113 is the composition, kit, or method of embodiment 112, wherein at least one or at least two reverse tcdB amplification oligomers comprise the sequence of any one of SEQ ID NOs: 317-338.

Embodiment 114 is the composition, kit, or method of any one of embodiments 93-113, wherein the tcdB detection oligomer comprises the sequence of any one of SEQ ID NOs: 281-298, with up to two mismatches.

Embodiment 115 is the composition, kit, or method of any one of embodiments 93-114, wherein the tcdB detection oligomer competes for hybridization to a tcdB nucleic acid under stringent conditions with an oligomer having a sequence consisting of SEQ ID NO: 299-316.

Embodiment 116 is the composition, kit, or method of embodiment 114 or 115, wherein the tcdB detection oligomer comprises the sequence of SEQ ID NO: 285, with up to two mismatches.

Embodiment 117 is the composition, kit, or method of embodiment 114 or 115, wherein the tcdB detection oligomer comprises the sequence of SEQ ID NO: 287, with up to two mismatches.

Embodiment 118 is the composition, kit, or method of embodiment 114 or 115, wherein the tcdB detection oligomer comprises the sequence of SEQ ID NO: 288, with up to two mismatches.

Embodiment 119 is the composition, kit, or method of anyone of embodiments 93-118, wherein the tcdB detection oligomer has no mismatches to the 1, 2, 3, 4, 5, 6, 7, 8, 9, or 10 5'-terminal nucleotides of any one of SEQ ID NO: 281-298.

Embodiment 120 is the composition, kit, or method of embodiment 119, wherein the tcdB detection oligomer comprises the sequence of any one of SEQ ID NOs: 281-298.

Embodiment 121 is the composition, kit, or method of embodiment 119, wherein the tcdB detection oligomer comprises the sequence of any one of SEQ ID NOs: 299-316.

Embodiment 122 is the composition, kit, or method of any one of embodiments 93-121, wherein the composition or kit further comprises a tcdB invader oligomer, wherein the tcdB invader oligomer competes for hybridization to a tcdB nucleic acid under stringent conditions with an oligomer having a sequence consisting of SEQ ID NO: 280 and/or the tcdB invader oligomer comprises the sequence of SEQ ID NO: 280, with up to two mismatches.

Embodiment 123 is the composition, kit, or method of embodiment 122, wherein the tcdB invader oligomer has no mismatches to the 1, 2, 3, 4, 5, 6, 7, 8, 9, or 10 3'-terminal nucleotides of any one of SEQ ID NO: 280.

Embodiment 124 is the composition, kit, or method of any one of the preceding embodiments, wherein the composition or kit further comprises forward and reverse cdtB amplification oligomers, and at least one cdtB detection oligomer, wherein: the forward and reverse cdtB amplification oligomers are configured to produce a cdtB amplicon having a size of from 80 to 400 nucleotides; and the cdtB detection oligomer is configured to specifically hybridize to the cdtB amplicon.

Embodiment 125 is the method of embodiment 124, further comprising detecting the presence of a *C. difficile* Cdt locus based at least in part on whether the cdtB detection oligomer hybridized to the cdtB amplicon.

Embodiment 126 is the composition, kit, or method of embodiment 124 or 125, wherein the forward or reverse cdtB amplification oligomer is an iPrimer and the cdtB detection oligomer is a primary probe.

Embodiment 127 is the composition, kit, or method of embodiment 124 or 125, wherein the cdtB detection oligomer is a primary probe and the composition or kit further comprises an invader oligomer.

Embodiment 128 is the composition, kit, or method of any one of embodiments 124-127, wherein the composition or kit comprises a forward cdtB amplification oligomer comprising the sequence of any one of SEQ ID NOs: 30-33 or 55, with up to two mismatches.

Embodiment 129 is the composition, kit, or method of any one of embodiments 124-128, wherein the forward cdtB amplification oligomer competes for hybridization to a cdtB nucleic acid under stringent conditions with an oligomer having a sequence consisting of SEQ ID NO: 30-33 or 55.

Embodiment 130 is the composition, kit, or method of embodiment 128 or 129, wherein the forward cdtB amplification oligomer comprises the sequence of SEQ ID NO: 33, with up to two mismatches.

Embodiment 131 is the composition, kit, or method of embodiment 128 or 129, wherein the forward cdtB amplification oligomer comprises the sequence of SEQ ID NO: 31, with up to two mismatches.

Embodiment 132 is the composition, kit, or method of any one of embodiments 124-131, wherein the forward cdtB amplification oligomer has no mismatches to the 1, 2, 3, 4, 5, 6, 7, 8, 9, or 10 3'-terminal nucleotides of any one of SEQ ID NO: 30-33 or 55.

Embodiment 133 is the composition, kit, or method of embodiment 132, wherein the forward cdtB amplification oligomer comprises the sequence of any one of SEQ ID NOs: 30-33 or 55.

Embodiment 134 is the composition, kit, or method of any one of embodiments 124-133, wherein the composition or kit comprises a reverse cdtB amplification oligomer comprising the sequence of any one of SEQ ID NOs: 40-41, 49-50, or 56, with up to two mismatches.

Embodiment 135 is the composition, kit, or method of any one of embodiments 124-134, wherein the reverse cdtB amplification oligomer competes for hybridization to a cdtB nucleic acid under stringent conditions with an oligomer having a sequence consisting of SEQ ID NO: 40-41, 49-50, or 56.

Embodiment 136 is the composition, kit, or method of embodiment 134 or 135, wherein the reverse cdtB amplification oligomer comprises the sequence of SEQ ID NO: 40, with up to two mismatches.

Embodiment 137 is the composition, kit, or method of embodiment 134 or 135, wherein the reverse cdtB amplification oligomer comprises the sequence of SEQ ID NO: 41, with up to two mismatches.

Embodiment 138 is the composition, kit, or method of embodiment 134 or 135, wherein the reverse cdtB amplification oligomer comprises the sequence of SEQ ID NO: 56, with up to two mismatches.

Embodiment 139 is the composition, kit, or method of anyone of embodiments 124-138, wherein at least one or at least two reverse cdtB amplification oligomers have no mismatches to the 1, 2, 3, 4, 5, 6, 7, 8, 9, or 10 3'-terminal nucleotides of any one of SEQ ID NO: 40-41, 49, 50, or 56.

Embodiment 140 is the composition, kit, or method of embodiment 139, wherein the composition or kit comprises a reverse cdtB amplification oligomer comprising the sequence of any one of SEQ ID NOs: 40-41, 49, 50, or 56.

Embodiment 141 is the composition, kit, or method of any one of embodiments 124-140, wherein the cdtB detection oligomer comprises the sequence of any one of SEQ ID NOs: 34-36, 43-45, 51, or 52, with up to two mismatches.

Embodiment 142 is the composition, kit, or method of anyone of embodiments 124-141, wherein the cdtB detection oligomer competes for hybridization to a cdtB nucleic acid under stringent conditions with an oligomer having a sequence consisting of SEQ ID NO: 37-39, 46-48, 53, or 54.

Embodiment 143 is the composition, kit, or method of embodiment 141 or 142, wherein the cdtB detection oligomer comprises the sequence of SEQ ID NO: 34, with up to two mismatches.

Embodiment 144 is the composition, kit, or method of embodiment 141 or 142, wherein the cdtB detection oligomer comprises the sequence of SEQ ID NO: 35, with up to two mismatches.

Embodiment 145 is the composition, kit, or method of embodiment 141 or 142, wherein the cdtB detection oligomer comprises the sequence of SEQ ID NO: 51, with up to two mismatches.

Embodiment 146 is the composition, kit, or method of anyone of embodiments 124-145, wherein the cdtB detection oligomer has no mismatches to the 1, 2, 3, 4, 5, 6, 7, 8, 9, or 10 5'-terminal nucleotides of any one of SEQ ID NO: 34-36, 43-45, 51, or 52.

Embodiment 147 is the composition, kit, or method of embodiment 146, wherein the cdtB detection oligomer comprises the sequence of any one of SEQ ID NOs: 34-36, 43-45, 51, or 52.

Embodiment 148 is the composition, kit, or method of embodiment 146, wherein the cdtB detection oligomer comprises the sequence of any one of SEQ ID NOs: 37-39, 46-48, 53, or 54.

Embodiment 149 is the composition, kit, or method of anyone of embodiments 124-148, wherein the composition or kit further comprises a cdtB invader oligomer, wherein the cdtB invader oligomer competes for hybridization to a cdtB nucleic acid under stringent conditions with an oligomer having a sequence consisting of SEQ ID NO: 42, and/or the cdtB invader oligomer comprises the sequence of SEQ ID NO: 42 with up to two mismatches.

Embodiment 150 is the composition, kit, or method of embodiment 149, wherein the cdtB invader oligomer has no mismatches to the 1, 2, 3, 4, 5, 6, 7, 8, 9, or 10 3'-terminal nucleotides of SEQ ID NO: 42.

Embodiment 151 is the composition, kit, or method of any one of the preceding embodiments, wherein the composition or kit further comprises forward and reverse cdtA amplification oligomers, and at least one cdtA detection oligomer, wherein:

the forward and reverse cdtA amplification oligomers are configured to produce a cdtA amplicon having a size of from 80 to 400 nucleotides; and the cdtA detection oligomer is configured to specifically hybridize to the cdtA amplicon.

Embodiment 152 is the method of embodiment 151, further comprising detecting the presence of a *C. difficile* Cdt locus based at least in part on whether the cdtA detection oligomer hybridized to the cdtA amplicon.

Embodiment 153 is the composition, kit, or method of embodiment 151 or 152, wherein the forward or reverse cdtA amplification oligomer is an iPrimer and the cdtA detection oligomer is a primary probe.

Embodiment 154 is the composition, kit, or method of embodiment 151 or 152, wherein the cdtA detection oligomer is a primary probe and the composition or kit further comprises an invader oligomer.

Embodiment 155 is the composition, kit, or method of anyone of embodiments 151-154, wherein the composition or kit comprises a forward cdtA amplification oligomer comprising the sequence of SEQ ID NO: 13, with up to two mismatches.

Embodiment 156 is the composition, kit, or method of anyone of embodiments 151-155, wherein the forward cdtA amplification oligomer competes for hybridization to a cdtA nucleic acid under stringent conditions with an oligomer having a sequence consisting of SEQ ID NO: 13.

Embodiment 157 is the composition, kit, or method of any one of embodiments 151-156, wherein the forward cdtA amplification oligomer has no mismatches to the 1, 2, 3, 4, 5, 6, 7, 8, 9, or 10 3'-terminal nucleotides of any one of SEQ ID NO: 13, or comprises the sequence of SEQ ID NO: 13.

Embodiment 158 is the composition, kit, or method of any one of embodiments 151-157, wherein the composition or kit comprises a reverse cdtA amplification oligomer comprising the sequence of any one of SEQ ID NOs: 21-29, with up to two mismatches.

Embodiment 159 is the composition, kit, or method of any one of embodiments 151-158, wherein the reverse cdtA amplification oligomer competes for hybridization to a cdtA nucleic acid under stringent conditions with an oligomer having a sequence consisting of SEQ ID NO: 21-29.

Embodiment 160 is the composition, kit, or method of any one of embodiments 151-159, wherein at least one or at least two reverse cdtA amplification oligomers have no mismatches to the 1, 2, 3, 4, 5, 6, 7, 8, 9, or 10 3'-terminal nucleotides of any one of SEQ ID NO: 21-29.

Embodiment 161 is the composition, kit, or method of any one of embodiments 151-160, wherein the composition or kit comprises a cdtA detection oligomer comprising the sequence of any one of SEQ ID NOs: 16 or 17, with up to two mismatches.

Embodiment 162 is the composition, kit, or method of any one of embodiments 151-161, wherein the cdtA detection oligomer competes for hybridization to a cdtA nucleic acid under stringent conditions with an oligomer having a sequence consisting of SEQ ID NO: 18-20.

Embodiment 163 is the composition, kit, or method of embodiment 161 or 162, wherein the cdtA detection oligomer comprises the sequence of SEQ ID NO: 16, with up to two mismatches.

Embodiment 164 is the composition, kit, or method of embodiment 161 or 162, wherein the cdtA detection oligomer comprises the sequence of SEQ ID NO: 17, with up to two mismatches.

Embodiment 165 is the composition, kit, or method of any one of embodiments 151-164, wherein the cdtA detection oligomer has no mismatches to the 1, 2, 3, 4, 5, 6, 7, 8, 9, or 10 5'-terminal nucleotides of any one of SEQ ID NO: 16 or 17.

Embodiment 166 is the composition, kit, or method of embodiment 165, wherein the cdtA detection oligomer comprises the sequence of any one of SEQ ID NOs: 16 or 17.

Embodiment 167 is the composition, kit, or method of embodiment 165, wherein the cdtA detection oligomer comprises the sequence of any one of SEQ ID NOs: 18-20.

Embodiment 168 is the composition, kit, or method of any one of embodiments 151-167, wherein the composition or kit further comprises a cdtA invader oligomer, wherein the cdtA invader oligomer competes for hybridization to a cdtA nucleic acid under stringent conditions with an oligomer having a sequence consisting of SEQ ID NO: 14 or 15, and/or the cdtA invader oligomer comprises the sequence of SEQ ID NO: 14 or 15 with up to two mismatches.

Embodiment 169 is the composition, kit, or method of embodiment 168, wherein the cdtA invader oligomer has no mismatches to the 1, 2, 3, 4, 5, 6, 7, 8, 9, or 10 3'-terminal nucleotides of any one of SEQ ID NO: 14 or 15.

Embodiment 170 is a detection oligomer comprising the sequence set forth in positions 7-18 of any one of SEQ ID NOs: 18-20, 37-39, 46-48, 53, 54, 58, 62, 68, 69, 138-182, 188-191, 201-204, 213-219, 238-242, or 299-316, wherein the detection oligomer further comprises sufficient additional sequence to specifically hybridize to a *C. difficile* tcdA, tcdB, tcdC, cdtA, or cdtB nucleic acid.

Embodiment 171 is the detection oligomer of embodiment 170, which is configured to specifically hybridize to the reverse complement of the sequence set forth in any one of SEQ ID NOs: 16, 17, 34-36, 43-45, 51, 52, 57, 61, 66, 67, 93-137, 184-187, 197-200, 206-212, 233-237, or 281-298.

Embodiment 172 is the detection oligomer of embodiment 170 or 171, comprising the sequence set forth in any one of SEQ ID NOs: 16, 17, 34-36, 43-45, 51, 52, 57, 61, 66, 67, 93-137, 184-187, 197-200, 206-212, 233-237, or 281-298 with up to two mismatches.

Embodiment 173 is the detection oligomer of embodiment 172, comprising the sequence set forth in any one of SEQ ID NOs: 16, 17, 34-36, 43-45, 51, 52, 57, 61, 66, 67, 93-137, 184-187, 197-200, 206-212, 233-237, or 281-298.

Embodiment 174 is the detection oligomer of anyone of embodiments 170-173, comprising the sequence set forth in any one of SEQ ID NOs: 18-20, 37-39, 46-48, 53, 54, 58, 62, 68, 69, 138-182, 188-191, 201-204, 213-219, 238-242, or 299-316 with up to two mismatches.

Embodiment 175 is the detection oligomer of embodiment 174, comprising the sequence set forth in any one of SEQ ID NOs: 18-20, 37-39, 46-48, 53, 54, 58, 62, 68, 69, 138-182, 188-191, 201-204, 213-219, 238-242, or 299-316.

Embodiment 176 is the composition, kit, method, or detection oligomer of any one of embodiments 1-89 or 93-175, wherein at least one detection oligomer is non-extendable.

Embodiment 177 is the composition, kit, method, or detection oligomer of any one of embodiments 1-89 or 93-176, wherein at least one detection oligomer comprises a label.

Embodiment 178 is the composition, kit, method, or detection oligomer of any one of embodiments 1-89 or 93-177, wherein at least one detection oligomer has a length of 15 to 55 nucleotides.

Embodiment 179 is a composition or kit comprising at least one detection oligomer of any one of embodiments 170-178 and at least one secondary detection oligomer, wherein the secondary detection oligomer comprises at least one label and is configured to interact with a fragment of the detection oligomer.

Embodiment 180 is the composition, kit, or method of anyone of embodiments 1-89 or 93-169, wherein the composition or kit further comprises at least one secondary detection oligomer that comprises a label and is configured to interact with a fragment of a detection oligomer.

Embodiment 181 is the composition, kit, or method of embodiment 179 or 180, wherein the secondary detection oligomer comprises at least two labels.

Embodiment 182 is the composition, kit, or method of embodiment 181, wherein the at least two labels include a FRET pair.

Embodiment 183 is the composition, kit, or method of embodiment 181 or 182, wherein the at least two labels include a quencher.

Embodiment 184 is the composition, kit, or method of anyone of embodiments 179-183, wherein the fragment of the detection oligomer is a 5'-terminal flap of at least six nucleotides.

Embodiment 185 is the composition, kit, or method of embodiment 184, wherein the one or more secondary detection oligomers are FRET cassettes.

Embodiment 186 is the composition, kit, or method of anyone of embodiments 180-184, wherein the kit or composition comprises at least a tcdB primary detection oligomer as recited in any one of embodiments 89, 93-96, or 114-123, and a tcdA primary detection oligomer as recited in any one of embodiments 2 or 80-86, and the one or more secondary detection oligomers include a secondary detection oligomer configured to generate a positive signal in the presence of a dB nucleic acid and in the presence of a tcdA nucleic acid.

Embodiment 187 is the composition, kit, or method of any one of embodiments 180-186, wherein the kit or composition comprises at least a first tcdC primary probe oligomer as recited in any one of embodiments 21-30 and a second tcdC primary probe oligomer as recited in any one of embodiments 38-46, and the one or more secondary detection oligomers include a secondary detection oligomer configured to generate a positive signal in the presence of a tcdC allele comprising a 117del mutation and in the presence of a tcdC allele comprising a 184T mutation.

Embodiment 188 is the composition, kit, or method of any one of embodiments 180-187, wherein the one or more secondary detection oligomers include a secondary detection oligomer comprising the sequence of SEQ ID NO: 10.

Embodiment 189 is the composition, kit, or method of any one of embodiments 180-188, wherein the one or more secondary detection oligomers include a secondary detection oligomer comprising the sequence of SEQ ID NO: 11.

Embodiment 190 is the composition, kit, or method of any one of embodiments 180-189, wherein the one or more secondary detection oligomers include a secondary detection oligomer comprising the sequence of SEQ ID NO: 12.

Embodiment 191 is the composition, kit, or method of any one of embodiments 1-169 or 176-190, wherein the composition or kit comprises a nuclease with structure-specific activity toward a three-strand structure formed by 3'-end invasion.

Embodiment 192 is the composition, kit, or method of any one of embodiments 1-169 or 176-191, wherein the composition or kit comprises a cleavase or 5'-nuclease.

Embodiment 193 is the composition, kit, or method of any one of embodiments 1-169 or 176-192, wherein the composition or kit comprises a FEN1 nuclease.

Embodiment 194 is the composition, kit, or method of any one of embodiments 1-169 or 176-193, wherein the composition or kit comprises a polymerase.

Embodiment 195 is the composition, kit, or method of any one of embodiments 1-169 or 176-194, wherein the composition or kit comprises a DNA polymerase.

Embodiment 196 is the composition, kit, or method of any one of embodiments 1-169 or 176-195, wherein the composition or kit comprises a thermostable DNA polymerase.

Embodiment 197 is the composition, kit, or method of embodiment 196, wherein the thermostable DNA polymerase is a hot-start DNA polymerase.

Embodiment 198 is the composition, kit, or method of any one of embodiments 1-169 or 176-197, wherein the composition or kit comprises NTPs.

Embodiment 199 is the composition, kit, or method of any one of embodiments 1-169 or 176-198, wherein composition or kit comprises deoxyribonucleotide triphosphates.

Embodiment 200 is a method of detecting at least one C. difficile nucleic acid comprising:
preparing a composition according to any one of embodiments 176-199, or comprising at least one detection oligomer of any one of embodiments 170-175, which further comprises a sample comprising or suspected of comprising C. difficile nucleic acid or at least one C. difficile amplicon;
detecting the presence of the C. difficile nucleic acid or the C. difficile amplicon by performing a hybridization assay; and determining whether the detection oligomer hybridized to the C. difficile nucleic acid or the C. difficile amplicon.

Embodiment 201 is the method of embodiment 200, wherein the composition comprises at least one secondary detection oligomer as recited in any one of embodiments 179-190, and the method comprises determining whether the detection oligomer hybridized to the C. difficile nucleic acid or the C. difficile amplicon at least in part by exposing the detection oligomer to a structure-specific nuclease and determining whether a fragment of the detection oligomer produced by the structure-specific nuclease interacts with the secondary detection oligomer.

Embodiment 202 is the method of embodiment 201, wherein the fragment of the detection oligomer is a 5'-terminal flap.

Embodiment 203 is the method of any one of embodiments 200-202, wherein the composition further comprises at least one invasive oligomer that hybridizes to a site in the C. difficile nucleic acid or the C. difficile amplicon that overlaps the hybridization site of the detection oligomer and, in the presence of the detection oligomer and the C. difficile nucleic acid or the C. difficile amplicon, forms a structure recognized for cleavage by the structure-specific nuclease.

Embodiment 204 is the method of embodiment 203, wherein the invasive oligomer competes for hybridization to the C. difficile nucleic acid or the C. difficile amplicon under stringent conditions with an oligomer having a sequence consisting of the sequence of any one of SEQ ID NOs: 14, 15, 40-42, 63-65, 74-76, 86-92, 183, 192-196, 205, 220, 221, 223-225, 260-280, or 317.

Embodiment 205 is the method of embodiment 217 or 218, wherein the invasive oligomer has a sequence comprising the sequence of any one of SEQ ID NOs: 14, 15, 40-42, 63-65, 74-76, 86-92, 183, 192-196, 205, 220, 221, 223-225, 260-280, or 317 with up to two mismatches.

Embodiment 206 is the composition, kit, detection oligomer, or method of any one of the preceding embodiments, wherein at least one oligomer comprises at least one methylated cytosine.

Embodiment 207 is the composition, kit, detection oligomer, or method of any one of the preceding embodiments, wherein the sequences of SEQ ID NOs include adenine methylation as indicated in the Table of Sequences.

Embodiment 208 is the composition, kit, detection oligomer, or method of any one of the preceding embodiments, wherein the sequences of SEQ ID NOs include cytosine methylation as indicated in the Table of Sequences.

Embodiment 209 is a composition of anyone of embodiments 1-2,4,10-30, 32-46, 49-64, 66-91, 93, 95-124, 126-151, 153-169, 179-199, or 206-208, or comprising a detection oligomer of any one of embodiments 170-175, which is aqueous, frozen, or lyophilized, or wherein at least one oligomer is bound to a solid substrate.

Embodiment 210 is the kit of anyone of embodiments 1-2,4,10-30, 32-46, 49-64, 66-91, 93, 95-124, 126-151, 153-169, 179-199, or 206-209, further comprising instructions for detecting at least one of a C. difficile tcdA, tcdB, tcdC, cdtA, or cdtB nucleic acid in a sample.

Embodiment 211 is the use of a composition or kit of any one of embodiments 1-2, 4, 10-30, 32-46, 49-64, 66-91, 93, 95-124, 126-151, 153-169, 179-199, or 206-210, or of a detection oligomer of any one of embodiments 170-175 for detecting at least one of a C. difficile tcdA, tcdB, tcdC, cdtA, or cdtB nucleic acid in a sample.

Section headings are provided for the convenience of the reader and are not to be interpreted to limit the scope of the disclosure.

DETAILED DESCRIPTION OF CERTAIN EMBODIMENTS

Overview

Oligomers for amplifying and/or detecting tcdA, tcdB, tcdC, cdtA, and cdtB target sequences of *C. difficile* are provided herein. In some embodiments, oligomers for detecting two or more of these genes can be used in a multiplex format so that a single reaction provides information about multiple genes. Certain oligomers can be used to specifically detect tcdC alleles associated with hypervirulence. In some embodiments, additional amplification oligomers or probes are used, e.g., to increase sensitivity or mitigate false negatives that may result from certain sequence polymorphisms.

In some embodiments, the oligomers are for use in performing invasive cleavage assays such as INVADER or INVADER PLUS assays. Such approaches can use a set of detection oligomers, comprising invasive and primary probe oligomers, to form a structure in which the 3' end of an invasive oligomer competes with the 5' flap of another oligomer for hybridization to the target sequence, resulting in a complex comprising a partially single-stranded primary probe. A cleavage agent is used that recognizes this structure and cleaves the primary probe, thus liberating the 5' flap for subsequent detection; this is referred to as an invasive cleavage reaction. In some embodiments, detection occurs by a second invasive cleavage reaction wherein the 5' flap hybridizes with a double-labeled oligomer (e.g., FRET cassette) and forms a substrate for the cleavage agent. Cleavage of the double-labeled oligomer can separate the two labels and thereby provide a detectable change in label behavior, such as a loss of quenching of a fluorophore. It has been found that this approach is suitable for discrimination of hypervirulent from non-hypervirulent tcdC alleles and also for multiplexing, facilitating a rapid and streamlined approach for assessing whether toxin-producing *C. difficile* nucleic acid is in a sample, whether the sample contains a tcdC allele associated with hypervirulence, and/or whether it has one, the other, or both of the Pathogenic locus and the Cdt locus.

Definitions

Before describing the present teachings in detail, it is to be understood that the disclosure is not limited to specific compositions or process steps, as such may vary. It should be noted that, as used in this specification and the appended claims, the singular form "a," "an," and "the" include plural references, and expressions such as "one or more items" include singular references unless the context clearly dictates otherwise. Thus, for example, reference to "an oligomer" includes a plurality of oligomers and the like; in a further example, a statement that "one or more secondary detection oligomers are FRET cassettes" includes a situation in which there is exactly one secondary detection oligomer and it is a FRET cassette. The conjunction "or" is to be interpreted in the inclusive sense, i.e., as equivalent to "and/or," unless the inclusive sense would be unreasonable in the context. When "at least one" member of a class (e.g., oligomer) is present, reference to "the" member (e.g., oligomer) refers to the present member (if only one) or at least one of the members (e.g., oligomers) present (if more than one).

Measured and measurable values are understood to be approximate, taking into account significant digits and the error associated with the measurement. All ranges are to be interpreted as encompassing the endpoints in the absence of express exclusions such as "not including the endpoints"; thus, for example, "within 10-15" includes the values 10 and 15. Also, the use of "comprise," "comprises," "comprising" "contain," "contains," "containing," "include," "includes," and "including" are not intended to be limiting. It is to be understood that both the foregoing general description and detailed description are exemplary and explanatory only and are not restrictive of the teachings. To the extent that any material incorporated by reference is inconsistent with the express content of this disclosure, the express content controls.

Unless specifically noted, embodiments in the specification that recite "comprising" various components are also contemplated as "consisting of" or "consisting essentially of" the recited components. "Consisting essentially of" means that additional component(s), composition(s) or method step(s) that do not materially change the basic and novel characteristics of the compositions and methods described herein can be included in those compositions or methods. Such characteristics include the ability to detect a toxigenic *C. difficile* nucleic acid sequence present in a sample with specificity that distinguishes the toxigenic *C. difficile* nucleic acid from other *Costridium* species and other known pathogens. In some embodiments, the characteristics include the ability to detect a *C. difficile* nucleic acid sequence at a sensitivity sufficient to detect as little as about 10 CFU (Colony Forming Units)/mL of toxigenic *C. difficile*. In some embodiments, the characteristics include the ability to detect a *C. difficile* nucleic acid sequence within about 60 minutes and/or within about 50 cycles from the beginning of an amplification reaction when a cycled amplification reaction is used.

Where a claim to a composition or kit recites an oligomer with a first given feature (e.g., competing for hybridization under stringent conditions for binding to a nucleic acid with an oligomer having a sequence consisting of a given sequence) and claims dependent thereon recite an oligomer with additional given features (e.g., comprising the sequence of at least one of a given list of SEQ ID NOs), then the composition or kit can comprise a plurality of oligomers that collectively have the features or an individual oligomer with the first and additional features (including but not necessarily limited to when the features are related; e.g., competing for hybridization under stringent conditions for binding to a nucleic acid with an oligomer having a sequence consisting of a given sequence would be related to comprising the sequence of a SEQ ID NO that overlaps with the given sequence).

A "sample" refers to material that may contain nucleic acid from *C. difficile*, including but not limited to biological, clinical, environmental, and food samples. Environmental samples include environmental material such as surface matter, soil, water and industrial samples, as well as samples obtained from food and dairy processing instruments, apparatus, equipment, utensils, disposable and non-disposable items. "Biological" or "clinical" samples refer to a tissue or material derived from a living or dead human or animal which may contain a *C. difficile* target nucleic acid, including, for example, body fluids, fecal samples and swabs thereof and colon or rectal biopsies or washes. A sample can be treated to physically, chemically, or mechanically disrupt tissue or cell structure to release intracellular nucleic acids into a solution which may contain enzymes, buffers, salts, detergents and the like, to prepare the sample for analysis. These examples are not to be construed as limiting the sample types applicable to the present disclosure.

"Nucleic acid" and "polynucleotide" refer to a multimeric compound comprising nucleosides or nucleoside analogs which have nitrogenous heterocyclic bases or base analogs linked together to form a polynucleotide, including conventional RNA, DNA, mixed RNA-DNA, and polymers that are analogs thereof. A nucleic acid "backbone" can be made up of a variety of linkages, including one or more of sugar-phosphodiester linkages, peptide-nucleic acid bonds ("peptide nucleic acids" or PNA; PCT No. WO 95/32305), phosphorothioate linkages, methylphosphonate linkages, or combinations thereof. Sugar moieties of a nucleic acid can be ribose, deoxyribose, or similar compounds with substitutions, e.g., 2' methoxy or 2' halide substitutions. Nitrogenous bases can be conventional bases (A, G, C, T, U), analogs thereof (e.g., inosine or others; see *The Biochemistry of the Nucleic Acids* 5-36, Adams et al., ed., 11$^{th}$ ed., 1992), derivatives of purines or pyrimidines (e.g., N$^4$-methyl guanine, N$^6$-methyladenine, deaza- or aza-purines, deaza- or aza-pyrimidines, pyrimidine bases with substituent groups at the 5 or 6 position (e.g., 5-methylcytosine), purine bases with a substituent at the 2, 6, or 8 positions, 2-amino-6-methylaminopurine, O$^6$-methylguanine, 4-thio-pyrimidines, 4-amino-pyrimidines, 4-dimethylhydrazine-pyrimidines, and O$^4$-alkyl-pyrimidines; U.S. Pat. No. 5,378,825 and PCT No. WO 93/13121). Nucleic acids can include one or more "abasic" residues where the backbone includes no nitrogenous base for position(s) of the polymer (U.S. Pat. No. 5,585,481). A nucleic acid can comprise only conventional RNA or DNA sugars, bases and linkages, or can include both conventional components and substitutions (e.g., conventional bases with 2' methoxy linkages, or polymers containing both conventional bases and one or more base analogs). Nucleic acid includes "locked nucleic acid" (LNA), an analogue containing one or more LNA nucleotide monomers with a bicyclic furanose unit locked in an RNA mimicking sugar conformation, which enhance hybridization affinity toward complementary RNA and DNA sequences (Vester and Wengel, 2004, *Biochemistry* 43(42):13233-41). Embodiments of oligomers that can affect stability of a hybridization complex include PNA oligomers, oligomers that include 2'-methoxy or 2'-fluoro substituted RNA, or oligomers that affect the overall charge, charge density, or steric associations of a hybridization complex, including oligomers that contain charged linkages (e.g., phosphorothioates) or neutral groups (e.g., methylphosphonates). Methylated cytosines such as 5-methylcytosines can be used in conjunction with any of the foregoing backbones/sugars/linkages including RNA or DNA backbones (or mixtures thereof) unless otherwise indicated. RNA and DNA equivalents have different sugar moieties (i.e., ribose versus deoxyribose) and can differ by the presence of uracil in RNA and thymine in DNA. The differences between RNA and DNA equivalents do not contribute to differences in homology because the equivalents have the same degree of complementarity to a particular sequence. It is understood that when referring to ranges for the length of an oligonucleotide, amplicon, or other nucleic acid, that the range is inclusive of all whole numbers (e.g., 19-25 contiguous nucleotides in length includes 19, 20, 21, 22, 23, 24, and 25).

"C residues" include methylated and unmethylated cytosines unless the context indicates otherwise. In some embodiments, methylated cytosines comprise or consist of 5-methylcytosines.

"A residues" include methylated and unmethylated adenines unless the context indicates otherwise. In some embodiments, methylated adenines comprise or consist of 2'-O-methyladenosine.

"Nucleic acid amplification" or simply "amplification" refers to any in vitro procedure that produces multiple copies of a target nucleic acid sequence, or its complementary sequence, or fragments thereof (i.e., an amplified sequence containing less than the complete target nucleic acid). Amplification methods include, for example, replicase-mediated amplification, polymerase chain reaction (PCR), ligase chain reaction (LCR), strand-displacement amplification (SDA), helicase-dependent amplification, and transcription-mediated amplification (TMA), also known as transcription-associated amplification. Replicase-mediated amplification uses self-replicating RNA molecules, and a replicase such as QB-replicase (see. e.g., U.S. Pat. No. 4,786,600, incorporated by reference herein). PCR amplification uses a DNA polymerase, pairs of primers, and thermal cycling to synthesize multiple copies of two complementary strands of dsDNA or from a cDNA (see. e.g., U.S. Pat. Nos. 4,683,195; 4,683,202; and 4,800,159; each incorporated by reference herein). LCR amplification uses four or more different oligonucleotides to amplify a target and its complementary strand by using multiple cycles of hybridization, ligation, and denaturation (see. e.g., U.S. Pat. Nos. 5,427,930 and 5,516,663, each incorporated by reference herein). SDA uses a primer that contains a recognition site for a restriction endonuclease and an endonuclease that nicks one strand of a hemimodified DNA duplex that includes the target sequence, whereby amplification occurs in a series of primer extension and strand displacement steps (see, e.g., U.S. Pat. Nos. 5,422,252; 5,547,861; and 5,648,211; each incorporated by reference herein). Helicase-dependent amplification uses a helicase to separate the two strands of a DNA duplex generating single-stranded templates, followed by hybridization of sequence-specific primers hybridize to the templates and extension by DNA polymerase to amplify the target sequence (see, e.g., U.S. Pat. No. 7,282, 328, incorporated by reference herein). Amplification may be linear or exponential.

Transcription associated amplification uses a DNA polymerase, an RNA polymerase, deoxyribonucleoside triphosphates, ribonucleoside triphosphates, a promoter-containing oligonucleotide, and optionally can include other oligonucleotides, to ultimately produce multiple RNA transcripts from a nucleic acid template (described in detail in U.S. Pat. Nos. 5,399,491 and 5,554,516, Kacian et al., U.S. Pat. No. 5,437,990, Burg et al., PCT Nos. WO 88/01302 and WO 88/10315, Gingeras et al., U.S. Pat. No. 5,130,238, Malek et al., U.S. Pat. Nos. 4,868,105 and 5,124,246, Urdea et al., PCT No. WO 94/03472, McDonough et al., PCT No. WO 95/03430, and Ryder et al.). Methods that use TMA are described in detail previously (U.S. Pat. Nos. 5,399,491 and 5,554,516).

In cyclic amplification methods that detect amplicons in real-time, the term "Threshold cycle" (Ct) is a measure of the emergence time of a signal associated with amplification of target, and may, for example, be approximately 10× standard deviation of the normalized reporter signal. Once an amplification reaches the "threshold cycle," generally there is considered to be a positive amplification product of a sequence to which the probe binds. Binding of the probe generally provides substantial information the identity of the product (e.g., that it is a tcdB or tcdA amplicon, as the case may be, or a member of a certain class of alleles of a gene in the case of one or more allele-specific probe(s)). The amplification product can additionally be further characterized through methods known to one of skill in the art, such as gel electrophoresis, nucleic acid sequencing, and other such analytical procedures.

An "oligomer" or "oligonucleotide" refers to a nucleic acid of generally less than 1,000 nucleotides (nt), including those in a size range having a lower limit of about 2 to 5 nt and an upper limit of about 500 to 900 nt. Some particular embodiments are oligomers in a size range with a lower limit of about 5 to 15, 16, 17, 18, 19, or 20 nt and an upper limit of about 50 to 600 nt, and other particular embodiments are in a size range with a lower limit of about 10 to 20 nt and an upper limit of about 22 to 100 nt. Oligomers can be purified from naturally occurring sources, but can be synthesized by using any well known enzymatic or chemical method. Oligomers can be referred to by a functional name (e.g., capture probe, primer or promoter primer) but those skilled in the art will understand that such terms refer to oligomers. Oligomers can form secondary and tertiary structures by self-hybridizing or by hybridizing to other polynucleotides. Such structures can include, but are not limited to, duplexes, hairpins, cruciforms, bends, and triplexes. Oligomers may be generated in any manner, including chemical synthesis, DNA replication, reverse transcription, PCR, or a combination thereof. In some embodiments, oligomers that form invasive cleavage structures are generated in a reaction (e.g., by extension of a primer in an enzymatic extension reaction).

By "amplicon" or "amplification product" is meant a nucleic acid molecule generated in a nucleic acid amplification reaction and which is derived from a target nucleic acid. An amplicon or amplification product contains a target nucleic acid sequence that can be of the same or opposite sense as the target nucleic acid. In some embodiments, an amplicon has a length of about 100-2000 nucleotides, about 100-1500 nucleotides, about 100-1000 nucleotides, about 100-800 nucleotides, about 100-700 nucleotides, about 100-600 nucleotides, or about 100-500 nucleotides.

An "amplification oligonucleotide" or "amplification oligomer" refers to an oligonucleotide that hybridizes to a target nucleic acid, or its complement, and participates in a nucleic acid amplification reaction, e.g., serving as a primer and/or promoter-primer. Particular amplification oligomers contain at least 10 contiguous bases, and optionally at least 11, 12, 13, 14, 15, 16, 17, 18, 19, or 20 contiguous bases, that are complementary to a region of the target nucleic acid sequence or its complementary strand. The contiguous bases can be at least 80%, at least 90%, or completely complementary to the target sequence to which the amplification oligomer binds. In some embodiments, an amplification oligomer comprises an intervening linker or non-complementary sequence between two segments of complementary sequence, e.g., wherein the two complementary segments of the oligomer collectively comprise at least 10 complementary bases, and optionally at least 11, 12, 13, 14, 15, 16, 17, 18, 19, or 20 complementary bases. One skilled in the art will understand that the recited ranges include all whole and rational numbers within the range (e.g., 92% or 98.377%). Particular amplification oligomers are 10 to 60 bases long and optionally can include modified nucleotides.

A "primer" refers to an oligomer that hybridizes to a template nucleic acid and has a 3' end that is extended by polymerization. A primer can be optionally modified, e.g., by including a 5' region that is non-complementary to the target sequence. Such modification can include functional additions, such as tags, promoters, or other sequences used or useful for manipulating or amplifying the primer or target oligonucleotide. A primer modified with a 5' promoter sequence can be referred to as a "promoter-primer." A person of ordinary skill in the art of molecular biology or biochemistry will understand that an oligomer that can function as a primer can be modified to include a 5' promoter sequence and then function as a promoter-primer, and, similarly, any promoter-primer can serve as a primer with or without its 5' promoter sequence.

"Detection oligomer" or "probe" refers to an oligomer that interacts with a target nucleic acid to form a detectable complex. Examples include invasive probes (also referred to as invader oligomers), iPrimers, and primary probes, discussed below. A probe's target sequence generally refers to the specific sequence within a larger sequence (e.g., gene, amplicon, locus, etc.) to which the probe hybridizes specifically. A detection oligomer can include target-specific sequences and a non-target-complementary sequence. Such non-target-complementary sequences can include sequences which will confer a desired secondary or tertiary structure, such as a flap or hairpin structure, which can be used to facilitate detection and/or amplification (e.g., U.S. Pat. Nos. 5,118,801, 5,312,728, 6,835,542, 6,849,412, 5,846,717, 5,985,557, 5,994,069, 6,001,567, 6,913,881, 6,090,543, and 7,482,127; WO 97/27214; WO 98/42873; Lyamichev et al., Nat. Biotech., 17:292 (1999); and Hall et al., PNAS, USA, 97:8272 (2000)). Probes of a defined sequence can be produced by techniques known to those of ordinary skill in the art, such as by chemical synthesis, and by in vitro or in vivo expression from recombinant nucleic acid molecules.

By "probe system" is meant a plurality of detection oligomers or probes for detecting a target sequence. In some embodiments, a probe system comprises at least primary and secondary probes, at least invasive and primary probes, or invasive, primary, and secondary probes. An "invasive probe" or "invader oligomer" refers to an oligonucleotide that hybridizes to a target nucleic acid at a location near the region of hybridization between a primary probe and the target nucleic acid, wherein the invasive probe oligonucleotide comprises a portion (e.g., a chemical moiety, or nucleotide, whether complementary to that target or not) that overlaps with the region of hybridization between the primary probe oligonucleotide and the target nucleic acid. An "iPrimer" is an invasive probe that is also an amplification oligomer and undergoes extension by a DNA polymerase—that is, the iPrimer can function as an invasive probe in the absence of extension, and it can also undergo extension during amplification, functioning as a primer. The "primary probe" for an invasive cleavage assay includes a target-specific region that hybridizes to the target nucleic acid, and further includes a "5' flap" region that is not complementary to the target nucleic acid. In general, detection can either be direct (i.e., probe hybridized directly to the target) or indirect (i.e., involving an intermediate structure that links a detectable label or detectably labeled molecule (e.g., a FRET cassette) to the target). In some embodiments, a primary probe comprises a target-hybridizing sequence and a non-target-complementary sequence. In some embodiments, a primary probe undergoes nucleolysis (e.g., cleavage, such as 5'-cleavage or endonucleolysis) upon hybridization to a target sequence in the presence of an appropriate cleavage agent, which can be a nuclease, such as structure-specific nuclease, e.g., a cleavase or 5'-nuclease. In some embodiments, such nucleolysis results in liberation of a "flap" or cleavage fragment from the primary probe that interacts with the secondary probe. In some embodiments, the secondary probe comprises at least one label. In some embodiments, the secondary probe comprises at least a pair of labels, such as an interacting pair of labels, e.g., a FRET pair or a fluorophore and quencher. In some embodiments, interaction of the secondary probe with a liberated flap of the primary probe results in a detectable change in the emission properties of the second probe, e.g., as discussed below with respect to INVADER® assays, FRET, and/or quenching. In some embodiments, a probe system comprises a primary probe and a secondary probe configured to interact with a liberated flap of the primary probe, e.g., the primary probe can be cleaved to give a liberated flap sufficiently complementary to the secondary probe or a segment thereof to form a complex.

By "hybridization" or "hybridize" is meant the ability of two completely or partially complementary nucleic acid strands to come together under specified hybridization assay conditions in a parallel or antiparallel orientation to form a stable structure having a double-stranded region. The two constituent strands of this double-stranded structure, sometimes called a hybrid, are held together by hydrogen bonds. Although these hydrogen bonds most commonly form between nucleotides containing the bases adenine and thymine or uracil (A and T or U) or cytosine and guanine (C and G) on single nucleic acid strands, base pairing can also form between bases which are not members of these "canonical" pairs. Non-canonical base pairing is well-known in the art. (See, e.g., R. L. P. Adams et al., *The Biochemistry of the Nucleic Acids* (11th ed. 1992).)

As used herein, "specific" means pertaining to only one (or to only a particularly indicated group), such as having a particular effect on only one (or on only a particularly indicated group), or affecting only one (or only a particularly indicated group) in a particular way. For example, a cleaved 5' flap specific for a FRET cassette will be able to hybridize to that FRET cassette, form an invasive cleavage structure, and promote a cleavage reaction, but will not be able to hybridize to a different FRET cassette (e.g., a FRET cassette having a different 5' flap-hybridizing sequence) to promote a cleavage reaction. In addition, specific may be used in relation to a combination of oligonucleotides, such as a set of amplification and detection oligonucleotides (e.g., a amplification oligonucleotides may amplify multiple target sequences non-specifically but the detection oligonucleotides will only detect a specific amplified sequence, thus making the combination specific).

As used herein, the term "specifically hybridizes" means that under given hybridization conditions a probe or primer detectably hybridizes substantially only to its target sequence(s) in a sample comprising the target sequence(s) (i.e., there is little or no detectable hybridization to non-targeted sequences). Notably, for example in the case of various polymorphic *C. difficile* toxin and toxin-related gene sequences, an oligomer or combination thereof can be configured to specifically hybridize to any one of a set of targets. Thus, an oligomer described as specifically hybridizing to a first tcdC allele can also (but does not necessarily) specifically hybridize to a second (or a second and third, etc.) tcdC allele. Amplification and detection oligomers that specifically hybridize to a target nucleic acid are useful to amplify and detect target nucleic acids, but not non-targeted nucleic acids, especially non-targeted nucleic acids of phylogenetically closely related organisms such as Clostridia other than *C. difficile* or in some cases alleles that give rise to a phenotype different from the phenotype associated with a targeted allele. Thus, the oligomer hybridizes to target nucleic acid to a sufficiently greater extent than to non-target nucleic acid to enable one having ordinary skill in the art to accurately amplify and/or detect the presence (or absence) of nucleic acid derived from the specified target (e.g., toxigenic *C. difficile*) as appropriate. In general, reducing the degree of complementarity between an oligonucleotide sequence and its target sequence will decrease the degree or rate of hybridization of the oligonucleotide to its target region. However, the inclusion of one or more non-complementary nucleosides or nucleobases may facilitate the ability of an oligonucleotide to discriminate against non-targeted nucleic acid sequences.

Specific hybridization can be measured using techniques known in the art and described herein, such as in the examples provided below. In some embodiments, there is at least a 10-fold difference between target and non-target hybridization signals in a test sample, at least a 100-fold difference, or at least a 1,000-fold difference. In some embodiments, non-target hybridization signals in a test sample are no more than the background signal level.

By "stringent hybridization conditions," or "stringent conditions" is meant conditions permitting an oligomer to preferentially hybridize to a target nucleic acid (e.g., *C. difficile* nucleic acid) and not to nucleic acid derived from a closely related non-targeted organisms. While the definition of stringent hybridization conditions does not vary, the actual reaction environment that can be used for stringent hybridization may vary depending upon factors including the GC content and length of the oligomer, the degree of similarity between the oligomer sequence and sequences of targeted and non-targeted nucleic acids that may be present in the test sample. Hybridization conditions include the temperature and the composition of the hybridization reagents or solutions. Exemplary hybridization assay conditions for amplifying and/or detecting target nucleic acids derived from one or more strains of *C. difficile* with the oligomers of the present disclosure correspond to a temperature of 63° C. to 72° C. or 65° C. to 69° C. when the salt concentration, such as a divalent salt, e.g., $MgCl_2$, is in the range of 5-21 mM. Additional details of hybridization conditions are set forth in the Examples section. Other acceptable stringent hybridization conditions could be easily ascertained by those having ordinary skill in the art.

"Label" or "detectable label" refers to a moiety or compound joined directly or indirectly to a probe that is detected or leads to a detectable signal. Direct joining can use covalent bonds or non-covalent interactions (e.g., hydrogen bonding hydrophobic or ionic interactions, and chelate or coordination complex formation) whereas indirect joining can use a bridging moiety or linker (e.g., via an antibody or additional oligonucleotide(s), which amplify a detectable signal. Any detectable moiety can be used, e.g., radionuclide, ligand such as biotin or avidin, enzyme, enzyme substrate, reactive group, chromophore such as a dye or particle (e.g., latex or metal bead) that imparts a detectable color, luminescent compound (e.g. bioluminescent, phosphorescent, or chemiluminescent compound), and fluorescent compound (i.e., fluorophore). Embodiments of fluorophores include those that absorb light (e.g., have a peak absorption wavelength) in the range of 495 to 690 nm and emit light (e.g., have a peak emission wavelength) in the range of 520 to 710 nm, which include those known as FAM™, TE™, HEX, CAL FLUOR™ (Orange or Red), CY, and QUASAR™ compounds. Fluorophores can be used in combination with a quencher molecule that absorbs light when in close proximity to the fluorophore to diminish background fluorescence. Such quenchers are well known in the art and include, e.g., BLACK HOLE QUENCHER™ (or BHQ™), Blackberry Quencher® (or BBQ-650®), Eclipse®, or TAMRA™ compounds. Particular embodiments include a "homogeneous detectable label" that is detectable in a homogeneous system in which bound labeled probe in a mixture exhibits a detectable change compared to unbound labeled probe, which allows the label to be detected without physically removing hybridized from unhybridized labeled probe (e.g., U.S. Pat. Nos. 5,283,174, 5,656,207, and 5,658,737). Exemplary homogeneous detectable labels include chemiluminescent compounds, including acridinium ester ("A") compounds, such as standard AE or AE derivatives which are well known (U.S. Pat. Nos. 5,656,207, 5,658,737, and 5,639,604). Methods of synthesizing labels, attaching labels to nucleic acid, and detecting signals from labels are known (e.g., Sambrook et al., *Molecular Cloning, A Laboratory Manual,* 2nd ed. (Cold Spring Harbor Laboratory Press, Cold Spring Harbor, NY, 1989) at Chapt. 10, and U.S. Pat. Nos. 5,658,737, 5,656,207, 5,547,842, 5,283, 174, 5,585,481, 5,639,604, and 4,581,333, and EP Pat. App. 0 747 706). Other detectably labeled probes include FRET cassettes, TaqMan™ probes, molecular torches, and molecular beacons. FRET cassettes are discussed in detail below. TaqMan™ probes include a donor and acceptor label wherein fluorescence is detected upon enzymatically degrading the probe during amplification in order to release the fluorophore from the presence of the quencher. Molecular torches and beacons exist in open and closed configurations wherein the closed configuration quenches the fluorophore and the open position separates the fluorophore from the quencher to allow a change in detectable fluorescent signal. Hybridization to target opens the otherwise closed probes.

Sequences are "sufficiently complementary" if they allow stable hybridization of two nucleic acid sequences, e.g., stable hybrids of probe and target sequences, although the sequences need not be completely complementary. That is, a "sufficiently complementary" sequence that hybridizes to another sequence by hydrogen bonding between a subset series of complementary nucleotides by using standard base pairing (e.g., G:C, A:T, or A:U), although the two sequences can contain one or more residues (including abasic positions) that are not complementary so long as the entire sequences in appropriate hybridization conditions to form a stable hybridization complex. Sufficiently complementary sequences can be at least 80%, at least 90%, or completely complementary in the sequences that hybridize together. Appropriate hybridization conditions are well known to those skilled in the art, can be predicted based on sequence composition, or can be determined empirically by using routine testing (e.g., Sambrook et al., *Molecular Coning, A Laboratory Manual,* 2$^{nd}$ ed. at §§ 1.90-1.91, 7.37-7.57, 9.47-9.51 and 11.47-11.57, particularly §§ 9.50-9.51, 11.12-11.13, 11.45-11.47 and 11.55-11.57).

A "non-extendable" oligomer includes a blocking moiety at or near its 3'-terminus to prevent extension. A blocking group near the 3' end is in some embodiments within five residues of the 3' end and is sufficiently large to limit binding of a polymerase to the oligomer, and other embodiments contain a blocking group covalently attached to the 3' terminus. Many different chemical groups can be used to block the 3' end, e.g., alkyl groups, non-nucleotide linkers, alkane-diol dideoxynucleotide residues (e.g., 3'-hexanediol residues), and cordycepin. Further examples of blocking moieties include a 3'-deoxy nucleotide (e.g., a 2',3'-dideoxy nucleotide); a 3'-phosphorylated nucleotide; a fluorophore, quencher, or other label that interferes with extension; an inverted nucleotide (e.g., linked to the preceding nucleotide through a 3'-to-3' phosphodiester, optionally with an exposed 5'-OH or phosphate); or a protein or peptide joined to the oligonucleotide so as to prevent further extension of a nascent nucleic acid chain by a polymerase. A non-extendable oligonucleotide of the present disclosure can be at least 10 bases in length, and can be up to 15, 20, 25, 30, 35, 40, 50 or more nucleotides in length. Non-extendable oligonucleotides that comprise a detectable label can be used as probes.

References, particularly in the claims, to "the sequence of SEQ ID NO: X" refer to the base sequence of the corresponding sequence listing entry and do not require identity of the backbone (e.g., RNA, 2'-O-Me RNA, or DNA) or base modifications (e.g., methylation of cytosine residues) unless otherwise indicated. Furthermore, T residues are understood to be interchangeable with U residues, and vice versa, unless otherwise indicated.

Unless otherwise indicated, "forward," "sense," "positive-sense," or "positive-strand" nucleic acid generally refers to the coding strand of an ORF (open reading frame) or non-coding nucleic acid on the same strand as the coding strand of the transcript, operon, mRNA, etc. of which it is a part, or otherwise of the closest ORF, and "reverse," "antisense," "negative-sense," "negative-strand" nucleic acid refers to the complement of a "sense," "positive-sense," or "positive-strand" nucleic acid. Exemplary sense-strand sequences are provided in SEQ ID NOs: 1-7 in the Sequence Table below. Unless otherwise indicated, "hybridizing to a nucleic acid" and the like includes hybridizing to either a sense or antisense strand thereof, e.g., either strand of a dsDNA sequence. Similarly, expressions such as "hybridization to a site comprising position X of SEQ ID NO: Y" and "competing for hybridization to SEQ ID NO: Y" can generally include hybridizing to either a sense or antisense strand of SEQ ID NO: Y; where a hybridized oligomer is configured to produce an amplicon, the proper orientation will be immediately apparent to one skilled in the art.

As used herein, the term "invasive cleavage structure" (or simply "cleavage structure") refers to a structure comprising (1) a target nucleic acid, (2) an upstream nucleic acid (e.g., an invasive probe oligonucleotide), and (3) a downstream nucleic acid (e.g., a primary probe oligonucleotide), where the upstream and downstream nucleic acids anneal to contiguous regions of the target nucleic acid, and where an overlap forms between the a 3' portion of the upstream nucleic acid and duplex formed between the downstream nucleic acid and the target nucleic acid. An overlap occurs where one or more bases from the upstream and downstream nucleic acids occupy the same position with respect to a target nucleic acid base, whether or not the overlapping base(s) of the upstream nucleic acid are complementary with the target nucleic acid, and whether or not those bases are natural bases or non-natural bases. In some embodiments, the 3' portion of the upstream nucleic acid that overlaps with the downstream duplex is a non-base chemical moiety such as an aromatic ring structure, as disclosed, for example, in U.S. Pat. No. 6,090,543. In some embodiments, one or more of the nucleic acids may be attached to each other, for example through a covalent linkage such as nucleic acid stem-loop, or through a non-nucleic acid chemical linkage (e.g., a multi-carbon chain). An invasive cleavage structure also is created when a cleaved 5' flap hybridizes to a FRET cassette (i.e., when the "target nucleic acid" and the "downstream nucleic acid" are covalently linked in a stem-loop configuration). The "target nucleic acid" sequence of a FRET cassette that hybridizes to a cleaved 5' flap can be referred to as a "5' flap-hybridizing sequence."

As used herein, an "INVADER assay" or "invasive cleavage assay" refers to an assay for detecting target nucleic acid sequences in which an invasive cleavage structure is formed and cleaved in the presence of the target sequence. In some embodiments, reagents for an invasive cleavage assay include: a cleavage agent, and oligonucleotides (e.g., an "invasive probe," a "primary probe," and a "FRET cassette"). In some embodiments the invasive probe is an amplification oligomer or extension product thereof. The invasive cleavage assay can combine two invasive signal amplification reactions (i.e., a "primary reaction" and a "secondary reaction") in series in a single reaction mixture. In some embodiments, detecting the presence of an invasive cleavage structure is achieved using a cleavage agent. The primary probe can be part of a probe system. In some embodiments, an additional portion of the primary probe comprises or consists of a 3' terminal nucleotide which is not complementary to the target nucleic acid and/or which is non-extendable. In some embodiments, an additional portion of the primary probe is configured to interact with a FRET cassette, e.g., comprises a FRET cassette interacting-sequence, e.g., which is not complementary to the target nucleic acid. In some embodiments, the reagents for an INVADER assay further comprise a nuclease, e.g., a cleavase, e.g., a FEN enzyme (e.g., Afu, Ave, RAD2 or XPG proteins) or other enzyme (e.g., a DNA polymerase with 5' nuclease activity, optionally with inactivated or reduced synthetic activity) wherein the nuclease has activity specific for a structure formed when both the invasive and primary probes are hybridized to a target sequence (e.g., a structure that can result when a duplex of the primary probe and the target undergoes 3'-end invasion by the invasive probe, wherein at least the 3' end and/or an intermediate portion of the invasive probe is hybridized, the 5' end of the primary probe is free, and an intermediate and/or 3'-terminal portion of the primary probe is hybridized). In some embodiments, the reagents for an INVADER assay further comprise a buffer solution. In some embodiments, the buffer solution comprises a source of divalent cations (e.g., Mn2+ and/or Mg2+ ions, such as a magnesium salt or manganese salt, e.g., MgCl$_2$, MnCl$_2$, magnesium acetate, manganese acetate, etc.). In some embodiments, the reagents for an INVADER assay further comprise at least one third oligomer, such as at least one amplification oligomer that together with the first oligomer is configured to produce an amplicon, e.g., via PCR. In such embodiments the primary probe can comprise a target-hybridizing sequence configured to specifically hybridize to the amplicon. In some embodiments, the reagents for an INVADER assay further comprise amplification reagents, such as PCR reagents. Embodiments of an INVADER assay in which the target sequence is amplified can be referred to as INVADER PLUS assays. Including amplification in the assay can provide a lower limit of detection. INVADER assays, cleavases, other nucleases, other possible INVADER/INVADER PLUS® reagents, etc., are discussed, for example, in U.S. Pat. Nos. 5,846,717, 5,985,557, 5,994,069, 6,001,567, 6,913,881, 6,090,543, 7,482,127, and 9,096,893; WO 97/27214; WO 98/42873; Lyamichev et al., Nat. Biotech., 17:292 (1999); Hall et al., PNAS, USA, 97:8272 (2000); and WO 2016/179093.

As used herein, the term "flap endonuclease" or "FEN" (e.g., "FEN enzyme") refers to a class of nucleolytic enzymes that act as structure-specific endonucleases on DNA structures with a duplex containing a single-stranded 5' overhang, or flap, on one of the strands that is displaced by another strand of nucleic acid, such that there are overlapping nucleotides at the junction between the single and double-stranded DNA. FEN enzymes catalyze hydrolytic cleavage of the phosphodiester bond 3' adjacent to the junction of single and double stranded DNA, releasing the overhang, or "flap" (see Trends Biochem. Sci. 23:331-336 (1998) and Ann. Rev. Biochem. 73: 589-615 (2004)). FEN enzymes may be individual enzymes, multi-subunit enzymes, or may exist as an activity of another enzyme or protein complex, such as a DNA polymerase. A flap endonuclease may be thermostable. Examples of FEN enzymes useful in the methods disclosed herein are described in U.S. Pat. Nos. 5,614,402; 5,795,763; 6,090,606; and in published PCT applications identified by WO 98/23774; WO 02/070755; WO 01/90337; and WO 03/073067, each of which is incorporated by reference in its entirety. Particular examples of commercially available FEN enzymes include the Cleavase® enzymes (Hologic, Inc.).

"Cassette," when used in reference to an INVADER assay and/or invasive cleavage assay or reaction, as used herein refers to an oligomer or combination of oligomers configured to generate a detectable signal in response to cleavage of a detection oligomer in an INVADER assay. In some embodiments, the cassette hybridizes to an cleavage product (e.g., a "flap") from cleavage of the detection oligomer (e.g., primary probe). In some embodiments, such hybridization results in a detectable change in fluorescence. In some embodiments, such hybridization forms a second invasive cleavage structure, such that the cassette can then be cleaved. In some embodiments, a cassette comprises an interacting pair of labels, e.g., a FRET pair (in which case the cassette is a "FRET cassette"). In some embodiments, a FRET cassette undergoes a detectable change in fluorescence properties upon hybridization to an cleavage product from cleavage of the detection oligomer. For example, a FRET cassette can increase fluorescence emission at a first wavelength and/or decrease fluorescence emission at a second wavelength based on a change in the average distance between labels upon hybridization to a cleavage product from cleavage of the detection oligomer. This can result from a decrease in energy transfer from a donor fluorophore (e.g., a decrease in quenching of a fluorophore or a decrease in energy transfer from a donor fluorophore to an acceptor fluorophore). In some embodiments, a FRET cassette adopts a hairpin conformation, wherein the interaction of the pair of labels substantially suppresses (e.g., quenches) a detectable energy emission (e.g., a fluorescent emission). In some embodiments, a FRET cassette comprises a portion that hybridizes to a complementary cleaved 5' flap of a primary probe to form an invasive cleavage structure that is a substrate for a cleavage agent (e.g., FEN enzyme). In some embodiments, cleavage of the FRET cassette by a cleavage agent separates the donor and acceptor moieties with the result of relieving the suppression and permitting generation of a signal.

A "117del tcdC allele" is an allele of *C. difficile* tcdC in which there is a deletion corresponding to position 117 of the wild-type tcdC open reading frame. Thus, for example, in the exemplary 117del sequence SEQ ID NO: 3, positions 112-121 are ATTTTGGCGT, while in the exemplary wild-type sequence fragment SEQ ID NO: 2, positions 112-122 are ATTTTAGGCGT. Position 117 has been observed to be polymorphic, with G and T known to occur there as well (see SEQ ID NOs: 1 and 4, respectively). Thus, a "117D tcdC allele" is one in which an A, G, or T is present at position 117 (D is the IUPAC ambiguity code for A, G, or T/U), and the individual non-deletion polymorphs are 117A, 117G, and 117T tcdC alleles. One skilled in the art can identify corresponding positions between sequence variants using known alignment methods, such as the Smith-Waterman or Needleman-Wunsch algorithms using standard parameters. Highly similar sequences such as SEQ ID NOs: 1-5 can alternatively be manually aligned.

A "184T tcdC allele" is an allele of *C. difficile* tcdC in which there is a T at the position corresponding to position 184 of the wild-type tcdC open reading frame. Thus, for example, in the exemplary 184T sequence SEQ ID NO: 5, positions 179-189 are CTAATTAAACA, while in the exemplary wild-type sequence fragment SEQ ID NO: 2, positions 179-189 are CTAACCAAACA. Position 183 is also polymorphic, and 184T and 184C alleles each can be either 183C or 183T (for example, SEQ ID NO: 2 is 183C 184C, SEQ ID NOs: 1 and 4 are 183T 184C, and SEQ ID NO: 5 is 183T 184T). Identification of corresponding positions is as discussed above.

Unless defined otherwise, all scientific and technical terms used herein have the same meaning as commonly understood by those skilled in the relevant art. General definitions can be found in technical books relevant to the art of molecular biology, e.g., DICTIONARY OF MICROBIOLOGY AND MOLECULAR BIOLOGY, 2nd ed. (Singleton et al., 1994, John Wiley & Sons, New York, NY) or THE HARPER COLLINS DICTIONARY OF BIOLOGY (Hale & Marham, 1991, Harper Perennial, New York, NY).

Exemplary Compositions, Kits, Methods, and Uses

The present disclosure provides oligomers, compositions, and kits, useful for amplifying and detecting *C. difficile* nucleic acids from a sample.

In some embodiments, oligomers are provided, e.g., in a kit or composition. Oligomers generally comprise a target-hybridizing region, e.g., configured to hybridize specifically to a *C. difficile* nucleic acid, such as a *C. difficile* toxin or toxin-related gene, for example, tdA, tcdB, tcdC, cdtA, or cdtB. While oligomers of different lengths and base composition can be used for amplifying *C. difficile* nucleic acids, in some embodiments oligomers in this disclosure have target-hybridizing regions from 10-60 bases in length, 12-50 bases in length, 12-40 bases in length, 12-35 bases in length, or 12-30 bases in length. In some embodiments, an oligomer comprises a second region of sequence in addition to the target-hybridizing region, which can be located 5' of the target-hybridizing region. In some embodiments, an oligomer does not comprise a second region of sequence. In some embodiments, the second region of sequence is a promoter. In some embodiments, the second region of sequence is configured to interact with a FRET cassette.

In some embodiments, a pair of oligomers is provided wherein one oligomer is configured to hybridize to a sense strand of a *C. difficile* nucleic acid and the other is configured to hybridize to an anti-sense strand of a *C. difficile* nucleic acid. Such oligomers include primer pairs for PCR or other forms of amplification.

In some embodiments, one or more oligomers, such as a primer set (defined as at least two primers configured to generate an amplicon from a target sequence) or a primer set and an additional oligomer (e.g., detection oligomer) which is optionally non-extendible and/or labeled (e.g., for use as a primary probe or part of a probe system, such as together with a FRET cassette), are configured to hybridize to at least one, two, three, or four *C. difficile* toxin or toxin-related genes, for example, tcdA, tcdB, tcdC, cdtA, or cdtB. When present, the additional oligomer (e.g., detection oligomer) can be configured to specifically hybridize to an amplicon produced by the primer set.

In some embodiments, a plurality of oligomers are provided which collectively hybridize to tcdA and tcdB; tcdC and tcdA; tcdB and tcdC; tcdC and cdtB; tcdB and cdtB; tcdA and cdtB; tcdA, tcdB, and tcdC; tcdA, tcdB, and cdtB; tcdA, cdtB, and tcdC; cdtB, tcdB, and tcdC; cdtB, tcdA, tcdB, and tcdC; tcdC and cdtA; tcdB and cdtA; tcdA and cdtA; tcdA, dB, and tcdC; tcdA, tcdB, and tcdA; tcdA, cdtA, and tcdC; cdtA, tcdB, and tcdC; cdtA, tcdA, tcdB, and tcdC; or cdtA, cdtB, tcdA, tcdB, and tcdC, it being understood that the foregoing gene names refer to *C. difficile* genes. In some embodiments, a plurality of primer sets is provided which collectively hybridize to any one of the foregoing combinations of genes. In some embodiments, a plurality of primer sets and additional oligomers (e.g., detection oligomers) which are optionally non-extendible and/or labeled (e.g., for use as a primary probe, optionally as part of a probe system, such as together with a FRET cassette) is provided which collectively hybridize to any one of the foregoing combinations of genes.

Exemplary cdtA, cdtB, tcdA, tcdB, and tcdC sequences are provided in the Sequence Table below. Additional exemplary sequences are provided, for example, in GenBank and can be accessed by one skilled in the art.

In some embodiments, one or more oligomers in a set, kit, composition, or reaction mixture comprise a methylated cytosine (e.g., 5-methylcytosine). In some embodiments, at least half of the cytosines in an oligomer are methylated. In some embodiments, all or substantially all (e.g., all but one or two) of the cytosines in an oligomer are methylated. In some embodiments, all or substantially all cytosines are methylated except for one or more cytosines at the 3' end or within 2, 3, 4, or 5 bases of the 3' end are unmethylated. Cytosine methylation can be used to modulate the affinity of an oligomer for a target and generally can result in an increased melting temperature for the hybridized complex.

Exemplary oligomer sets (primer pairs and detection oligomers, e.g., to be labeled or used as primary detection oligomers) and probe systems (primary and secondary detection oligomers) are set forth in the following tables. It should be understood that a detection oligomer in Table A, when used as a primary detection oligomer (e.g., with a structure-specific nuclease, such as in an invasive cleavage assay, e.g., an INVADER or INVADER PLUS® assay), can be combined with any secondary detection oligomer associated with that primary detection oligomer in Table B.

Table A. Exemplary oligomer sets. Oligomers are referred to by their SEQ ID NO (see the Sequence Table below). The allele(s) targeted by the exemplary detection

TABLE A

Exemplary oligomer sets. Oligomers are referred to by their SEQ ID NO (see the Sequence Table below). The allele(s) targeted by the exemplary detection oligomers for tcdC in Table A are indicated in parentheses. The oligomers can include methylation, labeling, and other non-sequence features noted in the Sequence Table.

| Oligomer 1 (e.g., forward primer) SEQ ID NO(s) | Oligomer 2 (e.g., reverse primer) SEQ ID NO(s) | Detection Oligomer (optionally labeled and/or non-extendable, e.g., probe) SEQ ID NO(s) |
|---|---|---|
| For targeting tcdC | | |
| 243 | one or more of 87-90 or 192-193 (reverse iPrimers) | 117del probes: one or more of 138, 141-171, 175-182 |
| 244 | same as above | same as above |
| 245 | same as above | same as above |
| 246 | same as above | same as above |
| 247 | same as above | same as above |
| 248 | same as above | same as above |
| 76 (forward iPrimer) | one or more of 251-259 (one or more of 251-255 if detecting 184T polymorphism in addition to 117del) | one or more of 188-191 |
| 243 | one or more of 251-259 (one or more of 251-255 if detecting 184T polymorphism in addition to 117del) | 117del probes: one or more of 138, 141-171, 175-182 with 86* and/or 184T probes: one or more of 201-204 with one or more of 194*, 195*, or 196*; or one or more of 213, 215, 217, or 218 with 205*; or one or more of 202, 204, 239, 240, 242 with 223* |
| 244 | same as above | same as above |
| 245 | same as above | same as above |
| 246 | same as above | same as above |
| 247 | same as above | same as above |
| 248 | same as above | same as above |
| 243 | 192 (reverse iPrimer) | 117del probes: one or more of 138, 141-171, 175-182 with 86* |
| 244 | same as above | same as above |
| 245 | same as above | same as above |
| 246 | same as above | same as above |
| 247 | same as above | same as above |
| 248 | same as above | same as above |
| one or more of 243, 244, 245, 246, 247, or 248 | 225 (reverse iPrimer) | 184T probes: one or more of 213, 215, 217, or 218 |
| same as above | 221 (reverse iPrimer) | 184T probes: one or more of 214, 216, or 219 |
| For targeting tcdA | | |
| 59 | one or more of 70, 72, or 73 | 62 with 63* |
| 60 | same as above | same as above |
| 64 (forward iPrimer) | same as above | same as above |
| 65 (forward iPrimer) | same as above | same as above |
| 64 (forward iPrimer) | One or more of 70-73 | one or more of 58, 68, or 69 |
| 65 (forward iPrimer) | same as above | same as above |
| For targeting tcdB | | |
| 260 (forward iPrimer) | one or more of 318-220, 322 or 328-338, e.g., 328-334 | one or more of 299-316 (e.g., 305 and at least one of 302, 304, or 306) |
| 261 (forward iPrimer) | same as above | same as above |
| 260 and 261 (forward iPrimers) | same as above | same as above |
| 321 | same as above | same as above |
| 260 and 321 (forward iPrimers) | same as above | same as above |
| 262 (forward iPrimer) | same as above | same as above |
| 263 (forward iPrimer) | same as above | same as above |
| 262 and 263 (forward iPrimers) | same as above | same as above |

TABLE A-continued

Exemplary oligomer sets. Oligomers are referred to by their SEQ ID NO (see the Sequence Table below). The allele(s) targeted by the exemplary detection oligomers for tcdC in Table A are indicated in parentheses. The oligomers can include methylation, labeling, and other non-sequence features noted in the Sequence Table.

| Oligomer 1 (e.g., forward primer) SEQ ID NO(s) | Oligomer 2 (e.g., reverse primer) SEQ ID NO(s) | Detection Oligomer (optionally labeled and/or non-extendable, e.g., probe) SEQ ID NO(s) |
|---|---|---|
| 264 | one or more of 322 or 332-338, e.g., 337 and 338 | one or more of 299, 312, or 316 with 280* |
| 265 | same as above | same as above |
| 266 | same as above | same as above |
| 268 | same as above | same as above |
| 269 | same as above | same as above |
| 270 | same as above | same as above |
| 271 | same as above | same as above |
| 272 | same as above | same as above |
| one or more of 264-279 or 339, e.g., a pair listed above | 317 (reverse iPrimer) | one or more of 299, 300, 308-312, or 316 |
| same as above | 323 (reverse iPrimer) | one or more of 300 or 307 |
| same as above | 324 (reverse iPrimer) | one or more of 299, 300, 308-312, or 316 |
| same as above | 325 (reverse iPrimer) | same as above |
| same as above | 324 and 325 (reverse iPrimers) | same as above |
| same as above | 324 and 326 (reverse iPrimers) | same as above |
| same as above | 326 (reverse iPrimer) | same as above |
| same as above | 336 (reverse iPrimer) | 300-306 or 308-311 |
| For targeting cdtA | | |
| 13 | one or more of 21-29 | one or more of 18-20 with 14* and/or 15* |
| For targeting cdtB | | |
| 30 (forward iPrimer if 47 used as probe) | one or more of 40 and 41 (reverse iPrimers if one or more of 37-39 used as probe) | one or more of 37-39 or 47 |
| 31 (forward iPrimer if 46 used as probe) | same as above | one or more of 37-39 or 46 |
| 32 (forward iPrimer if 46 used as probe) | same as above | same as above |
| 33 (forward iPrimer if 46 used as probe) | same as above | same as above |
| 30 (forward iPrimer if 47 used as probe) | one or more of 49, 50, and 56 | one or more of 38 with 42*; or 47; or 48 with 42* |
| 31 | same as above | one or more of 38 with 42*; or 46, 53, or 54; or 48 with 42* |
| 32 | same as above | same as above |
| 33 | same as above | same as above |

*used as an invasive oligomer to form a substrate for a structure-specific nuclease together with indicated detection oligomer The sets shown above are exemplary and not exclusive. For example, amplification oligomers should be oppositely oriented with convergent 3' ends, and detection oligomers should hybridize to an amplicon produced by the amplification oligomers (i.e., hybridization should occur in the region between amplification oligomer hybridization sites or in some cases overlapping the 3' end of an amplification oligomer hybridization site). In some embodiments, at least two forward primers targeting one of the genes referred to in Table A are used in combination. In some embodiments, at least two forward oligomers targeting tcdB are used in combination. Combinations of oligomers with different sequences can provide a benefit to assay sensitivity given the intraspecific heterogeneity of C. difficile sequences, including tcdB. See Example 2 below.

The detection oligomer SEQ ID NOs referred to in Table A (other than invasive oligomers) generally include 5' flap sequences, which are essentially arbitrary sequences that can interact with a FRET cassette after cleavage by a cleavage agent (see Table B below for exemplary secondary detection oligomers and 5' flap sequences that interact with them). Target-hybridizing sequences for the detection oligomers, which omit the 5' flap sequences, are also provided in the Sequence Table, and those skilled in the art will understand that the target hybridizing sequence of one detection oligomer can be paired with the 5' flap sequence of another detection oligomer or another 5' flap sequence that provides similar hybridization properties. Additionally, in some embodiments, the 5'-flap sequence may be omitted, such as in assay formats such as TaqMan where a 5'-flap is unnecessary in a detection oligomer. In some embodiments, a detection oligomer, such as a detection oligomer in a combination shown in Table A, is provided with a partially self-complementary sequence in place of the 5'-flap sequence, such as in the case of a molecular torch probe, discussed below.

Regarding tcdC, detection oligomers listed above are configured to detect (generate signal in the presence of) 117del or 184T alleles of tcdC, which are associated with hypervirulence. Thus, methods provided herein can be configured not to generate a positive signal in the presence of 117T 184C tcdC, or 117D 184C tcdC—that is, to the extent any signal is generated at all from the relevant detection system with such a tcdC allele, it is sufficiently low to be considered negative. The 117del primary probe and invasive oligomer (invader or iPrimer) can be configured so that the primary probe target-hybridizing sequence (e.g., SEQ ID NO: 93-137 or 184-187) hybridizes to a site on the opposite side of the deletion from the invasive oligomer, such that the 3' end of the invasive oligomer is close enough to the 5'-end of the target-hybridizing sequence to form an invasive cleavage structure when both are in a complex with a 117del allele, but not a 117D allele. SEQ ID NOs: 106 (primary probe target hybridizing sequence) and 88 (iPrimer) (in part) are shown below as examples, respectively, aligned with an excerpt of SEQ ID NO: 3, a 117del allele (position indicated with an asterisk), in which the deletion site is indicated with a dash. (As discussed elsewhere herein, the primary probe can have a nonextendable 3'-end to prevent extension.) The 5'-end of the primary probe target-hybridizing sequence and the 3'-end of the invasive oligomer (here, iPrimer) both occupy position 118, and there is a one-nucleotide offset between positions 112 and position 118 when aligning the probe (AAA—) and target (TTTT—) resulting in a bulge forming in the target strand between positions 112 and 118, thereby allowing for formation of an invasive cleavage structure and subsequent detection in an INVADER or INVADER PLUS assay. There would be a two-nucleotide offset if a 117D tcdC allele were present instead, which would destabilize the tertiary structure needed thereby reducing or eliminating the formation of an invasive cleavage structure and subsequent detection in an INVADER or INVADER PLUS assay, thus resulting in allele-specific detection. Thus, in some embodiments, an invasive oligomer and primary probe for detecting a 117del tcdC allele are provided that hybridize to sites that induce a bulge in the target sequence under the primary probe in a complex with a 117del allele, and substantially destabilize the invasive cleavage structure in a complex with a 117D allele. Notably, this approach should render the identity of the nucleotide at position 117 of a 117D allele essentially irrelevant because its effect on spacing rather than its base-pairing properties is what feeds into the assay outcome, thus reducing or eliminating possible errors that the various known non-hypervirulent polymorphisms at this position might otherwise cause.

| SEQ ID NO: | |
|---|---|
| 106 | 3'-AACGAGATGACCGTAAAUAAA--C-5' |
| 88 | 3'-CCACACAAAAAACCGTTA . . . -5' |
| 3 | 5'- . . . agggtattgctctactggcatttattttt-ggcgtgtttttggcaat . . . -3'<br>                                                       * |

Shown above are positions 1-22 of SEQ ID NO: 106, positions 11-29 of SEQ ID NO: 88, and positions 89-134 of SEQ ID NO: 3.

The 184T primary probe and invasive oligomer (invader or iPrimer) can be configured so that the primary probe target-hybridizing sequence (e.g., SEQ ID NO: 197-200 or 206-212) and the invasive oligomer hybridize to overlapping sites including position 184, e.g., such that the 5'-nucleotide of the primary probe (whose position corresponds to the 3'-terminal nucleotide of the invasive oligomer) can form a Watson-Crick base pair with the base at position 184 in a complex with a 184T allele, but not in a complex with a 184C allele. The absence of a Watson-Crick base pair at this position when the allele is 184C is intended to reduce or eliminate formation of a recognizable invasive cleavage structure that is formed when a 184T allele is present, and thus provide allele-specific detection. Shown below as examples are SEQ ID NOs: 198 (primary probe target-hybridizing sequence) and 194 (invader) (in part), along with an excerpt of the reverse complement of SEQ ID NO: 5, with an asterisk to mark position 184. Thus, in some embodiments, an invasive oligomer and primary probe for detecting a 184T tcdC allele are provided that hybridize to sites that overlap, wherein the nucleotide of the primary probe at the position corresponding to the 3'-terminal nucleotide of the invasive oligomer forms a Watson-Crick base pair in a complex with a 184T allele but not a 184C allele. In some embodiments, an invasive oligomer and primary probe for detecting a 184T tcdC allele are provided that hybridize to sites that overlap, wherein the 3'-penultimate nucleotide of the invasive oligomer forms a Watson-Crick base pair in a complex with a 183T allele but not a 183C allele.

5,656,744). A label, such as a fluorescent or chemiluminescent label, can be attached to the probe by a non-nucleotide linker (see. e.g., U.S. Pat. Nos. 5,585,481; 5,656,744; and 5,639,604). In some embodiments, an oligomer is provided that is non-extendible and hybridizes to a site in a *C. difficile* nucleic acid that overlaps the hybridization site of an additional oligomer in a kit or composition, such as an ampli-

| SEQ ID NO: | |
|---|---|
| 198 | 5'-TAAACATCAGTTATAGATTCTC-3' |
| 194 | 5'- . . . AGGAGGTCATTTCTAATa-3' |
| 5(rc) | 3'- . . . TCCTCCAGTAAAGATTAATTTGTAGTCAATATCTAAGAGTTTTTG . . . -5' |
| | * |

Shown above are positions 1-22 of SEQ ID NO: 198, positions 12-30 of SEQ ID NO: 194, and the reverse complement of positions 167-212 of SEQ ID NO: 5.

Table B.

Exemplary secondary detection oligomer pairings with primary detection oligomer 5'-flap sequences. Secondary detection oligomers are referred to by their SEQ ID NO (see the Sequence Table below). In some embodiments, a combination of a secondary detection oligomer in Table B with a compatible primary detection oligomer (primary probe) further comprises an invasive oligomer associated with the compatible primary detection oligomer in Table A.

| Primary Detection Oligomer 5' flap sequence | Secondary Detection Oligomer (e.g., FRET cassette) |
|---|---|
| aggccacggacg (e.g., 5'-flap sequence from SEQ ID NO: 37-39 or 53-54) | 10 |
| cgcgccgagg (e.g., 5'-flap sequence from SEQ ID NO: 138-167, 201-204, 213-216, 230-232, or 299) | 11 |
| acggacgcggag (e.g., 5'-flap sequence from SEQ ID NO: 69, 188, 190, 218-219, 240-242, or 300-316) | 12 |

In some embodiments, an oligomer is provided that comprises a label and/or is non-extendable. Such an oligomer can be used as a probe or as part of a probe system (e.g., as a FRET cassette in combination with a target-binding detection oligomer). In some embodiments, the labeled oligomer comprises a sequence corresponding to a SEQ ID NO listed in the Detection Oligomer column of Table A, or a target-hybridizing sequence thereof. In some embodiments, the label is a non-nucleotide label. Suitable labels include compounds that emit a detectable light signal, e.g., fluorophores or luminescent (e.g., chemiluminescent) compounds that can be detected in a homogeneous mixture. More than one label, and more than one type of label, can be present on a particular probe, or detection can rely on using a mixture of probes in which each probe is labeled with a compound that produces a detectable signal (see. e.g., U.S. Pat. Nos. 6,180,340 and 6,350,579). Labels can be attached to a probe by various means including covalent linkages, chelation, and ionic interactions. In some embodiments the label is covalently attached. For example, in some embodiments, a detection probe has an attached chemiluminescent label such as, e.g., an acridinium ester (AE) compound (see. e.g., U.S. Pat. Nos. 5,185,439; 5,639,604; 5,585,481; and fication oligomer (e.g., iPrimer) or an invasive oligomer that is not used as a primer. Hybridization of such oligomers can form a substrate for a structure-specific nuclease, e.g., as part of the detection mechanism in an INVADER or INVADER PLUS assay.

In some embodiments, a labeled oligomer (e.g., comprising a fluorescent label) further comprises a second label that interacts with the first label. For example, the second label can be a quencher. Such probes can be used (e.g., in TaqMan™ assays) where hybridization of the probe to a target or amplicon followed by nucleolysis by a polymerase comprising 5'-3' exonuclease activity results in liberation of the fluorescent label and thereby increased fluorescence, or fluorescence independent of the interaction with the second label. Such probes can also be used (e.g., in INVADER or INVADER PLUS assays (e.g., as FRET cassettes)). In some embodiments, the labeled oligomer has a SEQ ID NO listed in the Secondary Detection Oligomer column of Table B.

In some applications, one or more probes exhibiting at least some degree of self-complementarity are used to facilitate detection of probe:target duplexes in a test sample without first requiring the removal of unhybridized probe prior to detection. Specific embodiments of such detection probes include, for example, probes that form conformations held by intramolecular hybridization, such as conformations generally referred to as hairpins. Suitable hairpin probes include a "molecular torch" (see. e.g., U.S. Pat. Nos. 6,849,412; 6,835,542; 6,534,274; and 6,361,945) and a "molecular beacon" (see. e.g., U.S. Pat. Nos. 5,118,801 and 5,312,728). Molecular torches include distinct regions of self-complementarity (coined "the target binding domain" and "the target closing domain") which are connected by a joining region (e.g., a —($CH_2CH_2O$)$_3$-linker) and which hybridize to one another under predetermined hybridization assay conditions. When exposed to an appropriate target or denaturing conditions, the two complementary regions (which can be fully or partially complementary) of the molecular torch melt, leaving the target binding domain available for hybridization to a target sequence when the predetermined hybridization assay conditions are restored. Molecular torches are designed so that the target binding domain favors hybridization to the target sequence over the target closing domain. The target binding domain and the target closing domain of a molecular torch include interacting labels (e.g., fluorescent/quencher) positioned so that a different signal is produced when the molecular torch is self-hybridized as opposed to when the molecular torch is hybridized to a target nucleic acid, thereby permitting detection of probe:target duplexes in a test sample in the presence of unhybridized probe having a viable label associated therewith.

Examples of interacting donor/acceptor label pairs that can be used in connection with the disclosure include fluorescein/tetramethylrhodamine, IAEDANS/fluororescein, EDANS/DABCYL, coumarin/DABCYL, fluorescein/fluorescein, BODIPY® FL/BODIPY® FL, fluorescein/DABCYL, lucifer yellow/DABCYL, BODIPY®/DABCYL, eosine/DABCYL, erythrosine/DABCYL, tetramethylrhodamine/DABCYL, Texas Red/DABCYL, CY5/BHQ1®, CY5/BHQ2®, CY5/BHQ3®, CY5.5/BHQ3®, Quasar 670®/BHQ3®, Quasar 705®/BHQ3®, CY3/BHQ1®, CY3/BHQ2® and fluorescein/QSY7® dye. Those having an ordinary level of skill in the art will understand that when donor and acceptor dyes are different, energy transfer can be detected by the appearance of sensitized fluorescence of the acceptor or by quenching of donor fluorescence. Non-fluorescent acceptors such as DABCYL and the QSY7® dyes advantageously eliminate the potential problem of background fluorescence resulting from direct (i.e., non-sensitized) acceptor excitation. Exemplary fluorophore moieties that can be used as one member of a donor-acceptor pair include fluorescein, HEX, ROX, and the CY dyes (such as CY5). Exemplary quencher moieties that can be used as another member of a donor-acceptor pair include DABCYL, BLACKBERRY QUENCHER® which are available from Berry and Associates (Dexter, MI), and the BLACK HOLE QUENCHER® moieties which are available from Biosearch Technologies, Inc., (Novato, CA). One of ordinary skill in the art will be able to use appropriate pairings of donor and acceptor labels for use in various detection formats (e.g., FRET, TaqMan™, INVADER, etc).

In some embodiments, a detection oligomer (e.g., probe, primary probe, or labeled probe) is non-extendable. For example, the labeled oligomer can be rendered non-extendable by a 3'-adduct (e.g., 3'-phosphorylation or 3'-alkane-diol), having a 3'-terminal 3'-deoxynucleotide (e.g., a terminal 2',3'-dideoxynucleotide), having a 3'-terminal inverted nucleotide (e.g., in which the last nucleotide is inverted such that it is joined to the penultimate nucleotide by a 3' to 3' phosphodiester linkage or analog thereof such as a phosphorothioate), or having an attached fluorophore, quencher, or other label that interferes with extension (possibly but not necessarily attached via the 3' position of the terminal nucleotide). In some embodiments, the 3'-terminal nucleotide is not methylated. In some embodiments, a detection oligomer comprises a 3'-terminal adduct such as a 3'-alkanediol (e.g., hexanediol).

In some embodiments, an oligomer such as a detection oligomer is configured to specifically hybridize to an amplicon generated from C. difficile tcdA, tcdB, tcdC, cdtA, or cdtB (e.g., the oligomer comprises or consists of a target-hybridizing sequence sufficiently complementary to the amplicon for specific hybridization). The target-hybridizing sequence can include additional nucleotides beyond the sequence of any SEQ ID NO or variant thereof present in the oligomer.

Also provided by the disclosure is a reaction mixture for determining the presence or absence of a C. difficile target nucleic acid in a sample. A reaction mixture in accordance with the present disclosure comprises at least one or more of the following: an oligomer combination as described herein for amplification of at least one of C. difficile tcdA, tcdB, tcdC, cdtA, or cdtB or any of the combinations thereof noted above; and at least one detection probe oligomer as described herein for determining the presence or absence of at least one of C. difficile tcdA, tcdB, tcdC, cdtA, or cdtB or any of the combinations thereof noted above. The reaction mixture can further include a number of optional components such as, for example, capture probes (e.g., poly-(k) capture probes as described in US 2013/0209992, which is incorporated herein by reference). For an amplification reaction mixture, the reaction mixture will typically include other reagents suitable for performing in vitro amplification such as, buffers, salt solutions, appropriate nucleotide triphosphates (e.g., dATP, dCTP, dGTP, and one or both of dTTP or dUTP; and/or ATP, CTP, GTP and UTP), and/or enzymes (e.g., a thermostable DNA polymerase, and/or reverse transcriptase and/or RNA polymerase and/or FEN enzyme), and will typically include test sample components, in which a C. difficile nucleic acid may or may not be present. A reaction mixture can include amplification oligomers for at least one of C. difficile tcdA, tcdB, tcdC, cdtA, or cdtB or any of the combinations thereof noted above. In addition, for a reaction mixture that includes a detection probe together with an amplification oligomer combination, selection of amplification oligomers and detection probe oligomers for a reaction mixture are linked by a common target region (i.e., the reaction mixture will include a probe that binds to a sequence amplifiable by an amplification oligomer combination of the reaction mixture).

Also provided by the subject disclosure are kits for practicing the methods as described herein. A kit in accordance with the present disclosure comprises at least one or more of the following: an amplification oligomer combination as described herein for amplification of at least one of C. difficile tcdA, tcdB, tcdC, cdtA, or cdtB or any of the combinations thereof noted above; and at least one detection probe oligomer as described herein for determining the presence or absence of at least one of C. difficile tcdA, tcdB, tcdC, cdtA, or cdtB or any of the combinations thereof noted above. In some embodiments, any oligomer combination described herein is present in the kit. The kits can further include a number of optional components such as, for example, capture probes (e.g., poly-(k) capture probes as described in US 2013/0209992).

Other reagents that can be present in the kits include reagents suitable for performing in vitro amplification such as, e.g., buffers, salt solutions, appropriate nucleotide triphosphates (e.g., dATP, dCTP, dGTP, and one or both of dTTP or dUTP; and/or ATP, CTP, GTP and UTP), and/or enzymes (e.g., a thermostable DNA polymerase, and/or reverse transcriptase and/or RNA polymerase and/or FEN enzyme), and will typically include test sample components, in which a C. difficile nucleic acid may or may not be present. In addition, for a kit that includes a detection probe together with an amplification oligomer combination, selection of amplification oligomers and detection probe oligomers for a reaction mixture are linked by a common target region (i.e., the reaction mixture will include a probe that binds to a sequence amplifiable by an amplification oligomer combination of the reaction mixture). In certain embodiments, the kit further includes a set of instructions for practicing methods in accordance with the present disclosure, where the instructions can be associated with a package insert and/or the packaging of the kit or the components thereof.

Any method disclosed herein is also to be understood as a disclosure of corresponding uses of materials involved in the method directed to the purpose of the method. Any of the oligomers comprising C. difficile nucleic acid sequence and any combinations (e.g., kits and compositions, including but not limited to reaction mixtures) comprising such an oligomer are to be understood as also disclosed for use in detecting or quantifying toxigenic C. difficile, and for use in the preparation of a composition for detecting toxigenic C. difficile.

Broadly speaking methods can comprise one or more of the following components: target capture, in which C. difficile nucleic acid (e.g., from a sample, such as a clinical sample) is annealed to a capture oligomer (e.g., a specific or nonspecific capture oligomer); isolation (e.g., washing, to remove material not associated with a capture oligomer); amplification; and amplicon detection, which for example can be performed in real time with amplification. Certain embodiments involve each of the foregoing steps. Certain embodiments involve exponential amplification, optionally with a preceding linear amplification step. Certain embodiments involve exponential amplification and amplicon detection. Certain embodiments involve any two of the components listed above. Certain embodiments involve any two components listed adjacently above (e.g., washing and amplification, or amplification and detection).

In some embodiments, amplification comprises (1) contacting the sample with at least two oligomers for amplifying at least one of C. difficile tcdA, tcdB, tcdC, cdtA, or cdtB or any of the combinations thereof noted above, where the oligomers include at least two amplification oligomers as described above (e.g., one or more oriented in the sense direction and one or more oriented in the antisense direction for exponential amplification); (2) performing an in vitro nucleic acid amplification reaction, where any of at least one of C. difficile tcdA, tcdB, tcdC, cdtA, or cdtB or any of the combinations thereof noted above present in the sample is used as a template for generating an amplification product; and (3) detecting the presence or absence of the amplification product, thereby determining the presence or absence of at least one of C. difficile tdA, tcdB, tcdC, cdtA, or cdtB or any of the combinations thereof noted above in the sample.

A detection method in accordance with the present disclosure can further include the step of obtaining the sample to be subjected to subsequent steps of the method. In certain embodiments, "obtaining" a sample to be used includes, for example, receiving the sample at a testing facility or other location where one or more steps of the method are performed, receiving the sample from a subject or person providing or assisting in treatment of a subject, and/or retrieving the sample from a location (e.g., from storage or other depository) within a facility where one or more steps of the method are performed.

In certain embodiments, the method includes purifying C. difficile nucleic acid from other components (e.g., non-nucleic acid components) in a sample before an amplification (e.g., a capture step). Such purification can include methods of separating and/or concentrating organisms contained in a sample from other sample components, or removing or degrading non-nucleic acid sample components (e.g., protein, carbohydrate, salt, lipid, etc). In some embodiments, a sample such as a crude sample is contacted with a wash liquid (e.g., water, buffer, detergent solution, etc.), for example, by associating the sample with a swab and transferring the swab into the wash liquid, wherein at least some impurities are released into the wash liquid. Then at least partially purified sample can be released from the swab into a carrier liquid (e.g., water, buffer, a lysis solution, etc.). In some embodiments, RNA in the sample is degraded (e.g., with RNase and/or heat), and optionally the RNase is removed or inactivated and/or degraded RNA is removed.

In particular embodiments, purifying the nucleic acid includes capturing the nucleic acid to specifically or non-specifically separate the nucleic acid from other sample components. Non-specific target capture methods can involve selective precipitation of nucleic acids from a substantially aqueous mixture, adherence of nucleic acids to a support that is washed to remove other non-nucleic acid sample components, or other approaches for physically separating nucleic acids from a mixture that contains or is suspected of containing C. difficile nucleic acid and other sample components.

Target capture can occur in a solution phase mixture that contains one or more capture probe oligomers that hybridize to the C. difficile target sequence under hybridizing conditions. For embodiments wherein the capture probe oligomers comprise a capture probe tail, the C. difficile-target:capture-probe complex is captured by applying hybridization conditions so that the capture probe tail hybridizes to an immobilized probe, e.g., associated with a support. Certain embodiments use a particulate solid support, such as paramagnetic beads.

Isolation can follow capture, wherein the complex on the solid support is separated from other sample components. Isolation can be accomplished by any appropriate technique (e.g., washing a support associated with the C. difficile-sequence one or more times (e.g., 2 or 3 times) to remove other sample components and/or unbound oligomer). In embodiments using a particulate solid support, such as paramagnetic beads, particles associated with the C. difficile-target can be suspended in a washing solution and retrieved from the washing solution, in some embodiments by using magnetic attraction. To limit the number of handling steps, the C. difficile target nucleic acid can be amplified by simply mixing the C. difficile target sequence in the complex on the support with amplification oligomers and proceeding with amplification steps.

Exponentially amplifying a C. difficile sequence utilizes an in vitro amplification reaction using at least two amplification oligomers that flank a target region to be amplified. In some embodiments, at least two amplification oligomers as described above are provided. In some embodiments, a plurality of pairs of amplification oligomers is provided, wherein the plurality comprises oligomer pairs configured to hybridize to at least 2, 3, or 4 of tcdA, tcdB, tcdC, cdtA, and cdtB, or at least 2, 3, or 4 of tcdA, tcdB, tcdC, and cdtB. The amplification reaction can be cycled or isothermal. Suitable amplification methods include, for example, replicase-mediated amplification, polymerase chain reaction (PCR), ligase chain reaction (LCR), strand-displacement amplification (SDA), and transcription-mediated amplification (TMA).

A detection step can be performed using any of a variety of known techniques to detect a signal specifically associated with the amplified target sequence, such as by hybridizing the amplification product with a labeled detection probe and detecting a signal resulting from the labeled probe (including from label released from the probe following hybridization in some embodiments). In some embodiments, the labeled probe comprises a second moiety, such as a quencher or other moiety that interacts with the first label, as discussed above. The detection step can also provide additional information on the amplified sequence, such as all or a portion of its nucleic acid sequence. Detection can be performed after the amplification reaction is completed, or can be performed simultaneously with amplifying the target region (e.g., in real time). In one embodiment, the detection step allows homogeneous detection (e.g., detection of the hybridized probe without removal of unhybridized probe from the mixture (see. e.g., U.S. Pat. Nos. 5,639,604 and 5,283,174)). In some embodiments, the nucleic acids are associated with a surface that results in a physical change, such as a detectable electrical change. Amplified nucleic acids can be detected by concentrating them in or on a matrix and detecting the nucleic acids or dyes associated with them (e.g., an intercalating agent such as ethidium bromide or cyber green), or detecting an increase in dye associated with nucleic acid in solution phase. Other methods of detection can use nucleic acid detection probes that are configured to specifically hybridize to a sequence in the amplified product and detecting the presence of the probe: product complex, or by using a complex of probes that can amplify the detectable signal associated with the amplified products (e.g., U.S. Pat. Nos. 5,424,413; 5,451,503; and 5,849,481; each incorporated by reference herein). Directly or indirectly labeled probes that specifically associate with the amplified product provide a detectable signal that indicates the presence of the target nucleic acid in the sample. In particular, the amplified product will contain a target sequence in or complementary to a sequence in the *C. difficile* chromosome, and a probe will bind directly or indirectly to a sequence contained in the amplified product to indicate the presence of *C. difficile* nucleic acid in the tested sample.

In some embodiments, amplified product is detected through an invasive cleavage assay that provides means for forming an invasive cleavage structure that requires the presence of a target nucleic acid. The assay further involves cleaving the invasive cleavage structure to release distinctive cleavage products. A cleavage agent such as a FEN enzyme, for example, is used to cleave the target-dependent invasive cleavage structure, thereby resulting in cleavage products that indicate the presence of specific target nucleic acid sequences in the sample. When two oligonucleotides hybridize to a target nucleic acid strand such that they form an overlapping invasive cleavage structure, as defined above, invasive cleavage can occur. Through the interaction of a cleavage agent (e.g., FEN enzyme) and the upstream oligonucleotide (i.e., the invasive probe), the cleavage agent can be made to cleave the downstream oligonucleotide (i.e., the primary probe) at an internal site such that a distinctive fragment is produced. The fragment, sometimes referred to as a "liberated flap" or "cleaved 5' flap" or simply a "flap" can then itself interact with a secondary probe such as a FRET cassette (e.g., by participating as an invasive probe in a subsequent reaction that generates a detectable signal (e.g., a fluorescent signal)). Such embodiments are described in U.S. Pat. Nos. 5,846,717, 5,985,557, 5,994,069, 6,001,567, and 6,090,543, WO 97/27214, WO 98/42873, Nat. Biotech., 17:292 (1999), PNAS, 97:8272 (2000), and WO 2016/179093. More specifically, a plurality of INVADER reactions, e.g., combined in a single reaction mixture, can be used for the multiplex applications disclosed herein, including detection of two or more of tcdA, tcdB, tcdC, cdtA, and cdtB, or two or more of of tcdA, tcdB, tcdC, and cdtB. Additionally, an internal control can also be included in the multiplex amplification and detection procedure.

Invasive cleavage assays can be used for detecting specific target sequences in unamplified, as well as amplified DNA (e.g., PCR product(s)), including genomic DNA, RNA, or an amplicon thereof. The primary probe and the invasive probe hybridize in tandem to the target nucleic acid to form an overlapping structure. An unpaired "flap" is included on the 5' end of the primary probe. A cleavage agent (e.g. a FEN enzyme, such as the Cleavase® enzymes available from Hologic, Inc.) recognizes the overlap and cleaves off the unpaired 5' flap. In some embodiments, in a secondary reaction, this cleaved product serves as an invasive probe on a FRET cassette to again create a structure recognized by the structure-specific enzyme. When the two labels on a single FRET cassette are separated by cleavage, a detectable fluorescent signal above background fluorescence is produced. Consequently, cleavage of this second invasive cleavage structure results in an increase in fluorescence, indicating the presence of the target sequence.

Alternatively, in embodiments that detect the amplified product near or at the end of the amplification step, a linear detection probe can be used to provide a signal to indicate hybridization of the probe to the amplified product. One example of such detection uses a luminescentally labeled probe that hybridizes to target nucleic acid. The luminescent label is then hydrolyzed from non-hybridized probe. Detection is performed by chemiluminescence using a luminometer (see, e.g., International Patent Application Pub. No. WO 89/002476). In other embodiments that use real-time detection, the detection probe can be a hairpin probe such as a molecular beacon, molecular torch, or hybridization switch probe that is labeled with a reporter moiety that is detected when the probe binds to amplified product. Such probes can comprise target-hybridizing sequences and non-target-hybridizing sequences. Various forms of such probes are described, e.g., in U.S. Pat. Nos. 5,118,801; 5,312,728; 5,925,517; 6,150,097; 6,849,412; 6,835,542; 6,534,274; and 6,361,945; and US Patent Application Pub. Nos. 2006/0068417A1 and 2006/0194240A1).

In some embodiments, one or more of an internal amplification control polynucleotide ("internal control"; e.g., a plasmid, plasmid fragment, or other polynucleotide, generally with a sequence unrelated to *C. difficile* sequences, e.g., to tcdA, tcdB, tcdC, cdtA, and cdtB), and oligomers for amplifying and detecting the internal control are provided as components of a composition or kit disclosed herein and/or are used in a method disclosed herein. Detection of an amplicon from the internal control can serve to avoid false negatives due to instrument or reagent failures when no target sequences are detected.

Below is a table illustrating interpretation of various possible results obtained from methods according to this disclosure. In some embodiments, results are interpreted according to this table. U indicates that detection of an amplicon is expected but unnecessary to the call. In embodiments where reagents for amplifying and/or detecting one or more targets shown below are not used, such as cdtA or tcdA, the table can be applied as if the relevant column referred to the particular target being detected (e.g., cdtB or tcdB).

TABLE C

| Interpretation of Results | | | | | |
|---|---|---|---|---|---|
| Amplicon Detection Results | | | | Toxigenic | Hyper- |
| tcdA or tcdB | tcdC 117 del or tcdC 184T | cdtA or cdtB | Internal control | *C. difficile* Call | virulence Call |
| + | − | − | U | Positive | Negative |
| + | − | + | U | Positive | Negative |
| + | + | + | U | Positive | Positive |
| − | − | + | U | Positive | Negative |
| − | + | − | U | Negative | Negative |
| − | + | + | U | Positive | Negative |
| − | − | − | + | Negative | Negative |
| − | − | − | − | Invalid | Invalid |

Abbreviations are as defined above.

EXAMPLES

The following examples are provided to illustrate certain disclosed embodiments and are not to be construed as limiting the scope of this disclosure in any way.

All references to SEQ ID NOs in the Examples section include the cytosine methylation, labels, and other features indicated in the Table of Sequences below.

General Reagents and Methods. Unless otherwise indicated, non-specific target capture was used to isolate nucleic acid. Exemplary non-specific target capture reagents and procedures are disclosed in Becker et al., US2013/0209992A1. Target capture procedures were generally performed using a Panther or Panther Fusion™ instrument.

Unless otherwise indicated, amplifications were performed on a Panther Fusion™ instrument or an ABI 7500 Fast™ instrument. Unless otherwise indicated, amplifications were performed with combinations of oligomers disclosed above designed to detect sequences amplified from one or more of tcdA, tcdB, tcdC, cdtA, and cdtB. In some experiments, a set of primary probes for tcdC was used wherein a first primary probe targeted a site comprising position 117 of SEQ ID NO: 3 (to detect the 117del allele of tcdC) and a second primary probe targeted a site comprising position 184 of SEQ ID NO: 5 (to detect the 184T allele of tcdC). These sequences were detected with at least forward and reverse amplification oligomers and at least one primary detection oligomer configured to specifically hybridize to the target sequence(s) in INVADER PLUS assays as described above. In some reactions, one or more amplification oligomers or an extension product thereof served as an invasive probe, i.e., an iPrimer. In some reactions, a separate invasive probe was used. An internal control plasmid was also generally included in the reactions.

Cleavase used in these Examples was the Afu FEN-1 endonuclease described in U.S. Pat. No. 9,096,893.

Amplification reagents were dNTPs at 25 µM each, a commercially available hot-start Taq polymerase, $MgCl_2$, Cleavase, MOPS and Tris buffers, non-acetylated BSA, and other components supplied by Promega® Master Mix. Primers were supplied at a final concentration of 0.2-0.75 µM unless otherwise indicated. Oligomer annealing temperatures were from 65° C. to 69° C. and a standard extension temperature of 72° C. was used for 10 cycles, followed by a series of cycles having a 65° C. INVADER reaction step. Unless otherwise indicated, data was collected for 35 INVADER reaction cycles. "No detection" indicates that Ct had not occurred by the 35th cycle of collected data.

As noted above, detection of amplicons used INVADER PLUS chemistry. One or more FRET cassettes were included that collectively corresponded to the primary probes. Where two tcdC primary probes were used, one FRET cassette (e.g., SEQ ID NO: 11) was used that would interact with fragments generated from either tcdC primary probe. Where tcdA and/or tcdB primary probes were used, one FRET cassette (e.g., SEQ ID NO: 12) was used that would interact with fragments (liberated flaps) generated from either of the tcdA and tcdB primary probes. Where at least one cdtB primary probe was used, a FRET cassette (e.g., SEQ ID NO: 10) was used that would interact with fragments (liberated flaps) generated therefrom. The FRET cassettes were labeled with a interactive label pair in an energy transfer relationship, where fluorescence emission was quenched when both members of the label pair were attached to the FRET cassette. Thus, a positive signal for a given target was generally interpreted as indicating that a target sequence was present and amplified by a corresponding set of primers; that an invasive cleavage structure comprising a primer or detection oligomer (invader oligomer), the amplicon, and the corresponding primary probe had been formed and cleaved by Cleavase; that the flap thereby liberated from the primary probe formed an invasive cleavage structure with the corresponding FRET cassette, which was then cleaved by Cleavase, thereby allowing fluorescent detection of a labeled cleavage product of the FRET cassette.

Example 1. Detection of tcdC Alleles

The tcdC amplification and detection oligomers shown in the Table of Sequences were designed. Combinations of oligomers were tested with samples containing 0 (negative control), 5, 10, or 100 copies of *C. difficile* tcdC in 25 µL reactions. Reactions were generally run in triplicate.

TABLE D

| tcdC amplification oligomer sets | |
|---|---|
| Set | Oligomers (SEQ ID NOs) |
| 1 | 247 & 249 |
| 2 | 247 & 250 |
| 3 | 247 & 255 |
| 4 | 247 & 251 |
| 5 | 247 & 252 |
| 6 | 247 & 258 |

Set 1 gave signal that was near but not at the threshold at 100 copies, with no detection at lower values. Set 2 gave Ct values in the range of 31-35 at 100 copies no detection at 5 or 10 copies. Set 3 gave Ct values in the range of 29-32 at 100 copies and no detection at 5 or 10 copies. Set 4 gave Ct values in the range of 32-35 at 100 copies and no detection at 5 or 10 copies. Set 5 gave Ct values in the range of 31-32 at 100 copies (with detection in ⅔ triplicates) and no detection at 5 or 10 copies (with detection in ⅔ triplicates) and no detection at 5 or 10 copies. Set 6 gave Ct values in the range of 30-35 at 100 copies and no detection at 5 or 10 copies. Unless indicated otherwise, detection occurred in 3/3 triplicates.

The reactions were run in multiplex with tcdA, tcdB, and cdtB primers to confirm that the primer systems did not interfere with each other. Regardless of which tcdC oligomer set was used, detection of tcdA/B was consistent at a Ct in the range of 22-25 for the 100 copy reactions and detection of cdtB was consistent at a Ct in the range of 27-31 for the 100 copy reactions.

Invasive probe and primary detection oligomers targeting the 117del and 184T tcdC alleles (SEQ ID NOs: 86, 161, 165-167, 196, and 204) were tested in reactions with 10 copies of the relevant tcdC allele as follows (5 replicates each).

Cts in this paragraph are for detection of 117del tcdC. With SEQ ID NO: 86 and 161, Cts were about 35 with detection occurring in ⅖ replicates. With SEQ ID NO: 86 and 167, Cts were in the range of 30-35 with detection occurring in 5/5 replicates. With SEQ ID NO: 86 and 165, Cts were in the range of 32-35 with detection occurring in ⅘ replicates. With SEQ ID NO: 86 and 166, Cts were in the range of 30-34 with detection occurring in ⅘ replicates.

An exemplary pair of invasive probe and primary detection oligomers selected from those described above was also tested with 117T and 117A tcdC alleles. At 10, 100, and 1000 copies per reaction, the Ct was delayed by 12 cycles for 1000 copies per reaction with no detection for the 10 or 100 copy concentrations for the 117T allele relative to the 117del allele, indicating that the probe system could discriminate 117del tcdC (associated with hypervirulence) from 117T tcdC (not associated with hypervirulence). Additionally, the 117A tcdC allele (wild-type, not hypervirulent) did not generate positive signal at 10, 100, and 1000 copies per reaction, indicating that the system does not detect the 117A allele.

Detection of 184T tcdC was performed in duplicate unless otherwise noted. The template sequence used in these tests also contained a T at position 183, as in SEQ ID NO: 7, as the 184T polymorphism has been observed to coincide with a 183T polymorphism. Results are shown in the following table, given as ranges within which the observed Cts fell. "Copies" indicates copies per reaction.

TABLE E

Ct results for detection of 184T tcdC

| Invasive oligomer SEQ ID NO | Primary Probe SEQ ID NO | Ct (N/D = No Detection) | | |
|---|---|---|---|---|
| | | 100 copies | 1000 copies | 10,000 copies |
| 195 | 202 | N/D | N/D | 33-35 |
| 195 | 203 | 26-27 | 23-24 | 20-21 |
| 195 | 204 | N/D | N/D | 34-35 |
| 196 | 202 | 26-27 | 23-24 | 20-21 |
| 196 | 203 | N/D | 34-35 (1 of 2) | 31-33 |
| 196 | 204 | 25.5-26.5 | 22-23 | 19-20 |
| 205 | 215 | 24-25 | 21-22 | 17-18 |
| 205 | 216 | 31-32 | 28-29 | 24-25 |

Comparative reactions were performed with a wild-type, non-hypervirulent tcdC template (183C 184C, as in positions 183-184 of SEQ ID NO: 2) and a 183T 184C non-hypervirulent tcdC template (as in positions 183-184 of SEQ ID NO: 1) in duplicate at 10,000 copies per reaction. Results are shown below.

TABLE F

Ct results for detection of 183T 184C and 183C 184C tcdC

| Invasive oligomer SEQ ID NO | Primary Probe SEQ ID NO | tcdC allele (N/D = No Detection) | |
|---|---|---|---|
| | | 183T 184C | 183C 184C |
| 195 | 202 | N/D | N/D |
| 195 | 203 | 23-24 | N/D |
| 195 | 204 | N/D | N/D |

TABLE F-continued

Ct results for detection of 183T 184C and 183C 184C tcdC

| Invasive oligomer SEQ ID NO | Primary Probe SEQ ID NO | tcdC allele (N/D = No Detection) | |
|---|---|---|---|
| | | 183T 184C | 183C 184C |
| 196 | 202 | N/D | N/D |
| 196 | 203 | N/D | N/D |
| 196 | 204 | N/D | N/D |
| 205 | 215 | 32-34 | N/D |
| 205 | 216 | 23-24 | N/D |

Example 2. Detection of tcdB

Testing of forward amplification oligomers SEQ ID NOs: 266 and 269, reverse iPrimers SEQ ID NOs: 317 and 324, and a primary probe oligomer of SEQ ID NO: 312 gave a sensitivity (Ct) in the range of 26-28 for 10 copies per reaction and was compatible in multiplex with tcdC amplification and detection oligomers. Cross-reactivity was observed with template from another *Costridium* species, *C. soderllii* (strain ATCC9714 or JG6382).

Testing of an oligomer set including forward amplification oligomer SEQ ID NOs: 339, a reverse iPrimer selected from SEQ ID NOs: 323 and 327, and a primary probe oligomer selected from SEQ ID NO: 307 and 300 gave a sensitivity (Ct) of generally below 30 at 10 copies per reaction) but generated some signal in negative control reactions.

Two additional oligomer sets were tested, and results are shown below. tcdB oligomer set 1 included SEQ ID NOs: 274, 277, 305, 306, and 336; tcdB oligomer set 2 included SEQ ID NOs: 274, 275, 301, 305, and 336. Lysates from two different *C. difficile* strains (1: ATCC BAA-1805; and 2: CCUG20309) which had differing tcdB sequences were tested in duplicate using the indicated number of colony forming units (CFU) as input material.

TABLE G

Ct results for detection of tcdB in different strains

| Strain | CFU/reaction | tcdB oligomer set (N/D = No Detection) | |
|---|---|---|---|
| | | 1 | 2 |
| 1 | 100 | 26-27 | 25-26 |
| 1 | 10 | 29-30 | 28-29 |
| 1 | 1 | 32-34 | 30-31* |
| 2 | 1000 | 23-24 | 23-24 |
| 2 | 100 | 25-26 | 27-28 |
| 2 | 10 | 29-30 | N/D |
| 2 | 1 | 33-35* | N/D |

*detection in 1/2 duplicates tcdB oligomer sets 1 and 2 did not generate significant signal in negative control reactions, and were compatible in multiplex with tcdC amplification oligomers. No cross reactivity with *C. soderlii* was expected based on the number of mismatches between these oligomer sets and the *C. soderlii* tcsL sequence, which is the *C. soderlii* sequence most similar to *C. difficile* dB.

Example 3. Detection of cdtB

*C. difficile* can contain a binary toxin locus with the cdtA and cdtB binary toxin genes. Oligomer designs for detection of either binary toxin gene. It was found that cdtB designs could provide better specificity and performance in multiplex reactions. Some cross-reactivity was observed in initial experiments but subsequent testing with newly prepared synthetic target DNA essentially eliminated the cross-reactivity, suggesting that contamination of the original target DNA stock may have been responsible.

Representative cdtB oligomer sets, listed in the order of forward amplification oligomer, primary probe, and reverse iPrimer, are SEQ ID NO: 33, 37, and 40; or 31, 38, and 41; or permutations thereof e.g., in which SEQ ID NO: 33 is exchanged for SEQ ID NO: 31 or vice versa.

Results from a representative cdtB oligomer set were as shown below. In these experiments, data for 38 cycles of INVADER reaction were collected.

TABLE H

Ct results for detection of cdtB

| CFU/reaction | Ct |
|---|---|
| 1000 | 26-27 |
| 100 | 29-30 |
| 10 | 33-35 |
| 1 | 36-38 |

Example 4. Detection of tcdA

To avoid loss of sensitivity in the event of mutations that affect detection of tcdB (the Toxin B gene of the *C. difficile* pathogenic locus), oligomers for detection of tcdA were designed that can be multiplexed with oligomers for detecting tcdB and the other genes discussed above.

Exemplary tcdA oligomer sets contained SEQ ID NO: 64 or 65 as a forward iPrimer, SEQ ID NO: 68 or 69 as a primary probe, and any one of SEQ ID NO: 70-73 as a reverse primer. In the results shown below (Table 1), tcdA set 1 used SEQ ID NO: 64, 69, and 72; and tcdA set 2 used SEQ ID NO: 65, 69, and 72. Data were collected for 38 cycles of INVADER reaction. These results were performed in multiplex with tcdB, tcdC, and cdtB oligomer sets with 6, 12, or 25 copies of target DNA per reaction (n=8 for each condition); as noted above, a FRET cassette was used that detected cleavage of both tcdA and tcdB primary probes. The combined tcdA/tcdB detection performed well with both tcdA systems present. Additionally, the tcdA oligomers of set 1 were tested in the absence of tcdB oligomers with 100 copies of tcdA+ target per reaction (n=6, including 2 each of wild type, 184T, and 117del tcdC genotypes), and the results were positive with Cts of 27-28 and consistent with there being no negative impact from using the tcdA oligomers in multiplex. Target DNA was from *C. difficile* ATCC4118, which carries a 117del tcdC allele, at the indicated number of copies per reaction. Positivity indicates the proportion of replicates in which positive signal was observed. Regardless of which set was used, at least one of tcdA/B, tcdC, and cdtB were detected in every replicate. Negative controls were as expected (not shown).

TABLE I

Ct results for detection of tcdA/ B, tcdC, and cdtB in multiplex

| | tcdA oligomer set | | | |
|---|---|---|---|---|
| | 1 | | 2 | |
| Copies/reaction | tcdA/B Ct | Positivity | tcdA/B Ct | Positivity |
| 6 | 21-26 | 7/8 | 22-28 | 7/8 |
| 12 | 20-22 | 8/8 | 21-24 | 8/8 |
| 25 | 19-22 | 8/8 | 20-23 | 8/8 |
| | tcdC Ct | Positivity | tcdC Ct | Positivity |
| 6 | 28-32 | 7/8 | 28-33 | 5/8 |
| 12 | 27-32 | 7/8 | 28-37 | 7/8 |
| 25 | 26-34 | 8/8 | 26-31 | 8/8 |
| | cdtB Ct | Positivity | cdtB Ct | Positivity |
| 6 | 27-31 | 3/8 | 27-32 | 6/8 |
| 12 | 26-36 | 6/8 | 26-30 | 8/8 |
| 25 | 25-28 | 8/8 | 25-32 | 8/8 |

TABLE OF SEQUENCES

| SEQ ID NO | Description | Sequence 5'-3' |
|---|---|---|
| | Exemplary *C. difficile* sequences | |
| 1 | tcdC from GenBank DQ870676.1 (117 = G, 183 = T) | ATGTTTTCTAAAAAAAATGAGGGTAACGAATTTAGTAATGAAGGAAAAGGAAGCTCT AAGAAAATAATTAAATTCTTTAAGAGCACAAAGGGTATTGCTCTACTGGCATTTATT TTGGGCGTGTTTTTGGCAATATATCCTCACCAGCTTGTTCTGAAGACCATGAGGAGG TCATTTCTAATCAAACATCAGTTATAGATTCTCAAAAAACAGAAATAGAAACTTTAA ATAGCAAATTGTCTGATGCTGAACCATGGTTCAAAATGAAAGACGACGAAAAGAAAG CTATTGAAGCTGAAAATCAACGTAAAGCTGAAGAAGCTAAAAAGGCTGAAGAACAAC GTAAAAAAGAAGAAGAAGAGAAGAAAGGATATGATACTGGTATTACTTATGACCAAT TAGCTAGAACACCTGATGATTATAAGTACAAAAAGGTAAAATTTGAAGGTAAGGTTA TTCAAGTTATTGAAGATGGTGATGAGGTGCAAATAAGATTAGCTGTGTCTGGAAATT ATGATAAGGTCGTACTATGTAGTTATAAAAAATCAATAACTCCTTCAAGAGTGTTAG AGGATGATTACATAACTATAAGAGGTATAAGTGCTGGAACTATAACTTATGAATCAA CTATGGGTGGAAATATAACTATACCAGGGATAGCTGTGAGAAAATAAATTAA |
| 2 | tcdC from GenBank EU075382.1 (partial, 117 = a, 183 = C) | ATGTTTTCTAAAAAAAATGAGGGTAACGAATTTAGTAATGAAGGAAAAGGAAGCTCT AAGAAAATAATTAAATTCTTTAAGAGCACAAAGGGTATTGCTCTACTGGCATTTATT TTAGGCGTGTTTTTTGGCAATATATCCTCACCATCTTGTTCTGAAGACCATGAGGAG GTCATTTCTAACCAAACATCAGTTATAGATTCTCAAAAAACAGAAATAGAAACTTTA AATAGCAAATTGTCTGATGCTGAACCATGGTTCAAAATGAAAGACGACGAAAAGAAA GCTATTGAAGCTGAAAATCAACGTAAAGCTGAAGAAGCTAAAAAAGCTGAAGAAGCT AAAAAGGCTGAAGAACAACGCAAAAAAGAAGAAGAGGAGAAGAAAGGATATGATACT GGTATTACTTATGACCAATTAGCTAGAACACCTGATGATTATAAGTACAAAAAGGTA AAATTTGAAGGTAAGGTTATTCAA |
| 3 | tcdC 117delA (with dash at deletion site) | ATGTTTTCTAAAAAAAATGAGGGTAACGAATTTAGTAATGAAGGAAAAGGAAGCTCT AAGAAAATAATTAAATTCTTTAAGAGCACAAAGGGTATTGCTCTACTGGCATTTATT TT-GGCGTGTTTTTGGCAATATATCCTCACCAGCTTGTTCTGAAGACCATGAGGAG GTCATTTCTAATCAAACATCAGTTATAGATTCTCAAAAAACAGAAATAGAAACTTTA |

| TABLE OF SEQUENCES | | |
|---|---|---|
| SEQ ID NO | Description | Sequence 5'-3' |
| 4 | tcdC 117T | AATAGCAAATTGTCTGATGCTGAACCATGGTTCAAAATGAAAGACGACGAAAAGAAA<br>GCTATTGAAGCTGAAAATCAACGTAAAGCTGAAGAAGCTAAAAAGGCTGAAGAACAA<br>CGTAAAAAAGAAGAAGAAGAGAAGAAAGGATATGATACTGGTATTACTTATGACCAA<br>TTAGCTAGAACACCTGATGATTATAAGTACAAAAAGGTAAAATTTGAAGGTAAGGTT<br>ATTCAAGTTATTGAAGATGGTGATGAGGTGCAAATAAGATTAGCTGTGTCTGGAAAT<br>TATGATAAGGTCGTACTATGTAGTTATAAAAAATCAATAACTCCTTCAAGAGTGTTA<br>GAGGATGATTACATAACTATAAGAGGTATAAGTGCTGGAACTATAACTTATGAATCA<br>ACTATGGGTGGAAATATAACTATACCAGGGATAGCTGTAGAGAAAATAAATTAA<br>ATGTTTTCTAAAAAAAATGAGGGTAACGAATTTAGTAATGAAGGAAAAGGAAGCTAT<br>AAGAAAATAATTAAATTCTTTAAGAGCACAAAGGGTATTGCTCTACTGGCATTTATT<br>TTTGGCGTGTTTTTTGGCAATATATCCTCACCAGCTTGTTCTGAAGACCATGAGGAG<br>GTCATTTCTAATCAAACATCAGTTATAGATTCTCAAAAAACAGAAATAGAAACTTTA<br>AATAGCAAATTGTCTGATGCTGAACCATGGTTCAAAATGAAAGACGACGAAAAGAAA<br>GCTATTGAAGCTGAAAATCAACGTAAAGCTGAAGAAGCTAAAAAGGCTGAAGAACAA<br>CGTAAAAAAGAAGAAGAAGAGAAGAAAGGATATGATACTGGTATTACTTATGACCAA<br>TTAGCTAGAACACCTGATGATTATAAGTACAAAAAGGTAAAATTTGAAGGTAAGGTT<br>ATTCAAGTTATTGAAGATGGTGATGAGGTGCAAATAAGATTAGCTGTGTCTGGAAAT<br>TATGATAAGGTCGTACTATGTAGTTATAAAAAATCAATAACTCCTTCAAGAGTGTTA<br>GAGGATGATTACATAACTATAAGAGGTATAAGTGCTGGAACTATAACTTATGAATCA<br>ACTATGGGTGGAAATATAACTATACCAGGGATAGCTGTAGAGAAAATAAATTAA |
| 5 | tcdC<br>184C > T | ATGTTTTCTAAAAAAAATGAGGGTAACGAATTTAGTAATGAAGGAAAAGGAAGCTCT<br>AAGAAAATAATTAAATTCTTTAAGAGCACAAAGGGTATTGCTCTACTGGCATTTATT<br>TTGGGCGTGTTTTTTGGCAATATATCCTCACCAGCTTGTTCTGAAGACCATGAGGAG<br>GTCATTTCTAATTAAACATCAGTTATAGATTCTCAAAAAACAGAAATAGAAACTTTA<br>AATAGCAAATTGTCTGATGCTGAACCATGGTTCAAAATGAAAGACGACGAAAAGAAA<br>GCTATTGAAGCTGAAAATCAACGTAAAGCTGAAGAAGCTAAAAAGGCTGAAGAACAA<br>CGTAAAAAAGAAGAAGAAGAGAAGAAAGGATATGATACTGGTATTACTTATGACCAA<br>TTAGCTAGAACACCTGATGATTATAAGTACAAAAAGGTAAAATTTGAAGGTAAGGTT<br>ATTCAAGTTATTGAAGATGGTGATGAGGTGCAAATAAGATTAGCTGTGTCTGGAAAT<br>TATGATAAGGTCGTACTATGTAGTTATAAAAAATCAATAACTCCTTCAAGAGTGTTA<br>GAGGATGATTACATAACTATAAGAGGTATAAGTGCTGGAACTATAACTTATGAATCA<br>ACTATGGGTGGAAATATAACTATACCAGGGATAGCTGTAGAGAAAATAAATTAA |
| 6 | cdtB from<br>GenBank<br>HQ639679 | ATGAAAGTACAAATGAGGAATAAAAAGGTATTAAGTTTTTTAACACTTACAGCCATA<br>GTTAGTCAAGCATTAGCATATCCTGTATATGCTCAAACTAGTACAAGTAGCCATTCT<br>GATAATAAAAAAGAAATTATAAATGAAGACATACTCACAAACAACGGATTAATGGGA<br>TATTATTTCACAGACGAACACTTTAAAGATTTAAAATTAATGGCACCCATAAAAGAT<br>GGTAATTTAAAATTTGAAGAAAAGAAAGTAGATAAACTTCTAAATAAAGACAAATCA<br>AATGTAAAATCTATACGATGGACAGGAAGAATAATTCCTTCTAAGGATGGTGAATAT<br>ACATTATCAACTGATAGAGATGATATTTTAATGCAAGTAAATAATGAGAGTACTATA<br>TCAAATACACTTAAAGTTAATATGAAAAAGGGTAAAGAATATAAATTTAGAATAGAG<br>CTACAAGATAAAAATTTAGGTTCAATAGATAATTTATCATCACCAAATCTTTATTGG<br>GAATTAGATGGTATTAAGAAAATTATACCAGCAGAAAATTTATTCTTAAGAGATTAT<br>TCTAATATAGAAAAAAATGATCCATTTATCCCAAATAACAATTTCTTTGACCCAAGG<br>TTGATGTCTGATTGGGAAGACGAAGATTTGGATACAGATAATGATAATATACCAGAT<br>TCATATGAACGAAATGGATATACTATTAAGGACTTAATTGCAGTTAAGTGGGAAGAT<br>AGCTTTGCAGAACAAGGCTATAAGAAATATGTATCAAATTATTTAGAGTCAAATACT<br>GCTGGAGATCCATATACAGATTATGAAAAAGCTTCAGGTTCTTTTGACAAGGCTATA<br>AAGACCGAAGCAAGAGATCCGTTAGTTGCAGCGTATCCAATTGTTGGAGTAGGTATG<br>GAAAAATTAATTTATATCTACAAATGAACATGCCTCTACTGATCAAGGTAAAACTGTT<br>TCCAGAGCTACTACTAACAGTAAAACTGAATCTAATACAGCTGGTGTTTCTGTTAAT<br>GTAGGATATCAAATGGATTCACAGCTAATGTAACTACAAATTATTCCCATACAACA<br>GATAATTCAACTGCCGTTCAAGATAGTAATGGAGAATCATGGAATACTGGATTAAGT<br>ATAAACAAAGGAGAATCTGCATATATAAATGCAAATGTTAGATATTACAACACAGGT<br>ACTGCACCTATGTACAAAGTGACACCAACAACAAATTTAGTGTTAGATGGAGATACA<br>TTATCAACTATCAAAGCACAAGAAAATCAAATTGGCAATAATCTATCTCCTGGAGAT<br>ACTTATCCCAAAAAAGGGCTTTCACCTCTGGCTCTTAACACAATGGATCAATTTAGC<br>TCTAGACTGATTCCTATAAATTATGATCAATTAAAAAAATTAGATGCTGGAAAGCAA<br>ATTAAATTAGAAACAACACAAGTAAGTGGAAATTTTGGTACAAAAAATAGTTCTGGA<br>CAAATAGTAACAGAAGGAAATAGTTGGTCAGACTATATAAGTCAAATTGACAGTATT<br>TCTGCATCTATTATATTAGATACAGAGAATGAATCTTACGAAAGAAGAGTTACTGCT<br>AAAAATTTACAGAATCCAGAAGATAAAACACCTGAACTTACAATTGGAGAAGCAATT<br>GAAAAAGCTTTTGGCGCTACTAAAAAAGATGGTTTGTTATATTTTAATGATATACCA<br>ATAGATGAAAGTTGTGTTGAACTCATATTTGATGATAATACAGCCAATAAGATTAAA<br>GATAGTTTAAAAACTTTGTCTGATAAAAAGATATATAATGTTAAACTTGAAAGAGGA<br>ATGAATATACTTATAAAAACACCAACTTACTTTACTAATTTTGATGATTACAATAAT<br>TACCCTAGTACATGGAGTAATGTCAATACTACGAATCAAGATGGTTTACAAGGCTCA<br>GCAAATAAATTAAATGGTGAGACAAAGATTAAAATACCTATGTCTAAGCTAAAACCT<br>TATAAACGTTATGTTTTAGTGGATATTCAAAGGATCCTTTAACATCTAATTCAATA<br>ATTGTAAAGATAAAAGCAAAAGAAGAAAAACGGATTATTTGTTACCAGAACAAGGA<br>TATACAAAGTTTAGTTATGAATTTGAAACTACTGAAAAAGATTCTTCTAATATAGAG<br>ATAACATTAATTGGTAGTGGTACAACATACTTAGATAACTTATCTATTACAGAACTG<br>AATAGTACTCCTGAAATACTTAATGAACCAGAAGTTAAAATTCCAACTGACCAAGAA<br>ATAATAGATGCACATAAATATATTCTGCAGATTTAAATTTTAATCCAAGTACAGGA<br>AATGCTTATATAAATGGTATGTATTTTACACCAACACAAACTAATAAAGAAGCTCTC<br>GATTATATCCAAAAAATATAGAGTTGAAGCTACTTTACAATATTCTGGATTTAAAGAT |

TABLE OF SEQUENCES

| SEQ ID NO | Description | Sequence 5'-3' |
|---|---|---|
| | | ATTGGAACTAAAGATAAAGAAATGCGTAATTATTTAGGAGATCCAAATCAACCTAAA<br>AACTAATTATGTCAATCTTAGGAGTTATTTTACAGGTGGAGAAAATATTATGACATA<br>CAAGAAATTAAGAATATAGCAATTACTCCAGATGATAGAGAGTTATTAGTTCTTAGT<br>GTTGATTAG |
| 7 | tcdA from GenBank KC292125 | ATGTCTTTAATATCTAAAGAAGAGTTAATAAAACTCGCATATAGCATTAGACCAAGA<br>GAAAATGAGTATAAAACTATACTAACTAATTTAGACGAATATAATAAGTTAACTACA<br>AACAATAATGAAATAAATATTTACAATTAAAAAAACTAAATGAATCAATTGATGTT<br>TTTATGAATAAATATAAAACTTCAAGCAGAAATAGAGCACTCTCTAATCTAAAAAAA<br>GATATATTAAAAGAAGTAATTCTTATTAAAAATTCCAATACAAGCCCTGTAGAAAAA<br>AATTTACATTTTGTATGGATAGGTGGAGAAGTCAGTGATATTGCTCTTGAATACATA<br>AAACAATGGGCTGATATTAATGCAGAATATAATATTAAACTGTGGTATGATAGTGAA<br>GCATTCTTAGTAAATACACTAAAAAAGGCTATAGTTGAATCTTCTACCACTGAAGCA<br>TTACAGCTACTAGAGGAAGAGATTCAAAATGCTCAATTTGATAATATGAAATTTTAG<br>AAAAAAAGGATGGAATTTATATATGATAGACAAAAAAGGTTTATAAATTATTATAAA<br>TCTCAAATCAATAAACCTACAGTACCTACAATAGATGATATTATAAAGTCTCATCTA<br>GTATCTGAATATAATAGAGATGAAACTGTATTAGAATCATATAGAACAAATTCTTTG<br>AGAAAAATAAATAGTAATCATGGGATAGATATCAGGGCTAATAGTTTGTTACAGAA<br>GAAGAGTTATTAAATATTTATAGTCAGGAGTTGTTAAATCGTGGAAATTTAGCTGCA<br>GCATCTGACATAGTAAGATTATTAGCCCTAAAAAATTTTGGCGGAGTATATTTAGAT<br>GTTGATATGCTTCCAGGTATTCACTCTGATTTATTTAAAACAATATCTAGACCTAGC<br>TCTATTGGACTAGACCGTTGGGAAATGATAAAATTAGAGGGTATTATGAAGTATAAA<br>AAATATATAAATAATTATACATCAGAAAACTTTGATAAACTTGATCAACAATTAAAA<br>GATAATTTTAAACTCATTATAGAAAGTAAAAGTGAAAAATCTGAGATATTTTCTAAA<br>TTAGAAAATTTAAATGTATCTGATCTTGAAATTAAAATAGCTTTCGCTTTAGGCAGT<br>GTTATAAATCAAGCCTTGATATCAAACAAGGTTCATATCTTACTAACCTAGTAATA<br>GAACAAGTAAAAAATAGATATCAATTTTTAAACCAACACCTTAACCCAGCCATAGAG<br>TCTGATAATAACTTCACAGATACTACTAAAATTTTTCATGATTCATTATTTAATTCA<br>GCTACCGCAGAAAACTCTATGTTTTTAACAAAAATAGCACCCATACTTACAAGTAGGT<br>TTTATGCCAGAAGCTCGCTCCACAATAAGTTTAAGTGGTCCAGGAGCTTATGCGTCA<br>GCTTACTATGATTTCATAAATTTACAAGAAAATACTATAGAAAAAACTTTAAAAGCA<br>TCAGATTTAATAGAATTTAAATTCCCAGAAAATAATCTATCTCAATTGACAGAACAA<br>GAAATAAATAGTCTATGGAGCTTTGATCAAGCAAGTGCAAAATATCAATTTGAGAAA<br>TATGTAAGAGATTATACTGGTGGATCTCTTTCTGAAGACAATGGGGTAGACTTTAAT<br>AAAAAATACTGCCCTCGACAAAAACTATTTATTAAATAATAAAATTCCATCAAACAAT<br>GTAGAAGAAGCTGGAAGTAAAAATTATGTTCATTATATCATACAGTTACAAGGAGAT<br>GATATAAGTTATGAAGCAACATGCAATTTATTTTCTAAAAATCCTAAAAATAGTATT<br>ATTATACAACGAAATATGAATGAAAGTGCAAAAAGCTACTTTTTAAGTGATGATGGA<br>GAATCTATTTTAGAATTAAATAAAATATAGGATACCTGAAAGATTAAAAAATAAGGAA<br>AAAGTAAAAGTAACCTTTATTGGACATGGTAAAGATGAATTCAACACAAGCGAATTT<br>GCTAGATTAAGTGTAGATTCACTTTCCAATGAGATAAGTTCATTTTTAGATACCATA<br>AAATTAGATATATCACCTAAAAATGTAGAAGTAAACTTACTTGGATGTAATATGTTT<br>AGTTATGATTTTAATGTTGAAGAAACTTATCCTGGGAAGTTGCTATTAAGTATTATG<br>GACAAAATTACTTCCACTTTACCTGATGTAAATAAAAATTCTATTACTATAGGAGCA<br>AATCAATATGAAGTAAGAATTAATAGTGAGGGAAGAAAAGAACTTCTGGCTCACTCA<br>GGTAAATGGATAAATAAAGAAGAAGCTATTATGAGCGATTTATCTAGTAAAGAATAC<br>ATTTTTTTTGATTCTATAGATAATAAGCTAAAAGCAAAGTCCAAGAATATTCCAGGA<br>TTAGCATCAATATGAGAAGATATAAAAACATTATTACTTGATGCAAGTGTTAGTCCT<br>GATACAAAATTTATTTTAAATAATCTTAAGCTTAATATTGAATCTTCTATTGGTGAT<br>TACATTTATTATGAAAATTAGAGCCTGTTAAAAATATAATTCACAATTCTATAGAT<br>GATTTAATAGATGAGTTCAATCTACTTGAAATGTATCTGATGAATTATATGAATTA<br>AAAAAATTTAAATAATCTAGATGAGAAGTATTTAATATCTTTTGAAGATATCTCAAAA<br>AATAATTCAACTTACTCTGTAAGATTTATTAACAAAAGTAATGGTGAGTCAGTTTAT<br>GTAGAAACAGAAAAGAAATTTTTTGAAAATATAGCGAACATATTACAAAAGAAATA<br>AGTACTATAAAGAATAGTATAATTACAGATGTTAATGGTAATTTATTGGATAATATA<br>CAGTTAGATCATACTTCTCAAGTTAATACATTAAACGCAGCATTCTTTATTCAATCA<br>TTAATAGATTATAGTAGCAATAAAGATGTACTGAATGATTTAAGTACCTCAGTTAAG<br>GTTCAACTTTATGCTCAACTATTTAGTACAGGTTAAATACTATATATGACTCTATC<br>CAATTAGTAAATTTAATATCAAATGCAGTAAATGATACTATAAATGTACTACCTACA<br>ATAACAGAGGGGATACCTATTGTATCTACTATATTAGACGGAATAAACTTAGGTGCA<br>GCAATTAAGGAATTACTAGACGAACATGACCCATTACTAAAAAAAGAATTAGAAGCT<br>AAGGTGGGTGTTTTAGCAATAAATATGTCATTATCTATAGCTGCAACTGTAGCTTCA<br>ATTGTTGGAATAGGTGCTGAAGTTACTATTTTCTTATTACCTATAGCTGGTATATCT<br>GCAGGAATACCTTCATTAGTTAATAATGAATTAATATTGCATGATAAGGCAACTTCA<br>GTGGTAAACTATTTTAATCATTTGTCTGAATCTAAAAAATATGGCCCTCTTAAAACA<br>GAAGATGATAAAATTTTAGTTCCTATTGATGATTTAGTAATATCAGAAATAGATTTT<br>AATAATAATTCGATAAAACTAGGAACATGTAATATATTAGCAATGGAGGGGGGATCA<br>GGACACACAGTGACTGGTAATATAGATCACTTTTTCTCATCTCCATCTATAAGTTCT<br>CATATTCCTTCATTATCAATTTATTCTGCAATAGGTATAGAAACAGAAATCTAGAT<br>TTTTCAAAAAAAATAATGATGTTACCTAATGCTCCTTCAAGAGTGTTTTGGTGGGAA<br>ACTGGAGCAGTTCCAGGTTTAAGATCATTGGAAAATGACGGAACTAGATTACTTGAT<br>TCAATAAGAGATTTATACCCAGGTAAATTTTACTGGAGATTCTATGCTTTTTTCGAT<br>TATGCAATAACTACATTAAAACCAGTTTATGAAGACACTAATATTAAAATTAAACTA<br>GATAAAGATACTAGAAACTTCATAATGCCAACTATAACTACTAACGAATTAGAAAC<br>AAATTATCTATTCATTTGATGGAGCAGGAGGAACTTACTCTTTATTATTATCTTCAT<br>ATCCAATATCAACGAATATAAATTTATCTAAAGATGATTTATGGATATTTAATATTG |

TABLE OF SEQUENCES

| SEQ ID NO | Description | Sequence 5'-3' |
|---|---|---|
| | | ATAATGAAGTAAGAGAAATATCTATAGAAAATGGTACTATTAAAAAAGGAAAGTTAA<br>TAAAAGATGTTTTAAGTAAAATTGATATAAATAAAAATAAACTTATTATAGGCAATC<br>AAACAATAGATTTTTCAGGCGATATAGATAATAAAGATAGATATATATTCTTGACTT<br>GTGAGTTAGATGATAAAATTAGTTTAATAATAGAAATAAATCTTGTTGCAAAATCTT<br>ATAGTTTGTTATTGTCTGGGGATAAAAATTATTTGATATCCAATTTATCTAATACTA<br>TTGAGAAAATCAATACTTTAGGCCTAGATAGTAAAAATATAGCGTACAATTACACTG<br>ATGAATCTAATAATAAATATTTTGGAGCTATATCTAAACAAGTCAAAAAGCATAA<br>TACATTATAAAAAGACAGTAAAAATATATTAGAATTTTATAATGACAGTACATTAG<br>AATTTAACAGTAAAGATTTTATTGCTGAAGATATAAATGTATTTATGAAAGATGATA<br>TTAATACTATAACAGGAAAATACTATGTTGATAATAATACTGATAAAAGTATAGATT<br>TCTCTATTTCTTTAGTTAGTAAAAATCAAGTAAAAGTAAATGGATTATATTTAAATG<br>AATCCGTATACTCATCTTACCTTGATTTTGTGAAAAATTCAGATGGACACCATAATA<br>CTTCTAATTTTATGAATTTATTTTTGGACAATATAAGTTTCTGGAAATTGTTTGGGT<br>TTGAAAATATAAATTTTGTAATCGATAAATACTTTACCCTTGTTGGTAAAACTAATC<br>TTGGATATGTAGAATTTATTTGTGACAATAATAAAAATATAGATATATATTTTGGTG<br>AATGGAAAACATCGTCATCTAAAAGCACTATATTTAGCGGAAATGGTAGAAATGTTG<br>TAGTAGAGCCTATATATAATCCTGATACGGGTGAAGATATATCTACTTCACTAGATT<br>TTTCCTATGAACCTCTCTATGGAATAGATAGATATATAAATAAAGTATTGATAGCAC<br>CTGATTTATATACAAGTTTAATAAATATTAATACCAATTATTATTCAAATGAGTACT<br>ACCCTGAGATTATAGTTCTTAACCCAAATACATTCCACAAAAAGTAAATATAAATT<br>TAGATAGTTCTTCTTTTGAGTATAAATGGTCTACAGAAGGAAGTGACTTTATTTTAG<br>TTAGATACTTAGAAGAAGTAATAAAAAAATATTACAAAAAATAAGAATCAAAGGTA<br>TCTTATCTAATACTCAATCATTTAATAAAATGAGTATAGATTTTAAAGATATTAAAA<br>AACTATCATTAGGATATATAATGAGTAATTTTAAATCATTTAATTCTGAAAATGAAT<br>TAGATAGAGATCATTTAGGATTTAAAATAATAGATAATAAACTTATTACTATGATG<br>AAGATAGTAAATTAGTTAAAGGATTAATCAATATAAATAATTCATTATTCTATTTTG<br>ATCCTATAGAATTTAACTTAGTAACTGGATGGCAAACTATCAATGGTAAAAAATATT<br>ATTTTGATATAAATACTGGAGCAGCTTTAACTAGTTATAAAATTATTAATGGTAAAC<br>ACTTTTATTTTAATAATGATGGTGTGATGCAGTTGGGAGTATTTAAAGGACCTGATG<br>GATTTGAATATTTTGCACCTGCCAATACTCAAAATAATAACATAGAAGGTCAGGCTA<br>TAGTTTATCAAAGTAAATTCTTAACTTTGAATGGCAAAAAATATTATTTTGATAATG<br>ACTCAAAAGCAGTCACTGGATGGAGAATTATTAACAATGAGAAATATTACTTTAATC<br>CTAATAATGCTATTGCTGCAGTCGGATTGCAAGTAATTGACAATAATAAGTATTATT<br>TCAATCCTGACACTGCTATCATCTCAAAAGGTTGGCAGACTGTTAATGGTAGTAGAT<br>ACTACTTTGATACTGATACCGCTATTGCCTTTAATGGTTATAAAACTATTGATGGTA<br>AACACTTTTATTTTGATAGTGATTGTGTAGTGAAAATAGGTGTGTTTAGTACCTCTA<br>ATGGATTTGAATATTTTGCACCTGCTAATACTTATAATAATAACATAGAAGGTCAGG<br>CTATAGTTTATCAAAGTAAATTCTTAACTTTGAATGGTAAAAAATATTACTTTGATA<br>ATAACTCAAAAGCAGTTACCGGATGGCAAACTATTGATAGTAAAAAATATTACTTTA<br>ATACTAACACTGCTGAAGCAGCTACTGGATGGCAAACTATTGATGGTAAAAAATATT<br>ACTTTAATACTAACACTGCTGAAGCAGCTACTGGATGGCAAACTATTGATGGTAAAA<br>AATATTACTTTAATACTAACACTGCTATAGCTTCAACTGGTTATACAATTATTAATG<br>GTAAACATTTTTATTTTAATACTGATGGTATTATGCAGATAGGAGTGTTTAAAGGAC<br>CTAATGGATTTGAATATTTTGCACCTGCTAATACGGATGCTAACAACATAGAAGGTC<br>AAGCTATACTTTACCAAAATGAATTCTTAACTTTGAATAGTAAAAAATATTACTTTG<br>GTAGTGACTCAAAAGCAGTTACTGGATGGAGAATTATTAACAATAAGAAATATTACT<br>TTAATCCTAATAATGCTATTGCTGCAATTCATCTATGCACTATAAATAATGACAAGT<br>ATTACTTTAGTTATGATGGAATTCTTCAAAATGGATATATTACTATTGAAAGAAATA<br>ATTTCTATTTTGATGCTAATAATGAATCTAAAATGGTAACAGGAGTATTTAAAGGAC<br>CTAATGGATTTGAGTATTTTGCACCTGCTAATACTCACAATAATAACATAGAAGGTC<br>AGGCTATAGTTTACCAGAACAAATTCTTAACTTTGAATGGCAAAAAATATTATTTTG<br>ATAATGACTCAAAAGCAGTTACTGGATGGCAAACCATTGATGGTAAAAAATATTACT<br>TTAATCTTAACACTGCTGAAGCAGCTACTGGATGGCAAACTATTGATGGTAAAAAAT<br>ATTACTTTAATCTTAACACTGCTGAAGCAGCTACTGGATGGCAAACTATTGATGGTA<br>AAAAATATTACTTTAATACTAACACTTTCATAGCCTCAACTGGTTATACAAGTATTA<br>ATGGTAAACATTTTTATTTTAATACTGATGGTATTATGCAGATAGGAGTGTTTAAAG<br>GACCTAATGGATTTGAATACTTTGCACCTGCTAATACTCATAATAATAACATAGAAG<br>GTCAAGCTATACTTTACCAAAATAAATTCTTAACTTTGAATGGTAAAAAATATTACT<br>TTGGTAGTGACTCAAAAGCAGTTACCGGATTGCGAACTATTGATGGTAAAAAATATT<br>ACTTTAATACTAACACTGCTGTTGCAGTTACTGGATGGCAAACTATTAATGGTAAAA<br>AATACTACTTTAATACTAACACTTCTATAGCTTCAACTGGTTATACAATTATTAGTG<br>GTAAACATTTTTATTTTAATACTGATGGTATTATGCAGATAGGAGTGTTTAAAGGAC<br>CTGATGGATTTGAATACTTTGCACCTGCTAATACAGATGCTAACAATATAGAAGGTC<br>AAGCTATACGTTATCAAAATAGATTCCTATATTTACATGACAATATATATTATTTTG<br>GTAATAATTCAAAAGCGGCTACTGGTTGGGTAACTATTGATGGTAATAGATATTACT<br>TCGAGCCTAATACAGCTATGGGTGCGAATGGTTATAAAACTATTGATAATAAAACT<br>TTTACTTTAGAAATGGTTTACCTCAGATAGGAGTGTTTAAAGGGTCTAATGGATTTG<br>AATACTTTGCACCTGCTAATACGGATGCTAACAATATAGAAGGTCAAGCTATACGTT<br>ATCAAAATAGATTCCTACATTTACTTGGAAAAATATATTACTTTGGTAATAATTCAA<br>AAGCAGTTACTGGATGGCAAACTATTAATGGTAAAGTATATTACTTTATGCCTGATA<br>CTGCTATGGCTGCAGCTGGTGGACTTTTCGAGATTGATGGTGTTATATATTTCTTTG<br>GTGTTGATGGAGTAAAAGCCCCTGGGATATATGGCTAA |
| 8 | tcdB from GenBank KC292190 | ATGAGTTTAGTTAATAGAAAACAGTTAGAAAAAATGGCAAATGTAAGATTCGTACT<br>CAAGAAGATGAATATGTTGCAATATTGGATGCTTTAGAAGAATATCATAATATGTCA<br>GAGAATACTGTAGTCGAAAAATATTTAAAATTAAAAGATATAAATAGTTTAACAGAT |

TABLE OF SEQUENCES

| SEQ ID NO | Description | Sequence 5'-3' |
|---|---|---|
| | | ATTTATATAGATACATATAAAAAATCTGGTAGAAATAAAGCCTTAAAAAAATTTAAG<br>GAATATCTAGTTACAGAAGTATTAGAGCTAAAGAATAATAATTTAACTCCAGTTGAG<br>AAAAATTTACATTTGTTTGGATTGGAGGTCAAATAAATGACACTGCTATTAATTATA<br>TAAATCAATGGAAAGATGTAAATAGTGATTATAATGTTAATGTTTTTTATGATAGTA<br>ATGCATTTTTGATAAACACATTGAAAAAAACTGTAGTAGAATCAGCAATAAATGATA<br>CACTTGAATCATTTAGAGAAAACTTAAATGACCCTAGATTTGACTATAATAAATTCT<br>TCAGAAAACGTATGGAAATAATTTATGATAAACAGAAAAATTTCATAAACTACTATA<br>AAGCTCAAAGAGAAGAAAATCCTGAACTTATAATTGATGATATTGTAAAGACATATC<br>TTTCAAATGAGTATTCAAAGGAGATAGATGAACTTAATACCTATATTGAAGAATCCT<br>TAAATAAAATTACACAGAATAGTGGAAATGATGTTAGAAACTTTGAAGAATTTAAAA<br>ATGGAGAGTCATTCAACTTATATGAACAAGAGTTGGTAGAAAGGTGGAATTTAGCTG<br>CTGCTTCTGACATATTAAGAATATCTGCATTAAAAGAAATTGGTGGTATGTATTTAG<br>ATGTTGATATGTTACCAGGAATACAACCAGACTTATTTGAGTCTATAGAGAAACCTA<br>GTTCAGTAACAGTGGATTTTTGGGAAATGACAAAGTTAGAAGCTATAATGAAATACA<br>AAGAATATATACCAGAATATACCTCAGAACATTTTGACATGTTAGACGAAGAAGTTC<br>AAAGTAGTTTGAATCTGTTCTAGCTTCTAAGTCAGATAAATCAGAAATATTCTCATC<br>ACTTGGTGATATGGAGGCATCACCACTAGAAGTTAAAATTGCATTTAATAGTAAGGG<br>TATTATAAATCAAGGGCTAATTTCTGTGAAAGACTCATATTGTAGCAATTTAATAGT<br>AAAACAAATCGAGAATAGATATAAAATATTGAATAATAGTTTAAATCCAGCTATTAG<br>CGAGGATAATGATTTTAATACTACAACGAATACCTTTATTGATAGTATAATGGCTGA<br>AGCTAATGCAGATAATGGTAGATTTATGATGGAACTAGGAAAGTATTTAAGAGTTGG<br>TTTCTTCCCAGATGTTAAAACTACTATTAACTTAAGTGGCCCTGAAGCATATGCGGC<br>AGCTTATCAAGATTTATTAATGTTTAAAGAAGGCAGTATGAATATCCATTTGATAGA<br>AGCTGATTTAAGAAACTTTGAAATCTCTAAAACTAATATTTCTCAATCAACTGAACA<br>AGAAATGGCTAGCTTATGGTCATTTGACGATGCAAGAGCTAAAGGTCAATTTGAAGA<br>ATATAAAAGGAATTATTTTGAAGGTTCTCTTGGTGAAGATGATAATCTTGATTTTTC<br>TCAAAATATAGTAGTTGACAAGGAGTATCTTTTAGAAAAAATATCTTCATTAGCAAG<br>AAGTTCAGAGAGGATATATACACTATATTGTTCAGTTACAAGGAGATAAAATTAG<br>TTATGAAGCAGCATGTAACTTATTTGCAAAGACTCCTTATGATAGTGTACTGTTTCA<br>GAAAAATATAGAAGATTCAGAAATTGCATATTATTATAATCCTGGAGATGGTGAAAT<br>ACAAGAAATAGACAAGTATAAAATTCCAAGTATAATTTCTGATAGACCTAAGATTAA<br>ATTAACATTTATTGGTCATGGTAAAGATGAATTTAATACTGATATATTTGCAGGTTT<br>TGATGTAGATTCATTATCCACAGAAATAGAAGCAGCAATAGATTTAGCTAAAGAGGA<br>TATTTCTCCTAAGTCAATAGAAATAAATTTATTAGGATGTAATATGTTTAGCTACTC<br>TATCAACGTAGAGGAGACTTATCCTGGAAAATTATTACTTAAAGTTAAAGATAAAAT<br>ATCAGAATTAATGCCATCTATAAGTCAAGACTCTATTATAGTAAGTGCAAATCAATA<br>TGAAGTTAGAATAAATAGTGAAGGAAGAAGAGAATTATTGGATCATTCTGGTGAATG<br>GATAAATAAAGAAGAAAGTATTATAAAGGATATTTCATCAAAAGAATATATATCATT<br>TAATCCTAAAGAAAATAAAATTACAGTAAAATCTAAAAATTTACCTGAGCTATCTAC<br>ATTATTACAAGAAATTAGAAATAATTCTAATTCAAGTGATATTGAACTAGAAGAAAA<br>AGTAATGTTAACAGAATGTGAGATAAATGTTATTTCAAATATAGATACGCAAATTGT<br>TGAGGAAAGGATTGAAGAAGCTAAGAATTTAACTTCTGACTCTATTAATTATATAAA<br>AGATGAATTTAAACTAATAGAATCTATTTCTGATGCACTATGTGACTTAAAACAACA<br>GAATGAATTAGAAGATTCTCATTTTATATCTTTTGAGGACATATCAGAGACTGATGA<br>GGGATTTAGTATAAGATTTATTAATAAAGAAACTGGAGAATCTATATTTGTAGAAAC<br>TGAAAAAACAATATTCTCTGAATATGCTAATCATATAACTGAAGAGATTCTAAGAT<br>AAAAGGTACTATATTTGATACTGTAAATGGTAAGTTAGTAAAAAAGTAAATTTAGA<br>TACTACACACGAAGTAAATACTTTAAATGCTGCATTTTTTATACAATCATTAATAGA<br>ATATAATAGTTCTAAAGAATCTCTTAGTAATTTAAGTGTAGCAATGAAAGTCCAAGT<br>TTACGCTCAATTATTTAGTACTGGTTTAAATACTATTACAGATGCAGCCAAAGTTGT<br>TGAATTAGTATCAACTGCATTAGATGAAACTATAGACTTACTTCCTACATTATCTGA<br>AGGATTACCTATAATTGCAACTATTATAGATGGTGTAAGTTTAGGTGCAGCAATCAA<br>AGAGCTAAGTGAAACGAGTGACCCATTATTAAGCAAGAAATAGAAGGTAAGATAGG<br>TATAATGGCAGTAAATTTAACAACAGCTACAACTGCAATGATTACTTCATCTTTGGG<br>GATAGCTAGTGGATTTAGTATACTTTTAGTTCCTTTAGCAGGAATTTCAGCAGGTAT<br>ACCAAGCTTAGTAAACAATGAACTTGTACTTCGAGATAAGGCAACAAAGGTTGTAGA<br>TTATTTTAAACATGTTTCATTAGTTGAAACTGAAGGAGTATTTACTTTATTAGATGA<br>TAAAATAATGATGCCACAAGATGATTTAGTGATATCAGAAATAGATTTTAATAATAA<br>TTCAATAGTTTAGGTAAATGTGAAATCTGGAGAATGGAAGGTGGTTCAGGTCATAC<br>TGTAACTGATGATATAGATCACTTCTTTTCAGCACCATCAATAACATATAGAGAGCC<br>ACACTTATCTATATATGACGTATTGGAAGTACAAAAAGAAGAACTTGATTTGTCAAA<br>AGATTTAATGGTATTACCTAATGCTCCAAATAGAGTATTTGCTTGGGAAACAGGATG<br>GACACCAGGTTTAAGAAGCTTAGAAAATGATGGCACAAAACTGTTAGACCGTATAAG<br>AGATAACTATGAAGGTGAGTTTTATTGGAGATATTTTGCTTTTATAGCTGATGCTTT<br>AATAACAACATTAAAACCAAGATATGAAGATACTAATATAAGAATAAATTTAGATAG<br>TAATACTAGAAGTTTTATAGTTCCAATAATAACTACAGAATATATAAGAGAAAAATT<br>ATCATATTCTTTCTATGGTTCAGGAGGAACTTATGCATTGTCTCTTTCTCAATATAA<br>TATGGGTATAAATATAGAATTAAGTGAAAGTGATGTTTGGATTATAGATGTTGATAA<br>TGTTGTGAGAGATGTAACTATAGAATCTGATAAAATTAAAAAAGGTGATTTAATAGA<br>AGGTATTTTATCTACACTAAGTATTGAAGAGAATAAAATTATCTTAAATAGCCATGA<br>GATTAATTTTCTGGTGAGGTAAATGGAAGTAATGGATTTGTTTCTTTAACATTTTCA<br>ATTTTAGAAGGAATAAATGCAATTATAGAAGTTGATTTATTATCTAAATCATATAAA<br>TTACTTATTTCTGGCGAATTAAAAATATTGATGTTAAATTCAAATCATATTCAACAG<br>AAAATAGATTATATAGGATTCAATAGCGAATTACAGAAAAATATACCCATATAGCTTT<br>GTAGATAGTGAAGGAAAAGAGAATGGTTTTATTAATGGTTCAACAAAAGAAGGTTTA |

TABLE OF SEQUENCES

| SEQ ID NO | Description | Sequence 5'-3' |
|---|---|---|
| | | TTTGTATCTGAATTACCTGATGTAGTTCTTATAAGTAAGGTTTATATGGATGATAGT<br>AAGCCTTCATTTGGATATTATAGTAATAATTTGAAAGATGTCAAAGTTATAACTAAA<br>GATAATGTTAATATATTAACAGGTTATTATCTTAAGGATGATATAAAAATCTCTCTT<br>TCTTTGACTCTACAAGATGAAAAAACTATAAAGTTAAATAGTGTGCATTTAGATGAA<br>AGTGGAGTAGCTGAGATTTTGAAGTTCATGAATAGAAAAGGTAATACAAATACTTCA<br>GATTCTTTAATGAGCTTTTTAGAAAGTATGAATATAAAAAGTATTTTCGTTAATTTC<br>TTACAATCTAATATTAAGTTTATATTAGATGCTAATTTTATAATAAGTGGTACTACT<br>TCTATTGGCCAATTTGAGTTTATTTGTGATGAAAATGATAATATACAACCATATTTC<br>ATTAAGTTTAATACACTAGAAACTAATTATACTTTATATGTAGGAAATAGACAAAAT<br>ATGATAGTGGAACCAAATTATGATTTAGATGATTCTGGAGATATATCTTCAACTGTT<br>ATCAATTTCTCTCAAAAGTATCTTTATGGAATAGACAGTTGTGTTAATAAAGTTGTA<br>ATTTCACCAAATATTTATACAGATGAAATAAATATAACGCCTGTATATGAAACAAAT<br>AATACTTATCCAGAAGTTATTGTATTAGATGCAAATTATATAAATGAAAAAATAAAT<br>GTTAATATCAATGATCTATCTATACGATATGTATGGAGTAATGATGGTAATGATTTT<br>ATTCTTATGTCAACTAGTGAAGAAAATAAGGTGTCACAAGTTAAAATAAGATTCGTT<br>AATGTTTTTAAAGATAAGACTTTGGCAAATAAGCTATCTTTAACTTTAGTGATAAAC<br>AAGATGTACCTGTAAGTGAAATAATCTTATCATTTACACCTTCATATTATGAGGATG<br>GATTGATTGGCTATGATTTGGGTCTAGTTTCTTTATATAATGAGAAATTTTATATTA<br>ATAACTTTGGAATGATGGTATCTGGATTAATATATATTAATGATTCATTATATTATT<br>TTAAACCACCAGTAAATAATTTGATAACTGGATTTGTGACTGTAGGCGATGATAAAT<br>ACTACTTTAATCCAATTAATGGTGGAGCTGCTTCAATTGGAGAGACAATAATTGATG<br>ACAAAAATTATTATTTCAACCAAAGTGGAGTGTTACAAACAGGTGTATTTAGTACAG<br>AAGATGGATTTAAATATTTTGCCCCAGCTAATACACTTGATGAAAACCTAGAAGGAG<br>AAGCAATTGATTTTACTGGAAAATTAATTATTGACGAAAATATTTATTATTTTGATG<br>ATAATTATAGAGGAGCTGTAGAATGGAAAGAATTAGATGGTGAAATGCACTATTTTA<br>GCCCAGAAACAGGTAAAGCTTTTAAAGGTCTAAATCAAATAGGTGATGATAAATACT<br>ATTTCAATTCTGATGGAGTTATGCAAAAGGATTTGTTAGTATAAATGATAATAAAC<br>ACTATTTTGATGATTCTGGTGTTATGAAAGTAGGTTACACTGAAATAGATGGCAAGC<br>ATTTCTACTTTGCTGAAAACGGAGAAATGCAAATAGGAGTATTTAATACAGAAGATG<br>GATTTAAATATTTTGCTCATCATAATGAAGATTTAGGAAATGAAGAAGGTGAAGAAA<br>TCTCATATTCTGGTATATTAAATTTCAATAATAAAATTTACTATTTTGATGATTCAT<br>TTACAGCTGTAGTTGGATGGAAAGATTTAGAGGATGGTTCAAAGTATTATTTTGATG<br>AAGATACAGCAGAAGCATATATAGGTTTGTCATTAATAAATGATGGTCAATATTATT<br>TTAATGATGATGGAATTATGCAAGTTGGATTTGTCACTATAAATGATAAAGTCTTCT<br>ACTTTTCTGACTCTGGAATTATAGAATCTGGAGTACAAAACATAGATGACAATTATT<br>TCTATATAGATGATAATGGTATAGTTCAAATTGGTGTATTTGATACTTCAGATGGAT<br>ATAAATATTTTGCACCTGCTAATACTGTAAATGATAATATTTACGGACAAGCAGTTG<br>AATATAGTGGTTTAGTTAGAGTTGGGGAAGATGTATATTATTTTGGAGAAACATATA<br>CAATTGAGACTGGATGGATATATGATATGGAAATGAAAGTGATAAATATTATTTCA<br>ATCCAGAAACTAAAAAAGCATGCAAAGGTATTAATTTAATTGATGATATAAAATATT<br>ATTTTGATGAGAAGGGCATAATGAGAACGGGTCTTATATCATTTGAAAATAATAATT<br>ATTACTTTAATGAGAATGGTGAAATGCAATTTGGTTATATAAATATAGAAGATAAGA<br>TGTTCTATTTTGGTGAAGATGGTGTCATGCAGATTGGAGTATTTAATACACCAGATG<br>GATTTAAATACTTTGCACATCAAAATACTTTGGATGAGAATTTTGAGGGAGAATCAA<br>TAAACTATACTGGTTGGTTAGATTTAGATGAAAAGAGATATTATTTTACAGATGAAT<br>ATATTGCAGCAACTGGTTCAGTTATTATTGATGGTGAGGAGTATTATTTTGATCCTG<br>ATACAGCTCAATTAGTGATTAGTGAATAG |
| 9 | cdtA from GenBank HQ639679 | ATGAAAAAATTTAGAAAACATAAAAGTATTAGTAATTGTATATCTATATTGTTGATA<br>TTTATATCTAACTTTAGGTAGTTTGTTACCTAATAACATTTATGCACAAGACTTACAA<br>AGCTATAGTGAAAAAGTTTGCAATACTACTTACAAGGCTCCTATAGAAAGACCAGAA<br>GATTTTCTTAAAGATAAAGAAAGGGCTAAAGAATGGGAAAGAAAAGAAGCAGAAAGA<br>ATAGAGCAAAAACTTGAAAGATCTGAAAAAGAAGCATTAGAATCATATAAAAAAGAT<br>TCTGTAGAAATAAATAAATATTCTCAGACAAGAAATTATTTTTATGATTATCAAATA<br>GAAGCAAATTCTCGAGAAAAAGAATATAGAGAACTTCGAAATGCTATATCAAAAAAT<br>AAAATAGATAAACCTATGTATGTCTATTATTTTGAATCTCCAGAAAAATTTGCATTT<br>AATAAAGTAATAAGAACAGAAAATCAAAACGAAATTTCATTAGAAAAATTTAATGAG<br>TTTAAAGAAACTATACAAAACAAATTATTTAAGCAAGATGGATTTAAAGAAATTTCT<br>TTATATGAACCTGGAAAAGGTGATGAAGAACCTACACCATTACTTATGCACTTAAAA<br>TTACCTAGAAATACTGGTATGTTACCATATACAAATACTAACAATGTAAGTACATTA<br>ATAGAGCAAGGATATAGTATAAAAATAGATAAAATTGTTCGTATAGTTATAGATGGG<br>AAACATTATATTAAAGCAGAAGCATCTGTTGTAAGTAGTCTTGATTTTAAGGATGAT<br>GTAAGTAAGGGGGACTCTTGGGGTAAAGCAAATTATAATGATTGGAGTAATAAATTA<br>ACACCTAATGAACTTGCTGATGTAAATGATTATATGCGTGGAGGATATACTGCAATT<br>AATAATTATTTAATATCAAATGGTCCAGTAAATAACCCTAACCCAGAATTAGATTCT<br>AAAATCACAAACATTGAAAATGCATTAAAACGTGAACCTATTCCAACTAATTTAACT<br>GTATATAGAAGATCTGGTCCTCAAGAATTTGGTTTAACCCTTACTTCCCCTGAATAT<br>GATTTTAACAAACCAGAAAATATAGATGCTTTTAAATCAAAATGGGAAGGACAAACA<br>CTGTCTTATCCAAACTTTATTAGTACTAGTATTGGTAGTGTGAATATGAGTGCATTT<br>GCTAAAAGAAAAATAGTACTACGTATAACTATACCTAAAGGTTCTCCTGGAGCCTAT<br>CTATCAGCTATTCCAGGTTATGCAGGTGAATATGAAGTACTTTTAAATCATGGAAGC<br>AAATTTAAAATCAGTAAAATTGATTCTTACAAAGATGGCGCTATAACAAAATTAATT<br>GTTGATGCAACATTGATACCTTAA |

-continued

TABLE OF SEQUENCES

| SEQ ID NO | Description | Sequence 5'-3' |
|---|---|---|
| | FRET cassettes | |
| 10 | Exemplary cdtB FRET cassette | Red-TCT-Ecl-AGCCGGTTTTCCGGCTGAGACGTCCGTGGCCT-Hexanediol |
| 11 | Exemplary tcdC FRET cassette | HEX-TCT-BBQdT-AGCCGGTTTTCCGGCTGAGCCTCGGCGCG-Hexanediol |
| 12 | Exemplary tcdB/tcdA FRET cassette | FAM-TCT-BBQdT-AGCCGGTTTTCCGGCTGAGACTCCGCGTCCGT-Hexanediol |
| | Binary Toxin oligomers | |
| 13 | cdtA Forward Primer | GAGCAAGGATATAGTAAAAATAGATAAAATTGTTCGTATAGTTATAGATGG |
| 14 | cdtA Invader | TATATTAAAGCAGAAGCATCTGTTGTAAGTAGTCTTGt |
| 15 | cdtA Invader | TATATTAAAGCAGAAGCATCTGTTGTAAGTAGTCTTGc |
| 16 | THS for cdtA probe | ATTTTAAGGATGATGTAAGTAAGGGAG |
| 17 | THS for cdtA probe | CGATTTTAAGGATGATGTAAGTAAGGG |
| 18 | cdtA Primary Probe | CGCGAGGCCGATTTTAAGGATGATGTAAGTAAGGGAG-hexanediol |
| 19 | cdtA Primary Probe | AGGCCACGGACGATTTTAAGGATGATGTAAGTAAGGGAG-hexanediol |
| 20 | cdtA Primary Probe | AGGCCACGGACGATTTTAAGGATGATGTAAGTAAGGG-hexanediol |
| 21 | cdtA Reverse Primer | ACTCCAATCACTATAATTTGCTTTACCCCAAG |
| 22 | cdtA Reverse Primer | CGCATATAATCATTTACATCAGCAAGTTCATTAGGT |
| 23 | cdtA Reverse Primer | ATTTGCTTTACCCCAAGAGTCTCCC |
| 24 | cdtA Reverse Primer | GCTTTACCCCAAGAGTCTCCC |
| 25 | cdtA Reverse Primer | ACTCCAATCACTATAATTTGCTTTACCCCAAGAGTC |
| 26 | cdtA Reverse Primer | CAATCACTATAATTTGCTTTACCCCAAGAGTC |
| 27 | cdtA Reverse Primer | AGGTGTTAATTTATTACTCCAATCACTATAATTTGCTTTACC |
| 28 | cdtA Reverse Primer | TGTTAATTTATTACTCCAATCACTATAATTTGCTTTACC |
| 29 | cdtA Reverse Primer | GTTCATTAGGTGTTAATTTATTACTCCAATCACTATAATTTGC |
| 30 | Forward Primer | GTTGATGTCTGATTGGGAAGACGAAGATTTGG |
| 31 | Forward Primer | TTTGACCCAAGGTTGATGTCTGATTGG |
| 32 | Forward Primer | GACCCAAGGTTGATGTCTGATTGG |
| 33 | Forward Primer | CTTTGACCCAAGGTTGATGTCTGATTGG |
| 34 | THS for cdtB probe | CGTTCATATGAATCTGGTATATTATCATTATC |
| 35 | THS for cdtB probe | GTTCATATGAATCTGGTATATTATCATTATCT |
| 36 | THS for cdtB probe | CGTTCATATGAATCTGGTATATTATC |
| 37 | cdtB Primary Probe | aggccacggacgCGTTCATATGAATCTGGTATATTATCATTATC-hexanediol |
| 38 | cdtB Primary Probe | aggccacggacgGTTCATATGAATCTGGTATATTATCATTATCT-hexanediol |
| 39 | cdtB Primary Probe | aggccacggacgCGTTCATATGAATCTGGTATATTATC-hexanediol |
| 40 | cdtB Reverse iPrimer | CACTTAACTGCAATTAAGTCCTTAATAGTATATCCATTTC |
| 41 | cdtB Reverse iPrimer | ACTTAACTGCAATTAAGTCCTTAATAGTATATCCATTTCG |
| 42 | cdtB Invader | ACTTAACTGCAATTAAGTCCTTAATAGTATATCCATTTCt |
| 43 | THS for cdtB probe | GGAAGACGAAGATTTGGATAC |
| 44 | THS for cdtB probe | GATACAGATAATGATAATATACCAGATTCATAT |
| 45 | THS for cdtB probe | GTTCATATGAATCTGGTATATTATCATTATCT |
| 46 | cdtB Primary Probe | CGCGAGGCCGGGAAGACGAAGATTTGGATAC-hexanediol |
| 47 | cdtB Primary Probe | CGCGAGGCCGGATACAGATAATGATAATATACCAGATTCATAT-hexanediol |
| 48 | cdtB Primary Probe | CGCGAGGCCGGTTCATATGAATCTGGTATATTATCATTATCT-hexanediol |
| 49 | cdtB Reverse Primer | CATAATCTGTATATGGATCTCCAGCAGTATTTGACTC |
| 50 | cdtB Reverse Primer | GACTCTAAATAATTTGATACATATTTCTTATAGCCTTGTTCTGC |
| 51 | cdtB Primary Probe | GGAAGACGAAGATTTGGATAC |
| 52 | cdtB Primary Probe | GGAAGACGAAGATTTGGATACA |
| 53 | cdtB Primary Probe | AGGCCACGGACGGGAAGACGAAGATTTGGATAC-hexanediol |
| 54 | cdtB Primary Probe | AGGCCACGGACGGGAAGACGAAGATTTGGATACA-hexanediol |
| 55 | cdtB Froward Primer | GATCCATTTATCCCAAATAAC |
| 56 | cdtB Reverse Primer | CATATTTCTTATAGCCTTGTTCTG |
| | tcdA oligomers | |
| 57 | THS for tcdA Probe | GAATAAACTTAGGTGCAGCAA |
| 58 | tcdA Primary Probe | TCCGCGCGTCCGAATAAACTTAGGTGCAGCAA-hexanediol |
| 59 | tcdA Forward Primer | CTTTATGCTCAACTATTTAGTAC |
| 60 | tcdA Forward Primer | CAGTAAATGATACTATAAATGTACTAC |
| 61 | THS for tcdA Probe | CTAGACGAACATGACCCAT |
| 62 | tcdA Primary Probe | acggacgcggagCTAGACGAACATGACCCAT-hexanediol |
| 63 | tcdA Invader | ATAAACTTAGGTGCAGCAATTAAGGAATTAa |
| 64 | tcdA Forward iPrimer | CAGAGGGGATACCTATTGTATCTACTATATTAGACGG |
| 65 | tcdA Forward iPrimer | GAGGGGATACCTATTGTATCTACTATTAGACGG |
| 66 | THS for tcdA Probe | CTAGACGAACATGACCCAT |
| 67 | THS for tcdA Probe | GAATAAACTTAGGTGCAGCAA |
| 68 | tcdA Primary Probe | cgcgccgaggCTAGACGAACATGACCCAT-hexanediol |
| 69 | tcdA Primary Probe | acggacgcggagGAATAAACTTAGGTGCAGCAA-hexanediol |
| 70 | tcdA Reverse Primer | GTAACTTCAGCACCTATTCCAACAATTGAAGCTAC |
| 71 | tcdA Reverse Primer | AGTAATGGGTCATGTTCGTCTAGTAATTCC |

-continued

TABLE OF SEQUENCES

| SEQ ID NO | Description | Sequence 5'-3' |
|---|---|---|
| 72 | tcdA Reverse Primer | GACATATTTATTGCTAAAACACCCACCTTAGCTTC |
| 73 | tcdA Reverse Primer | GATATACCAGCTATAGGTAATAAG |
| | tcdC oligomers | |
| 74 | tcdC 117 Invader | GGTGAGGATATATTGCCAAAAAACACGCg |
| 75 | tcdC 117 Invader | ACAAAGGGTATTGCTCTACTGGCATTTATTTTc |
| 76 | tcdC 117 Iprimer (N = A, C, T, or G) | ACAAAGGGTATTGCTCTACTGGCATTTATTTTG |
| 77 | Not Used | |
| 78 | Not Used | |
| 79 | Not Used | |
| 80 | Not Used | |
| 81 | Not Used | |
| 82 | Not Used | |
| 83 | Not Used | |
| 84 | Not Used | |
| 85 | Not Used | |
| 86 | tcdC 117del Invader | GGTGAGGATATTGCCAAAAAACACACg |
| 87 | tcdC 117del Revese iPrimer | GGTGAGGATATATTGCCAAAAAACACACCA |
| 88 | tcdC 117del Revese iPrimer | GGTGAGGATATATTGCCAAAAAACACACC |
| 89 | tcdC 117del Revese iPrimer | GGTGAGGATATATTGCCAAAAAACACGC |
| 90 | tcdC 117del Revese iPrimer | GGTGAGGATATATTGCCAAAAAACACAC |
| 91 | tcdC 117del Revese iPrimer | GGTGAGGATATATTGCCAAAAAACACG |
| 92 | tcdC 117del Revese iPrimer | GGTGAGGATATATTGCCAAAAAACACA |
| 93 | THS for tcdC 117del Probe | CAAAATAAATGCCAGTAGAGC |
| 94 | THS for tcdC 117del Probe | AAAATAAATGCCAGTAGAGCAATAT |
| 95 | THS for tcdC 117del Probe | AAAATAAATGCCAGTAGAGCAATATC |
| 96 | THS for tcdC 117del Probe | CAAAATAAATGCCAGTAGAG |
| 97 | THS for tcdC 117del Probe | CAAAATAAATGCCAGTAGA |
| 98 | THS for tcdC 117del Probe | CAAAATAAATGCCAGTAGAGCAA |
| 99 | THS for tcdC 117del Probe | CAAAATAAATGCCAGTAGAGCAATAC |
| 100 | THS for tcdC 117del Probe | CAAATAAATGCCAGTAGAGCAA |
| 101 | THS for tcdC 117del Probe | CAATAAATGCCAGTAGAGCAA |
| 102 | THS for tcdC 117del Probe | CATAAATGCCAGTAGAGCAA |
| 103 | THS for tcdC 117del Probe w/methoxy | CAAAAUAAATGCCAGTAGAGCAA |
| 104 | THS for tcdC 117del Probe w/methoxy | CAAmAATAAATGCCAGTAGAGCAA |
| 105 | THS for tcdC 117del Probe w/methoxy | CAmAAATAAATGCCAGTAGAGCAA |
| 106 | THS for tcdC 117del Probe w/methoxy | CAAAUAAATGCCAGTAGAGCAA |
| 107 | THS for tcdC 117del Probe w/methoxy | CAAUAAATGCCAGTAGAGCAA |
| 108 | THS for tcdC 117del Probe w/methoxy | CAUAAATGCCAGTAGAGCAA |
| 109 | THS for tcdC 117del Probe w/methoxy | CAAmAUAAATGCCAGTAGAGCAA |
| 110 | THS for tcdC 117del Probe w/methoxy | CAAAUmAAATGCCAGTAGAGCAA |

TABLE OF SEQUENCES

| SEQ ID NO | Description | Sequence 5'-3' |
|---|---|---|
| 111 | THS for tcdC 117del Probe w/methoxy | CAAmAUmAAATGCCAGTAGAGCAA |
| 112 | THS for tcdC 117del Probe w/methoxy | CmAAATAAATGCCAGTAGAGCAA |
| 113 | THS for tcdC 117del Probe w/methoxy | CmAAAATAAATGCCAGTAGAGCAA |
| 114 | THS for tcdC 117del Probe w/methoxy | CmAAAUAAATGCCAGTAGAGCAA |
| 115 | THS for tcdC 117del Probe w/methoxy | CmAAAAUAAATGCCAGTAGAGCAA |
| 116 | THS for tcdC 117del Probe w/methoxy | CAAAUmAAATGCCAGTAGAGCAATA |
| 117 | THS for tcdC 117del Probe w/methoxy | CAAAUmAAATGCCAGTAGAGCAATAC |
| 118 | THS for tcdC 117del Probe w/methoxy | CAAAUmAAATGCCAGTAGAGCAATACC |
| 119 | THS for tcdC 117del Probe w/methoxy | CAAAUmAAATGCCAGTAGAGCAATACCC |
| 120 | THS for tcdC 117del Probe w/methoxy | CAAAUmAAATGmCmCAGTAGAGmCAATA |
| 121 | THS for tcdC 117del Probe w/methoxy | mCAAAUmAAATGmCmCAGTAGAGmCAATA |
| 122 | THS for tcdC 117del Probe w/methoxy | mCAAAUmAAATGCCAGTAGAGCAATA |
| 123 | THS for tcdC 117del Probe | CAAAATAAATGCCAGTAGAGC |
| 124 | THS for tcdC 117del Probe | CAAAATAAATGCCAGTAGAGC |
| 125 | THS for tcdC 117del Probe | CAAAATAAATGCCAGTAGAG |
| 126 | THS for tcdC 117del Probe | CAAAATAAATGCCAGTAGA |
| 127 | THS for tcdC 117del Probe | AAAATAAATGCCAGTAGAGCAATAC |
| 128 | THS for tcdC 117del Probe | AAAATAAATGCCAGTAGAGCAATAT |
| 129 | THS for tcdC 117del Probe | AAAATAAATGCCAGTAGAGCAATATC |
| 130 | THS for tcdC 117del Probe with abasic linker | C(abasic)AAATAAATGCCAGTAGAGCAA |
| 131 | THS for tcdC 117del Probe with abasic linker | CA(abasic)AATAAATGCCAGTAGAGCAA |
| 132 | THS for tcdC 117del Probe with abasic linker | C(sp9)AAATAAATGCCAGTAGAGCAA |
| 133 | THS for tcdC 117del Probe with abasic linker | CA(sp9)AATAAATGCCAGTAGAGCAA |
| 134 | THS for tcdC 117del Probe with abasic linker | C(abasic)AAATAAATGCCAGTAGAGC |
| 135 | THS for tcdC 117del Probe with abasic linker | CA(abasic)AATAAATGCCAGTAGAGC |
| 136 | THS for tcdC 117del Probe with abasic linker | C(sp9)AAATAAATGCCAGTAGAGC |
| 137 | THS for tcdC 117del Probe with abasic linker | CA(sp9)AATAAATGCCAGTAGAGC |

-continued

TABLE OF SEQUENCES

| SEQ ID NO | Description | Sequence 5'-3' |
|---|---|---|
| 138 | tcdC 117del Primary Probe | cgcgccgaggCAAAATAAATGCCAGTAGAGC-hexanediol |
| 139 | tcdC 117del Primary Probe | cgcgccgaagAAAATAAATGCCAGTAGAGCAATAT-hexanediol |
| 140 | tcdC 117del Primary Probe | cgcgccgaggAAAATAAATGCCAGTAGAGCAATATC-hexanediol |
| 141 | tcdC 117del Primary Probe | cgcgccgaggCAAAATAAATGCCAGTAGAG-hexanediol |
| 142 | tcdC 117del Primary Probe | cgcgccgaggCAAAATAAATGCCAGTAGA-hexanediol |
| 143 | tcdC 117del Primary Probe | cgcgccgaggCAAAATAAATGCCAGTAGAGCAA-hexanediol |
| 144 | tcdC 117del Primary Probe | cgcgccgaggCAAAATAAATGCCAGTAGAGCAATAC-hexanediol |
| 145 | tcdC 117del Primary Probe | cgcgccgaggCAAATAAATGCCAGTAGAGCAA-hexanediol |
| 146 | tcdC 117del Primary Probe | cgcgccgaggCAATAAATGCCAGTAGAGCAA-hexanediol |
| 147 | tcdC 117del Primary Probe | cgcgccgaggCATAAATGCCAGTAGAGCAA-hexanediol |
| 148 | tcdC 117del Primary Probe w/methoxy | cgcgccgaggCAAAAUAAATGCCAGTAGAGCAA-hexanediol |
| 149 | tcdC 117del Primary Probe w/methoxy | cgcgccgaggCAAmAATAAATGCCAGTAGAGCAA-hexanediol |
| 150 | tcdC 117del Primary Probe w/methoxy | cgcgccgaggCAmAAATAAATGCCAGTAGAGCAA-hexanediol |
| 151 | tcdC 117del Primary Probe w/methoxy | cgcgccgaggCAAAUAAATGCCAGTAGAGCAA-hexanediol |
| 152 | tcdC 117del Primary Probe w/methoxy | cgcgccgaggCAAUAAATGCCAGTAGAGCAA-hexanediol |
| 153 | tcdC 117del Primary Probe w/methoxy | cgcgccgaggCAUAAATGCCAGTAGAGCAA-hexanediol |
| 154 | tcdC 117del Primary Probe w/methoxy | cgcgccgaggCAAmAUAAATGCCAGTAGAGCAA-hexanediol |
| 155 | tcdC 117del Primary Probe w/methoxy | cgcgccgaggCAAmAUmAAATGCCAGTAGAGCAA-hexanediol |
| 156 | tcdC 117del Primary Probe w/methoxy | cgcgccgaggCAAmAUmAAATGCCAGTAGAGCAA-hexanediol |
| 157 | tcdC 117del Primary Probe w/methoxy | cgcgccgaggCmAAATAAATGCCAGTAGAGCAA-hexanediol |
| 158 | tcdC 117del Primary Probe w/methoxy | cgcgccgaggCmAAAATAAATGCCAGTAGAGCAA-hexanediol |
| 159 | tcdC 117del Primary Probe w/methoxy | cgcgccgaggCmAAAUAAATGCCAGTAGAGCAA-hexanediol |
| 160 | tcdC 117del Primary Probe w/methoxy | cgcgccgaggCmAAAAUAAATGCCAGTAGAGCAA-hexanediol |
| 161 | tcdC 117del Primary Probe w/methoxy | cgcgccgaggCAAAUmAAATGCCAGTAGAGCAATA-hexanediol |
| 162 | tcdC 117del Primary Probe w/methoxy | cgcgccgaggCAAAUmAAATGCCAGTAGAGCAATAC-hexanediol |
| 163 | tcdC 117del Primary Probe w/methoxy | cgcgccgaggCAAAUmAAATGCCAGTAGAGCAATACC-hexanediol |
| 164 | tcdC 117del Primary Probe w/methoxy | cgcgccgaggCAAAUmAAATGCCAGTAGAGCAATACCC-hexanediol |
| 165 | tcdC 117del Primary Probe w/methoxy | cgcgccgaggCAAAUmAAATGmCmCAGTAGAGmCAATA-hexanediol |
| 166 | tcdC 117del Primary Probe w/methoxy | cgcgccgaggmCAAAUmAAATGmCmCAGTAGAGmCAATA-hexanediol |
| 167 | tcdC 117del Primary Probe w/methoxy | cgcgccgaggmCAAAUmAAATGCCAGTAGAGCAATA-hexanediol |
| 168 | tcdC 117del Primary Probe | atgacgtggcagacCAAAATAAATGCCAGTAGAGC-hexanediol |
| 169 | tcdC 117del Primary Probe | acggacgcggagCAAAATAAATGCCAGTAGAGC-hexanediol |
| 170 | tcdC 117del Primary Probe | acggacgcggagCAAAATAAATGCCAGTAGAG-hexanediol |
| 171 | tcdC 117del Primary Probe | acggacgcggagCAAAATAAATGCCAGTAGA-hexanediol |
| 172 | tcdC 117del Primary Probe | acggacgcggagAAAATAAATGCCAGTAGAGCAATAC-hexanediol |
| 173 | tcdC 117del Primary Probe | acggacgcggagAAAATAAATCCAGTAGAGCAATAT-hexanediol |
| 174 | tcdC 117del Primary Probe | acggacgcggagAAAATAAATGCCAGTAGAGCAATATC-hexanediol |

-continued

| TABLE OF SEQUENCES | | |
|---|---|---|
| SEQ ID NO | Description | Sequence 5'-3' |
| 175 | tcdC 117del Primary Probe with abasic linker | acggacgcggagC(abasic)AAATAAATGCCAGTAGAGCAA-hexanediol |
| 176 | tcdC 117del Primary Probe with abasic linker | acggacgcggagCA(abasic)AATAAATGCCAGTAGAGCAA-hexanediol |
| 177 | tcdC 117del Primary Probe with C9 linker | acggacgcggagC(sp9)AAATAAATGCCAGTAGAGCAA-hexanediol |
| 178 | tcdC 117del Primary Probe with C9 linker | acggacgcggagCA(sp9)AATAAATGCCAGTAGAGCAA-hexanediol |
| 179 | tcdC 117del Primary Probe with abasic linker | acggacgcggagC(abasic)AAATAAATGCCAGTAGAGC-hexanediol |
| 180 | tcdC 117del Primary Probe with abasic linker | acggacgcggagCA(abasic)AATAAATGCCAGTAGAGC-hexanediol |
| 181 | tcdC 117del Primary Probe with C9 linker | acggacgcggagC(sp9)AAATAAATGCCAGTAGAGC-hexanediol |
| 182 | tcdC 117del Primary Probe with C9 linker | acggacgcggagCA(sp9)AATAAATGCCAGTAGAGC-hexanediol |
| 183 | tcdC 117del Invader | ACAAAGGGTATTGCTCTACTGGCATTTATTTc |
| 184 | THS for tcdC 117del Primary Probe | TGGtGTGTTTTTTGGCAATAT |
| 185 | THS for tcdC 117del Primary Probe | GGtGTGTTTTTTGGCAATATATC |
| 186 | THS for tcdC 117del Primary Probe | GGtGTGTTTTTTGGCAATAT |
| 187 | THS for tcdC 117del Primary Probe | GGtGTGTTTTTTGGCAATATAC |
| 188 | tcdC 117del Primary Probe | acggacgcggagTGGtGTGTTTTTTGGCAATAT-hexanediol |
| 189 | tcdC 117del Primary Probe | atgacgtggcagacGGtGTGTTTTTTGGCAATATAC-hexanediol |
| 190 | tcdC 117del Primary Probe | atgacgtggcagacGGtGTGTTTTTTGGCAATAT-hexanediol |
| 191 | tcdC 117del Primary Probe | acggacgcggagGGtGTGTTTTTTGGCAATATATC-hexanediol |
| 192 | tcdC 117del Reverse iPrimer | GGTGAGGATATATTGCCAAAAAACACGCC |
| 193 | tcdC 117del Reverse iPrimer | GGTGAGGATATATTGCCAAAAAACACGCCA |
| 194 | tcdC 183/184 Invader | CTGAAGACCATGAGGAGGTCATTTCTAATa |
| 195 | tcdC 183/184 Invader | GTTCTGAAGACCATGAGGAGGTCATTTCTAAG |
| 196 | tcdC 183/184 Invader | GTTCTGAAGACCATGAGGAGGTCATTTCTAATG |
| 197 | THS for tcdC 184/184 CC > TT Primary Probe | TTAAACATCAGTTATAGATTCTC |
| 198 | THS for tcdC 184/184 CC > TT Primary Probe | TAAACATCAGTTATAGATTCTC |
| 199 | THS for tcdC 184/184 CC > TT Primary Probe | TTAAACATCAGTTATAGATTCTC |
| 200 | THS for tcdC 184/184 CC > TT Primary Probe | TAAAmCATCAGTTATAGATTCTC |
| 201 | tcdC 184/184 CC > TT Primary Probe | cgcgccgaggTTAAACATCAGTTATAGATTCTC-hexanediol |
| 202 | tcdC 184/184 CC > TT Primary Probe | cgcgccgaggTAAACATCAGTTATAGATTCTC-hexanediol |
| 203 | tcdC 184/184 CC > TT Primary Probe | cgcgccgaggTTAAACATCAGTTATAGATTCTC-hexanediol |
| 204 | tcdC 184/184 CC > TT Primary Probe | cgcgccgaggTAAAmCATCAGTTATAGATTCTC-hexanediol |

-continued

TABLE OF SEQUENCES

| SEQ ID NO | Description | Sequence 5'-3' |
|---|---|---|
| 205 | tcdC 184 Invader | GTTTCTATTTCTGTTTTTTGAGAATCTATAACTGATGTTTt |
| 206 | THS for tcdC 183C > T 184C > T Primary Probe | AATTAGAAATGACCTCCTCATGG |
| 207 | THS for tcdC 183C > T 184C > T Primary Probe | ATTAGAAATGACCTCCTCATGGT |
| 208 | THS for tcdC 183C > T 184C > T Primary Probe | AATTAGAAATGACCTCCTC |
| 209 | THS for tcdC 183C > T 184C > T Primary Probe | ATTAGAAATGACCTCCTC |
| 210 | THS for tcdC 183C > T 184C > T Primary Probe | AATTAGAAATGACCTCCTCATGG |
| 211 | THS for tcdC 183C > T 184C > T Primary Probe | AATTAGAAATGACCTCCTCATGG |
| 212 | THS for tcdC 183C > T 184C > T Primary Probe | ATTAGAAATGACCTCCTCATGGT |
| 213 | tcdC 183C > T 184C > T Primary Probe | cgcgccgaggAATTAGAAATGACCTCCTCATGG-hexanediol |
| 214 | tcdC 183C > T 184C > T Primary Probe | cgcgccgaggATTAGAAATGACCTCCTCATGGT-hexanediol |
| 215 | tcdC 183C > T 184C > T Primary Probe | cgcgccgaggAATTAGAAATGACCTCCTC-hexanediol |
| 216 | tcdC 183C > T 184C > T Primary Probe | cgcgccgaggATTAGAAATGACCTCCTC-hexanediol |
| 217 | tcdC 183C > T 184C > T Primary Probe | atgacgtggcagacAATTAGAAATGACCTCCTCATGG-hexanediol |
| 218 | tcdC 183C > T 184C > T Primary Probe | acggacgcggagAATTAGAAATGACCTCCTCATGG-hexanediol |
| 219 | tcdC 183C > T 184C > T Primary Probe | acggacgcggagATTAGAAATGACCTCCTCATGGT-hexanediol |
| 220 | tcdC 183T Forward iPrimer (+) | CTTGTTCTGAAGACCATGAGGAGGTCATTTCTAAT |
| 221 | tcdC 184 Forward iPrimer (-) | GTTTCTATTTCTGTTTTTTGAGAATCTATAACTGATGTTTAA |
| 222 | tcdC 184 Forward Primer | GCAATATATCCTCACCAGCTTGTTCTGAAG |
| 223 | tcdC 184 Invader | GAAGACCATGAGGAGGTCATTTCTAACa |
| 224 | Not Used | Not Used |
| 225 | tcdC 184 Iprimer 2 (-) | GTTTCTATTTCTGTTTTTTGAGAATCTATAACTGATGTTTA |
| 226 | Not Used | |
| 227 | Not Used | |
| 228 | Not Used | |
| 229 | Not Used | |
| 230 | Not Used | |
| 231 | Not Used | |
| 232 | Not Used | |
| 233 | THS for tcdC 184C > T Primary Probe | AGTTAGAAATGACCTCCTCATG |
| 234 | THS for tcdC 184C > T Primary Probe | TAAACATCAGTTATAGATTCTCAAAAAGC |
| 235 | THS for tcdC 184C > T Primary Probe | TAAACATCAGTTATAGATTCTCAAAAAGC |
| 236 | THS for tcdC 184C > T Primary Probe | AGTTAGAAATGACCTCCTCATG |
| 237 | THS for tcdC 184C > T Primary Probe | TAAACATCAGTTATAGATTCTC |

-continued

| SEQ ID NO | Description | Sequence 5'-3' |
|---|---|---|
| 238 | tcdC 184C > T Primary Probe | atgacgtggcagacAGTTAGAAATGACCTCCTCATG-hexanediol |
| 239 | tcdC 184C > T Primary Probe | atgacgtggcagacTAAACATCAGTTATAGATTCTCAAAAAGC-hexanediol |
| 240 | tcdC 184C > T Primary Probe | acggacgcggagTAAACATCAGTTATAGATTCTCAAAAAGC-hexanediol |
| 241 | tcdC 184C > T Primary Probe | acggacgcggagAGTTAGAAATGACCTCCTCATG-hexanediol |
| 242 | tcdC 184C > T Primary Probe | acggacgcggagTAAACATCAGTTATAGATTCTC-hexanediol |
| 243 | tcdC Forward Primer | GGAAAAGGAAGCTCTAAGAAAATAATTAAATTCTTTAAGAGC |
| 244 | tcdC Forward Primer | GGAAGCTCTAAGAAAATAATTAAATTCTTTAAGAGCACAAAGGG |
| 245 | tcdC Forward Primer | GGTAAmCGAATTTAGTAATGAA |
| 246 | tcdC Forward Primer | GGTAAmCGAATTTAGTAATGAA |
| 247 | tcdC Forward Primer | GGAAGCTCTAAGAAAATAATTAAATTCTTTAAGAGCACAAAGG |
| 248 | tcdC Forward Primer | GGTAACGAATTTAGTAATGAAGGAAAAGGAAGC |
| 249 | tcdC Reverse Primer | GTTCAGCATCAGACAATTTGCTATTTAAAGTTTCTATTTC |
| 250 | tcdC Reverse Primer | GAACCATGGTTCAGCATCAGACAATTTGC |
| 251 | tcdC Reverse Primer | CTTTCTTTTCGTCGTCTTTCATTTTGAACCATGG |
| 252 | tcdC Reverse Primer | CAATAGCTTTCTTTTCGTCGTCTTTCATTTTGAACC |
| 253 | tcdC Reverse Primer | TCATAAGTAATACCAGTATCATATC |
| 254 | tcdC Reverse Primer | TCATAAGTAATACCAGTATCATATCC |
| 255 | tcdC Reverse Primer | GTCGTCTTTCATTTTGAACCATGGTTCAGC |
| 256 | tcdC Reverse Primer | GTTTCTATTTCTGTTTTTTGAGAATCTATAACTGATGTTTGA |
| 257 | tcdC Reverse Primer | CCTCCTCATGGTCTTCAGAACAAG |
| 258 | tcdC Reverse Primer | CCTCCTCATGGTCTTCAGAACAAGC |
| 259 | tcdC Reverse Primer | GACCTCCTCATGGTCTTCAGAACAAG | tcdB oligomers

| 260 | tcdB Forward iPrimer | GTAAGTTTAGGTGCAGCAATCAAAGAGCT |
|---|---|---|
| 261 | tcdB Forward iPrimer | GTAAGTTTAGGTGCAGCAATCAAAGAGTT |
| 262 | tcdB Forward iPrimer | GGATTACCTGTAATTGCTACTATTATAGATGGTGTAAGT |
| 263 | tcdB Forward iPrimer | GATTACCTGTAATTGCTACTATTATAGATGGTGTAAGT |
| 264 | tcdB Forward Primer | GTGTAAGTTTAGGTGCAGCAATCAAAGAG |
| 265 | tcdB Forward Primer | GGTGCAGCAATCAAAGAG |
| 266 | tcdB Forward Primer | TGGTGTAAGTTTAGGTGCAGCAATCAAAGAG |
| 267 | tcdB Forward Primer | GATTGGAGGGTCAAATAAATGACACTGCTATTAAT |
| 268 | tcdB Forward Primer | ATAGATGGTGTAAGTTTAGGTGCAGCAATC |
| 269 | tcdB Forward Primer | TGGTGTAAGTTTAGGTGCATCAATTAAAGAG |
| 270 | tcdB Forward Primer | GGTGCAGCAATCAAAGAGCTAAGTG |
| 271 | tcdB Forward Primer | GTAAGTTTAGGTGCATCAATTAAAGAGTTGAGTG |
| 272 | tcdB Forward Primer | GTGTAAGTTTAGGTGCATCAATTAAAGAGTTGAGTG |
| 273 | tcdB Forward Primer | GTGGATTTAGTATACTTTTAGTTC |
| 274 | tcdB Forward Primer | GTATTACCTAATGCTCCAAATAGAGTATTTGCTTG |
| 275 | tcdB Forward Primer | CCTAATGCCCAGATAGAGTATTTGGCTG |
| 276 | tcdB Forward Primer | GCCCCAGATAGAATCTTTGGCTG |
| 277 | tcdB Forward Primer | CTAATGCCCCAGATAGAATCTTTGGCTG |
| 278 | tcdB Forward Primer | CTTGATTTGTCAAAAGATTTAATG |
| 279 | tcdB Forward Primer | mCTTGATTTATmCAAAAGATTTAATG |
| 280 | tcdB Invader | TTTACTGCCATTATACCTATCTTAGCTTCTATTTa |
| 281 | THS for tcdB Primary Probe | CTTGTCTTAATAATGGGTCACT |
| 282 | THS for tcdB Primary Probe | TAATTATATAAATCAATGGAAAGATGTAAATAGTG |
| 283 | THS for tcdB Primary Probe | GGGAAAGAGGATGGACG |
| 284 | THS for tcdB Primary Probe | GGGAAAGAGGATGGACGC |
| 285 | THS for tcdB Primary Probe | GGGAAAGAGGATGGAC |
| 286 | THS for tcdB Primary Probe | GGGAAAGAGGATGGACGCCAG |
| 287 | THS for tcdB Primary Probe | GGGAAACAGGATGGACACC |
| 288 | THS for tcdB Primary Probe | GGGAAAGAGGATGGACGCC |
| 289 | THS for tcdB Primary Probe | ATTATAGTCACTATTTACATCTTTCCATTGATTTATAT |
| 290 | THS for tcdB Primary Probe | CAAAGAGCTAAGTGAAACCAGTGAC |
| 291 | THS for tcdB Primary Probe | CAAAGAGCTAAGTGAAACCAGTGACC |
| 292 | THS for tcdB Primary Probe | CAAAGAGCTAAGTGAAACCAGTGACCC |

-continued

TABLE OF SEQUENCES

| SEQ ID NO | Description | Sequence 5'-3' |
|---|---|---|
| 293 | THS for tcdB Primary Probe | TAAGTGAAACCAGTGACCCATTATTAAGAC |
| 294 | THS for tcdB Primary Probe | CTTGTCTTAATAATGGGTCACT |
| 295 | THS for tcdB Primary Probe | TGAGTGAAACCAGTGACCCATTATTAAGAC |
| 296 | THS for tcdB Primary Probe | TTTAGGTGCATCAATTAAAGAGTTG |
| 297 | THS for tcdB Primary Probe | TTTAGGTGCAGCAATTAAAGAGTTA |
| 298 | THS for tcdB Primary Probe | CTTGTmCTTAATAATGGGTmCAmCT |
| 299 | tcdB Primary Probe | cgcgccgaggCTTGTCTTAATAATGGGTCACT-hexanediol |
| 300 | tcdB Primary Probe | acggacgcggagTAATTATATAAATCAATGGAAAGATGTAAATAGTG-hexanediol |
| 301 | tcdB Primary Probe | acggacgcggagGGGAAAGAGGATGGACG-hexanediol |
| 302 | tcdB Primary Probe | acggacgcggagGGGAAAGAGGATGGACGC-hexanediol |
| 303 | tcdB Primary Probe | acggacgcggagGGGAAAGAGGATGGAC-hexanediol |
| 304 | tcdB Primary Probe | acggacgcggagGGGAAAGAGGATGGACGCCAG-hexanediol |
| 305 | tcdB Primary Probe | acggacgcggagGGGAAACAGGATGGACACC-hexanediol |
| 306 | tcdB Primary Probe | acggacgcggagGGGAAAGAGGATGGACGCC-hexanediol |
| 307 | tcdB Primary Probe | acggacgcggagATTATAGTCACTATTTACATCTTTCCATTGATTTATAT-hexanediol |
| 308 | tcdB Primary Probe | ACGGACGCGGAGCAAAGAGCTAAGTGAAACCAGTGAC-hexanediol |
| 309 | tcdB Primary Probe | ACGGACGCGGAGCAAAGAGCTAAGTGAAACCAGTGACC-hexanediol |
| 310 | tcdB Primary Probe | ACGGACGCGGAGCAAAGAGCTAAGTGAAACCAGTGACCC-hexanediol |
| 311 | tcdB Primary Probe | ACGGACGCGGAGTAAGTGAAACCAGTGACCCATTATTAAGAC-hexanediol |
| 312 | tcdB Primary Probe | acggacgcggagCTTGTCTTAATAATGGGTCACT-hexanediol |
| 313 | tcdB Primary Probe | ACGGACGCGGAGTGAGTGAAACCAGTGACCCATTATTAAGAC-hexanediol |
| 314 | tcdB Primary Probe | acggacgcggagTTTAGGTGCATCAATTAAAGAGTTG-hexanediol |
| 315 | tcdB Primary Probe | acggacgcggagTTTAGGTGCAGCAATTAAAGAGTTA-hexanediol |
| 316 | tcdB Primary Probe | acggacgcggagCTTGTmCTTAATAATGGGTmCAmCT-hexanediol |
| 317 | tcdB Reverse iPrimer | TTTACTGCCATTATACCTATCTTAGCTTCTATTTC |
| 318 | tcdB Reverse Primer | CTGCCATTATACCTATCTTAGCTTCTATTTCTTGTC |
| 319 | tcdB Reverse Primer | CTGCCATTATACCTATCTTAGCTTCTATTTCTTG |
| 320 | tcdB Reverse Primer | CTGCCATTATACCTATTTTGCTTCTATTTCTTG |
| 321 | tcdB Forward Primer | GTAAGTTTAGGTGCATCAATTAAAGAGTT |
| 322 | tcdB Reverse Primer | GAACTAAAAGTATACTAAATCCACTAGC |
| 323 | tcdB Reverse iPrimer | TCAATGTGTTTATCAAAAATGCATTACTATCATAAAAAACATTAACA |
| 324 | tcdB Reverse iPrimer | TTTACTGCCATTATACCTATTTTTGCTTCTATTTC |
| 325 | tcdB Reverse iPrimer | TTTACTGCCATTATACCTATTTTTGGCTTCTATTTC |
| 326 | tcdB Reverse iPrimer | GTTTACTGCCATTATACCTATTTTTGGCTTCTATTTC |
| 327 | tcdB Reverse Primer | CAATGTGTTTATCAAAAATGCATTACTATCATAAAAAACATTAACAT |
| 328 | tcdB Reverse Primer | CTATTTCTTGTCTTAATAATGGGTCACTTGTTTCAC |
| 329 | tcdB Reverse Primer | CTTGTCTTAATAATGGGTCACTTGTTTCAC |
| 330 | tcdB Reverse Primer | CTATTTCTTGTCTTAATAATGGGTCACTAGTTTCAC |
| 331 | tcdB Reverse Primer | CTTGTCTTAATAATGGGTCACTAGTTTCAC |
| 332 | tcdB Reverse Primer | CCTGCTGAAATTCCTGCTAAAGGAACTAAAAGTATACTAAATCC |
| 333 | tcdB Reverse Primer | CCTGCTGAAATTCCTGCTAAAGGAACTAAAAGTATACTAAATC |
| 334 | tcdB Reverse Primer | ACCTGCTGAAATTCCTGCTAAAGGAACTAAAAGTATAC |
| 335 | tcdB Reverse Primer | AGTTTTGTACCATCATTTTCTAAGCTTCTTAAACC |
| 336 | tcdB Reverse Primer | CAGTTTTGTGCCATCATTTTCTAAGCTTCTTAAACC |
| 337 | tcdB Reverse Primer | CTCTTATACGGTCTAACAG |
| 338 | tcdB Reverse Primer | mCTCTTATAmCGGTCTAATAG |
| 339 | tcdB Forward Primer | TGGATTGGAGGTCAAATAAATGATACTGCTATT |

[1]lowercase bases have RNA backbone; uppercase bases have DNA backbone; mC indicates a 5-methylated cytosine; 2'-O-Methyladenosine; Hdiol = Hexanediol, HEX = Hexochloro-Fluorescein, FAM = Fluorescein, Red = Redmond Red fluorphore, BBQdT = Blackberry Quencher 650 dT, Ecl = Eclipse Quencher. C9 (also referred to as sp9) indicates spacer 9 linker (triethylene glycol chain).

What is claimed is:

1. A composition or kit comprising:

a detection oligomer comprising the sequence set forth in positions 7-18 of SEQ ID NO: 305, wherein the detection oligomer further comprises sufficient additional sequence to specifically hybridize to a C. difficile tcdB nucleic acid, and wherein the detection oligomer is non-extendable; and at least one secondary detection oligomer, comprising a secondary detection oligomer that is configured to interact with a fragment of the detection oligomer, comprises at least two labels, and comprises the sequence of SEQ ID NO: 12.

2. The composition or kit of claim 1, wherein the detection oligomer comprises the sequence set forth in SEQ ID NO: 305.

3. The composition or kit of claim 1, wherein the detection oligomer comprises a label.

4. The composition or kit of claim 1, wherein the detection oligomer has a length of 15 to 55 nucleotides.

5. The composition or kit of claim 1, wherein the at least two labels include a FRET pair.

6. The composition or kit of claim 1, wherein the at least two labels include a quencher.

7. The composition or kit of claim 1, wherein the fragment of the detection oligomer is a 5'-terminal flap of at least six nucleotides.

8. The composition or kit of claim 1, wherein the composition or kit comprises a plurality of secondary detection oligomers, wherein the secondary detection oligomers comprise FRET cassettes.

9. The composition or kit of claim 1, wherein the kit or composition further comprises a tedA primary detection oligomer configured to specifically hybridize to a tedA amplicon having a size from 80 to 400 nucleotides; and at least one additional secondary detection oligomer, wherein the secondary detection oligomers include a secondary detection oligomer configured to generate a positive signal in the presence of a tcdB nucleic acid and in the presence of a tcdA nucleic acid.

10. The composition or kit of claim 1, wherein the composition or kit comprises a nuclease with structure-specific activity toward a three-strand structure formed by 3'-end invasion.

11. The composition or kit of claim 1, wherein the composition or kit comprises a flap endonuclease or 5'-nuclease.

12. The composition or kit of claim 1, wherein the composition or kit comprises a FEN1 nuclease.

\* \* \* \* \*